US008802679B2

(12) United States Patent
Yoshihara et al.

(10) Patent No.: US 8,802,679 B2
(45) Date of Patent: Aug. 12, 2014

(54) GLYCINE COMPOUND

(75) Inventors: Kousei Yoshihara, Tokyo (JP); Daisuke Suzuki, Tokyo (JP); Susumu Yamaki, Tokyo (JP); Yuji Koga, Tokyo (JP); Norio Seki, Tokyo (JP); Jiro Fujiyasu, Tokyo (JP); Masahiro Neya, Kobe (JP)

(73) Assignee: Astellas Pharma Inc., Tokyo (JP)

( * ) Notice: Subject to any disclaimer, the term of this patent is extended or adjusted under 35 U.S.C. 154(b) by 159 days.

(21) Appl. No.: 13/394,505

(22) PCT Filed: Sep. 15, 2010

(86) PCT No.: PCT/JP2010/065918
§ 371 (c)(1),
(2), (4) Date: Mar. 6, 2012

(87) PCT Pub. No.: WO2011/034078
PCT Pub. Date: Mar. 24, 2011

(65) Prior Publication Data
US 2012/0184520 A1    Jul. 19, 2012

(30) Foreign Application Priority Data

Sep. 16, 2009 (JP) ................................ 2009-214991

(51) Int. Cl.
*A61K 31/497* (2006.01)
*C07D 403/14* (2006.01)

(52) U.S. Cl.
USPC .................. 514/252.14; 514/252.18; 544/295

(58) Field of Classification Search
CPC ... C07D 403/04; C07D 403/14; C07D 401/14
USPC .......................... 544/295; 514/252.14, 252.18
See application file for complete search history.

(56) References Cited

U.S. PATENT DOCUMENTS

| 4,888,283 | A | 12/1989 | Bertini et al. |
|---|---|---|---|
| 6,451,800 | B1 | 9/2002 | Ajito et al. |
| 2002/0173521 | A1 | 11/2002 | Smith et al. |
| 2004/0106792 | A1 | 6/2004 | Tauri et al. |
| 2005/0096359 | A1 | 5/2005 | Cho et al. |
| 2007/0066646 | A1 | 3/2007 | Clauzel et al. |
| 2009/0118502 | A1 | 5/2009 | Zhou et al. |
| 2009/0156646 | A1 | 6/2009 | Sasaki et al. |

FOREIGN PATENT DOCUMENTS

| CN | 1921841 A | 2/2007 |
|---|---|---|
| EP | 1 295 867 A1 | 3/2003 |
| JP | 61 239891 | 10/1986 |
| JP | 2000 178243 | 6/2000 |
| JP | 2002 80439 | 3/2002 |
| JP | 2007 500707 | 1/2007 |
| WO | 93 23023 | 11/1993 |
| WO | WO 98/50029 A1 | 11/1998 |
| WO | WO 98/50030 A1 | 11/1998 |
| WO | WO 98/50031 A1 | 11/1998 |
| WO | WO 99/38849 A1 | 8/1999 |
| WO | 02 02090 | 1/2002 |
| WO | 02 02541 | 1/2002 |
| WO | 02 38152 | 5/2002 |
| WO | 02 38153 | 5/2002 |
| WO | WO 03/057671 A1 | 7/2003 |
| WO | 2004 067521 | 8/2004 |
| WO | 2005 072738 | 8/2005 |
| WO | 2005 082343 | 9/2005 |
| WO | 2005 087236 | 9/2005 |
| WO | WO 2006/013209 A2 | 2/2006 |
| WO | 2007 018319 | 2/2007 |
| WO | WO 2007/119463 A1 | 10/2007 |
| WO | 2008 104077 | 9/2008 |
| WO | 2009 055002 | 4/2009 |

OTHER PUBLICATIONS

Purandare, A.V., et al., "Pyrazole inhibitors of coactivator associated arginine methyltransferase 1 (CARM1)," Bioorganic and Medicinal Chemistry Letters, vol. 18, No. 15, pp. 4438-4441, (2008).

Olivieri, A., et al., "L-lysine as a recognition molecule for the VAP-1 function of SSAO," Journal of Neural Transmission, vol. 114, pp. 747-749, (2007).

Boomsma, F., et al., "Circulating semicarbazide-sensitive amine oxidase is raised both in Type I (insulin-dependent), in Type II (non-insulin dependent) diabetes mellitus and even in childhood Type I diabetes at first clinical diagnosis," Diabetologia, vol. 42, pp. 233-237, (1999).

Garpenstrand, H., et al., "Elevated plasma semicarbazide-sensitive amine oxidase (SSAO) activity in Type 2 diabetes mellitus complicated by retinopathy," Diabetic Medicine, vol. 16, pp. 514-521, (1999).

Yu, P.H., et al., "Aminoguanidine inhibits semicarbazide-sensitive amine oxidase activity: implications for advanced glycation and diabetic complications," Diabetologia, vol. 40, pp. 1243-1250, (1997).

Nemcsik, J., et al., "Alteration of serum semicarbazide-sensitive amine oxidase activity in chronic renal failure," Journal of Neural Transmission, vol. 114, pp. 841-843, (2007).

International Search Report Issued Oct. 12, 2010 in PCT/JP10/65918 Filed Sep. 15, 2010.

Combined Office Action and Search Report issued Jun. 26, 2013 in Chinese Patent Application No. 201080041470.2 (with English translation and English translation of category of cited documents).

Israeli Office Action issued Sep. 3, 2013 in Patent Application No. 218394 with English Translation.

Office Action issued on Jul. 31, 2013 in the corresponding Thai Patent Application No. 1201001152.

Extended European Search Report Issued Jan. 30, 2013 in Patent Application No. 10817191.9.

*Primary Examiner* — Rebecca Anderson
(74) *Attorney, Agent, or Firm* — Oblon, Spivak, McClelland, Maier & Neustadt, L.L.P.

(57) ABSTRACT

Compounds of formula (I) defined herein exhibit VAP-1 inhibitory activity, and as a result, are useful for preventing and/or treating VAP-1-related diseases, in particular, diabetic nephropathy or diabetic macular edema, thereby completing the present invention.

12 Claims, No Drawings

GLYCINE COMPOUND

CROSS REFERENCES TO RELATED APPLICATIONS

This application is a 371 of International Patent Application No. PCT/JP2010/065919, filed on Sep. 15, 2010, and claims priority to Japanese Patent Application No. 2009-214991, filed on Sep. 16, 2009.

TECHNICAL FIELD

The present invention relates to a glycine compound which is useful as an active ingredient of a pharmaceutical composition, in particular, a pharmaceutical composition for preventing and/or treating vascular adhesion protein-1 (which will be hereinafter abbreviated as VAP-1)-related diseases.

BACKGROUND ART

VAP-1 is an amine oxidase (semicarbazide sensitive amine oxidase, SSAO) which is abundant in human plasma (Non-Patent Document 1), and shows remarkably increased expression in vascular endothelium and vascular smooth muscle of the inflammatory region. While the physiological role of VAP-1 has not been clarified until recently, VAP-1 gene was cloned in 1998, and VAP-1 has been reported to be a membrane protein that regulates rolling and migration of lymphocytes and NK cells as an adhesion molecule under regulation of expression by inflammatory cytokines. Although the amine as a substrate is unknown, it is considered to be methylamine generated in any part of biological body. It is also known that hydrogen peroxide and aldehydes produced due to the amine oxidase activity in the molecule are important factors of adhesion activity.

A recent report has documented that the VAP-1 enzyme activity in plasma increases in patients with diabetes mellitus, whether type I or type II, and the increase is particularly remarkable in the patients with diabetes mellitus suffering from retinopathy complications (Non-Patent Documents 2 and 3).

In addition, it has been reported that VAP-1 is related to the following diseases:

(1) cirrhosis, essential stabilized hypertension, diabetes mellitus, and arthrosis (Patent Documents 1 and 2);

(2) endothelium damage (in diabetes mellitus, arteriosclerosis, and hypertension), cardiovascular diseases related to diabetes mellitus and uremia, pain related to gout and arthritis, and retinopathy (in diabetes mellitus patients) (Patent Document 3);

(3) (connective tissue) inflammatory diseases or conditions (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematosus, systemic sclerosis, eosinophilic fasciitis, polymyositis, dermatomyositis, polymyalgia rheumatica, vasculitis, temporal arteritis, polyarteritis nodosa, Wegener's granulomatosis, mixed connective tissue disease, and juvenile rheumatoid arthritis); gastrointestinal inflammatory diseases or conditions [Crohn's disease, ulcerative colitis, irritable bowel syndrome (spastic colon), fibrotic conditions of the liver, inflammation of the oral mucosa (stomatitis), and recurrent aphtous stomatitis]; central nervous system inflammatory diseases or conditions (multiple sclerosis, Alzheimer's disease, and ischemia-reperfusion injury related to ischemic stroke); pulmonary inflammatory diseases or conditions (asthma, adult respiratory distress syndrome, and chronic obstructive pulmonary disease); (chronic) skin inflammatory diseases or conditions (psoriasis, allergic lesions, lichen planus, pityriasis rosea, contact dermatitis, atopic dermatitis, and pityriasis rubra pilaris); diseases related to carbohydrate metabolism (diabetes mellitus and complications from diabetes mellitus) including microvascular and macrovascular diseases (arteriosclerosis, vascular retinopathies, retinopathy, nephropathy, nephrotic syndrome and neuropathy (polyneuropathy, mononeuropathies and autonomic neuropathy), foot ulcers, joint problems, and increased risk of infection); diseases related to aberrations in adipocyte differentiation or function or smooth muscle cell function (arteriosclerosis and obesity); vascular diseases [atheromatous arteriosclerosis, nonatheromatous arteriosclerosis, ischemic heart disease including myocardial infarction and peripheral arterial occlusion, Raynaud's disease and phenomenon, and thromboangiitis obliterans (Buerger's disease)]; chronic arthritis; inflammatory bowel diseases; and skin dermatoses (Patent Documents 4, 5, and 6, and Non-Patent Documents 4 and 5);

(4) diabetes mellitus (Patent Document 7);

(5) SSAO-mediated complications [diabetes mellitus (insulin dependent diabetes mellitus (IDDM) and non-insulin dependent diabetes mellitus (NIDDM)) and vascular complications (heart attack, angina, strokes, amputations, blindness, and renal insufficiency)], and macular edema (for example, diabetic and non-diabetic macular edema) (Patent Documents 8 and 11); and (6) hepatitis, transplantation, and the like.

Under the present circumstances, a drug for treating or preventing the above diseases has been demanded.

Furthermore, Patent Document 9 discloses that a compound represented by the formula (A) has a VAP-1 inhibitory activity.

[Chem. 10]

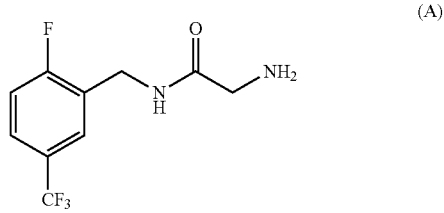

(A)

In addition, Patent Document 10 discloses that a compound represented by the formula (B) has a VAP-1 inhibitory activity.

[Chem. 11]

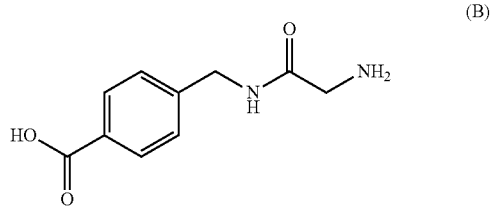

(B)

RELATED ART

Patent Document

[Patent Document 1] JP-A-61-239891
[Patent Document 2] U.S. Pat. No. 4,888,283
[Patent Document 3] Pamphlet of International Publication WO 93/23023
[Patent Document 4] Pamphlet of International Publication WO 02/02090
[Patent Document 5] Pamphlet of International Publication WO 02/02541
[Patent Document 6] U.S. Unexamined Patent Application Publication No. 2002/0173521
[Patent Document 7] Pamphlet of International Publication WO 02/38152
[Patent Document 8] Pamphlet of International Publication WO 02/38153
[Patent Document 9] Pamphlet of International Publication WO 05/082343
[Patent Document 10] Pamphlet of International Publication WO 09/055,002
[Patent Document 11] Pamphlet of International Publication WO 04/067521

Non-Patent Document

[Non-Patent Document 1] J Neural Transm, Vol. 114, pp. 747-749, 2007
[Non-Patent Document 2] Diabetologia, Vol. 42, pp. 233-237, 1999
[Non-Patent Document 3] Diabetic Medicine, Vol. 16, pp. 514-521, 1999
[Non-Patent Document 4] Diabetologia, Vol. 40, pp. 1243-1250, 1997
[Non-Patent Document 5] J Neural Transm, Vol. 114, pp. 841-843, 2007

DISCLOSURE OF INVENTION

Technical Problem

Problems to Be Solved by the Invention

The present invention provides a compound which is useful as an active ingredient of a pharmaceutical composition, in particular, a pharmaceutical composition for preventing and/or treating VAP-1-related diseases.

Means for Solving the Problems

The present inventors have conducted intensive studies on a compound having a VAP-1 inhibitory activity, and as a result, they have found that a compound of the formula (I) or a salt thereof exhibits an excellent VAP-1 inhibitory activity and is useful for preventing and/or treating VAP-1-related diseases, in particular, diabetic nephropathy or diabetic macular edema, thereby completing the present invention.

That is, the present invention relates to the compound of the formula (I) or a salt thereof, and a pharmaceutical composition comprising the compound of the formula (I) or a salt thereof, and an excipient.

[Chem. 12]

(I)

(wherein
$R^1$ is H or lower alkyl which may be substituted,
$R^2$ is halogen,
$R^3$ and $R^4$ are the same as or different from each other, and are H or halogen,
m is 0, 1, 2, 3, or 4,
$Y^1$ and $Y^2$ are the same as or different from each other, and are N or $CR^Y$,
$R^Y$ is H or halogen,
X is H, halogen, Z—$(CR^{11}R^{12})_n$—, $R^{13}R^{14}N$—$SO_2$—, or lower alkenyl which may be substituted,
n is 0 or 1,
$R^{11}$ and $R^{12}$ are the same as or different from each other, and are H, or $R^{11}$ and $R^{12}$ are combined together to form oxo (=O),
$R^{13}$ and $R^{14}$ are the same as or different from each other, and are H or lower alkyl,
Z is $R^{Z1}R^{Z2}N$—, $R^{Z3}O$—, or

[Chem. 13]

$R^{Z1}$ and $R^{Z2}$ are the same as or different from each other, and are H, —C(=O)—$R^{Z11}$, —C(=O)—O—$R^{Z11}$, —C(=O)—$NH_2$, —C(=O)—$NHR^{Z11}$, —C(=O)—N$(R^{Z11})_2$, —$SO_2$— (lower alkyl which may be substituted), —$SO_2$— (aryl which may be substituted), lower alkyl which may be substituted, or a hetero ring group which may be substituted,
$R^{Z11}$'s are the same as or different from each other, and are lower alkyl which may be substituted, cycloalkyl which may be substituted, or a hetero ring group which may be substituted,
$R^{Z3}$ is lower alkyl which may be substituted or a hetero ring group which may be substituted,
p is 0, 1, or 2,
q is 1 or 2,
E is CH or N,
G is $CR^{G1}R^{G2}$, $NR^{G3}$, O, or $SO_2$,
$R^{G1}$ and $R^{G2}$ are the same as or different from each other, and are H, OH, $NH_2$, —C(=O)—$R^{G31}$, —C(=O)—O—$R^{G31}$, —C(=O)—$NHR^{G31}$, —C(=O)—N$(R^{G31})_2$, —$SO_2$—$R^{G31}$, amino which may be substituted, or lower alkyl which may be substituted, cycloalkyl which may be substituted, aryl which may be substituted, or a hetero ring group which may be substituted,
$R^{G3}$ is H, $NH_2$, —C(=O)—$R^{G31}$, —C(=O)—O—$R^{G31}$, —C(=O)—$NHR^{G31}$, —C(=O)—N$(R^{G31})$, —$SO_2$—$R^{G31}$, or lower alkyl which may be substituted, cycloalkyl which may be substituted, aryl which may be substituted, or a hetero ring group which may be substituted,
$R^{G31}$'s are the same as or different from each other, and are lower alkyl which may be substituted, cycloalkyl which may be substituted, aryl which may be substituted, or a hetero ring group which may be substituted, and
$R^{21}$, $R^{22}$, $R^{23}$, $R^{24}$, $R^{25}$ and $R^{26}$ are the same as or different from each other, and are H, OH, halogen, $NH_2$, amino which may be substituted, or lower alkyl which may be substituted,
in which $R^{G1}$ or $R^{G2}$ may be combined with either $R^{21}$ or $R^{22}$ to form a new bond, or $R^{G1}$, $R^{G2}$, $R^{21}$, and $R^{22}$ may be combined together to form a nitrogen-containing hetero ring group which may be substituted, and $R^{G3}$, $R^{21}$, and $R^{22}$ may be combined together to form a nitrogen-containing hetero ring group which may be substituted.)

Moreover, unless specified otherwise, in the case where the symbols of the chemical formulae in the present specification are also used in other chemical formulae, the same symbols denote the same meanings.

The present invention relates to a pharmaceutical composition comprising the compound of the formula (I) or a salt thereof, and an excipient.

Furthermore, the present invention relates to pharmaceutical composition, in particular, a pharmaceutical composition for preventing and/or treating VAP-1-related diseases, which includes the compound of the formula (I) or a salt thereof, and an excipient.

In addition, the present invention relates to use of the compound of the formula (I) or a salt thereof for the preparation of a pharmaceutical composition for preventing and/or treating VAP-1-related diseases, use of the compound of the formula (I) or a salt thereof for preventing and/or treating VAP-1-related diseases, the compound of the formula (I) or a salt thereof for preventing and/or treating VAP-1-related diseases, and a method for preventing and/or treating VAP-1-related diseases, including administering to a patient an effective amount of the compound of the formula (I) or a salt thereof.

Effects of the Invention

The compound of the formula (I) or a salt thereof has a VAP-1 inhibitory action, and can be used as an agent for preventing and/or treating VAP-1-related diseases.

Further, the VAP-1-related diseases refer to diseases selected from the group consisting of:

(1) cirrhosis, essential stabilized hypertension, diabetes mellitus, and arthrosis;
(2) endothelium damage (in diabetes mellitus, arteriosclerosis, and hypertension), cardiovascular diseases related to diabetes mellitus and uremia, pain related to gout and arthritis, and retinopathy (in diabetes mellitus patients);
(3) (connective tissue) inflammatory diseases or conditions (rheumatoid arthritis, ankylosing spondylitis, psoriatic arthritis and osteoarthritis or degenerative joint disease, Reiter's syndrome, Sjogren's syndrome, Behcet's syndrome, relapsing polychondritis, systemic lupus erythematosus, discoid lupus erythematosus, systemic sclerosis, eosinophilic fasciitis, polymyositis, dermatomyositis, polymyalgia rheumatica, vasculitis, temporal arteritis, polyarteritis nodosa, Wegener's granulomatosis, mixed connective tissue disease, and juvenile rheumatoid arthritis); gastrointestinal inflammatory diseases or conditions [Crohn's disease, ulcerative colitis, irritable bowel syndrome (spastic colon), fibrotic conditions of the liver, inflammation of the oral mucosa (stomatitis), and recurrent aphtous stomatitis]; central nervous system inflammatory diseases or conditions (multiple sclerosis, Alzheimer's disease, and ischemia-reperfusion injury related to ischemic stroke); pulmonary inflammatory diseases or conditions (asthma, adult respiratory distress syndrome, and chronic obstructive pulmonary disease); (chronic) skin inflammatory diseases or conditions (psoriasis, allergic lesions, lichen planus, pityriasis rosea, contact dermatitis, atopic dermatitis, and pityriasis rubra pilaris); diseases related to carbohydrate metabolism (diabetes mellitus and complications from diabetes mellitus) including microvascular and macrovascular diseases (arteriosclerosis, vascular retinopathies, retinopathy, nephropathy, nephrotic syndrome and neuropathy (polyneuropathy, mononeuropathies and autonomic neuropathy), foot ulcers, joint problems, and increased risk of infection); diseases related to aberrations in adipocyte differentiation or function or smooth muscle cell function (arteriosclerosis and obesity); vascular diseases [atheromatous arteriosclerosis, nonatheromatous arteriosclerosis, ischemic heart disease including myocardial infarction and peripheral arterial occlusion, Raynaud's disease and phenomenon, and thromboangiitis obliterans (Buerger's disease)]; chronic arthritis; inflammatory bowel diseases; and skin dermatoses;
(4) diabetes mellitus;
(5) SSAO-mediated complications [diabetes mellitus (insulin dependent diabetes mellitus (IDDM) and non-insulin dependent diabetes mellitus (NIDDM)) and vascular complications (heart attack, angina, strokes, amputations, blindness, and renal insufficiency)], macular edema (for example, diabetic and non-diabetic macular edema); and
(6) hepatitis, transplantation, and the like.

EMBODIMENTS FOR CARRYING OUT THE INVENTION

Hereinafter, the present invention will be described in detail.

In the present specification, the "lower alkyl" refers to linear or branched alkyl having 1 to 6 carbon atoms (which is hereinafter simply referred to as $C_{1-6}$), for example, methyl, ethyl, n-propyl, isopropyl, n-butyl, isobutyl, sec-butyl, tert-butyl, n-pentyl, n-hexyl, or the like. In another embodiment, it is $C_{1-4}$ alkyl, and in a still another embodiment, $C_{1-3}$ alkyl.

The "lower alkenyl" refers to linear or branched $C_{2-6}$ alkenyl, for example, vinyl, propenyl, butenyl, pentenyl, 1-methylvinyl, 1-methyl-2-propenyl, 1,3-butadienyl, 1,3-pentadienyl, or the like. In another embodiment, it is $C_{2-4}$ alkenyl, and in a still embodiment, $C_{2-3}$ alkenyl.

The "cycloalkyl" refers to a $C_{3-10}$ saturated hydrocarbon ring group, which may have a bridge. It is, for example, cyclopropyl, cyclobutyl, cyclopentyl, cyclohexyl, cycloheptyl, cyclooctyl, adamantyl, or the like. In another embodiment, it is $C_{3-8}$ cycloalkyl, and in a still another embodiment, $C_{3-6}$ cycloalkyl.

The "aryl" refers to a $C_{6-14}$ monocyclic to tricyclic aromatic hydrocarbon ring group, and includes a ring group fused with $C_{5-8}$ cycloalkene at its double bond site. It is, for example, phenyl, naphthyl, 5-tetrahydronaphthyl, 4-indenyl, 1-fluorenyl, or the like. In an embodiment, it is phenyl.

The "hetero ring" means a ring group selected from i) a monocyclic 3- to 8-membered, and in another embodiment, 5- to 7-membered hetero ring, containing 1 to 4 hetero atoms selected from oxygen, sulfur, and nitrogen, and ii) a bi- to tricyclic hetero ring containing 1 to 5 hetero atoms selected from oxygen, sulfur, and nitrogen, formed by condensation with one or two rings in which the monocyclic hetero ring is selected from a monocyclic hetero ring, a benzene ring, $C_{5-8}$ cycloalkane, and $C_{5-8}$ cycloalkene. The ring atom, sulfur or nitrogen, may be oxidized to form an oxide or a dioxide.

Examples of the "hetero ring group" include the following embodiments (1) Monocyclic saturated hetero ring groups
(a) those containing 1 to 4 nitrogen atoms, for example, azepanyl, diazepanyl, aziridinyl, azetidinyl, pyrrolidinyl, imidazolidinyl, piperidyl, pyrazolidinyl, piperazinyl, azocanyl, hexamethyleneimino, homopiperazinyl, and the like;
(b) those containing 1 to 3 nitrogen atoms and 1 to 2 sulfur atoms and/or 1 to 2 oxygen atoms, for example, thiomorpholinyl, thiazolidinyl, isothiazolidinyl, oxazolidinyl, morpholinyl, and the like;
(c) those containing 1 to 2 sulfur atoms, for example, tetrahydropyranyl and the like;
(d) those containing 1 to 2 sulfur atoms and 1 to 2 oxygen atoms, for example, oxathiolanyl and the like;
(e) those containing 1 to 2 oxygen atoms, for example, oxiranyl, oxetanyl, dioxolanyl, tetrahydrofuranyl, tetrahydropyranyl, 1,4-dioxanyl, and the like;
(2) Monocyclic unsaturated hetero ring groups
(a) those containing 1 to 4 nitrogen atoms, for example, pyrrolyl, 2-pyrrolinyl, imidazolyl, 2-imidazolinyl, pyrazolyl, 2-pyrazolinyl, pyridyl, dihydropyridyl, tetrahydropyridinyl, pyrimidinyl, pyrazinyl, pyridazinyl, triazolyl, tetrazolyl, triazinyl, dihydrotriazinyl, azepinyl, and the like;
(b) those containing 1 to 3 nitrogen atoms and 1 to 2 sulfur atoms and/or 1 to 2 oxygen atoms, for example, thiazolyl, isothiazolyl, thiadiazolyl, dihydrothiazinyl, oxazolyl, isoxazolyl, oxadiazolyl, oxazinyl, and the like;
(c) those containing 1 to 2 sulfur atoms, for example, thienyl, thiepinyl, dihydrodithiopyranyl, dihydrodithionyl, 2H-thiopyranyl, and the like;
(d) those containing 1 to 2 sulfur atoms and 1 to 2 oxygen atoms, for example, dihydroxathiopyranyl and the like;
(e) those containing 1 to 2 oxygen atoms, for example, furyl, dihydrofuryl, pyranyl, 2H-pyranyl, oxepinyl, dioxolyl, and the like;
(3) Fused polycyclic saturated hetero ring groups
(a) those containing 1 to 5 nitrogen atoms, for example, quinuclidinyl, 7-azabicyclo[2.2.1]heptyl, 3-azabicyclo[3.2.2]nonanyl, and the like;
(b) those containing 1 to 4 nitrogen atoms and 1 to 3 sulfur atoms and/or 1 to 3 oxygen atoms, for example, trithiadiazaindenyl, dioxoloimidazolidinyl, and the like;
(c) those containing 1 to 3 sulfur atoms and/or 1 to 3 oxygen atoms, for example, 2,6-dioxabicyclo[3.2.2]oct-7-yl and the like;
(4) Fused polycyclic unsaturated hetero ring groups
(a) those containing 1 to 5 nitrogen atoms, for example, indolyl, isoindolyl, indolinyl, indolidinyl, benzoimidazolyl, dihydrobenzoimidazolyl, tetrahydrobenzoimidazolyl, quinolyl, tetrahydroquinolyl, isoquinolyl, tetrahydroisoquinolyl, indazolyl, imidazopyridyl, benzotriazolyl, tetrazolopyridazinyl, carbazolyl, acridinyl, quinoxalinyl, dihydroquinoxalinyl, tetrahydroquinoxalinyl, phthalazinyl, dihydroindazolyl, benzopyrimidinyl, naphthyridinyl, quinazolinyl, cinnolinyl, pyridopyrrolidinyl, triazolopiperidinyl, 9,10-dihydroacridine, and the like;
(b) those containing 1 to 4 nitrogen atoms and 1 to 3 sulfur atoms and/or 1 to 3 oxygen atoms, for example, benzothiazolyl, dihydrobenzothiazolyl, benzothiadiazolyl, imidazothiazolyl, imidazothiadiazolyl, benzoxazolyl, dihydrobenzoxazolyl, dihydrobenzoxadinyl, benzoxadiazolyl, benzoisothiazolyl, benzoisoxazolyl, thiazolopiperidinyl, 5,6-dihydro-4H-pyrrolo[3,4-d][1,3]thiazol-2-yl, 10H-phenothiazine, and the like;
(c) those containing 1 to 3 sulfur atoms, for example, benzothienyl, benzodithiopyranyl, chromanyl, dibenzo[b,d]thienyl, and the like;
(d) those containing 1 to 3 sulfur atoms and 1 to 3 oxygen atoms, for example, benzoxathiopyranyl, phenoxazinyl, and the like;
(e) those containing 1 to 3 oxygen atoms, for example, benzodioxolyl, benzofuranyl, dihydrobenzofuranyl, isobenzofuranyl, chromanyl, chromenyl, isochromenyl, dibenzo[b,d]furanyl, methylenedioxyphenyl, ethylenedioxyphenyl, xanthenyl, and the like;
etc.

Further, the "hetero ring group" in (1) to (4) above is described as a monovalent group, but this may represent a divalent or higher group in some cases.

The "monocyclic hetero ring group" refers to a hetero ring group which has one ring structure not fused with other rings as in (1) and (2), among the "hetero ring groups above.

The "nitrogen-containing hetero ring group" refers to one containing at least one nitrogen atom, as in (1)(a), (1)(b), (2)(a), (2)(b), (3)(a), (3)(b), (4)(a), (4)(b), and the like, among the "hetero ring groups" above.

The expression "$R^{G1}$, $R^{G2}$, $R^{21}$, and $R^{22}$ are combined together to a form a nitrogen-containing hetero ring group" indicates that $R^{G1}$, $R^{G2}$, $R^{21}$, and $R^{22}$ are combined with carbon atoms to which they are bonded to form a nitrogen-containing hetero ring group.

Examples of the nitrogen-containing hetero ring group include:

[Chem. 14]

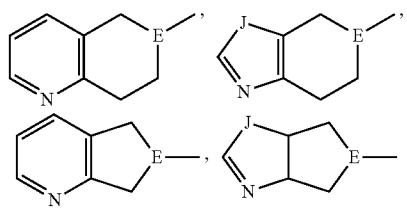

(wherein J represents S, O, or NH), and the like, and in another embodiment,

[Chem. 15]

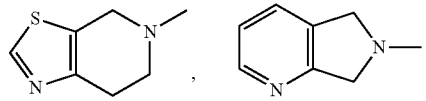

The expression "$R^{G3}$, $R^{21}$, and $R^{22}$ are combined together to form a nitrogen-containing hetero ring group" indicates that $R^{G3}$, $R^{21}$, and $R^{22}$ are combined with carbon atoms and nitrogen atoms to which they are bonded to form a nitrogen-containing hetero ring group.

Examples of the nitrogen-containing hetero ring group include:

[Chem. 16]

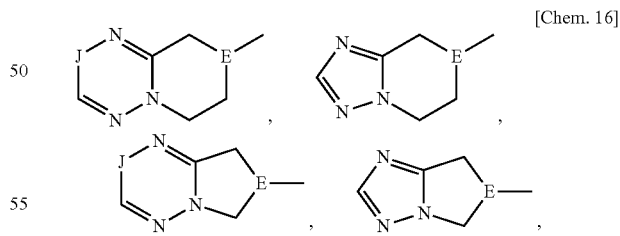

(wherein J represents S, O, or NH), and the like, and in another embodiment,

[Chem. 17]

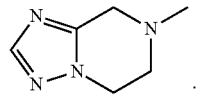

The expression "$R^{G1}$ or $R^{G2}$ may be combined with either $R^{21}$ or $R^{22}$ to form a new bond" indicates that $R^{G1}$ or $R^{G2}$ of

[Chem. 18]

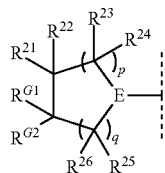

is combined with either $R^{21}$ or $R^{22}$ to form a new bond, thereby forming a double bond,

[Chem. 19]

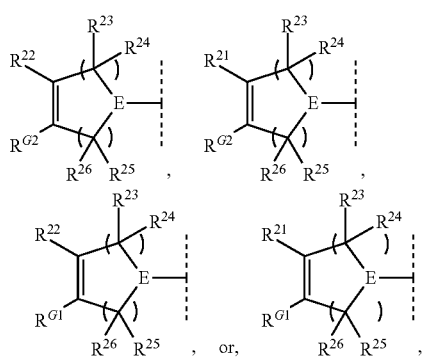

The "halogen" means F, Cl, Br, or I, and preferably F.

The expression "which may be substituted" represents non-substitution or substitution with 1 to 5 substituents". Further, if it has a plurality of substituents, the substituents may be the same as or different from one other.

Examples of the substituents in "aryl which may be substituted", "cycloalkyl which may be substituted", and "hetero ring group which may be substituted" in $R^{G3}$ include the groups shown in (a) to (j) below and oxo (=O); in another embodiment, the groups shown in (a) to (j) below; and in a still another embodiment, the groups shown in (a), (b), (d), (g), (f), and (j) below, and oxo (=O).

(a) halogen.
(b) —OH, —O-lower alkyl (in which the lower alkyl may be substituted with 1 to 3 OH, halogen, —O-lower alkyl (in which the lower alkyl may be substituted with one or more —COOH groups), or aryl groups).
(c) amino which may be substituted with one or more lower alkyl groups (in which the lower alkyl may be substituted with one or more aryl groups), or nitro.
(d) —CHO, —CO-lower alkyl (in which the lower alkyl may be substituted with 1 to 3 halogen atoms), —CO-cycloalkyl (in which cycloalkyl may be substituted with one or more —O-lower alkyl groups), —CO-aryl, a —CO-monocyclic saturated hetero ring group, or cyano.
(e) aryl or cycloalkyl; further, these groups may be substituted with 1 to 5 halogen atoms.
(f) a hetero ring group, and in another embodiment, a monocyclic hetero ring group; further, these hetero ring groups and monocyclic hetero ring groups may be substituted with halogen or lower alkyl (in which the lower alkyl may be substituted with one or more aryl groups).
(g) —COOH, —COO-lower alkyl (in which the lower alkyl may be substituted with 1 to 3 halogen atoms).
(h) —CONH$_2$, —CONH(lower alkyl) (in which the lower alkyl may be substituted with 1 to 3 halogen atoms), —CONH(lower alkyl)$_2$ (in which the lower alkyl may be substituted with 1 to 3 halogen atoms).
(i) —O—CO-lower alkyl (in which the lower alkyl may be substituted with 1 to 3 halogen atoms or aryl groups), —O—CO—O-lower alkyl (in which the lower alkyl may be substituted with 1 to 3 halogen atoms).
(j) lower alkyl or lower alkenyl, which may be each substituted with one or more groups selected from the substituents shown in (a) to (i) above.

The substituents that can be used in the "lower alkyl which may be substituted" in $R^1$ include the groups shown in (a) to (i) above and oxo (=O), and in another embodiment, the groups shown in (a) above.

The substituents that can be used in the "lower alkenyl which may be substituted" in X include the groups shown in (a) to (i) above and oxo (=O), and in another embodiment, the groups shown in (g) above.

The substituents that can be used in the "lower alkyl which may be substituted" in $R^{Z1}$ and $R^{Z2}$ include the groups shown in (a) to (i) above and oxo (=O), and in another embodiment, the groups shown in (a) and (b) above.

The substituents that can be used in the "aryl which may be substituted" in $R^{Z1}$ and $R^{Z2}$ include the groups shown in (a) to (j) above and oxo (=O), and in another embodiment, the groups shown in (a), (b), and (j) above.

The substituents that can be used in the "hetero ring group which may be substituted" in $R^{Z1}$ and $R^{Z2}$ include the groups shown in (a) to (j) above and oxo (=O), and in another embodiment, the groups shown in (j) above and oxo (=O).

The substituents that can be used in the "lower alkyl which may be substituted" in $R^{Z3}$ include the groups shown in (a) to (i) above and oxo (=O), and in another embodiment, the groups shown in (a) and (b) above.

The substituents that can be used in the "hetero ring group which may be substituted" in $R^{Z3}$ include the groups shown in (a) to (j) above and oxo (=O), and in another embodiment, the groups shown in (f) and (j) above and oxo (=O).

The substituents that can be used in the "lower alkyl which may be substituted" in $R^{Z1}$ include the groups shown in (a) to (i) above and oxo (=O), and in another embodiment, the groups shown in (b), (c), (f), and (i) above.

The substituents that can be used in the "cycloalkyl which may be substituted" and the "hetero ring group which may be substituted" in $R^{Z11}$ include the groups shown in (a) to (j) above and oxo (=O), and in another embodiment, the groups shown in (b), (c), (d), (f), (i), and (j) above and oxo (=O).

The substituents that can be used in the "lower alkyl which may be substituted" in $R^{G1}$ and $R^{G2}$ include the groups shown in (a) to (i) above and oxo (=O), and in another embodiment, the groups shown in (a), (b), (c), (g), and (i).

The substituents that can be used in the "amino which may be substituted" in $R^{G1}$ and $R^{G2}$ include the groups shown in (j) above.

The substituents that can be used in the "aryl which may be substituted" in $R^{G1}$ and $R^{G2}$ include the groups shown in (a) to (j) above, and in another embodiment, the groups shown in (a), (b), (c), (f), (g), and (j).

The substituents that can be used in the "cycloalkyl which may be substituted", the "hetero ring group which may be substituted", "$R^{G1}$, $R^{G2}$, $R^{21}$, and $R^{22}$ which may be substituted are combined together to form a nitrogen-containing hetero ring group" and "$R^{G3}$, $R^{21}$, and $R^{22}$ which may be substituted are combined together to form a nitrogen-containing hetero ring group" in $R^{G1}$ and $R^{G2}$ include the groups shown in (a) to (j) above and oxo (=O), and in another embodiment, the groups shown in (a), (b), (c), (f), (g), and (j) and oxo (=O).

The substituents that can be used in the "lower alkyl which may be substituted" in $R^{G3}$ include the groups shown in (a) to (i) above and oxo (=O), and in another embodiment, the groups shown in (a), (c), (b), and (f).

The substituents that can be used in the "lower alkyl which may be substituted" in $R^{G31}$ include the groups shown in (a) to (i) above and oxo (=O), and in another embodiment, the groups shown in (a), (b), (d), and (g).

The substituents that can be used in the "aryl which may be substituted" in $R^{G31}$ include the groups shown in (a) to (j) above, and in another embodiment, the groups shown in (a), (b), (d), (g), (f), and (j).

The substituents that can be used in the "cycloalkyl which may be substituted" and the "hetero ring group which may be substituted" in $R^{G31}$ include the groups shown in (a) to (j) above and oxo (=O), and in another embodiment, the groups shown in (a), (b), (d), (g), (f), and (j), and oxo (=O).

The substituents that can be used in the "lower alkyl which may be substituted" in $R^{21}$, $R^{22}$, $R^{23}$, $R^{24}$, $R^{25}$, and $R^{26}$ include the groups shown in (a) to (j) above and oxo (=O), and in another embodiment, the groups shown in (a), (b), (c), (g), and (j).

The substituents that can be used in the "amino which may be substituted" in $R^{21}$, $R^{22}$, $R^{23}$, $R^{24}$, $R^{25}$, and $R^{26}$ include the groups shown in (j) above.

Embodiments of the compound (1) include the following compounds or salts thereof.

(1) The compound, wherein $Y^1$ and $Y^2$ are both $CR^Y$, and $R^Y$'s are both H.
(2) The compound, wherein $Y^1$ and $Y^2$ are both N.
(3) The compound, wherein $Y^1$ is N, $Y^2$ is $CR^Y$, and $R^Y$ is H.
(4) The compound, wherein $R^1$ is lower alkyl which may be substituted.
(5) The compound, wherein $R^1$ is methyl, ethyl, propyl, or isopropyl.
(6) The compound, wherein X is $Z—(CR^{11}R^{12})_n—$, n is 0, and Z is

[Chem. 20]

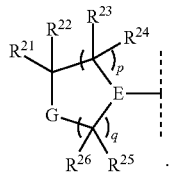

(7) The compound as described in (6), wherein E is N, G is, $CR^{G1}R^{G2}$, O, or $SO_2$, p is 1, and q is 1 or 2.
(8) The compound, wherein X is $Z—(CR^{11}R^{12})_n—$, n is 0, Z is

[Chem. 21]

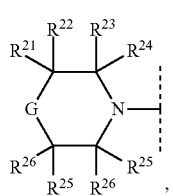

G is O or $SO_2$, and $R^{21}$, $R^{22}$, $R^{23}$, $R^{24}$, $R^{25}$, and $R^{26}$ are the same as or different from each other, and are H or lower alkyl which may be substituted.
(9) The compound as described in (8), wherein G is O or $SO_2$, and $R^{21}$, $R^{22}$, $R^{23}$, $R^{24}$, $R^{25}$ and $R^{26}$ are the same as or different from each other, and are H, methyl, or hydroxymethyl.

(10) The compound, wherein X is $Z—(CR^{11}R^{12})_n—$, n is 0, Z is

[Chem. 22]

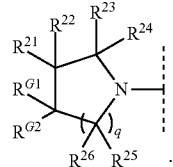

(11) The compound as described in (10), wherein $R^{G1}$ and $R^{G2}$ are the same as or different from each other, and are H, OH, or a hetero ring group which may be substituted, $R^{21}$, $R^{22}$, $R^{23}$, $R^{24}$, $R^{25}$, and $R^{26}$ are H, or $R^{G1}$, $R^{G2}$, $R^{21}$, and $R^{22}$ are combined together to form a nitrogen-containing hetero ring group which may be substituted, and
$R^{G1}$ or $R^{G2}$ may be combined with either $R^{21}$ or $R^{22}$ to form a new bond.
(12) The compound as described in (10), wherein $R^{G1}$ and $R^{G2}$ are the same as or different from each other, and are H, OH, or pyridine or morpholine which may be substituted,
$R^{21}$, $R^{22}$, $R^{23}$, $R^{24}$, $R^{25}$, and $R^{26}$ are H or F, or
$R^{G1}$, $R^{G2}$, $R^{21}$ and $R^{22}$ are combined together to form pyridine or thiazole which may be substituted, and
$R^{G1}$ or $R^{G2}$ may be combined with either $R^{21}$ or $R^{22}$ to form a new bond.
(13) The compound as described in (10), wherein $R^{G1}$ and $R^{G2}$ are the same as or different from each other, and are H, OH, pyridin-3-yl or morpholin-4-yl, or, $R^{G1}$, $R^{G2}$, $R^{21}$ and $R^{22}$ are combined with carbon atoms to which they are bonded to form

[Chem. 23]

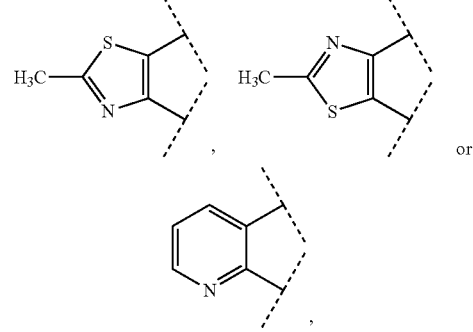

and $R^{21}$, $R^{22}$, $R^{23}$, $R^{24}$, $R^{25}$ and $R^{26}$ are H or F.
(14) The compound as described in (6), wherein E is, N, G is $NR^{G3}$, p is 1, and q is 2.
(15) The compound as described in (6), wherein Z is

[Chem. 24]

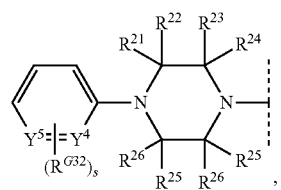

$R^{21}$, $R^{22}$, $R^{23}$, $R^{24}$, $R^{25}$ and $R^{26}$ are H, $Y^4$ is N or $CR^{Y41}$, $Y^5$ is N or $CR^{Y51}$, $R^{Y41}$, $R^{Y51}$, and $R^{G32}$ are H, halogen, —OH, —O-lower alkyl (in which the lower alkyl may be substituted with 1 to 3 OH, halogen, —O-lower alkyl (in which the lower alkyl may be substituted with one or more —COOH groups), or aryl groups), —CHO, —CO-lower alkyl (in which the lower alkyl may be substituted with 1 to 3 halogen atoms), —CO-cycloalkyl (in which cycloalkyl may be substituted with one or more —O-lower alkyl groups), —CO-aryl, a —CO-monocyclic saturated hetero ring group, cyano, —COOH, —COO-lower alkyl (in which the lower alkyl may be substituted with 1 to 3 halogen atoms), lower alkyl which may be substituted with —COOH or —O-lower alkyl (in which the lower alkyl may be substituted with one or more —COOH groups), or lower alkenyl which may be substituted with —COOH or —O-lower alkyl (in which the lower alkyl may be substituted with one or more —COOH groups), and s is 0, 1, 2, or 3.

(16) The compound as described in (6), wherein Z is

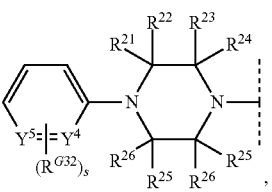

[Chem. 25]

$R^{21}$, $R^{22}$, $R^{23}$, $R^{24}$, $R^{25}$ and $R^{26}$ are H, and

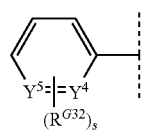

[Chem. 26]

is 3-methylpyridin-2-yl, 5-(2-carboxyvinyl)-3-methyl-pyridin-2-yl, 5-(2-carboxyethyl)-3-methyl-pyridin-2-yl, 5-carboxy-3-chloro-pyridin-2-yl, 5-(2-carboxyvinyl)-3-chloro-pyridin-2-yl, 4-carboxy-6-chloro-phenyl, 6-cyanopyridin-3-yl, 2-methylpyridin-3-yl, or 3-chloropyridin-2-yl.

(17) The compound, wherein $R^3$ and $R^4$ are H.
(18) The compound, wherein m is 0.

Furthermore, other embodiments of the compound (1) of the present invention include the compounds or salts thereof including the combinations of two or more of the groups as described in (1) to (18), and specifically the following compounds or salts thereof.

(19) The compound as described in (6) to (9) and (14) to (16), wherein $Y^1$ and $Y^2$ are both $CR^Y$, and $R^Y$s are both H.
(20) The compound as described in (19), wherein m is 0.
(21) The compound as described in (19), wherein $R^3$ and $R^4$ are H.
(22) The compound as described in (19), wherein $R^3$ and $R^4$ are H, and m is 0.
(23) The compound as described in (6) to (16), wherein $Y^1$ and $Y^2$ are both N.
(24) The compound as described in (23), wherein m is 0.
(25) The compound as described in (23), wherein $R^3$ and $R^4$ are H.
(26) The compound as described in (23), wherein $R^3$ and $R^4$ are H, and m is 0.
(27) The compound as described in (6) to (9) and (14) to (16), wherein $Y^1$ is N, $Y^2$ is $CR^Y$, and $R^Y$ is H.
(28) The compound as described in (26), wherein m is 0.
(29) The compound as described in (26), wherein $R^3$ and $R^4$ are H.
(30) The compound as described in (26), wherein $R^3$ and $R^4$ are H, and m is O, Still further embodiments of the compound of the present invention are shown below.
(31) The compound as described in (6), wherein Z is

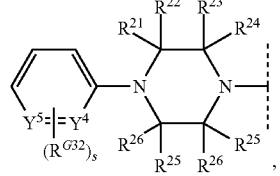

[Chem. 27]

$R^{21}$, $R^{22}$, $R^{23}$, $R^{24}$, $R^{25}$ and $R^{26}$ are H, $Y^4$ is N or $CR^{Y41}$, $Y^5$ is N or $CR^{Y51}$, $R^{Y41}$, $R^{Y51}$, and $R^{G32}$ are H, halogen, —OH, —O-lower alkyl (in which the lower alkyl may be substituted with 1 to 3 OH, halogen, —O-lower alkyl (in which the lower alkyl may be substituted with one or more —COOH groups), or aryl groups), —CHO, —CO-lower alkyl (in which the lower alkyl may be substituted with 1 to 3 halogen atoms), —CO-cycloalkyl (in which cycloalkyl may be substituted with one or more —O-lower alkyl groups), —CO-aryl, a —CO-monocyclic saturated hetero ring group, cyano, —COOH, —COO-lower alkyl (in which the lower alkyl may be substituted with 1 to 3 halogen atoms), —NH$_2$, NH(lower alkyl), N(lower alkyl)$_2$, or lower alkyl which may be substituted with —COOH or —O-lower alkyl (in which the lower alkyl may be substituted with one or more —COOH groups), or lower alkenyl which may be substituted with —COOH or —O-lower alkyl (in which the lower alkyl may be substituted with one or more —COOH groups), and s is 0, 1, 2, or 3.
(32) The compound as described in (31), wherein $Y^4$ is N or $CR^{Y41}$, $Y^5$ is N or $CR^{Y51}$, $R^{Y41}$, $R^{Y51}$ and $R^{G32}$ are H, halogen, —COOH, lower alkyl, —O-lower alkyl, cyano, —COOH, —COO-lower alkyl, —NH$_2$, NH(lower alkyl), N(lower alkyl)$_2$, or lower alkyl which may be substituted with halogen, OH, —COOH, or —O-lower alkyl (in which the lower alkyl may be substituted with —COOH groups), or lower alkenyl which may be substituted with halogen, OH, —COOH, or —O-lower alkyl, and s is 0, 1, 2, or 3.
(33) The compound as described in (31), wherein $Y^4$ is N or $CR^{Y41}$, $Y^5$ is N or $CR^{Y51}$, $R^{Y41}$, $R^{Y51}$, and $R^{G32}$ are H, F, Cl, Br, methyl, methoxy, —COOH, —NH$_2$, —N(CH$_3$)$_2$, ethoxycarbonyl, hydroxymethyl, 2-carboxyethyl, trifluoromethyl, carboxymethoxymethyl, or cyano.
(34) The compound as described in (6), wherein Z is

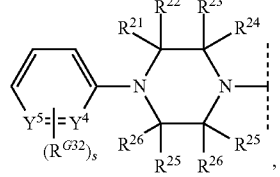

[Chem. 28]

$R^{21}$, $R^{22}$, $R^{23}$, $R^{24}$, $R^{25}$ and $R^{26}$ are H, and

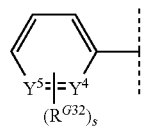

[Chem. 29]

is phenyl, 4-aminophenyl, 4-dimethylaminophenyl, 4-carboxyphenyl, 4-carboxy-6-chloro-phenyl, 4-methylphenyl, 4-fluorophenyl, 4-chlorophenyl, 2-fluorophenyl, 2-methylphenyl, 2,4-difluorophenyl, 2-methoxyphenyl, 3-methylpyridin-2-yl, 3-trifluoromethylpyridin-2-yl, 3-cyano-6-methylpyridin-2-yl, 5-[(E)-2-carboxyvinyl]-3-methylpyridin-2-yl, 5-carboxy-3-chloropyridin-2-yl, 5-[(E)-2-carboxyvinyl]-3-chloropyridin-2-yl, 3-carboxymethoxymethylpyridin-2-yl, 5-(2-carboxyethyl)-3-methylpyridin-2-yl, 5-carboxypyridin-2-yl, pyridin-2-yl, 5-ethoxycarbonylpyridin-2-yl, 5-cyanopyridin-2-yl, 3-cyanopyridin-2-yl, 3-chloropyridin-2-yl, 5-trifluoromethylpyridin-2-yl, 3-fluoropyridin-2-yl, 5-fluoropyridin-2-yl, 5-chloropyridin-2-yl, 5-bromopyridin-2-yl, 3-methoxypyridin-2-yl, 3-hydroxymethylpyridin-2-yl, 5-methylpyridin-2-yl, 4-methylpyridin-2-yl, 5-carboxy-3-methylpyridin-2-yl, 6-methylpyridin-2-yl, 542-carboxyethyl)-3-hydroxymethylpyridin-2-yl, 5-[(E)-2-carboxyvinyl]-3-hydroxymethylpyridin-2-yl, 5-[(E)-2-carboxyvinyl]-pyridin-2-yl, 5-(2-carboxyethyl)pyridin-2-yl, 6-chloropyridin-3-yl, 4-methylpyridin-3-yl, 5-ethoxycarbonylpyridin-3-yl, 5-methylpyridin-3-yl, 2-methylpyridin-3-yl, pyridin-3-yl, 6-aminopyridin-3-yl, 5-chloropyridin-3-yl, 5-carboxypyridin-3-yl, or 6-cyanopyridin-3-yl, 6-chloropyrimidin-3-yl, or pyrimidin-3-yl.

(35) The compound as described in (31), wherein $Y^4$ is $CR^{Y41}$, $Y^5$ is $CR^{Y51}$, $R^{Y41}$, $R^{Y51}$, and $R^{G32}$ are H, halogen, —COOH, lower alkyl, —O-lower alkyl, —COOH, —COO-lower alkyl, —NH$_2$, NH(lower alkyl), or N(lower alkyl)$_2$, and s is 0, 1, 2, or 3.

(36) The compound as described in (31), wherein $Y^4$ is $CR^{Y41}$, $Y^5$ is $CR^{Y51}$, $R^{Y41}$, $R^{Y51}$, and $R^{G32}$ are H, F, Cl, methyl, methoxy, —COOH, —NH$_2$, or —N(CH$_3$)$_2$, and s is 0, 1, 2, or 3.

(37) The compound as described in (34), wherein

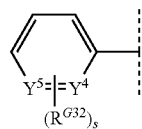

[Chem. 30]

is phenyl, 4-aminophenyl, 4-dimethylaminophenyl, 4-carboxyphenyl, 4-carboxy-6-chloro-phenyl, 4-methylphenyl, 4-fluorophenyl, 4-chlorophenyl, 2-fluorophenyl, 2-methylphenyl, 2,4-difluorophenyl, or 2-methoxyphenyl.

(38) The compound as described in (31), wherein $Y^4$ is N, $Y^5$ is $CR^{Y51}$, $R^{Y51}$ and $R^{G32}$ are H, halogen, —O-lower alkyl (in which the lower alkyl may be substituted with 1 to 3 OH, halogen, —O-lower alkyl (in which the lower alkyl may be substituted with one or more —COOH groups), or aryl groups), cyano, —COOH, —COO-lower alkyl (in which the lower alkyl may be substituted with 1 to 3 halogen atoms), lower alkyl which may be substituted with halogen, OH, —COOH or —O-lower alkyl (in which the lower alkyl may be substituted with one or more —COOH groups), lower alkenyl which may be substituted with halogen, OH, —COOH or —O-lower alkyl (in which the lower alkyl may be substituted with one or more —COOH groups), and s is 0, 1, 2, or 3.

(39) The compound as described in (31), wherein $Y^4$ is N, $Y^5$ is $CR^{Y51}$, $R^{Y51}$ and $R^{G32}$ are H, halogen, —O-lower alkyl, cyano, —COOH, —COO-lower alkyl, lower alkyl which may be substituted with halogen, OH, —COOH, or —O-lower alkyl (in which the lower alkyl may be substituted with —COOH groups), or lower alkenyl which may be substituted with halogen, OH, —COOH, or —O-lower alkyl, and s is 0, 1, 2, or 3.

(40) The compound as described in (31), wherein $Y^4$ is N, $Y^5$ is $CR^{Y51}$, $R^{Y51}$ and $R^{G32}$ are H, F, Cl, Br, methoxy, cyano, —COOH, ethoxycarbonyl, hydroxymethyl, 2-carboxyethyl, trifluoromethyl, carboxymethoxymethyl, or 2-carboxyvinyl, and s is 0, 1, 2, or 3.

(41) The compound as described in (34), wherein

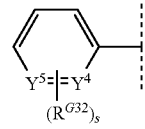

[Chem. 31]

is 3-methylpyridin-2-yl, 3-trifluoromethylpyridin-2-yl, 3-cyano-6-methylpyridin-2-yl, 5-[(E)-2-carboxyvinyl]-3-methylpyridin-2-yl, 5-carboxy-3-chloropyridin-2-yl, 5-[(E)-2-carboxyvinyl]-3-chloropyridin-2-yl, 3-carboxymethoxymethylpyridin-2-yl, 542-carboxyethyl)-3-methylpyridin-2-yl, 5-carboxypyridin-2-yl, pyridin-2-yl, 5-ethoxycarbonylpyridin-2-yl, 5-cyanopyridin-2-yl, 3-cyanopyridin-2-yl, 3-chloropyridin-2-yl, 5-trifluoromethylpyridin-2-yl, 3-fluoropyridin-2-yl, 5-fluoropyridin-2-yl, 5-chloropyridin-2-yl, 5-bromopyridin-2-yl, 3-methoxypyridin-2-yl, 3-hydroxymethylpyridin-2-yl, 5-methylpyridin-2-yl, 4-methylpyridin-2-yl, 5-carboxy-3-methylpyridin-2-yl, 6-methylpyridin-2-yl, 5-(2-carboxyethyl)-3-hydroxymethylpyridin-2-yl, 5-[(E)-2-carboxyvinyl]-3-hydroxymethylpyridin-2-yl, 5-[(E)-2-carboxyvinyl]-pyridin-2-yl, or 5-(2-carboxyethyl)pyridin-2-yl.

(42) The compound as described in (31), wherein $Y^4$ is $CR^{Y41}$, $Y^5$ is N, $R^{Y41}$ and $R^{G32}$ are H, halogen, cyano, —COOH, —COO-lower alkyl (in which the lower alkyl may be substituted with 1 to 3 halogen atoms), or lower alkyl which may be substituted with —COOH or —O-lower alkyl (in which the lower alkyl may be substituted with one or more —COOH groups), and s is 0, 1, 2, or 3.

(43) The compound as described in (31), wherein $Y^4$ is $CR^{Y41}$, $Y^5$ is N, $R^{Y41}$ and $R^{G32}$ are H, halogen, cyano, —COOH, —COO-lower alkyl, —NH$_2$, NH(lower alkyl), N(lower alkyl)$_2$, or lower alkyl, and s is 0, 1, 2, or 3.

(44) The compound as described in (31), wherein $Y^4$ is $CR^{Y41}$, $Y^5$ is N, $R^{Y41}$ and $R^{G32}$ are H, chloro, cyano, —COOH, ethoxycarbonyl, —NH$_2$, or methyl, and s is 0, 1, 2, or 3.

(45) The compound as described in (34), wherein

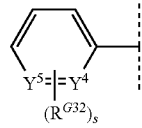

is 6-chloropyridin-3-yl, 4-methylpyridin-3-yl, 5-ethoxy-carbonylpyridin-3-yl, 5-methylpyridin-3-yl, 2-methylpyridin-3-yl, pyridin-3-yl, 6-aminopyridin-3-yl, 5-chloropyridin-3-yl, 5-carboxypyridin-3-yl, or 6-cyanopyridin-3-yl.

(46) The compound as described in (31), wherein $Y^4$ is N, $Y^5$ is N, $R^{G32}$ is H, halogen, and s is 0, 1, 2, or 3.

(47) The compound as described in (31), wherein $Y^4$ is N, $Y^5$ is N, $R^{G32}$ is H, Cl, and s is 0, 1, 2, or 3.

(48) The compound as described in (34), wherein

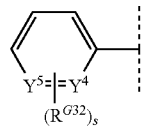

is 6-chloropyrimidin-3-yl or pyrimidin-3-yl.

(49) The compound as described in (19) to (30), or (31) to (48), wherein $R^1$ is lower alkyl which may be substituted.

(50) The compound as described in (19) to (30), or (31) to (48), wherein $R^1$ is methyl, ethyl, propyl, or isopropyl.

(51) The compound as described in (31) to (50), wherein m is 0.

(52) The compound as described in (31) to (51), wherein $R^3$ and $R^4$ are H.

(53) The compound as described in (31) to (51), wherein $R^3$ and $R^4$ are H, and m is 0.

Specific examples of the compound included in the present invention include the following compounds or salts thereof.

N-methyl-N-[3-(2-morpholin-4-ylpyrimidin-5-yl)benzyl]glycinamide,
N-methyl-N-[3-(2-pyrrolidin-1-ylpyrimidin-5-yl)benzyl]glycinamide,
N-(3-{2-[(2R,6S)-2,6-dimethylmorpholin-4-yl]pyrimidin-5-yl}benzyl)-N-methylglycinamide,
N-(3-{2-[2-(hydroxymethyl)morpholin-4-yl]pyrimidin-5-yl}benzyl)-N-methylglycinamide,
N-(3-{6-[(2R,6S)-2,6-dimethylmorpholin-4-yl]pyridin-3-yl}benzyl)-N-methylglycinamide,
N-{3-[2-(4-hydroxypiperidin-1-yl)pyrimidin-5-yl]benzyl}-N-methylglycinamide,
N-{3-[2-(1,1-dioxidothiomorpholin-4-yl)pyrimidin-5-yl]benzyl}-N-methylglycinamide,
N-methyl-N-{3-[2-(4-morpholin-4-yl-piperidin-1-yl)pyrimidin-5-yl]benzyl}glycinamide,
N-{3-[2-(3',6'-dihydro-3,4'-bipyridin-1'(2'H)-yl)pyrimidin-5-yl]benzyl}-N-methylglycinamide,
N-methyl-N-{3-[2-(4-pyridin-3-ylpiperidin-1-yl)pyrimidin-5-yl]benzyl}glycinamide,
N-methyl-N-(3-{2-[4-(3-methylpyridin-2-yl)piperazin-1-yl]pyrimidin-5-yl}benzyl)glycinamide,
(2E)-3-(6-{4-[5-(3-{[glycyl(methyl)amino]methyl}phenyl)pyrimidin-2-yl]piperazin-1-yl}-5-methylpyridin-3-yl)acrylic acid,
3-(6-{-4-[5-(3-{[glycyl(methyl)amino]methyl}phenyl)pyrimidin-2-yl]piperazin-1-yl}-5-methylpyridin-3-yl)propionic acid,
5-chloro-6-{4-[5-(3-{glycyl(methyl)amino]methyl}phenyl)pyrimidin-2-yl]piperazin-1-yl}nicotinic acid,
(2E)-3-(5-chloro-6-{-4-[5-(3-{[glycyl(methyl)amino]methyl}phenyl)pyrimidin-2-yl]piperazin-1-yl}pyridin-3-yl)acrylic acid,
3-chloro-4-{4-[5-(3-{[glycyl(methyl)amino]methyl}phenyl)pyrimidin-2-yl]piperazin-1-yl}benzoic acid,
N-(3-{2-[4-(6-cyanopyridin-3-yl)piperidin-1-yl]pyrimidin-5-yl}benzyl)-N-methylglycinamide,
N-methyl-N-(3-{2-[4-(2-methylpyridin-3-yl)piperidin-1-yl]pyrimidin-5-yl}benzyl)glycinamide,
N-(3-{2-[4-(3-chloropyridin-2-yl)piperazin-1-yl]pyrimidin-5-yl}benzyl)-N-methylglycinamide,
N-methyl-N-{3-[2-(2-methyl-6,7-dihydro[1,3]thiazolo[5,4-c]pyridin-5(4H)-yl)pyrimidin-5-yl]benzyl}glycinamide,
N-{3-[2-(5,7-dihydro-6H-pyrrolo[3,4-b]pyridin-6-yl)pyrimidin-5-yl]benzyl}-N-methylglycinamide, or
N-(3-{2-[(3S)-3-fluoropyrrolidin-1-yl]pyrimidin-5-yl}benzyl)-N-methylglycinamide.

The compound of the formula (I) may exist in the form of tautomers or geometrical isomers depending on the kind of substituents. In the present specification, the compound of the formula (I) shall be described in only one form of isomer, yet the present invention includes other isomers, isolated forms of the isomers, or a mixture thereof.

In addition, the compound of the formula (I) may have asymmetric carbon atoms or axial asymmetry in some cases, and correspondingly, it may exist in the form of optical isomers based thereon. The present invention includes both an isolated form of the optical isomers of the compound of the formula (I) or a mixture thereof.

Moreover, the present invention also includes a pharmaceutically acceptable prodrug of the compound represented by the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Drug Design, 163-198.

Furthermore, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditolyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, and polymorphic crystalline substances of the compound of the formula (I) and a salt thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituents thereof and by applying various known synthesis methods. During the preparation, replacing the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis (4$^{th}$ Ed., 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, the prodrug of the compound of the formula (I) can be prepared by introducing a specific group or by carrying out the reaction using the obtained compound of the formula (I) at the stage from a starting material to an intermediate, just as in the case of the above-mentioned protective group. The reaction can be carried out using methods known to those skilled in the art, such as ordinary esterification, amidation, dehydration, and the like.

Hereinbelow, the representative preparation methods for the compound of the formula (I) will be described. Each of the production processes may also be carried out with reference to the References appended in the present description. Further, the preparation methods of the present invention are not limited to the examples as shown below.

(Production Process 1)

[Chem. 34]

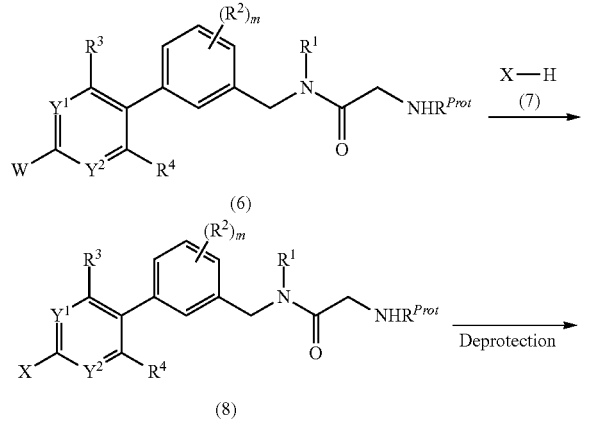

(wherein W represents a leaving group, and $R^{Prot}$ represents a protective group.)

When X is $R^{Z1}R^{Z2}N-$, $R^{Z3}O-$, or

[Chem. 35]

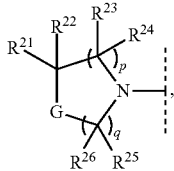

the compound (1a) of the present invention can be obtained by reaction of a compound (6) with X—H (7), followed by a deprotection reaction. Here, examples of the leaving group W include halogen, a methanesulfonyloxy group, a p-toluenesulfonyloxy group, a methoxy group, an ethoxy group, and the like, and examples of the protective group $R^{Prot}$ include a tert-butoxycarbonyl group, a benzyloxycarbonyl group, and the like.

First, the compound (8) can be obtained by the reaction of the compound (6) with X—H (7).

In this reaction, a mixture of the compound (6) and the compound (7) in an equivalent amount or in an excess amount is stirred in a range of from cooling to heating and refluxing, and preferably at 0° C. to 80° C., usually for 0.1 hours to 5 days in a solvent which is inert to the reaction or without a solvent. The solvent used herein is not particularly limited, but examples thereof include aromatic hydrocarbons such as benzene, toluene, xylene, and the like, ethers such as diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile and a mixture thereof. It may be advantageous in some cases for the smooth progress of the reaction to carry out the reaction in the presence of an organic base such as triethylamine, N,N-diisopropylethylamine, N-methylmorpholine, and the like, or an inorganic base such as potassium carbonate, sodium carbonate, potassium hydroxide, and the like.

Furthermore, the reaction may be carried out using a catalyst which is not particularly limited, but includes catalysts used for an Ullmann reaction, a Buchwald-Hartwig reaction, or the like. The catalyst as used herein is not particularly limited, but a suitable combination of tris(dibenzylideneacetone)palladium, tetrakis(triphenylphosphine) palladium, or the like with 4,5-bis(diphenylphosphino)-9,9'-dimethylxanthene (Xantphos), 2-dicyclohexylphosphino-2',6'-dimethoxybiphenyl (SPhos), 2-dicyclohexylphosphino-2',4',6'-triisopropylbiphenyl (XPhos), and the like can be used.

Next, the deprotection reaction of the compound (8) can be carried out with reference to, for example, the method as described in "Greene's Protective Groups in Organic Synthesis (4$^{th}$ edition, 2006)" above.

[Document]

Synthesis 2006, 4, 629-632

(Production Process 2)

[Chem. 36]

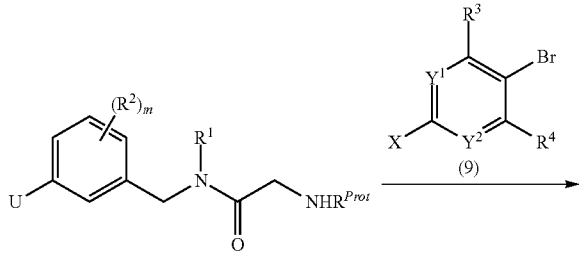

(Starting Material Synthesis 1)

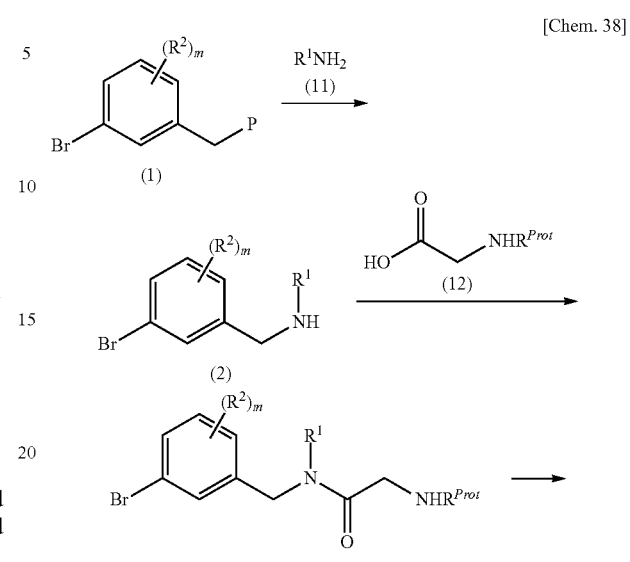

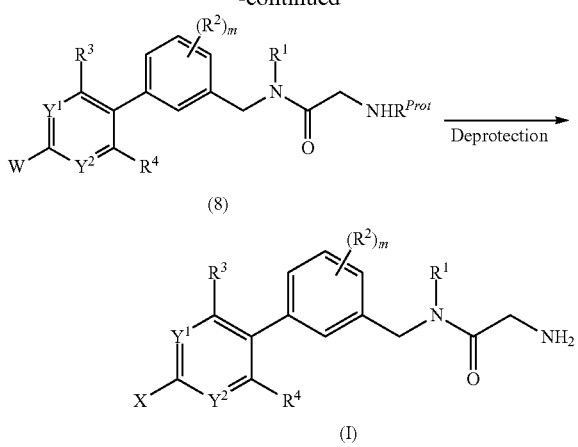

(wherein U represents a boric ester substituent.)

The compound (1) of the present invention can be obtained by the coupling reaction of a compound (4) with a compound (9), followed by a deprotection reaction.

The present reaction can be carried out under the same reaction condition as for the coupling reaction described in (Starting Material Synthesis 1) as described later.

(Production Process 3)

[Chem. 37]

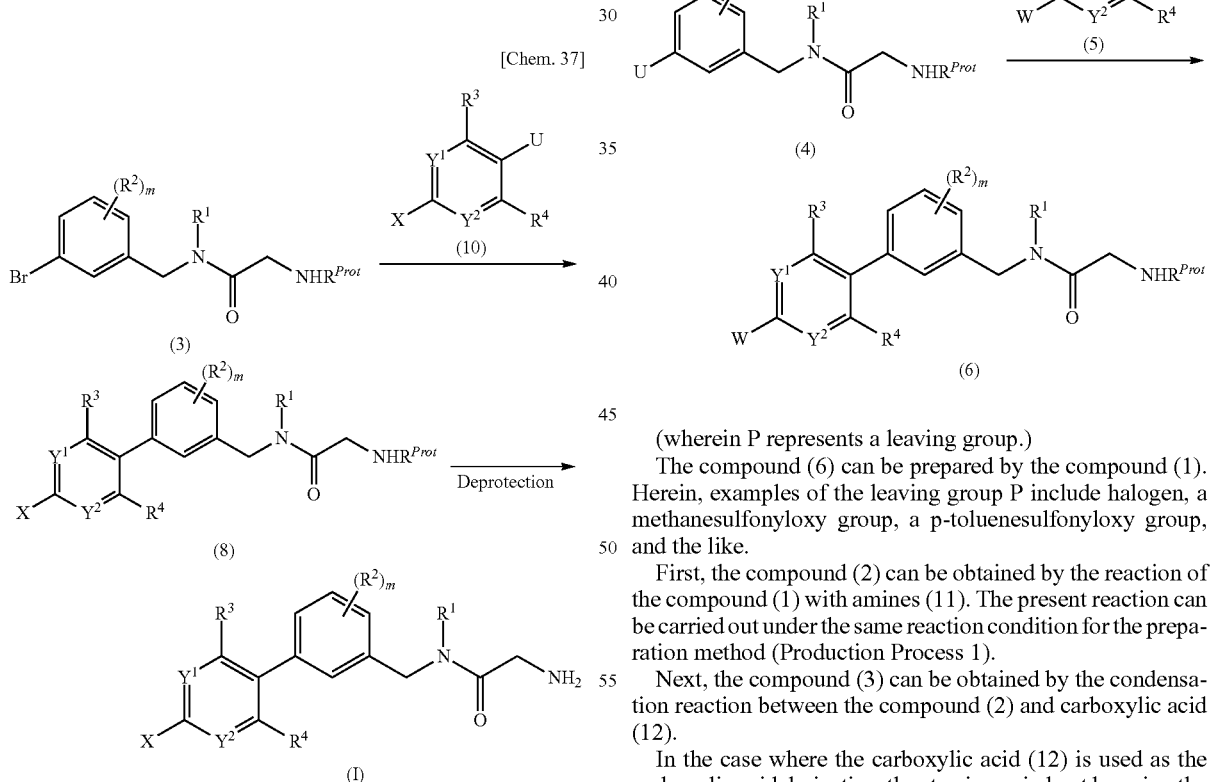

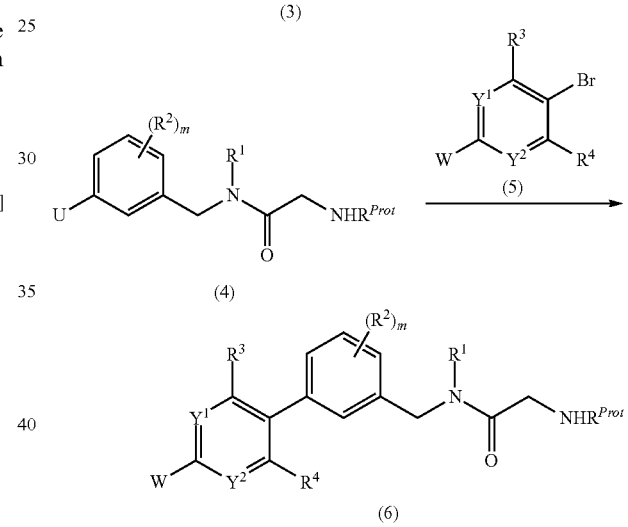

The compound (8) can be obtained by the coupling reaction of a compound (3) with a compound (10), followed by a deprotection reaction.

The present reaction can be carried out under the same reaction condition as for the coupling reaction described in (Starting Material Synthesis 1) as described later.

(wherein P represents a leaving group.)

The compound (6) can be prepared by the compound (1). Herein, examples of the leaving group P include halogen, a methanesulfonyloxy group, a p-toluenesulfonyloxy group, and the like.

First, the compound (2) can be obtained by the reaction of the compound (1) with amines (11). The present reaction can be carried out under the same reaction condition for the preparation method (Production Process 1).

Next, the compound (3) can be obtained by the condensation reaction between the compound (2) and carboxylic acid (12).

In the case where the carboxylic acid (12) is used as the carboxylic acid derivative, the step is carried out by using the compound (2) with the carboxylic acid (12) in an equivalent amount or in an excess amount, and stirring the mixture thereof in a range of from cooling to heating, preferably at a temperature from $-20°$ C. to $60°$ C., usually for about 0.1 hours to 5 days, in a solvent which is inert to the reaction, in the presence of a condensing agent. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran, dioxane, dimethoxyethane, and the like, DMF, DMSO, EtOAc, acetonitrile or water, and a mixture thereof. Examples of the condensing agent include, but are not limited to, 1-(3-dimethylaminopropyl)-3-ethylcarbodiimide, dicyclohexylcarbodiimide, carbonyldiimidazole, diphenylphosphonyl azide, and phosphorus oxychloride. It may be sometimes preferable for the reaction to use an additive (for example, 1-hydroxybenzotriazole). It is sometimes advantageous for smooth progress of the reaction to carry out the reaction in the presence of organic bases such as triethylamine, N,N-diisopropylethylamine, N-methylmorpholine, DBU, and the like, or inorganic bases such as potassium carbonate, sodium carbonate, potassium hydroxide, and the like.

Furthermore, it is also possible to use a method in which a reactive derivative of the carboxylic acid (12) is used, and reacted with the compound (2). Examples of the reactive derivative of the carboxylic acid include acid halides that can be obtained by the reaction with a halogenating agent such as phosphorus oxychloride, thionyl chloride, and the like, mixed acid anhydrides that can be obtained by the reaction with isobutyl chloroformate or the like, active esters that can be obtained by condensation with 1-hydroxybenzotriazole or the like, etc. The reaction of the reactive derivative with the benzyl amine derivative (2) can be carried out in a range of from cooling to heating, and preferably from −20° C. to 60° C., in a solvent which is inert to the reaction, such as halogenated hydrocarbons, aromatic hydrocarbons, ethers, and the like.

In addition, the compound (4) can be prepared by subjecting the compound (3) to a boronic acid esterification reaction.

In this reaction, a mixture of the compound (3) and a boric ester reagent in an equivalent amount or in an excess amount is stirred in a range of from cooling to heating, and preferably −20° C. to 60° C., in a solvent which is inert to the reaction, usually for 0.1 hours to 5 days, in the presence of an organic metal compound. The solvent as used herein is not particularly limited, but examples thereof include aromatic hydrocarbons such as benzene, toluene, xylene, and the like, halogenated hydrocarbons such as dichloromethane, 1,2-dichloroethane or chloroform, and the like, ethers such as diethyl ether, tetrahydrofuran, dioxane, dimethoxyethane, and the like, DMF, DMSO, EtOAc, acetonitrile, or water, and a mixture thereof. Examples of the boronic acid esterification reagent include triisopropyl borate, tributyl borate, and the like. Examples of the organic metal compound used in the present reaction include organic lithium compounds such as n-butyl lithium and the like.

Next, the compound (6) can be obtained by subjecting the compound (4) to a coupling reaction.

In this reaction, a mixture of the compound (4) and the compound (5) in an equivalent amount or in an excess amount is stirred in a range of from cooling to heating under reflux, and preferably 0° C. to 80° C., in a solvent which is inert to the reaction or without a solvent, usually for 0.1 hours to 5 days. The solvent as used herein is not particularly limited, but examples thereof include aromatic hydrocarbons such as benzene, toluene, xylene, and the like, ethers such as dimethyl ether, diethyl ether, tetrahydrofuran, dioxane, dimethoxyethane, and the like, halogenated hydrocarbons such as dichloromethane, 1,2-dichloroethane, chloroform, and the like, N,N-dimethylformamide, dimethylsulfoxide, ethyl acetate, acetonitrile and a mixture thereof. It is sometimes advantageous for smooth progress of the reaction to carry out the reaction in the presence of organic bases such as triethylamine, N,N-diisopropylethylamine, N-methylmorpholine, and the like, or inorganic bases such as potassium carbonate, sodium carbonate, potassium hydroxide, and the like.

Furthermore, the Suzuki-Miyaura cross-coupling reaction can also be carried out using, for example, a catalyst used for the Suzuki-Miyaura cross-coupling reaction, but is not limited thereto. The catalyst as used herein is not particularly limited, but may be tetrakis(triphenylphosphine)palladium (0), palladium(II) acetate, dichloro[1,1'-bis(diphenylphosphenylphosphino)ferrocene]palladium (II), bistriphenylphosphine palladium(II) chloride, or the like. Further, the coupling reaction can also be carried out using metal palladium(0).

[Document]

"Organic Functional Group Preparations", S. R. Sandler and W. Karo, 2$^{nd}$ edition, Vol. 1, Academic Press Inc., 1991

The Chemical Society of Japan, "Courses in Experimental Chemistry (5$^{th}$ edition)" Vol. 14 (2005) (Maruzen)

(Starting Material Synthesis 2)

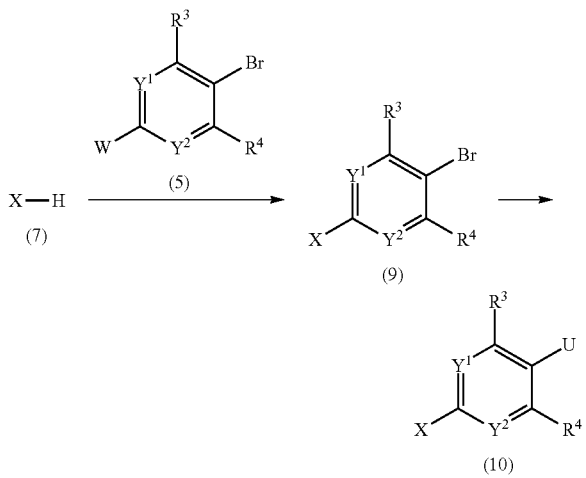

[Chem. 39]

The compound (10) can be prepared by the reaction of a compound (7) with a compound (5), followed by a boronic acid esterification reaction.

The present reaction can be carried out by the method as in Starting Material Synthesis 1 as described above.

The compounds of the formula (I) can be isolated and purified as their free compounds, salts, hydrates, solvates, or polymorphic crystalline substances thereof. The salts of the compound of the formula (I) can be prepared by carrying out the treatment of a conventional salt forming reaction.

Isolation and purification are carried out by employing ordinary chemical operations such as extraction, fractional crystallization, various types of fractional chromatography, and the like.

Various isomers can be prepared by selecting an appropriate starting compound or separated by using the difference in the physicochemical properties between the isomers. For example, the optical isomers can be obtained by means of a general method for designing optical resolution of racemic products (for example, fractional crystallization for inducing diastereomer salts with optically active bases or acids, chromatography using a chiral column or the like, and others), and further, the isomers can also be prepared from an appropriate optically active starting compound.

The pharmacological activity of the compound of the formula (I) was confirmed by the tests shown below.

Test Example 1

Inhibitory Effect of Compound on Human VAP-1 Enzyme (SSAO) Activity

A human VAP-1 enzyme (SSAO) activity was measured by a radiochemistry-enzymatic assay using $^{14}$C-benzylamine as an artificial substrate. An enzyme suspension prepared from CHO (Chinese Hamster Ovary) cells stably expressing a human VAP-1 enzyme (SSAO) was preincubated with the compound of the present invention in a 96-well microplate at room temperature for 30 minutes. Subsequently, the enzyme suspension was incubated with $^{14}$C-benzylamine (a final concentration of $1 \times 10^{-5}$ mol/L) to a final volume of 50 mL at 37° C. for 1 hour. The enzymatic reaction was stopped by the addition of 2 mol/L (50 µL) of citric acid. The oxidation products were extracted directly in a 200-µL toluene scintillator, and the radioactivity was measured with a scintillation spectrometer.

Test Example 2

Inhibitory Effect of Compound on Rat VAP-1 Enzyme (SSAO) Activity

A rat VAP-enzyme 1 (SSAO) activity was measured by a radiochemistry-enzymatic assay using $^{14}$C-benzylamine as an artificial substrate. An enzyme suspension prepared from CHO (Chinese Hamster Ovary) cells stably expressing a rat VAP-enzyme 1 (SSAO) was preincubated with the compound of the present invention in a 96-well microplate at room temperature for 30 minutes. Subsequently, the enzyme suspension was incubated with $^{14}$C-benzylamine (a final concentration of $1 \times 10^{-5}$ mol/L) to a final volume of 50 mL at 37° C. for 1 hour. The enzymatic reaction was stopped by the addition of 2 mol/L (50 µL) of citric acid. The oxidation products were extracted directly in a 200-µL toluene scintillator, and the radioactivity was measured with a scintillation spectrometer.

The results are shown in Table 1. In addition, the inhibitory activity is expressed in $IC_{50}$ (nmol/L).

TABLE 1

| Ex | Human (nM) | Rat (nM) |
|---|---|---|
| 3 | 32 | 22 |
| 16 | 49 | 7.4 |
| 19 | 6.9 | 6.9 |
| 32 | 18 | 10 |
| 33 | 31 | 21 |
| 51 | 48 | 21 |
| 66 | 9.4 | 5.2 |
| 69 | 32 | 9.8 |
| 75 | 49 | 3.6 |
| 78 | 61 | 61 |
| 79 | 66 | 34 |
| 80 | 81 | 39 |
| 84 | 140 | 15 |
| 91 | 18 | 12 |
| 95 | 11 | 5.8 |
| 102 | 20 | 12 |
| 147 | 72 | 44 |
| 190 | 23 | 19 |
| 191 | 7 | 14 |
| 261 | 17 | 21 |
| 216 | 90 | 40 |
| 263 | 25 | 15 |

From these test, it was confirmed that the compound of the present invention has an extremely high inhibitory activity on human and rat VAP-1. Further, a few of the compounds of the present invention were evaluated for their inhibitory activity on the human platelet MAO, but it became evident that they do not inhibit the enzyme.

Test Example 3

Eight-week to twelve-week Wistar male rats were fasted for 20 hours, and orally administered with a test drug (1 mg/1 kg). Heparin blood collection from the tail vein was performed immediately before the administration, and at 1 h, 3 h, 6 h, and 12 h after the administration. The resulting blood was subjected to centrifugation at 14000 rpm for 5 minutes to separate plasma, and the VAP-1 enzyme activity in the resulting plasma was measured by a radio-enzyme assay method.

For the radio-enzyme assay method, $^{14}$C-benzylamine which is a synthetic substrate (10 µM) was reacted with the resulting plasma at 37° C., and the resulting metabolite was extracted with a mixture of toluene/ethyl acetate. The radioactivity was measured and taken as a VAP-1 enzyme activity in the plasma. The effect of the test drug was calculated from the ratio (%) of the VAP-1 activity after the administration of the test drug relative to the VAP-1 activity in the plasma immediately before the administration (100%).

Reference Document Diabetologia (1997) 40 1243-1250

TABLE 2

| | Inhibition Ratio (%) | | | |
|---|---|---|---|---|
| Ex | 1 h | 3 h | 6 h | 12 h |
| 3 | 65 | 77 | 71 | 47 |
| 16 | 83 | 83 | 53 | 42 |
| 19 | 84 | 79 | 75 | 63 |
| 32 | 68 | 70 | 58 | 45 |
| 33 | 84 | 87 | 97 | 83 |
| 51 | 30 | 37 | 43 | 32 |
| 66 | 78 | 81 | 74 | 67 |
| 69 | 72 | 56 | 39 | 24 |
| 75 | 78 | 58 | 38 | 24 |
| 78 | 31 | 18 | 3 | −4 |
| 79 | 24 | 21 | 15 | 14 |
| 80 | 48 | 43 | 26 | 21 |
| 84 | 16 | 20 | 17 | NT |
| 91 | 68 | 68 | 68 | 44 |
| 95 | 70 | 67 | 71 | 21 |
| 102 | 65 | 62 | 71 | 40 |
| 147 | 70 | 79 | 75 | 66 |
| 190 | 42 | 48 | 41 | 11 |
| 191 | 35 | 43 | 48 | 20 |
| 216 | 25 | −7 | 15 | 25 |
| 261 | 36 | 44 | 45 | 32 |
| 263 | 97 | 95 | 80 | 75 |

Test Example 4

Effect on Albuminuria in Rats with Diabetes

Seven- to eight-week SD rats (having weights up to 200 to 250 g) during fasting were used and fasted for 20 hours and then intraperitoneally administered with 60 mg/ml/kg of streptozotocin (STZ) prepared from a 2 mmol/l citric acid buffer (pH 4.5). At the same time, the control rats were injected with the same amount of a 2 mmol/l citric acid buffer (pH 4.5). The blood glucose value was measured using a colorimetric method, and the rats that had showed a value of 350 mg/dl blood glucose levels on day 3 after the treatment with STZ was diagnosed with diabetes mellitus.

The test substance was given daily for 4 weeks after the treatment with STZ. After 4 weeks of the treatment with the test substance, 24-hour urine collection was performed using metabolic cages.

Test Example 5

Effect on Eye Permeability in Rats with Diabetes

Seven- to eight-week SD rats (having weights up to 200 to 250 g) during fasting were used and fasted for 20 hours and then intraperitoneally administered with 60 mg/ml/kg of streptozotocin (STZ) prepared from a 2 mmol/l citric acid buffer (pH 4.5). At the same time, the control rats were injected with the same amount of a 2 mmol/l citric acid buffer (pH 4.5). The blood glucose value was measured using a colorimetric method, and the rats that had showed a value of 350 mg/dl blood glucose levels on day 3 after the treatment with STZ was diagnosed with diabetes mellitus.

The test substance was given daily for 4 weeks after the treatment with STZ. After 4 weeks of the treatment with the test substance, the eye vascular permeability was examined after 24 hours from the date of the final administration. The eye permeability was examined on the basis of the colorant leakage into the vitreous body in the eye after 30 minutes from the tail vein administration of 40 mg/ml/kg of a sodium fluorescein solution. The permeability as an index of the evaluation was expressed in the intravitreal concentration/plasma concentration of the fluorescein. Measurement of the fluorescein was carried out using a fluorescent plate reader.

After the result of the tests above, it was confirmed that the compound of the formula (I) constantly exhibits a VAP-1 activity in blood even in the oral administration test with rats. Therefore, the compound can be used for treatment of VAP-1-related diseases or the like.

A pharmaceutical composition containing one or more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, ophthalmic solutions, eye ointments, transdermal liquid preparations, ointments, transdermal patches, transmucosal liquid preparations, transmucosal patches, inhalers, and the like.

The solid composition for use in the oral administration is used in the form of tablets, powders, granules, or the like. In such a solid composition, one or more active ingredient(s) are mixed with at least one inactive excipient. In a conventional method, the composition may contain inactive additives, such as a lubricant, a disintegrating agent, a stabilizer, or a solubilization assisting agent. If necessary, tablets or pills may be coated with sugar or a film of a gastric or enteric coating substance.

The liquid composition for oral administration contains pharmaceutically acceptable emulsions, solutions, suspensions, syrups, elixirs, or the like, and also contains generally used inert diluents, for example, purified water or ethanol. In addition to the inert diluent, the liquid composition may also contain auxiliary agents, such as a solubilization assisting agent, a moistening agent, and a suspending agent, sweeteners, flavors, aromatics, or antiseptics.

The injections for parenteral administration include sterile aqueous or non-aqueous solutions, suspensions and emulsions. The aqueous solvent includes, for example, distilled water for injection and physiological saline. Examples of the non-aqueous solvent include alcohols such as ethanol. Such a composition may further contain a tonicity agent, an antiseptic, a moistening agent, an emulsifying agent, a dispersing agent, a stabilizer, or a solubilizing aid. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, poultices, sprays, lotions, eye drops, eye ointments, and the like. The agents contain generally used ointment bases, lotion bases, aqueous or non-aqueous liquid preparations, suspensions, emulsions, and the like.

As the transmucosal agents such as an inhaler, a transnasal agent, and the like, those in the form of a solid, liquid, or semi-solid state are used, and can be prepared in accordance with a conventionally known method. For example, a known excipient, and also a pH adjusting agent, an antiseptic, a surfactant, a lubricant, a stabilizer, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a known device or sprayer, such as a measured administration inhalation device, and the like. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, carbon dioxide, and the like.

In oral administration, the daily dose is generally from about 0.001 to 100 mg/kg, preferably from 0.1 to 30 mg/kg, and more preferably 0.1 to 10 mg/kg, per body weight, administered in one portion or in 2 to 4 divided portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to the individual case by taking the symptoms, the age, and the gender, and the like into consideration.

The compound of the formula (I) can be used in combination with various agents for treating the diseases for which the compound of the formula (I) is considered to be effective. The combined preparation may be administered simultaneously, or separately and continuously, or at a desired time interval. The preparations to be administered simultaneously may be a blend, or may be prepared individually.

EXAMPLES

Hereinbelow, the preparation methods for the compound of the formula (I) will be described in more detail with reference to Examples. Further, the present invention is not limited to only the preparation methods of the specific Examples and Preparation Examples below, but the compound of the formula (I) can be prepared by any combination of the preparation methods or the methods that are apparent to a person skilled in the art.

Furthermore, the following abbreviations may be used in some cases in the Examples, Preparation Examples, and Tables below.

Rf: Preparation Example No.,
Ex: Example No.,
Data: Physicochemical data,
ESI+: representing m/z values in ESI-MS (positive ions), and representing [M+H]$^+$ peaks unless otherwise specified,
ESI−: representing m/z values in ESI-MS (negative ions), and representing [M−H]$^-$ peaks unless otherwise specified,
APCI+: representing m/z values in APCI-MS (positive ions), and representing [M+H]$^+$ peaks unless otherwise specified,
APCI−: representing m/z values in APCI-MS (negative ions), and representing [M−H]$^-$ peaks unless otherwise specified,
FAB+: representing m/z values in FAB-MS (positive ions), and representing [M+H]$^+$ peaks unless otherwise specified,
FAB−: representing m/z values in FAB-MS (negative ions), and representing [M−H]$^-$ peaks unless otherwise specified,
EI+: representing m/z values in EI-MS (positive ions), and representing [M]$^+$ peaks unless otherwise specified,
EI−: representing m/z values in EI-MS (negative ions), and representing [M]$^-$ peaks unless otherwise specified,
NMR-DMSO-$d_6$: δ (ppm) in $^1$H-NMR in DMSO-$d_6$,
NMR-CDCl$_3$: δ (ppm) in $^1$H-NMR in CDCl$_3$,
Powder X-ray diffraction curve using Cu—Kα rays: measured under the condition of using MAC Science MXP18TAHF22, tube: Cu, tube current: 200 mA, tube voltage: 40 kV sampling interval: 0.020°, scanning rate: 3°/min, wavelength: 1.54056 Angstrom, measurement diffraction angle range (2θ): 3 to 40°, or using RIGAKU RINT-TTRII, tube: Cu, tube current: 50 mA, tube voltage: 300 kV, sampling interval: 0.020°, scanning rate: 4°/min, wavelength: 1.54056 Angstrom, measurement diffraction angle range (2θ): 2.5 to 40°,
Structure: Structural formula,
Syn: Preparation method (in which the numeral shows that the compound is prepared by the same preparation method as the compound having the Example No. and R prefixed before the numeral shows that the compound is prepared by the same preparation method as the compound having the Preparation Example No.),
Acid: indicating that the compound represented by a structural formula forms a salt with an acid as described, and the numeral before the acid mean the ratio of the acid. For example, ½FA means formation of a hemifumarate, and 2HCl means formation of dihydrochloride,
L-TA: L-tartaric acid,
OA: oxalic acid,
FA: fumaric acid,
½FA: hemifumaric acid,
SA: succinic acid,
AA: acetic acid,
HCl: hydrochloric acid,
HBr: hydrobromic acid,
Boc: tert-butoxycarbonyl group,
DMSO: dimethylsulfoxide,
THF: tetrahydrofuran,
EtOAc: ethyl acetate,
MgSO$_4$: anhydrous magnesium sulfate,
DMF: N,N-dimethylformamide,
Na$_2$SO$_4$: anhydrous sodium sulfate,
MeOH: methanol,
EtOH: ethanol
CHCl$_3$: chloroform,
K$_2$CO$_3$: potassium carbonate,
NaH: sodium hydride (60% mineral oil suspension),
NMP: N-methyl-2-pyrrolidone,
WSC: 1-(3-dimethylaminopropyl)-3-ethylcarbodiimide,
HOBt: 1-hydroxybenzotriazole,
TEA: triethylamine,
DIPEA: diisopropylethylamine,
MeCN: acetonitrile,
TFA: trifluoroacetic acid,
DME: 1,2-dimethoxyethane,
M: mol/L.

Preparation Example 1

To 80% ethylamine/MeOH (1.1 g) was added 1-bromo-3-(bromomethyl)benzene (1 g) in five divided portions at room temperature, followed by stirring at room temperature overnight. The reaction mixture was concentrated under reduced pressure, and the obtained residue was subjected to liquid separation with chloroform and a saturated aqueous sodium hydrogen carbonate solution. The organic layer was separated, and then the aqueous layer was extracted with CHCl$_3$ again. These organic layers were combined, dried over Na$_2$SO$_4$, and then concentrated under reduced pressure. The obtained residue was purified by silica gel column chromatography (NH silica, 3% MeOH/CHCl$_3$) to obtain N-(3-bromobenzyl)ethanamine (610 mg) as a colorless oil.

Preparation Example 2

To a solution of 1-(3-bromophenyl)-N-methylmethanamine (12.0 g) and N-(tert-butoxycarbonyl)glycine (11.5 g) in dichloroethane (80 ml) were added HOBt (9.7 g) and WSC hydrochloride (13.7 g), followed by stirring at room temperature overnight. To the reaction mixture was added a saturated aqueous sodium hydrogen carbonate solution, followed by extraction with CHCl$_3$. The mixture was dried over Na$_2$SO$_4$ and then concentrated under reduced pressure. The obtained residue was purified by silica gel column chromatography (CHCl$_3$/MeOH) to obtain tert-butyl {2-[(3-bromobenzyl)(methyl)amino]-2-oxoethyl}carbamate (21.3 g).

Preparation Example 7

To a solution of tert-butyl {2-[(3-bromobenzyl)amino]-2-oxoethyl}carbamate (1.0 g) and bis(pinacolato)diboron (777 mg) in dioxane (15 ml) were added potassium acetate (858 mg) and dichlorobis(triphenylphosphine)palladium(II) (102 mg), followed by stirring at 80° C. overnight. The reaction mixture was filtrated and the solvent was concentrated under reduced pressure. The obtained residue was purified by silica gel column chromatography (hexane/EtOAc=10/1 to ⅕) to obtain tert-butyl (2-oxo-2-{[3-(4,4,5,5-tetramethyl-1,3,2-dioxaborolan-2-yl)benzyl]amino}ethyl)carbamate (1.06 g) as a colorless oil.

Preparation Example 10

Under a nitrogen atmosphere, tert-butyl {2-[(3-bromobenzyl)amino]-2-oxoethyl}carbamate (237 mg) and 4-[4-(4,4,5,5-tetramethyl-1,3,2-dioxaborolan-2-yl)phenyl]pyrrolidine (275 mg) were dissolved in DME (3 ml) and water (1.5 ml), and tetrakis(triphenylphosphine)palladium (23 mg) and sodium carbonate (210 mg) were added thereto, followed by stirring at 90° C. for 36 hours. The reaction mixture was concentrated under reduced pressure, and the obtained residue was subjected to liquid separation with CHCl$_3$ and water. The organic layer was separated, and then the aqueous layer was extracted with CHCl$_3$ again. These organic layers were combined and dried over Na$_2$SO$_4$, and then the solvent was evaporated under reduced pressure. The obtained residue was purified by silica gel column chromatography (2% MeOH/CHCl$_3$) to obtain tert-butyl (2-{methyl[3-(2-pyrrolidin-1-ylpyrimidin-5-yl)benzyl]amino}-2-oxoethyl)carbamate (260 mg) as a colorless oil.

Preparation Example 16

Under an argon atmosphere, (4-bromophenyl)methanol (3.0 g) and bis(pinacolato)diboron (4.5 g) was dissolved in dioxane (35 ml), and dichlorobis(triphenylphosphine)palladium(II) (567 mg) and potassium acetate (4.7 g) were added thereto, followed by stirring at 80° C. for 1 day. The reaction mixture was concentrated under reduced pressure, and then a saturated aqueous sodium hydrogen carbonate solution was added thereto, followed by extraction with CHCl$_3$. The organic layer was dried over Na$_2$SO$_4$ and concentrated under reduced pressure. The obtained residue was dissolved in DME (35 ml) and water (18 ml), and tert-butyl {2-[(3-bromobenzyl)(methyl)amino]-2-oxoethyl}carbamate (3.5 g) was added thereto under an argon atmosphere. In addition, sodium carbonate (3.1 g) and tetrakis(triphenylphosphine)palladium (339 mg) were added thereto, followed by stirring at 70° C. for 1 day. The reaction mixture was concentrated under reduced pressure, and then a saturated aqueous sodium hydrogen carbonate solution was added thereto, followed by extraction with CHCl$_3$. The organic layer was dried over Na$_2$SO$_4$ and concentrated under reduced pressure. The obtained residue was purified by silica gel column chromatography (hexane/EtOAc) to obtain tert-butyl {2-[{[4'-(hydroxymethyl)biphenyl-3-yl]methyl}(methyl)amino]-2-oxoethyl}carbamate (2.8 g).

Preparation Example 50 tert-butyl (2-{[3-(2-Chloropyrimidin-5-yl)benzyl](methyl)amino}-2-oxoethyl)carbamate (250 mg) was dissolved in DMF (5 ml), and 4-piperidin-4-ylmorpholine (218 mg) and K$_2$CO$_3$ (265 mg) were added thereto, followed by stirring at room temperature for 3 days. To the reaction mixture was added water, followed by extraction with EtOAc, and then the organic layer was dried over MgSO$_4$ and evaporated under reduced pressure. The obtained residue was purified by silica gel column chromatography (0% to 5% MeOH/CHCl$_3$) to obtain tert-butyl [2-(methyl{3-[2-(4-morpholin-4-ylpiperidin-1-yl)pyrimidin-5-yl]benzyl}amino)-2-oxoethyl]carbamate (285 mg).

Preparation Example 91 tert-Butyl 4-(2-fluoroethyl)piperazine-1-carboxylate (460 mg) was dissolved in EtOAc (5 ml), and 4 M hydrogen chloride/EtOAc (2.5 ml) was added thereto. After stirring at room temperature for 7 hours, the precipitated solid was collected by filtration to obtain 1-(2-fluoroethyl)piperazine dihydrochloride (406 mg).

Preparation Example 94

3-Bromo-2-methylpyridine (500 mg) and tert-butyl piperazine-1-carboxylate (650 mg) were dissolved in toluene (7.5 ml), and (1E,4E)-1,5-diphenylpenta-1,4-dien-3-one_palladium (3:2) (40 mg), 1,1'-binaphthalene-2,2'-diylbis(diphenylphosphine) (18 mg), and 2-methylpropan-2-ol sodium (391 mg) were added thereto in this order under a nitrogen atmosphere, followed by warming to 100° C. and stirring overnight. The reaction mixture was subjected to liquid separation with CHCl$_3$ and water, the organic layer was dried over Na$_2$SO$_4$, and then the solvent was evaporated. The obtained residue was purified by silica gel column chromatography (CHCl$_3$ to 5% MeOH/CHCl$_3$) to obtain tert-butyl 4-(2-methylpyridin-3-yl)piperazine-1-carboxylate (790 mg) as a pale yellow oil.

Preparation Example 107

Under an argon atmosphere, tert-butyl piperazine-1-carboxylate (10 g) and 2-bromo-3-methylpyridine were dissolved in toluene (150 ml), and tris(dibenzylideneacetone)dipalladium (1.25 g), 1,1'-binaphthalene-2,2'-diylbis(diphenylphosphine) (2.5 g), and 2-methylpropan-2-ol sodium (6.5 g) were added thereto, followed by stirring at 100° C. for 5 hours. To the reaction mixture was added a saturated aqueous sodium hydrogen carbonate solution, followed by extraction with EtOAc. The organic layer was dried over Na$_2$SO$_4$ and the solvent was concentrated under reduced pressure. The obtained residue was purified by silica gel column chromatography (hexane/EtOAc). The product was dissolved in MeOH, and 4 M hydrogen chloride/EtOAc was added thereto, followed by stirring at room temperature overnight. The reaction mixture was concentrated under reduced pressure, and then EtOAc was added thereto. The obtained solid was collected by filtration to obtain 1-(3-methylpyridin-2-yl)piperazine dihydrochloride (8.3 g).

Preparation Example 111

5-Bromo-2-fluoropyridine (3.0 g) was dissolved in DMF (18 ml), and K$_2$CO$_3$ (1.31 g) and tert-butyl piperazine-1-carboxylate (1.76 g) were added thereto, followed by stirring at 130° C. for 3 days. The reaction mixture was concentrated under reduced pressure, and then a saturated aqueous sodium hydrogen carbonate solution was added thereto, followed by extraction with CHCl$_3$. The organic layer was dried over Na$_2$SO$_4$ and the solvent was concentrated under reduced pressure. The obtained residue was purified by silica gel column chromatography (hexane/EtOAc) to obtain tert-butyl 4-(5-bromopyridin-2-yl)piperazine-1-carboxylate (1.21 g).

Preparation Example 112

2-Chloro-3-(trifluoromethyl)pyridine (1.07 g) and tert-butyl piperazine-1-carboxylate (1.0 g) was dissolved in DMF (10 ml), and K$_2$CO$_3$ (3.0 g) was added thereto, followed by stirring at 80° C. overnight. The reaction mixture was concentrated under reduced pressure, and then a saturated aqueous sodium hydrogen carbonate solution was added thereto, followed by extraction with CHCl$_3$. The organic layer was dried over Na$_2$SO$_4$ and the solvent was concentrated under reduced pressure. The obtained residue was purified by silica gel column chromatography (hexane/EtOAc). The product was dissolved in MeOH (16 ml), and 4 M hydrogen chloride/EtOAc (8 ml) was added thereto, followed by stirring at room temperature overnight. The reaction mixture was concentrated under reduced pressure, then EtOAc was added thereto, and the solid was collected by filtration to obtain 1-[3-(trifluoromethyl)pyridin-2-yl]piperazine dihydrochloride (858 mg).

Preparation Example 123

6-[4-(tert-Butoxycarbonyl)piperazin-1-yl]nicotinic acid (934 mg) was dissolved in dioxane (12 ml), and 4 M hydrogen chloride/dioxane (7 ml) was added thereto, followed by stirring at room temperature overnight. The precipitated solid was collected by filtration to obtain 6-piperazin-1-yl nicotinic acid dihydrochloride (850 mg).

Preparation Example 143 tert-Butyl 4-{5-[(1E)-3-ethoxy-3-oxoprop-1-en-1-yl]-3-methylpyridin-2-yl}piperazine-1-carboxylate (305 mg) was dissolved in EtOH (4 ml), and 4 M hydrogen chloride/EtOAc (2 ml) was added thereto, followed by stirring at room temperature overnight. The reaction mixture was concentrated under reduced pressure and then suspended in DMF (4 ml), and $K_2CO_3$ (636 mg) and tert-butyl (2-{[3-(2-chloropyrimidin-5-yl)benzyl]methyl)amino}-2-oxoethyl)carbamate (300 mg) were added thereto, followed by stirring at 80° C. overnight. The reaction mixture was concentrated under reduced pressure, and then a saturated aqueous sodium hydrogen carbonate solution was added thereto, followed by extraction with $CHCl_3$. The organic layer was dried over $Na_2SO_4$ and the solvent was concentrated under reduced pressure. The obtained residue was purified by silica gel column chromatography ($CHCl_3$/MeOH) to obtain ethyl (2E)-3-[6-(4-{5-[3-({[N-(tert-butoxycarbonyl)glycyl](methyl)amino}methyl)phenyl]pyrimidin-2-yl}piperazin-1-yl)-5-methylpyridin-3-yl]acrylate (451 mg).

Preparation Example 145 tert-Butyl 3',6'-dihydro-3,4'-bipyridine-1'(2'H)-carboxylate (606 mg) was dissolved in MeOH (15 ml), and 4 M hydrogen chloride/EtOAc (6 ml) was added thereto, followed by stirring at room temperature for 5 hours. The reaction mixture was concentrated under reduced pressure and then suspended in DMF (8 ml), and $K_2CO_3$ (2.5 g) and 5-bromo-2-fluoropyridine (400 mg) were added thereto, followed by stirring at 80° C. overnight. The reaction mixture was concentrated under reduced pressure, and then a saturated aqueous sodium hydrogen carbonate solution was added thereto, followed by extraction with $CHCl_3$. The organic layer was dried over $Na_2SO_4$ and the solvent was concentrated under reduced pressure. The obtained residue was purified by silica gel column chromatography ($CHCl_3$/MeOH) to obtain 5-bromo-3',6'-dihydro-2'H-2,1':4',3"-terpyridine (170 mg).

Preparation Example 146 tert-Butyl 4-pyridin-3-ylpiperazine-1-carboxylate (680 mg) was dissolved in MeOH (15 ml), and 4 M hydrogen chloride/EtOAc (6.5 ml) was added thereto, followed by stirring at room temperature overnight. Then, the solvent was evaporated under reduced pressure. To a mixture of the obtained residue and DMF (20 ml) was added $K_2CO_3$ (1.8 g), and then 5-bromo-2-fluoropyridine (910 mg) was added thereto. After stirring at 60° C. overnight, water was added thereto, followed by extraction with EtOAc. The organic layer was dried over $MgSO_4$ and then evaporated under reduced pressure. The obtained residue was purified by silica gel column chromatography (0% to 5% MeOH/$CHCl_3$) to obtain 1-(5-bromopyridin-2-yl)-4-pyridin-3-ylpiperazine (173 mg).

Preparation Example 147

Piperazine (1.13 g) and 2-chloro-6-methylnicotinonitrile (500 mg) were dissolved in DMF (15 ml), and $K_2CO_3$ (1.36 g) was added thereto, followed by stirring at 60° C. overnight. The reaction mixture was concentrated under reduced pressure, and then a saturated aqueous sodium hydrogen carbonate solution was added thereto, followed by extraction with $CHCl_3$. The organic layer was dried over $Na_2SO_4$, and the solvent was concentrated under reduced pressure. The obtained residue was purified by silica gel column chromatography ($CHCl_3$/MeOH) to obtain 6-methyl-2-piperazin-1-ylnicotinonitrile (628 mg).

Preparation Example 159

5-Bromo-2-chloropyrimidine (400 mg) was dissolved in DMF (4 ml), and thiomorpholine 1,1-dioxide (308 mg) and $K_2CO_3$ (857 mg) were added thereto, followed by stirring at room temperature for 2 hours. The reaction mixture was concentrated under reduced pressure, and then a saturated aqueous sodium hydrogen carbonate solution was added thereto, followed by extraction with $CHCl_3$. The organic layer was dried over $Na_2SO_4$ and then concentrated under reduced pressure. The obtained residue was purified by silica gel column chromatography ($CHCl_3$/MeOH) to obtain 4-(5-bromopyrimidin-2-yl)thiomorpholine 1,1-dioxide (191 mg).

Preparation Example 160

Under an argon atmosphere, to a solution of tert-butyl 4-(4-bromophenyl)piperazine-1-carboxylate (993 mg) and bis(pinacolato)diboron (813 mg) in dioxane (20 ml) were added potassium acetate (1.03 g) and dichlorobis(triphenylphosphine)palladium(II) (102 mg), followed by stirring at 80° C. for 24 hours. To the reaction mixture was added a saturated aqueous sodium hydrogen carbonate solution, followed by extraction with $CHCl_3$. The organic layer was dried over $Na_2SO_4$, and the solvent was concentrated under reduced pressure. The obtained residue was purified by silica gel column chromatography ($CHCl_3$/MeOH) to obtain tert-butyl 4-[4-(4,4,5,5-tetramethyl-1,3,2-dioxaborolan-2-yl)phenyl]piperazine-1-carboxylate (900 mg).

Preparation Example 162 tert-Butyl {2-[(3-bromobenzyl)amino]-2-oxoethyl}carbamate (274 mg), 4-[4-(4,4,5,5-tetramethyl-1,3,2-dioxaborolan-2-yl)phenyl]morpholine (222 mg), sodium carbonate (81 mg), tetrakis(triphenylphosphine)palladium (88 mg), DME (5 ml), and water (2.5 ml) were put into a 50-ml recovery flask, followed by stirring at 80° C. for 10 hours under a nitrogen atmosphere. The reaction mixture was cooled to room temperature and concentrated under reduced pressure. The obtained residue was subjected to liquid separation with $CHCl_3$ and water. The organic layer was separated, and then the aqueous layer was extracted with $CHCl_3$ again. These organic layers were combined, dried over $Na_2SO_4$, and then concentrated under reduced pressure. The obtained residue was purified by silica gel column chromatography (2% MeOH/$CHCl_3$) to obtain tert-butyl (2-{methyl[(4'-morpholin-4-ylbiphenyl-3-yl)methyl]amino}-2-oxoethyl)carbamate (270 mg) as a pale yellow oil.

Preparation Example 171 rel-(2R,6S)-4-(5-Bromopyrimidin-2-yl)-2,6-dimethylmorpholine (118 mg) and tert-butyl (2-{methyl[3-(4,4,5,5-tetramethyl-1,3,2-dioxaborolan-2-yl)benzyl]amino}-2-oxoethyl)carbamate (175 mg) were dissolved in DME (2 ml) and water (1 ml), and tetrakis(triphenylphosphine)palladium (15 mg) and sodium carbonate (137 mg) were added thereto, followed by stirring at 80° C. for 24 hours. The obtained residue was subjected to liquid separation with CHCl₃ and water. The organic layer was separated, and then the aqueous layer was extracted with CHCl₃ again. These organic layers were combined, dried over Na₂SO₄, and then concentrated under reduced pressure. The obtained residue was purified by silica gel column chromatography (2% MeOH/CHCl₃) to obtain tert-butyl rel-{2-[(3-{2-[(2R,6S)-2,6-dimethylmorpholin-4-yl]pyrimidin-5-yl}benzyl)(methyl)amino]-2-oxoethyl]carbamate (190 mg) as a colorless oil.

Preparation Example 200 tert-Butyl (2-{methyl[3-(2-piperazin-1-ylpyrimidin-5-yl)benzyl]amino}-2-oxoethyl)carbamate (200 mg) and ethyl 6-chloronicotinate (169 mg) were dissolved in NMP (4 ml), and N,N-dibutylbutan-1-amine (252 mg) was added thereto, followed by stirring at 100° C. overnight. To the reaction mixture was added water, followed by extraction with EtOAc. The organic layer was washed with saturated brine and dried over MgSO₄, and then the solvent was evaporated under reduced pressure. The obtained residue was purified by silica gel column chromatography (0% to 8% CHCl₃/MeOH) to obtain ethyl 6-(4-{5-[3-({[N-(tert-butoxycarbonyl)glycyl](methyl)amino}methyl)phenyl]pyrimidin-2-yl}piperazin-1-yl)nicotinate (100 mg).

Preparation Example 215

1-{5-[3-({[N-(tert-Butoxycarbonyl)glycyl](methyl)amino}methyl)phenyl]pyrimidin-2-yl}piperidine-4-carboxylic acid (200 mg) and N-methylcyclohexanamine (94 mg) were suspended in methylene chloride (4 ml), and WSC hydrochloride (159 mg) and HOBt (112 mg) were added thereto, followed by stirring at room temperature for 3 hours. The reaction mixture was subjected to liquid separation with CHCl₃ and a saturated aqueous sodium hydrogen carbonate solution. The organic layer was separated, and then the aqueous layer was extracted with CHCl₃ again. These organic layers were combined and dried over Na₂SO₄, and then the solvent was evaporated under reduced pressure. The obtained residue was purified by silica gel column chromatography (0% to 5% MeOH/CHCl₃) to obtain tert-butyl (2-{[3-(2-{4-[cyclohexyl(methyl)carbamoyl]piperidin-1-yl}pyrimidin-5-yl)benzyl](methyl)amino}-2-oxoethyl)carbamate (169 mg).

Preparation Example 228 tert-Butyl (2-{[(4'-aminobiphenyl-3-yl)methyl](methyl)amino}-2-oxoethyl)carbamate (300 mg) was dissolved in DMF (6 ml), and nicotinic acid (150 mg), WSC hydrochloride (233 mg), and HOBt (165 mg) were added thereto, followed by stirring at room temperature for 20 hours. Water was added thereto, followed by extraction with EtOAc. The organic layer was dried over MgSO₄, and then the solvent was evaporated under reduced pressure. The obtained residue was purified by silica gel column chromatography (CHCl₃/MeOH=20/1) to obtain tert-butyl {2-[methyl({4'-[(pyridin-3-ylcarbonyl)amino]biphenyl-3-yl}methyl)amino]-2-oxoethyl}carbamate (328 mg).

Preparation Example 233 tert-Butyl (2-{[(4'-aminobiphenyl-3-yl)methyl](methyl)amino}-2-oxoethyl)carbamate (200 mg) and pyridine (64 mg) were dissolved in methylene chloride (6 ml), followed by ice-cooling. Dimethylcarbamoylchloride (64 mg) was added thereto, followed by warming to room temperature and stirring for 1 hour. The reaction mixture was subjected to liquid separation with CHCl₃ and water. The organic layer was separated, and then the aqueous layer was extracted with CHCl₃ again. These organic layers were combined and dried over sodium sulfate, and the solvent was evaporated. The obtained residue was purified by silica gel column chromatography (2% MeOH/CHCl₃) to obtain tert-butyl {2-[({4'-[(dimethylcarbamoyl)amino]biphenyl-3-yl}methyl)(methyl)amino]-2-oxoethyl}carbamate (220 mg) as a colorless oil.

Preparation Example 235

To a mixture of 2-(methylamino)ethanol (41 mg), sodium triacetoxyborohydride (166 mg), acetic acid (9 mg), and dichloromethane (4 ml) was added tert-butyl (2-{[(4'-formylbiphenyl-3-yl)methyl](methyl)amino}-2-oxoethyl)carbamate (200 mg), followed by stirring for 5 hours. To the reaction mixture was added CHCl₃-saturated aqueous sodium hydrogen carbonate solution, the organic layer was dried over Na₂SO₄, and then the solvent was evaporated. The obtained residue was purified by silica gel column chromatography (3% MeOH/chloroform) to obtain tert-butyl (2-{[(4'-{[(2-hydroxyethyl)(methyl)amino]methyl}biphenyl-3-yl)methyl](methyl)amino}-2-oxoethyl)carbamate (230 mg) as a colorless oil.

Preparation Example 240 tert-Butyl (2-{methyl[3-(2-piperazin-1-ylpyrimidin-5-yl)benzyl]amino}-2-oxoethyl)carbamate (200 mg) and TEA (92 mg) were dissolved in dichloromethane, followed by ice-cooling. Isopropyl chlorocarbonate (83 mg) was added thereto, followed by stirring at room temperature for 4 hours. Water was added thereto, followed by extraction with chloroform. The organic layer was dried over MgSO₄, and then the solvent was evaporated under reduced pressure. The obtained residue was purified by silica gel column chromatography to obtain isopropyl 4-{5-[3-({[N-(tert-butoxycarbonyl)glycyl](methyl)amino}methyl)phenyl]pyrimidin-2-yl}piperazine-1-carboxylate (155 mg).

Preparation Example 254

Ethyl 4-(4-{5-[3-({[N-(tert-butoxycarbonyl)glycyl](methyl)amino}methyl)phenyl]pyrimidin-2-yl}piperazin-1-yl)benzoate (451 mg) was dissolved in EtOH (5 ml) and THF (5 ml), and a 1 M aqueous NaOH solution (2 ml) was added thereto, followed by stirring at room temperature for 3 hours. After neutralization with 1 M hydrochloric acid (2 ml), water was added thereto, followed by extraction with CHCl₃. The organic layer was dried over Na₂SO₄ and the solvent was concentrated under reduced pressure. The obtained residue was purified by silica gel column chromatography (CHCl₃/MeOH) to obtain 4-(4-{5-[3-({[N-(tert-butoxycarbonyl)glycyl](methyl)amino}methyl)phenyl]pyrimidin-2-yl}piperazin-1-yl)benzoic acid (269 mg).

Preparation Example 256 tert-Butyl 4-(5-bromopyridin-2-yl)piperazine-1-carboxylate (800 mg) was dissolved in DMF (4 ml), and ethyl acrylate (368 mg), palladium(II) acetate (27 mg), tris(2-methylphenyl)phosphine (290 mg), and DIPEA (1.26 g) were added thereto, followed by stirring at 100° C. for 3 hours. The reaction mixture was concentrated under reduced pressure, and then EtOAc was added thereto. The insoluble material was removed by filtration. The filtrate was concentrated under reduced pressure, and then the obtained residue was purified by silica gel column chromatography (hexane/EtOAc) to obtain tert-butyl 4-{5-[(1E)-3-ethoxy-3-oxoprop-1-en-1-yl]pyridin-2-yl}piperazine-1-carboxylate (790 mg).

Preparation Example 257 tert-Butyl (2-{[(4'-cyanobiphenyl-3-yl)methyl](methyl)amino}-2-oxoethyl)carbamate (1.3 g) was dissolved in MeOH (20 ml), and a 28% aqueous ammonia solution (2 ml) was added thereto. Then, Raney nickel (205 mg) was added thereto under an argon atmosphere, followed by stirring at room temperature overnight under a hydrogen atmosphere at 1 atm. The reaction mixture was filtered and washed with water, and then the filtrate was extracted with CHCl$_3$. The organic layer was concentrated under reduced pressure, and then the obtained residue was purified by silica gel column chromatography (0 to 10% MeOH/CHCl$_3$) to obtain tert-butyl {2-[{[4'-(aminomethyl)biphenyl-3-yl]methyl}(methyl)amino]-2-oxoethyl}carbamate (900 mg).

Preparation Example 258

Under an argon atmosphere, 1-(4-iodophenyl)azepane (200 mg) and triisopropylborate (162 mg) were dissolved in THF (2 ml), followed by cooling to −78° C. A 1.59 M butyl lithium/hexane solution (0.5 ml) was added thereto, followed by elevating the temperature to 0° C. over 1 hour, and further stirring at the same temperature for 1 hour. To the reaction mixture was added a saturated aqueous ammonium chloride solution, followed by extraction with EtOAc. The organic layer was dried over Na$_2$SO$_4$ and concentrated under reduced pressure. The obtained residue was purified by silica gel column chromatography (CHCl$_3$/MeOH) to obtain (4-azepan-1-ylphenyl)boronic acid (52 mg).

Preparation Example 259

Under an argon atmosphere, 1,4-diiodiobenzene (2 g), azepane (1.2 g), and 2-(dimethylamino)ethanol (5.3 g) were mixed, and tripotassium phosphate (2.8 g) and copper (77 mg) were added thereto, followed by stirring at 60° C. for 2 days. To the reaction mixture was added a saturated aqueous sodium hydrogen carbonate solution, followed by extraction with CHCl$_3$. The organic layer was dried over Na$_2$SO$_4$ and concentrated under reduced pressure. The obtained residue was purified by silica gel column chromatography (hexane/EtOAc) to obtain 1-(4-iodophenyl)azepane (300 mg).

Preparation Example 260

To a solution of tert-butyl {2-[{[4'-(hydroxymethyl)]biphenyl-3-yl]methyl}(methyl)amino]-2-oxoethyl}carbamate (1.4 g) in 1,2-dichloroethane (15 ml) was added TEA (472 mg), followed by cooling at 0° C. in an ice bath. Methanesulfonyl chloride (518 mg) was added dropwise, followed by warming to room temperature and stirring for 2 hours. To the reaction mixture was added saturated brine, followed by extraction with CHCl$_3$. The organic layer was dried over Na$_2$SO$_4$, and concentrated under reduced pressure. The obtained residue was purified by silica gel column chromatography (hexane/EtOAc) to obtain [3'-({[N-(tert-butoxycarbonyl)glycyl](methylamino)amino}methyl)biphenyl-4-yl]methylmethanesulfonate (1.0 g).

Preparation Example 264

Under an argon atmosphere, tert-butyl (2-{methyl[3-(2-piperazin-1-ylpyrimidin-5-yl)benzyl]amino}-2-oxoethyl)carbamate (200 mg) and 6-bromonicotinonitrile (124 mg) were dissolved in toluene (6 ml), and tris(dibenzylideneacetone)dipalladium (124 mg), 1,1'-binaphthalene-2,2'-diylbis(diphenylphosphine) (169 mg), and cesium carbonate (222 mg) were added thereto, followed by stirring at 100° C. for 6 hours. The solvent was evaporated under reduced pressure, and the obtained residue was purified by silica gel column chromatography (0% to 7% MeOH/CHCl$_3$) to obtain tert-butyl {2-[(3-{2-[4-(5-cyanopyridin-2-yl)piperazin-1-yl]pyrimidin-5-yl}benzyl)(methyl)amino]-2-oxoethyl}carbamate (122 mg).

Preparation Example 268

6-Chloronicotinic acid was dissolved in N,N-dimethylacetamide (10 ml), and tert-butyl piperazine-1-carboxylate (1.2 g) and DIPEA (1.6 g) were added thereto, followed by stirring at 130° C. for 3 days. The reaction mixture was concentrated under reduced pressure, and to the obtained residue was added a 1 M aqueous NaOH solution, followed by washing with CHCl$_3$. The pH of the aqueous layer was adjusted to around 6 to 7 by the addition of 1 M hydrochloric acid, followed by extraction with CHCl$_3$. The organic layer was dried over Na$_2$SO$_4$ and the solvent was concentrated under reduced pressure. The obtained residue was purified by silica gel column chromatography (CHCl$_3$/MeOH) to obtain 6-[4-(tert-butoxycarbonyl)piperazin-1-yl]nicotinic acid (934 mg).

Preparation Example 270

3-Chloro-4-fluorobenzoic acid (1 g) was dissolved in N,N-dimethylacetamide (10 ml), and tert-butyl piperazine-1-carboxylate (1.3 g) and DIPEA (1.9 g) were added thereto, followed by stirring at 130° C. overnight. The reaction mixture was concentrated under reduced pressure, and a 1 M aqueous NaOH solution was added thereto, followed by washing with EtOAc. The pH of the aqueous layer was adjusted to around 6 to 7 by the addition of 1 M hydrochloric acid, followed by extraction with CHCl$_3$. The organic layer was dried over Na$_2$SO$_4$ and the solvent was concentrated under reduced pressure. The obtained residue was purified by silica gel column chromatography (CHCl$_3$/MeOH). The product was dissolved in dioxane (10 ml), and 4 M hydrogen chloride/dioxane (10 ml) was added thereto, followed by stirring at room temperature overnight. The precipitated solid was collected by filtration to obtain 3-chloro-4-piperazin-1-yl benzoic acid hydrochloride (142 mg).

Preparation Example 271

Under ice-cooling, 6-(4-{5-[3-({[N-(tert-butoxycarbonyl)glycyl](methyl)amino}methyl)phenyl]pyrimidin-2-yl}piperazin-1-yl)-5-chloronicotinic acid (303 mg), THF (9 ml), and TEA (65 mg) were mixed, and isobutyl chlorocarbonate (77 mg) was added thereto, followed by stirring at the same temperature for 1.5 hours. The reaction mixture was cooled to −78° C., and a solution of sodium borohydride (77 mg) in water (1.1 ml) was added thereto, followed by warming to 0° C. and stirring for 30 minutes. To the reaction mixture was added water, followed by extraction with EtOAc, and the organic layer was washed with water and saturated brine, and dried over $Na_2SO_4$. Under reduced pressure, the solvent was evaporated, and the obtained residue was purified by silica gel column chromatography (NH silica) to obtain tert-butyl (2-{[3-(2-{4-[3-chloro-5-(hydroxymethyl)pyridin-2-yl]piperazin-1-yl}pyrimidin-5-yl)benzyl](methyl)amino}-2-oxoethyl)carbamate (296 mg).

Preparation Example 272 tert-Butyl (2-{[3-(2-{4-[3-chloro-5-(hydroxymethyl)pyridin-2-yl]piperazin-1-yl}pyrimidin-5-yl)benzyl](methyl)amino}-2-oxoethyl)carbamate (288 mg) was dissolved in dichloromethane (8 ml), and manganese dioxide (1.16 g) was added thereto, followed by stirring at room temperature for 1.5 hours. Manganese dioxide (220 mg) was added thereto, followed by additionally stirring at room temperature for 1 hour. The reaction mixture was filtered using Celite as a filtration assistant, and the filtrate was concentrated under reduced pressure. The obtained residue was purified by silica gel column chromatography ($CHCl_3$/MeOH=100/0 to 96/4) to obtain tert-butyl {2-[(3-{2-[4-(3-chloro-5-formylpyridin-2-yl)piperazin-1-yl]pyrimidin-5-yl}benzyl)(methyl)amino]-2-oxoethyl}carbamate (235 mg).

Preparation Example 275

Ethyl (diethylphosphoryl)acetate (471 mg) was dissolved in THF (15 ml), and NaH (98 mg) was added thereto, followed by stirring at room temperature for 30 minutes. A solution of tert-butyl 4-(5-formyl-3-methylpyridin-2-yl)piperazine-1-carboxylate (493 mg) in THF (5 ml) was added thereto, followed by stirring at room temperature for 3 hours. To the reaction mixture was added water, followed by extraction with $CHCl_3$. The organic layer was dried over $Na_2SO_4$ and the solvent was concentrated under reduced pressure. The obtained residue was purified by silica gel column chromatography ($CHCl_3$/MeOH) to obtain tert-butyl 4-{5-[(1E)-3-ethoxy-3-oxoprop-1-en-1-yl]-3-methylpyridin-2-yl}piperazine-1-carboxylate (305 mg).

Preparation Example 276 tert-Butyl 4-(4-nitrophenyl)piperazine-1-carboxylate (500 mg) was dissolved in EtOH (5 ml), and THF (5 ml) and 10% Pd/C (25 mg) was added thereto, followed by stirring for 4 hours under a hydrogen atmosphere. After filtration using Celite as a filtration assistant, the filtrate was concentrated under reduced pressure. The obtained residue was dissolved in MeOH, and 4 M hydrogen chloride/EtOAc (3.8 ml) was added thereto. After stirring at room temperature overnight, the solvent was evaporated under reduced pressure. To a mixture of the obtained residue and DMF (5 ml) was added $K_2CO_3$ (424 mg), and then tert-butyl (2-{[3-(2-chloropyrimidin-5-yl)benzyl](methyl)amino}-2-oxoethyl)carbamate (200 mg) was added thereto. After stirring at 60° C. overnight, water was added thereto, followed by extraction with EtOAc. The organic layer was dried over $MgSO_4$ and evaporated under reduced pressure. The obtained residue was purified by silica gel column chromatography (0% to 8% MeOH/$CHCl_3$) to obtain tert-butyl {2-[(3-{2-[4-(4-aminophenyl)piperazin-1-yl]pyrimidin-5-yl}benzyl)(methyl)amino]-2-oxoethyl}carbamate (228 mg).

Preparation Example 277 tert-Butyl 4-(4,4,5,5-tetramethyl-1,3,2-dioxaborolan-2-yl)-3,6-dihydropyridine-1(2H)-carboxylate (400 mg) and 3-bromopyridine (226 mg) were dissolved in DMF (4 ml), and $K_2CO_3$ (536 mg) and a 1,1'-bis(diphenylphosphino)ferrocene-palladium(II) dichloride-dichloromethane complex were added, followed by stirring at 80° C. overnight. The reaction mixture was concentrated under reduced pressure, and then a saturated aqueous sodium hydrogen carbonate solution was added thereto, followed by extraction with $CHCl_3$. The organic layer was dried over $Na_2SO_4$ and the solvent was concentrated under reduced pressure. The obtained residue was purified by silica gel column chromatography ($CHCl_3$/MeOH) to obtain tert-butyl 3',6'-dihydro-3,4'-bipyridine-1'(2'H)-carboxylate (249 mg).

Preparation Example 283

Ethyl (2E)-3-[6-(4-{5-[3-({[N-(tert-butoxycarbonyl)glycyl](methyl)amino}methyl)phenyl]pyrimidin-2-yl}piperazin-1-yl)-5-methylpyridin-3-yl]acrylate (250 mg) was dissolved in EtOH (4 ml), and 10% Pd/C (80 mg) was added thereto under a hydrogen atmosphere at 1 atm, followed by stirring at room temperature overnight. The mixture was filtrated using Celite as a filtration assistant to remove the catalyst, and then the filtrate was concentrated under reduced pressure. The obtained residue was purified by silica gel column chromatography (hexane/EtOAc) to obtain ethyl 3-[6-(4-{5-[3-({[N-(tert-butoxycarbonyl)glycyl](methyl)amino}methyl)phenyl]pyrimidin-2-yl}piperazin-1-yl)-5-methylpyridin-3-yl]propanoate (163 mg).

Preparation Example 285 tert-Butyl 4-pyrimidin-2-yl-3,6-dihydropyridine-1(2H)-carboxylate (233 mg) was dissolved in EtOH (5 ml), and 10% Pd/C was added thereto, followed by stirring for 4 hours under a hydrogen atmosphere. The mixture was filtered using Celite as a filtration assistant and the solvent was evaporated under reduced pressure. The obtained residue was purified by silica gel column chromatography (hexane/EtOAc). The obtained oily substance was dissolved in MeOH (5 ml), and 4 M hydrogen chloride/EtOAc (2.2 ml) was added thereto. After stirring at room temperature overnight, the solvent was evaporated under reduced pressure. To a mixture of the obtained residue and DMF (8 ml) was added $K_2CO_3$ (138 mg), and then tert-butyl (2-{[3-(2-chloropyrimidin-5-yl)benzyl](methyl)amino}-2-oxoethyl)carbamate (269 mg) was added thereto, followed by stirring at 60° C. overnight. To the reaction mixture was added water, followed by extraction with EtOAc. The organic layer was dried over $MgSO_4$ and evaporated under reduced pressure. The obtained residue was purified by silica gel column chromatography (0% to 5% MeOH/$CHCl_3$) to obtain tert-butyl[2-(methyl{3-[2-(4-pyrimidin-2-ylpiperidin-1-yl)pyrimidin-5-yl]benzyl}amino)-2-oxoethyl]carbamate (361 mg).

Preparation Example 286 tert-Butyl 3',6'-dihydro-4,4'-bipyridine-1'(2'H)-carboxylate (213 mg) was dissolved in EtOH (4 ml), and 10% Pd/C (20 mg) was added thereto, followed by stirring for 4 hours under a hydrogen atmosphere. The mixture was filtered using Celite as a filtration assistant and the solvent was evaporated under reduced pressure. The obtained residue was purified by silica gel column chromatography. The obtained oily substance was dissolved in MeOH (4 ml), and 4 M hydrogen chloride/EtOAc (2 ml) was added thereto. After stirring at room temperature overnight, the solvent was evaporated under reduced pressure. To a mixture of the obtained residue and DMF (4 ml) was added K$_2$CO$_3$ (904 mg), and then 5-bromo-2-fluoropyridine (432 mg) was added thereto, followed by stirring at 60° C. overnight. To the reaction mixture was added water, followed by extraction with EtOAc. The organic layer was dried over MgSO$_4$ and evaporated under reduced pressure. The obtained residue was purified by silica gel column chromatography to obtain 5-bromo-2-(4-pyridin-4-ylpiperidin-1-yl)pyridine (121 mg).

Preparation Example 287

NaH (230 mg) was suspended in DMF (10 ml), and a solution of 5-bromopyrimidine-2-amine in DMF (5 ml) and a solution of cyclohexyl isocyanate (791 mg) in DMF (5 ml) were added dropwise thereto in this order under ice-cooling, followed by stirring at the same temperature for 30 minutes. The obtained solid was collected by filtration and washed with diethyl ether to obtain 1-(5-bromopyrimidin-2-yl)-3-cyclohexylurea (1.47 g).

Preparation Example 289 tert-Butyl (2-{[3-(2-chloropyrimidin-5-yl)benzyl](methyl)amino}-2-oxoethyl)carbamate (2.35 g) was dissolved in DMF (50 ml), and piperazine was added thereto, followed by stirring at room temperature overnight. To the reaction mixture was added water, followed by extraction with EtOAc, and then the organic layer was dried over MgSO$_4$ and evaporated under reduced pressure. The obtained residue was purified by silica gel column chromatography (0% to 10% MeOH/CHCl$_3$) to obtain tert-butyl (2-{methyl[3-(2-piperazin-1-ylpyrimidin-5-yl)benzyl]amino}-2-oxoethyl)carbamate (1.8 g).

Preparation Example 296 tert-Butyl (2-{[(4'-aminobiphenyl-3-yl)methyl](methyl) amino]-2-oxoethyl}carbamate (240 mg) was dissolved in a mixed solution of EtOAc (10 ml)/saturated aqueous sodium hydrogen carbonate solution (10 ml), followed by ice-cooling. A solution of cyclohexanecarbonyl chloride (142 mg) in EtOAc (5 ml) was added dropwise thereto. The reaction mixture was returned to room temperature and stirred for 24 hours, and then to the reaction mixture was added water, followed by extraction with EtOAc. The organic layer was dried over MgSO$_4$ and evaporated under reduced pressure. The obtained residue was purified by silica gel column chromatography (EtOAc/hexane=2/1) to obtain tert-butyl {2-[({4'-[(cyclohexylcarbonyl)amino]biphenyl-3-yl}methyl) (methyl)amino]-2-oxoethyl}carbamate (311 mg).

Preparation Example 301

4-Bromo-3-chloroaniline (500 mg) was dissolved in DMF (10 ml), and bis(2-bromoethyl)ether (1.12 g), K$_2$CO$_3$ (1.34 g), and potassium iodide (80 mg) were added thereto, followed by stirring at 80° C. for 2 days. To the reaction mixture was added water, followed by extraction with EtOAc. The organic layer was dried over MgSO$_4$ and then the solvent was evaporated under reduced pressure. The obtained residue was purified by silica gel column chromatography (0% to 20% EtOAc/hexane) to obtain 4-(4-bromo-3-chlorophenyl)morpholine (263 mg).

Preparation Example 302

1H-Pyrazole (460 mg) was dissolved in DMF (10 ml), and NaH (118 mg) was added thereto. After 10 minutes, tert-butyl 4-{[(4-methylphenyl)sulfonyl]oxy}piperidine-1-carboxylate (800 mg) was added thereto, followed by stirring at 60° C. for 5 hours. To the reaction mixture were added several drops of water, followed by concentration under reduced pressure. A saturated aqueous sodium hydrogen carbonate solution was added thereto, followed by extraction with CHCl$_3$. The organic layer was dried over Na$_2$SO$_4$ and the solvent was concentrated under reduced pressure. The obtained residue was purified by silica gel column chromatography (hexane/EtOAc). The product was dissolved in EtOH (15 ml), and 4 M hydrogen chloride/EtOAc (5.6 ml) was added thereto, followed by stirring at room temperature overnight. The reaction mixture was concentrated under reduced pressure to obtain 4-(1H-pyrazol-1-yl)piperidine dihydrochloride (148 mg).

Preparation Example 303

To an ice-cooled solution of tert-butyl (2-{[(4'-aminobiphenyl-3-yl)methyl](methyl)amino]-2-oxoethyl}carbamate (200 mg) in dichloromethane (4 ml) was added 2-propyl isocyanate (55 mg), followed by stirring at room temperature for 2 hours. To the reaction mixture was added water, followed by stirring, and the organic layer was purified by silica gel column chromatography (2% MeOH/CHCl$_3$) to obtain tert-butyl {2-[({4'-[(isopropylcarbamoyl)amino]biphenyl-3-yl}methyl)(methyl)amino]-2-oxoethyl}carbamate (240 mg) as a colorless oil.

Preparation Example 305

To a mixture of 4-nitrophenyl(3'-{[{[(tert-butoxycarbonyl) amino]acetyl}(methyl)amino]methyl}biphenyl-4-yl)carbamate (150 mg), DIPEA (36 mg), and dichloromethane (3 ml) was added 1-methylpiperazine (28 mg), followed by stirring at 50° C. for 5 hours. The reaction mixture was subjected to liquid separation with CHCl$_3$-water, and the aqueous layer was extracted with CHCl$_3$. The combined organic layer was dried over Na$_2$SO$_4$, and then the solvent was evaporated. The obtained residue was purified by silica gel column chromatography (2% MeOH/CHCl$_3$) to obtain tert-butyl (2-{methyl [(4'-{[(4-methylpiperazin-1-yl)carbonyl]amino}biphenyl-3-yl)methyl]amino}-2-oxoethyl)carbamate (132 mg) as a pale yellow oil.

Preparation Example 306

Pyridin-4-ylmethanol (112 mg) was dissolved in DMF (4 ml), and NaH (45 mg) was added thereto under ice-cooling. After stirring at the same temperature for 30 minutes, tert-butyl (2-{[3-(2-chloropyrimidin-5-yl)benzyl](methyl) amino}-2-oxoethyl)carbamate (200 mg) was added thereto, followed by stirring at room temperature for 2 hours. To the reaction mixture was added water, followed by extraction with EtOAc. The organic layer was dried over MgSO$_4$ and evaporated under reduced pressure. The obtained residue was purified by silica gel column chromatography (0% to 7% MeOH/CHCl$_3$) to obtain tert-butyl[2-(methyl{3-[2-(pyridin-4-ylmethoxy)pyrimidin-5-yl]benzyl}amino)-2-oxoethyl] carbamate (237 mg).

Preparation Example 309

2-Fluoroethyl 4-methylbenzenesulfonate (1 g) was dissolved in DMF (20 ml), and tert-butyl piperazine-1-carboxylate (939 mg) and K$_2$CO$_3$ (1.90 g) were added thereto, followed by stirring at 70° C. overnight. To the reaction mixture was added water, followed by extraction with EtOAc. The organic layer was dried over MgSO$_4$, and then the solvent was evaporated under reduced pressure. The obtained residue was purified by silica gel column chromatography (0% to 5% MeOH/CHCl$_3$) to obtain tert-butyl 4-(2-fluoromethyl)piperazine-1-carboxylate (463 mg).

Preparation Example 313

A mixture of 2-bromo-1-(4-bromophenyl)ethanone (550 mg), pyridine-3-carbothioamide (273 mg), and EtOH (20 ml) was heated under reflux for 2 hours. Thereafter, the mixture was cooled to room temperature, and the precipitated crystal was collected by filtration. This was washed with EtOH to obtain 3-[4-(4-bromophenyl)-1,3-thiazol-2-yl]pyridine hydrochloride (450 mg) as a pale yellow crystal.

Preparation Example 314 tert-Butyl piperazine-1-carboxylate (500 mg) was dissolved in NMP (10 ml), and 4-chloro-2-methylpyridine (685 mg) and tri-n-butylamine (498 mg) were added thereto, followed by stirring at 150° C. overnight. To the reaction mixture was added water, followed by extraction with EtOAc. The organic layer was dried over MgSO$_4$, and then the solvent was evaporated under reduced pressure. The obtained residue was purified by silica gel column chromatography to obtain tert-butyl 4-(2-methylpyridin-4-yl)piperazine-1-carboxylate (667 mg).

Preparation Example 315

Under an argon atmosphere, to a mixture of tert-butyl 4-{[(trifluoromethyl)sulfonyl]oxy}-3,6-dihydropyridine-1(2H)-carboxylate (1.82 g), pyridin-4-yl boronic acid (473 mg), and DME (35 ml) were added tetrakis(triphenylphosphine)palladium (317 mg), cesium carbonate (5.37 g), and water (9 ml), followed by stirring at 80° C. overnight. To the reaction mixture was added water, followed by extraction with EtOAc. The organic layer was dried over MgSO$_4$ and then evaporated under reduced pressure. The obtained residue was purified by silica gel column chromatography to obtain tert-butyl 3,6-dihydro-4,4'-bipyridine-1(2H)-carboxylate (1.28 g).

Preparation Example 317

To a mixture of tert-butyl 4-(5-bromo-3-formylpyridin-2-yl)piperazine-1-carboxylate (1 g) and MeOH (20 ml) was added sodium borohydride (153 mg). After stirring at room temperature for 2 hours, the solvent was evaporated under reduced pressure. To the obtained residue was added water, followed by extraction with EtOAc. The organic layer was dried over MgSO$_4$, and then the solvent was evaporated under reduced pressure. The obtained residue was purified by silica gel column chromatography to obtain tert-butyl 4-[5-bromo-3-(hydroxymethyl)pyridin-2-yl]piperazine-1-carboxylate (922 mg).

Preparation Example 318 tert-Butyl 4-(6-chloro-5-methylpyrimidin-4-yl)piperazine-1-carboxylate (400 mg) was dissolved in EtOH (8 ml), and 10% Pd/C (40 mg) was added thereto, followed by stirring at room temperature overnight under a hydrogen atmosphere. To the reaction mixture was added TEA (129 mg) and filtered using Celite as a filtration assistant, and the filtrate was evaporated under reduced pressure. The obtained residue was purified by silica gel column chromatography (10% to 80% EtOAc/hexane) to obtain tert-butyl 4-(5-methylpyrimidin-4-yl)piperazine-1-carboxylate (255 mg).

Preparation Example 322 tert-Butyl (2-{methyl[3-(2-piperazin-1-ylpyrimidin-5-yl)benzyl]amino}-2-oxoethyl)carbamate (200 mg) was dissolved in DMF (4 ml), and dihydrofuran-2,5-dione (50 mg) and K$_2$CO$_3$ (125 mg) were added thereto, followed by stirring at room temperature for 1 hour. Water and 1 M hydrochloric acid were added thereto, followed by extraction with EtOAc. The organic layer was dried over MgSO$_4$, and then the solvent was evaporated under reduced pressure. The obtained residue was purified by silica gel column chromatography to obtain 4-(4-{5-[3-({[N-(tert-butoxycarbonyl)glycyl](methyl)amino}methyl)phenyl]pyrimidin-2-yl}piperazin-1-yl)-4-oxobutanoic acid (168 mg).

Preparation Example 324 tert-Butyl 4-(2-hydroxyethyl)piperidine-1-carboxylate (500 mg) was dissolved in THF (5 ml), and NaH (174 mg) was added thereto under ice-cooling, and subsequently, ethyl iodide (680 mg) was added thereto, followed by elevating the temperature to room temperature and stirring overnight. To the reaction mixture was added water, followed by extraction with EtOAc. The organic layer was dried over MgSO$_4$ and the solvent was evaporated under reduced pressure. The obtained residue was purified by silica gel column chromatography (5% to 20% EtOAc/hexane) to obtain tert-butyl 4-(2-ethoxyethyl)piperidine-1-carboxylate (496 mg).

Preparation Example 325 tert-Butyl (2-{methyl[(4'-piperazin-1-ylbiphenyl-3-yl)methyl]amino}-2-oxoethyl)carbamate (180 mg) was dissolved in dichloromethane (3.6 ml), and TEA (125 mg) was added thereto under ice-cooling. Subsequently, ethyl iodide (128 mg) was added thereto, followed by stirring at room temperature overnight. To the reaction mixture was added water, followed by extraction with CHCl$_3$. The organic layer was dried over MgSO$_4$, and then the solvent was evaporated under reduced pressure. The obtained residue was purified by silica gel column chromatography (2% MeOH/CHCl$_3$) to obtain tert-butyl {2-[{[4'-(4-ethylpiperazin-1-yl)biphenyl-3-yl]methyl}(methyl)amino]-2-oxoethyl}carbamate (137 mg).

Preparation Example 326

Under an argon atmosphere, a solution of 2 M isopropylmagnesium chloride in THF (5.5 ml) was cooled to −78° C., and a solution of 2,5-dibromo-3-methylpyridine (2.5 g) in THF (10 ml) was added dropwise. After stirring at the same temperature for 30 minutes, a solution of morpholine-4-carboaldehyde (1.26 g) in THF (5 ml) was added dropwise thereto, followed by elevating the temperature to 0° C. over 30 minutes, followed by stirring at 0° C. for 2 hours. To the reaction mixture was added water, followed by extraction with EtOAc. The organic layer was dried over Na$_2$SO$_4$ and the solvent was concentrated under reduced pressure. The obtained residue was purified by silica gel column chromatography (hexane/EtOAc) to obtain 6-bromo-5-methyl nicotine aldehyde (1.42 g).

Preparation Example 327 tert-Butyl 4-(3-formylpyridin-2-yl)piperazine-1-carboxylate (1.88 g) was dissolved in acetic acid (20 ml), and bromine (1.03 g) was added dropwise thereto, followed by stirring at room temperature for 30 minutes. The solvent was evaporated under reduced pressure. The obtained residue was subjected to liquid separation by the addition of CHCl₃ and a 1 M aqueous NaOH solution. The organic layer was dried over MgSO₄ and the solvent was evaporated under reduced pressure. The obtained residue was purified by silica gel column chromatography to obtain tert-butyl 4-(5-bromo-3-formylpyridin-2-yl)piperazine-1-carboxylate (2.05 g).

Preparation Example 328

Ethyl glycolate (116 mg) was dissolved in DMF (4 ml), and NaH (73 mg) was added thereto under ice-cooling. After stirring at the same temperature for 10 minutes, a solution of 4-nitrophenyl 4-{5-[3-({[N-(tert-butoxycarbonyl)glycyl](methyl)amino}methyl)phenyl]pyrimidin-2-yl}piperazine-1-carboxylate (340 mg) in DMF (3 ml) was added thereto, followed by stirring at room temperature overnight. To the reaction mixture was added water, followed by extraction with EtOAc. The organic layer was dried over MgSO₄, and then the solvent was evaporated under reduced pressure. The obtained residue was purified by silica gel column chromatography to obtain 2-ethoxy-2-oxoethyl 4-{5-[3-({[N-(tert-butoxycarbonyl)glycyl](methyl)amino}methyl)phenyl]pyrimidin-2-yl}piperazine-1-carboxylate (35 mg).

Preparation Example 329 tert-Butyl (2-{methyl[3-(2-piperazin-1-ylpyrimidin-5-yl)benzyl]amino}-2-oxoethyl(carbamate (2.18 g) was dissolved in dioxane (50 ml), and a 1 M aqueous sodium hydrogen carbonate solution (19.8 ml) was added thereto. 4-Nitrophenylchlorocarbonate (1.10 g) was added thereto, followed by stirring at room temperature for 3 hours. The reaction mixture was concentrated under reduced pressure, and then the organic layer was extracted by the addition of CHCl₃ and water. The organic layer was dried over Na₂SO₄ and the solvent was concentrated under reduced pressure. The obtained residue was purified by silica gel column chromatography (hexane/EtOAc) to obtain 4-nitrophenyl 4-{5-[3-({[N-(tert-butoxycarbonyl)glycyl](methyl)amino}methyl)phenyl]pyrimidin-2-yl}piperazine-1-carboxylate (2.89 g).

Preparation Example 330

Under an argon atmosphere, a solution of tert-butyl 4-(5-bromo-3-methylpyridin-2-yl)piperazine-1-carboxylate (400 mg) in THF (8 ml) was cooled to −78° C., and 1.63 M n-butyl lithium (0.9 ml) was added dropwise thereto, followed by stirring at the same temperature for 1 hour. Crushed dry ice was put into another flask, and THF (30 ml) was poured thereinto. The mixture to which n-BuLi had been added dropwise immediately before was added thereto, followed by stirring as it was for 1 hour. To the reaction mixture was added water and 1 M hydrochloric acid, and the pH of the aqueous layer was adjusted to around 5.0. The aqueous layer was extracted with EtOAc, the organic layer was separated, and then the aqueous layer was extracted with CHCl₃ again. These organic layers were combined and dried over Na₂SO₄, and the solvent was concentrated under reduced pressure. The obtained residue was purified by silica gel column chromatography (CHCl₃/MeOH) to obtain 6-[4-(tert-butoxycarbonyl)piperazin-1-yl]-5-methylnicotinic acid (169 mg).

Preparation Example 336

Benzyl 4-phenylpiperazine-1-carboxylate (2.1 g) was dissolved in DMF (80 ml), and N-bromosuccinimide (1.4 g) was added thereto, followed by stirring at room temperature for 2 hours. The reaction mixture was concentrated under reduced pressure and subjected to liquid separation by the addition of CHCl₃ and a saturated aqueous sodium hydrogen carbonate solution. The organic layer was separated and dried over Na₂SO₄, and then the solvent was evaporated under reduced pressure. The obtained residue was purified by silica gel column chromatography (hexane/EtOAc) to obtain benzyl 4-(4-bromophenyl)piperazine-1-carboxylate (2.3 g).

Preparation Example 338

Benzyl 4-[3'-({[N-(tert-butoxycarbonyl)glycyl](methyl)amino}methyl)biphenyl-4-yl]piperazine-1-carboxylate (1.5 g) was dissolved in a mixed solution of MeOH (15 ml) and THF (15 ml). 10% Pd—C (150 mg) was added thereto, followed by stirring at room temperature for 1 day under a hydrogen atmosphere. The reaction mixture was filtered using Celite as a filtration assistant, and the filtrate was concentrated under reduced pressure. The obtained residue was purified by silica gel column chromatography to obtain tert-butyl (2-{methyl [(4'-piperazin-1-ylbiphenyl-3-yl)methyl]amino}-2-oxoethyl)carbamate (860 mg).

The Preparation Example Compounds as shown in Tables below were prepared in the same manner as the methods of Preparation Examples above, using each of the corresponding starting materials. The structures, the preparation methods, and the physicochemical data of Preparation Example Compounds are shown in Tables below.

TABLE 3

| Rf | Syn | Structure | Acid |
|---|---|---|---|
| 1 | R1 | Br-phenyl-CH₂-NH-CH₃ structure | — |
| 2 | R2 | Br-phenyl-CH₂-N(CH₃)-C(O)-CH₂-NH-Boc structure | — |
| 3 | R2 | Br-phenyl-CH₂-N(CH₂CH₃)-C(O)-CH₂-NH-Boc structure | — |
| 4 | R2 | Br-pyridyl-CH₂-N(CH₃)-C(O)-CH₂-NH-Boc structure | — |
| 5 | R2 | tetrahydropyran-CH₂-NH-C(O)-pyrimidine-Br structure | — |

TABLE 3-continued
| Rf | Syn | Structure | Acid |
|----|-----|-----------|------|
| 6 | R2 | 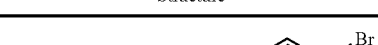 | — |
| 7 | R7 | 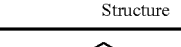 | — |
TABLE 4
| Rf | Syn | Structure | Acid |
|----|-----|-----------|------|
| 8 | R7 | 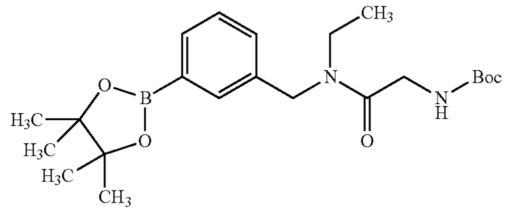 [SMILES: CCN(Cc1cccc(B2OC(C)(C)C(C)(C)O2)c1)C(=O)CNC(=O)OC(C)(C)C] | — |
| 9 | R7 | 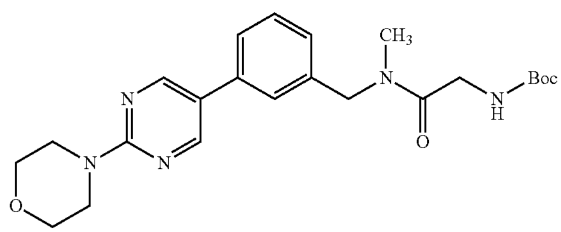 [SMILES: CN(Cc1cccc(-c2cnc(N3CCOCC3)nc2)c1)C(=O)CNC(=O)OC(C)(C)C] | — |
| 10 | R10 | 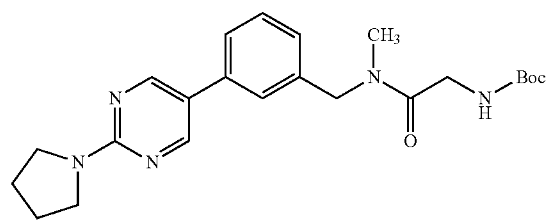 [SMILES: CN(Cc1cccc(-c2cnc(N3CCCC3)nc2)c1)C(=O)CNC(=O)OC(C)(C)C] | — |
| 11 | R10 | 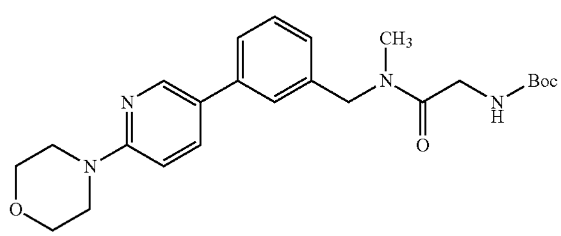 | — |
| 12 | R10 | 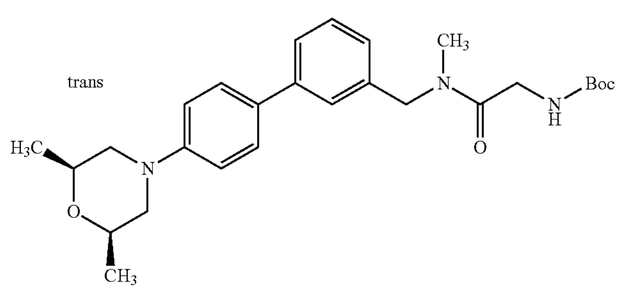 [SMILES: C[C@@H]1CN(c2ccc(-c3cccc(CN(C)C(=O)CNC(=O)OC(C)(C)C)c3)cc2)C[C@H](C)O1] | — |

TABLE 5

| Rf | Syn | Structure | Acid |
|----|-----|-----------|------|
| 13 | R10 | 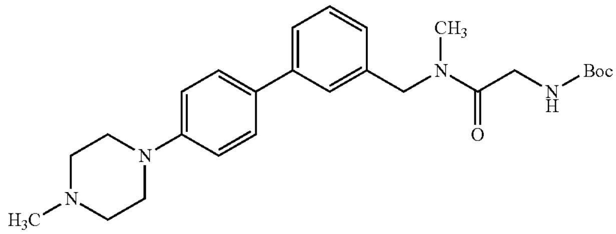 [SMILES: CN1CCN(c2ccc(-c3cccc(CN(C)C(=O)CNC(=O)OC(C)(C)C)c3)cc2)CC1] | — |
| 14 | R10 | 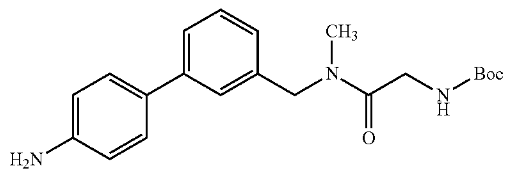 [SMILES: CN(Cc1cccc(-c2ccc(N)cc2)c1)C(=O)CNC(=O)OC(C)(C)C] | — |
| 15 | R10 | 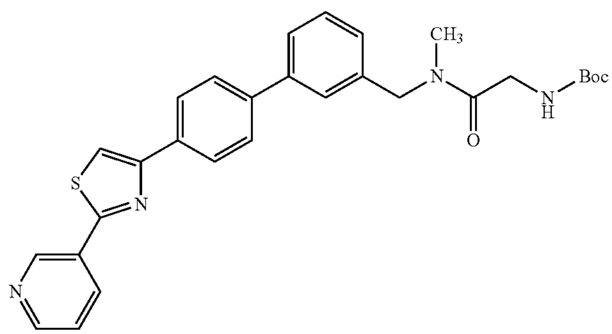 [SMILES: CN(Cc1cccc(-c2ccc(-c3csc(-c4cccnc4)n3)cc2)c1)C(=O)CNC(=O)OC(C)(C)C] | — |
| 16 | R16 | 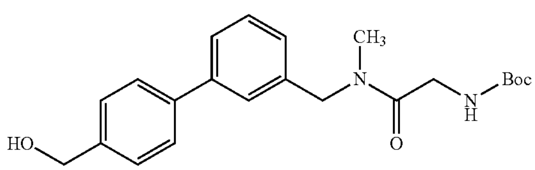 [SMILES: CN(Cc1cccc(-c2ccc(CO)cc2)c1)C(=O)CNC(=O)OC(C)(C)C] | — |
| 17 | R17 | 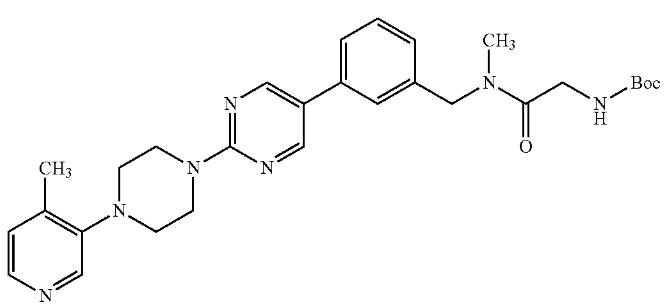 [SMILES: Cc1ccncc1N1CCN(c2ncc(-c3cccc(CN(C)C(=O)CNC(=O)OC(C)(C)C)c3)cn2)CC1] | — |

TABLE 6
| Rf | Syn | Structure | Acid |
|---|---|---|---|
| 18 | R17 | 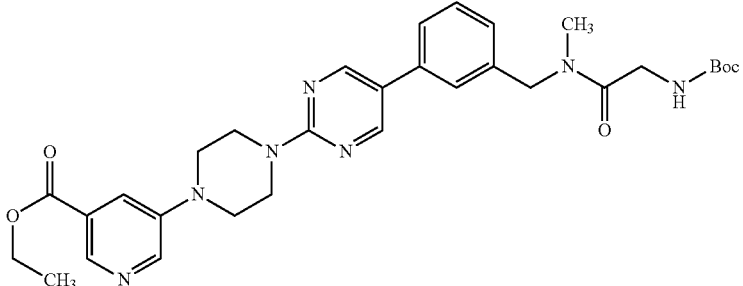 | — |
| 19 | R17 | 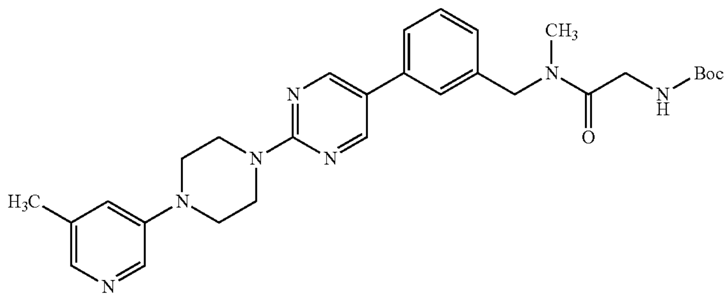 [SMILES: Cc1cncc(N2CCN(c3ncc(-c4cccc(CN(C)C(=O)CNC(=O)OC(C)(C)C)c4)cn3)CC2)c1] | — |
| 20 | R17 | 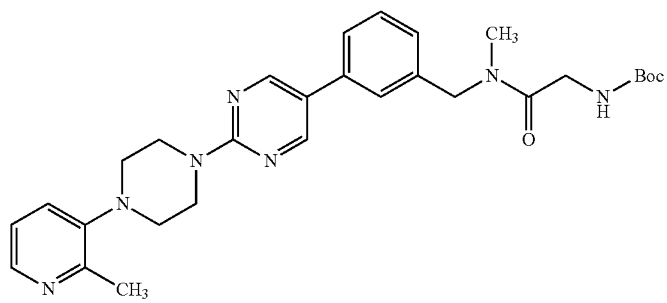 [SMILES: Cc1ncccc1N1CCN(c2ncc(-c3cccc(CN(C)C(=O)CNC(=O)OC(C)(C)C)c3)cn2)CC1] | — |
| 21 | R17 | 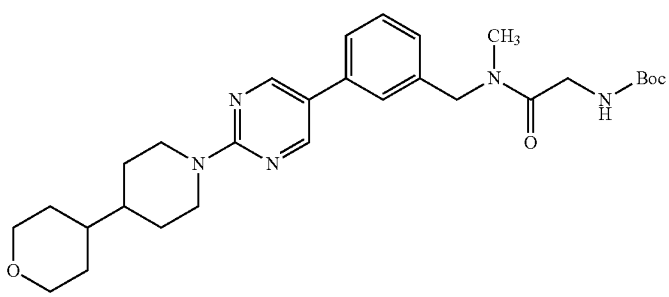 [SMILES: CN(Cc1cccc(-c2cnc(N3CCC(C4CCOCC4)CC3)nc2)c1)C(=O)CNC(=O)OC(C)(C)C] | — |
| 22 | R17 | 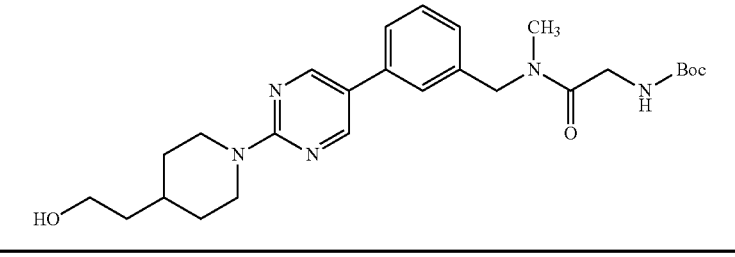 | — |

TABLE 7
| Rf | Syn | Structure | Acid |
|----|-----|-----------|------|
| 23 | R17 | 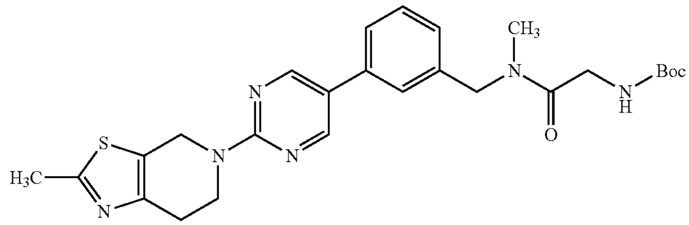 [SMILES: Cc1nc2c(s1)CN(c1ncc(-c3cccc(CN(C)C(=O)CNC(=O)OC(C)(C)C)c3)cn1)CC2] | — |
| 24 | R17 | 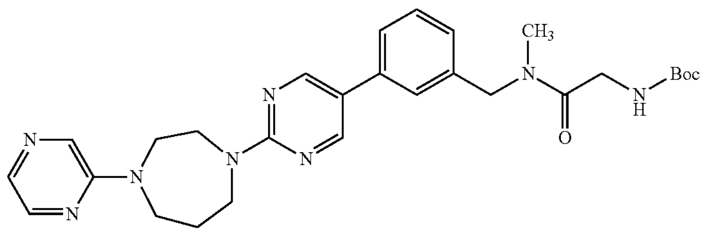 [SMILES: CN(Cc1cccc(-c2cnc(N3CCCN(c4cnccn4)CC3)nc2)c1)C(=O)CNC(=O)OC(C)(C)C] | — |
| 25 | R17 | 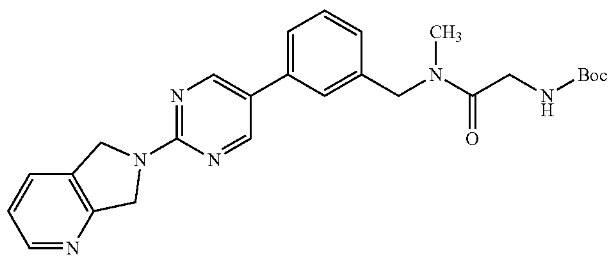 [SMILES: CN(Cc1cccc(-c2cnc(N3Cc4cccnc4C3)nc2)c1)C(=O)CNC(=O)OC(C)(C)C] | — |
| 26 | R17 | 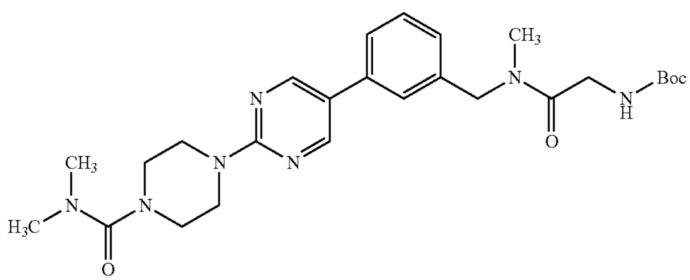 | — |
| 27 | R17 | 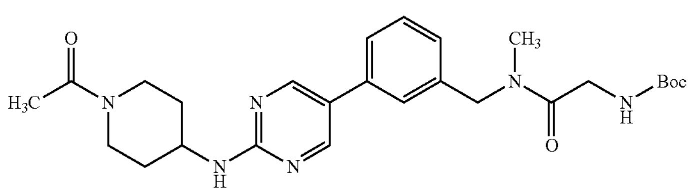 [SMILES: CC(=O)N1CCC(Nc2ncc(-c3cccc(CN(C)C(=O)CNC(=O)OC(C)(C)C)c3)cn2)CC1] | — |
TABLE 8
| Rf | Syn | Structure | Acid |
|----|-----|-----------|------|
| 28 | R17 | 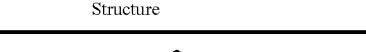 | — |

TABLE 8-continued

| Rf | Syn | Structure | Acid |
|----|-----|-----------|------|
| 29 | R17 | 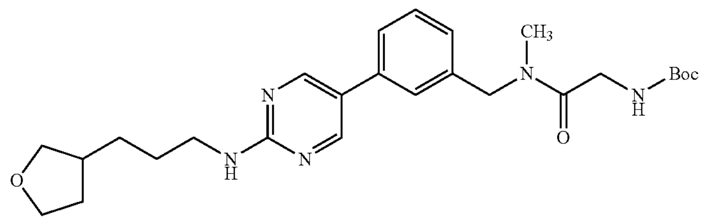 [SMILES: CN(Cc1cccc(-c2cnc(NCCCC3CCOC3)nc2)c1)C(=O)CNC(=O)OC(C)(C)C] | — |
| 30 | R17 | 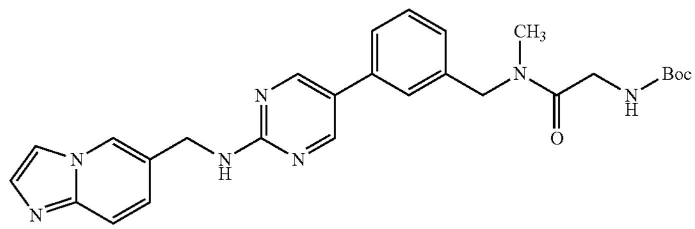 [SMILES: CN(Cc1cccc(-c2cnc(NCc3ccc4nccn4c3)nc2)c1)C(=O)CNC(=O)OC(C)(C)C] | — |
| 31 | R17 | 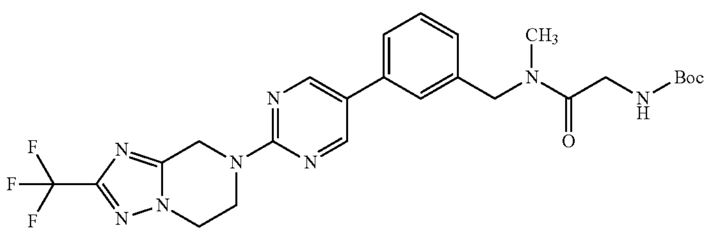 [SMILES: CN(Cc1cccc(-c2cnc(N3CCn4nc(C(F)(F)F)nc4C3)nc2)c1)C(=O)CNC(=O)OC(C)(C)C] | — |
| 32 | R17 | 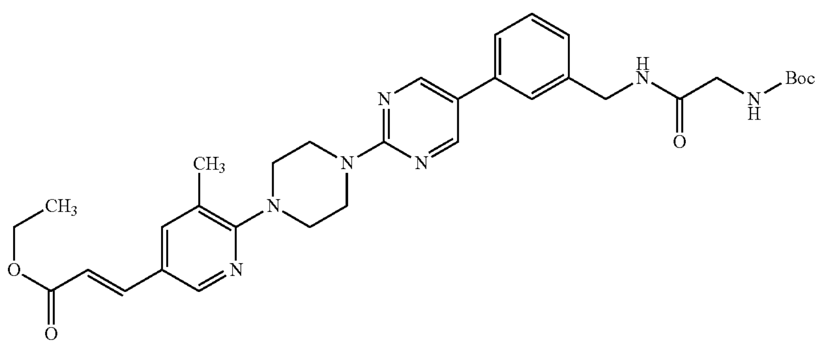 [SMILES: CCOC(=O)/C=C/c1cnc(N2CCN(c3ncc(-c4cccc(CNC(=O)CNC(=O)OC(C)(C)C)c4)cn3)CC2)c(C)c1] | — |

TABLE 9

| Rf | Syn | Structure | Acid |
|----|-----|-----------|------|
| 33 | R17 | 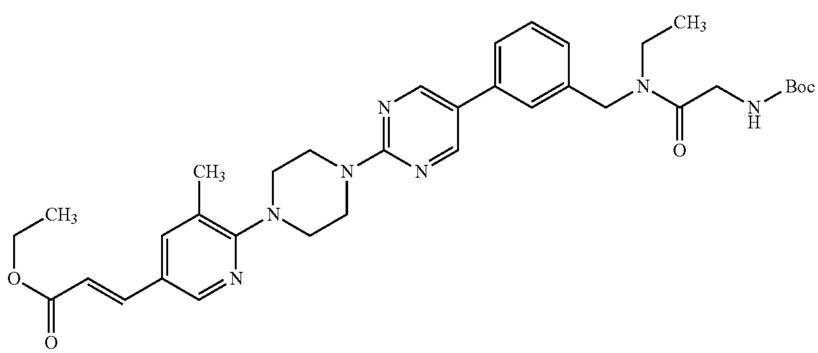 [SMILES: CCOC(=O)/C=C/c1cnc(N2CCN(c3ncc(-c4cccc(CN(CC)C(=O)CNC(=O)OC(C)(C)C)c4)cn3)CC2)c(C)c1] | — |

TABLE 9-continued

| Rf | Syn | Structure | Acid |
|---|---|---|---|
| 34 | R17 | (structure) | — |
| 35 | R17 | (structure) | — |
| 36 | R17 | (structure) | — |
| 37 | R17 | (structure) | — |

TABLE 10

| Rf | Syn | Structure | Acid |
|---|---|---|---|
| 38 | R17 | (structure) | — |

TABLE 10-continued

| Rf | Syn | Structure | Acid |
|----|-----|-----------|------|
| 39 | R17 | 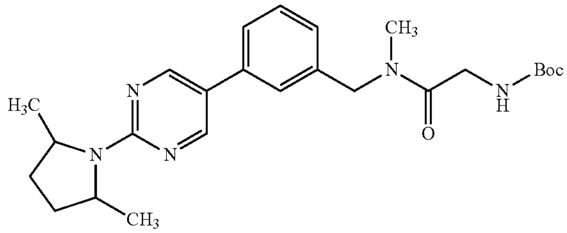 [SMILES: CC1CCC(C)N1c1ncc(-c2cccc(CN(C)C(=O)CNC(=O)OC(C)(C)C)c2)cn1] | — |
| 40 | R17 | 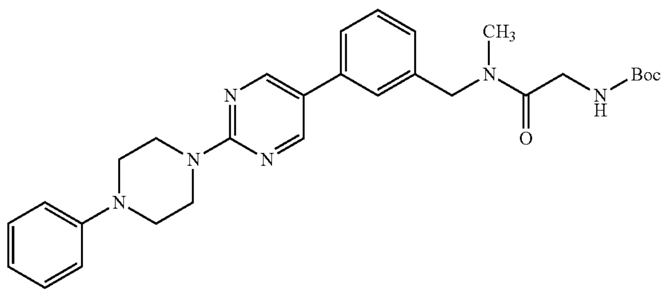 [SMILES: CN(Cc1cccc(-c2cnc(N3CCN(c4ccccc4)CC3)nc2)c1)C(=O)CNC(=O)OC(C)(C)C] | — |
| 41 | R17 | 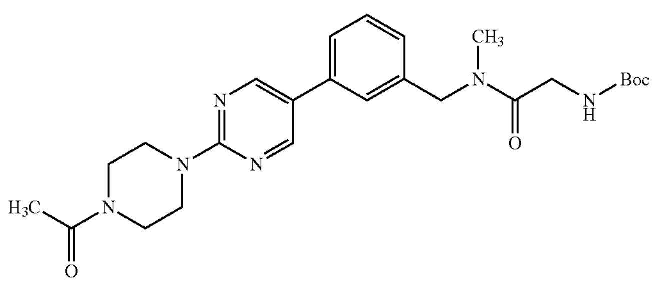 [SMILES: CC(=O)N1CCN(c2ncc(-c3cccc(CN(C)C(=O)CNC(=O)OC(C)(C)C)c3)cn2)CC1] | — |
| 42 | R17 | 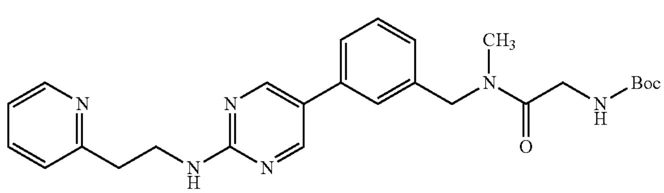 [SMILES: CN(Cc1cccc(-c2cnc(NCCc3ccccn3)nc2)c1)C(=O)CNC(=O)OC(C)(C)C] | — |

TABLE 11

| Rf | Syn | Structure | Acid |
|----|-----|-----------|------|
| 43 | R17 | 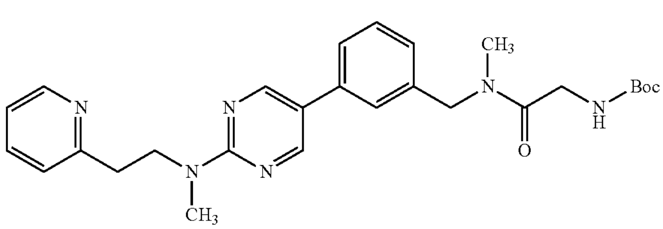 [SMILES: CN(Cc1cccc(-c2cnc(N(C)CCc3ccccn3)nc2)c1)C(=O)CNC(=O)OC(C)(C)C] | — |

TABLE 11-continued
| Rf | Syn | Structure | Acid |
|----|-----|-----------|------|
| 44 | R17 | 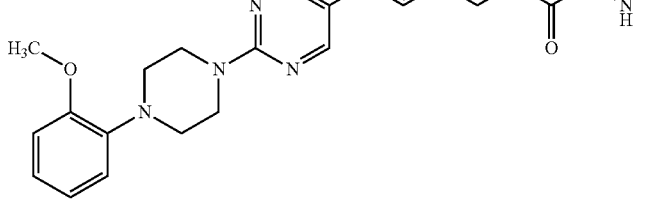 | — |
| 45 | R17 | 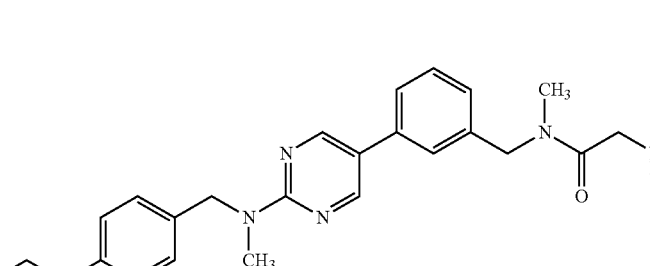 | — |
| 46 | R17 | 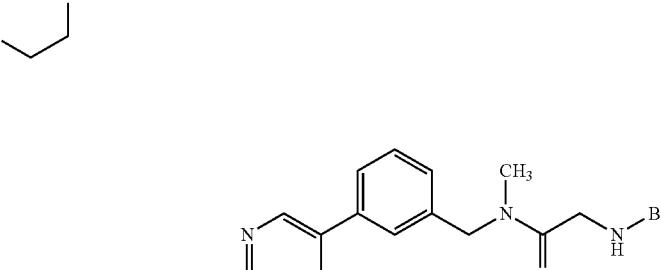 | — |
| 47 | R17 | 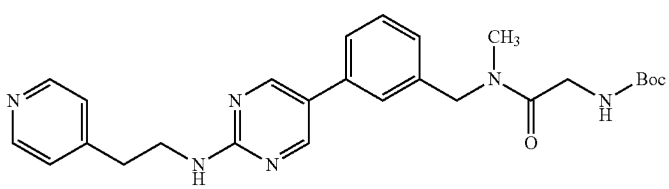 [SMILES: CN(Cc1cccc(-c2cnc(NCCc3ccncc3)nc2)c1)C(=O)CNC(=O)OC(C)(C)C] | — |
TABLE 12
| Rf | Syn | Structure | Acid |
|----|-----|-----------|------|
| 48 | R17 | 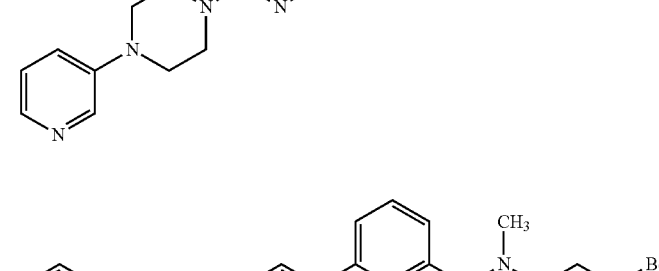 | — |

TABLE 12-continued
| Rf | Syn | Structure | Acid |
|----|-----|-----------|------|
| 49 | R17 | 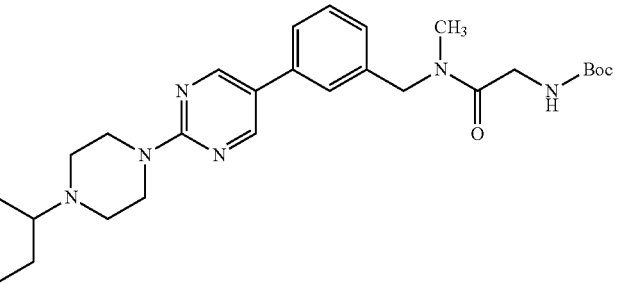 | — |
| 50 | R17 | 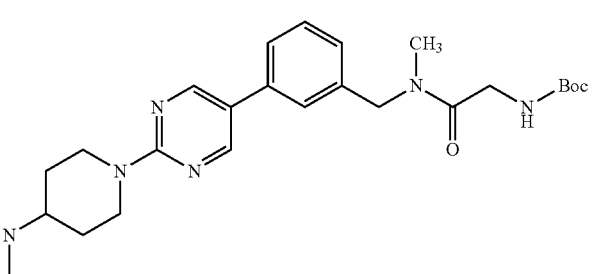 | — |
| 51 | R17 | 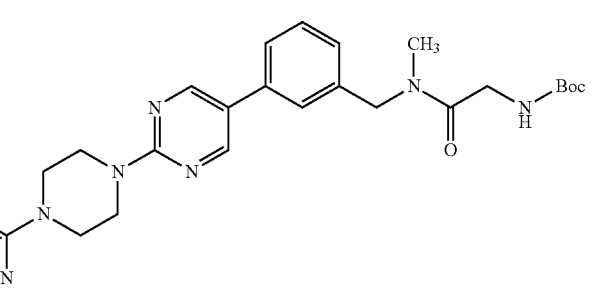 | — |
TABLE 13
| Rf | Syn | Structure | Acid |
|----|-----|-----------|------|
| 52 | R17 | 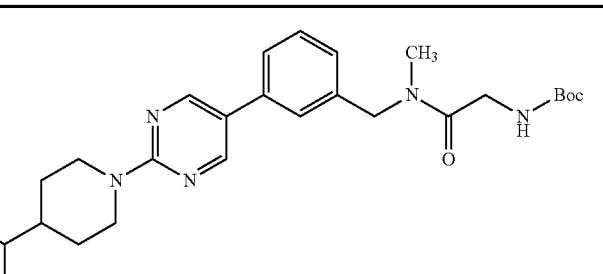 | — |

TABLE 13-continued

| Rf | Syn | Structure | Acid |
|----|-----|-----------|------|
| 53 | R17 | 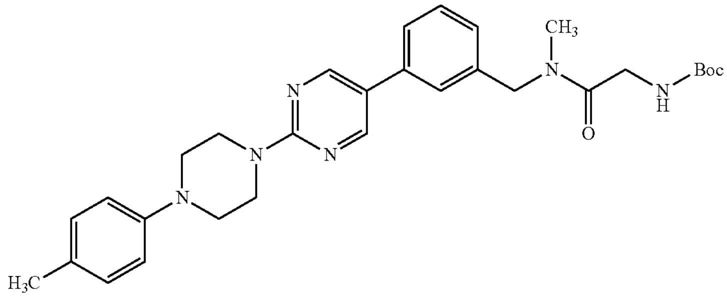 | — |
| 54 | R17 | 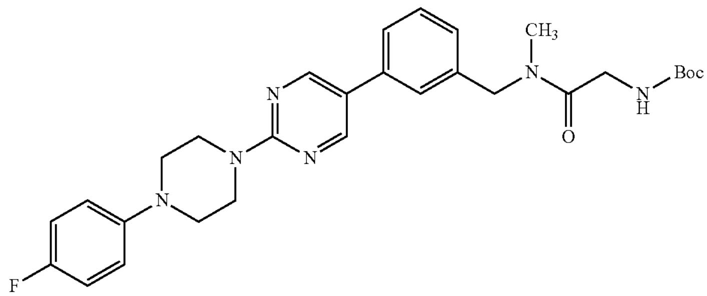 | — |
| 55 | R17 | 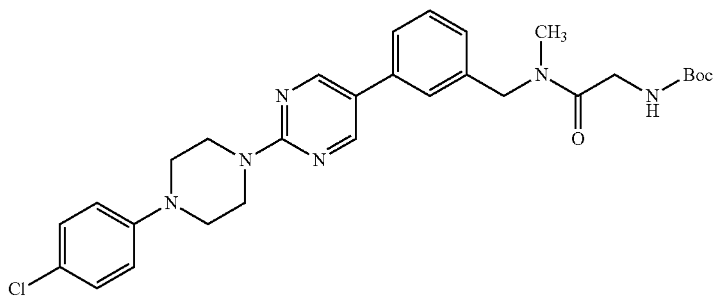 [SMILES: CN(Cc1cccc(-c2cnc(N3CCN(c4ccc(Cl)cc4)CC3)nc2)c1)C(=O)CNC(=O)OC(C)(C)C] | — |
| 56 | R17 | 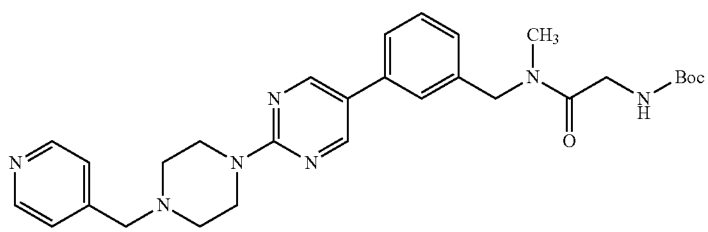 [SMILES: CN(Cc1cccc(-c2cnc(N3CCN(Cc4ccncc4)CC3)nc2)c1)C(=O)CNC(=O)OC(C)(C)C] | — |

TABLE 14

| Rf | Syn | Structure | Acid |
|----|-----|-----------|------|
| 57 | R17 | 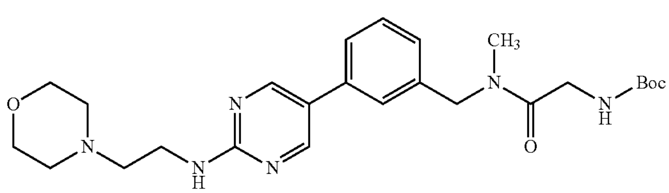 [SMILES: CN(Cc1cccc(-c2cnc(NCCN3CCOCC3)nc2)c1)C(=O)CNC(=O)OC(C)(C)C] | — |

TABLE 14-continued

| Rf | Syn | Structure | Acid |
|----|-----|-----------|------|
| 58 | R17 | 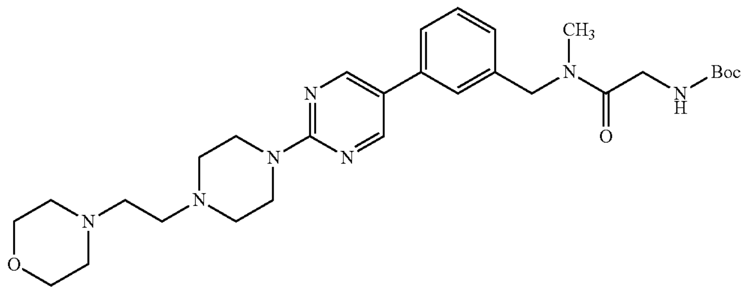 [SMILES: CN(Cc1cccc(-c2cnc(N3CCN(CCN4CCOCC4)CC3)nc2)c1)C(=O)CNC(=O)OC(C)(C)C] | — |
| 59 | R17 | cis | — |
| 60 | R17 | 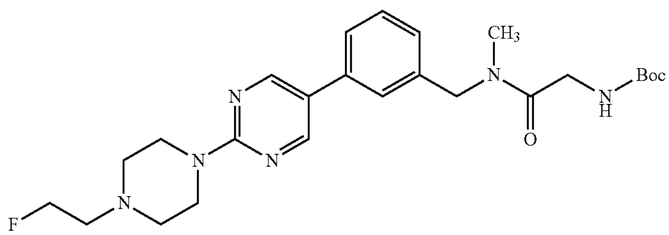 [SMILES: CN(Cc1cccc(-c2cnc(N3CCN(CCF)CC3)nc2)c1)C(=O)CNC(=O)OC(C)(C)C] | — |
| 61 | R17 | 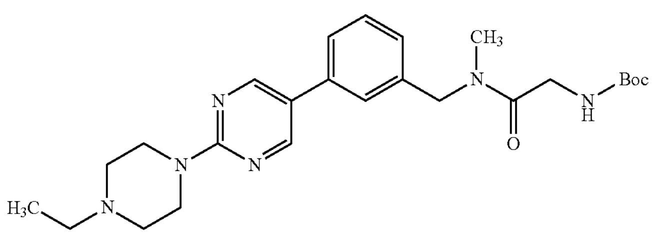 [SMILES: CCN1CCN(c2ncc(-c3cccc(CN(C)C(=O)CNC(=O)OC(C)(C)C)c3)cn2)CC1] | — |
| 62 | R17 | 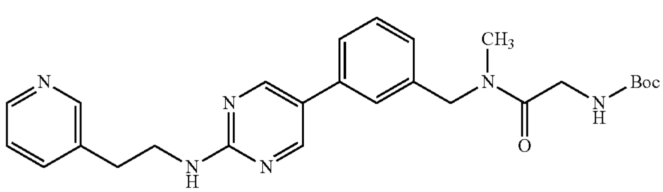 [SMILES: CN(Cc1cccc(-c2cnc(NCCc3cccnc3)nc2)c1)C(=O)CNC(=O)OC(C)(C)C] | — |

TABLE 15
| Rf | Syn | Structure | Acid |
|----|-----|-----------|------|
| 63 | R17 | 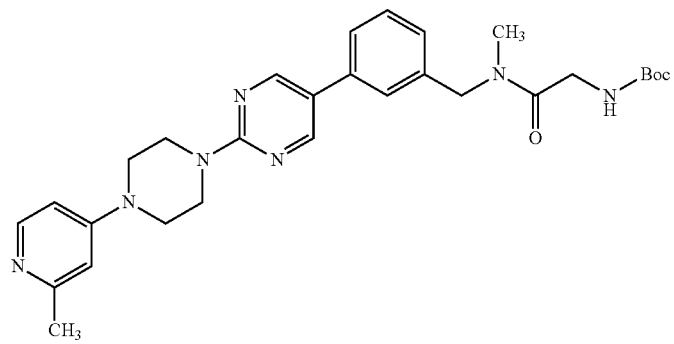 [SMILES: Cc1cc(N2CCN(c3ncc(-c4cccc(CN(C)C(=O)CNC(=O)OC(C)(C)C)c4)cn3)CC2)ccn1] | — |
| 64 | R17 | 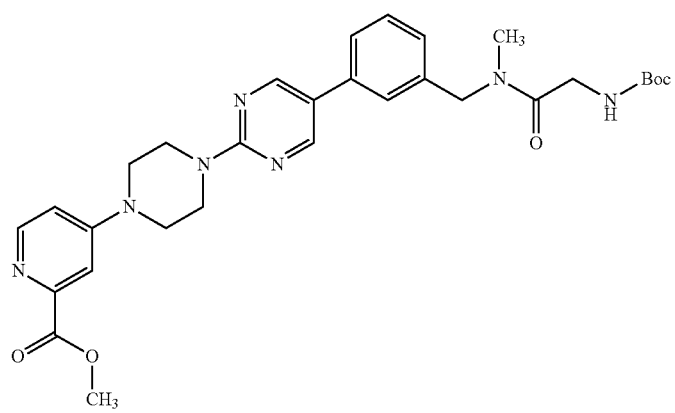 [SMILES: COC(=O)c1cc(N2CCN(c3ncc(-c4cccc(CN(C)C(=O)CNC(=O)OC(C)(C)C)c4)cn3)CC2)ccn1] | — |
| 65 | R17 | 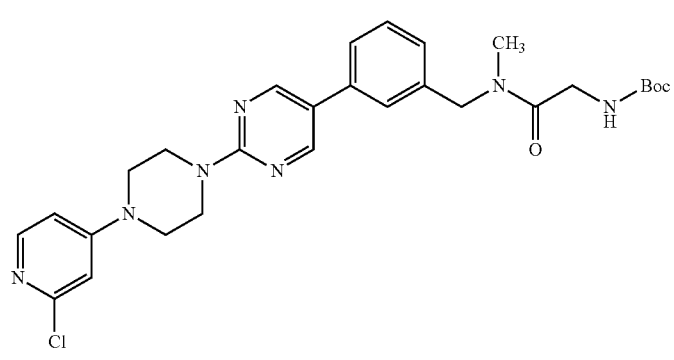 [SMILES: CN(Cc1cccc(-c2cnc(N3CCN(c4ccnc(Cl)c4)CC3)nc2)c1)C(=O)CNC(=O)OC(C)(C)C] | — |
| 66 | R17 | 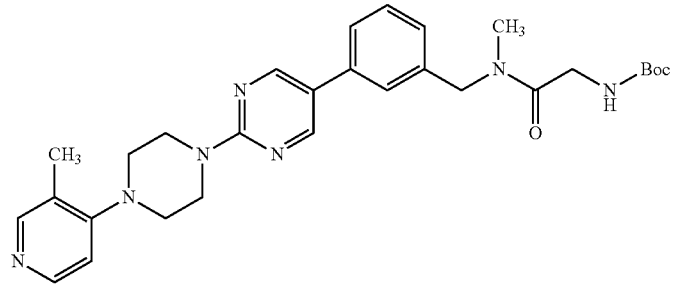 [SMILES: Cc1cnccc1N1CCN(c2ncc(-c3cccc(CN(C)C(=O)CNC(=O)OC(C)(C)C)c3)cn2)CC1] | — |

TABLE 16
| Rf | Syn | Structure | Acid |
|----|-----|-----------|------|
| 67 | R17 | 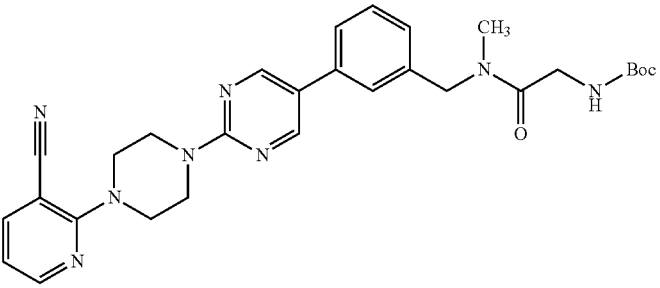 [SMILES: CN(Cc1cccc(-c2cnc(N3CCN(c4ncccc4C#N)CC3)nc2)c1)C(=O)CNC(=O)OC(C)(C)C] | — |
| 68 | R17 | 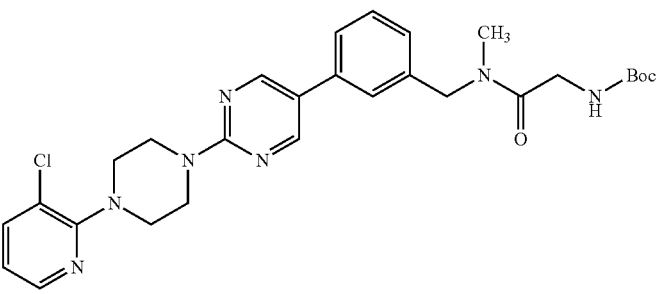 [SMILES: CN(Cc1cccc(-c2cnc(N3CCN(c4ncccc4Cl)CC3)nc2)c1)C(=O)CNC(=O)OC(C)(C)C] | — |
| 69 | R17 | 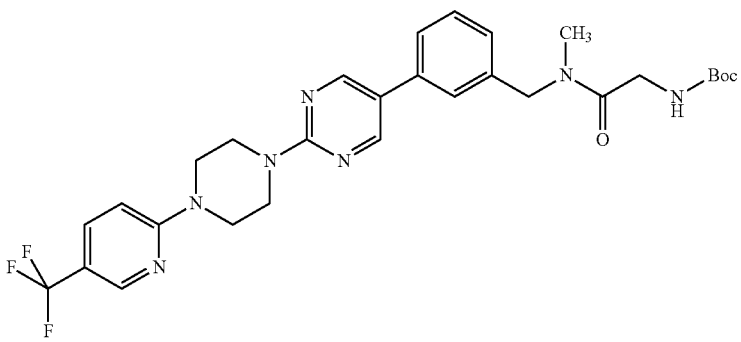 [SMILES: CN(Cc1cccc(-c2cnc(N3CCN(c4ccc(C(F)(F)F)cn4)CC3)nc2)c1)C(=O)CNC(=O)OC(C)(C)C] | — |
| 70 | R17 | 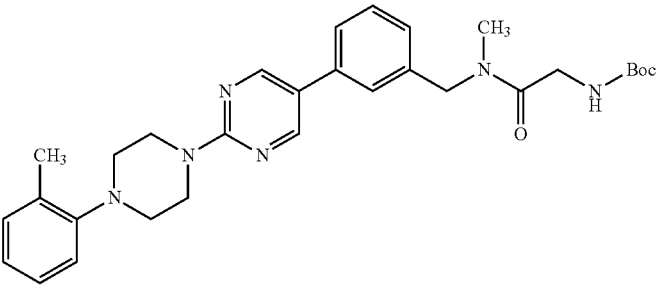 | — |

TABLE 17

| Rf | Syn | Structure | Acid |
|----|-----|-----------|------|
| 71 | R17 | 3-fluoropyridin-2-yl piperazine pyrimidine phenyl CH2-N(CH3)-C(=O)-CH2-NHBoc | — |
| 72 | R17 | 2,4-difluorophenyl piperazine pyrimidine phenyl CH2-N(CH3)-C(=O)-CH2-NHBoc | — |
| 73 | R17 | 2,6-dimethylpyridin-4-yl piperazine pyrimidine phenyl CH2-N(CH3)-C(=O)-CH2-NHBoc | — |
| 74 | R17 | 5-chloropyridin-2-yl piperazine pyrimidine phenyl CH2-N(CH3)-C(=O)-CH2-NHBoc | — |

TABLE 18
| Rf | Syn | Structure | Acid |
|----|-----|-----------|------|
| 75 | R17 | 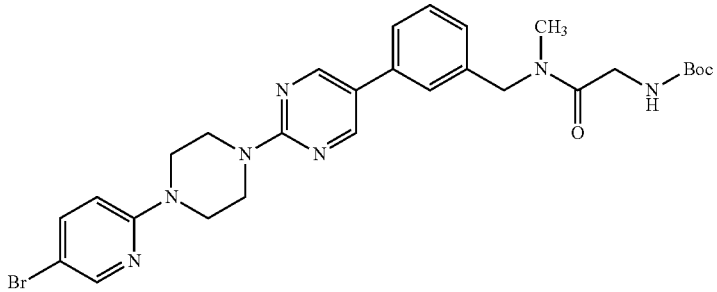 [SMILES: CN(Cc1cccc(-c2cnc(N3CCN(c4ccc(Br)cn4)CC3)nc2)c1)C(=O)CNC(=O)OC(C)(C)C] | — |
| 76 | R17 | 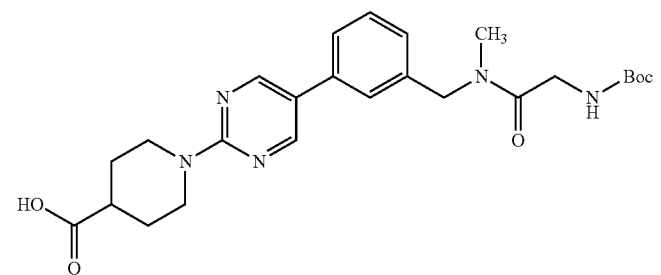 [SMILES: CN(Cc1cccc(-c2cnc(N3CCC(C(=O)O)CC3)nc2)c1)C(=O)CNC(=O)OC(C)(C)C] | — |
| 77 | R17 | 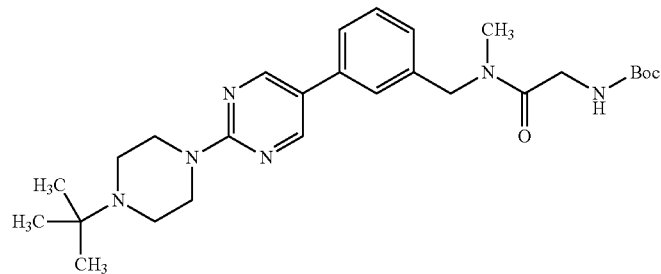 [SMILES: CN(Cc1cccc(-c2cnc(N3CCN(C(C)(C)C)CC3)nc2)c1)C(=O)CNC(=O)OC(C)(C)C] | — |
| 78 | R17 | 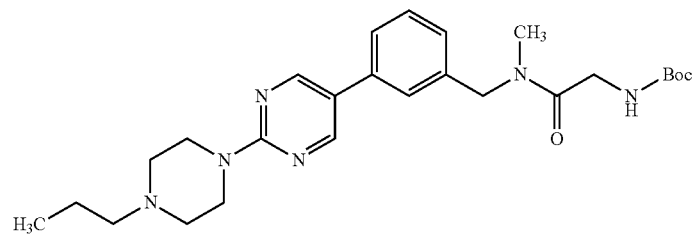 [SMILES: CCCN1CCN(c2ncc(-c3cccc(CN(C)C(=O)CNC(=O)OC(C)(C)C)c3)cn2)CC1] | — |
| 79 | R17 | 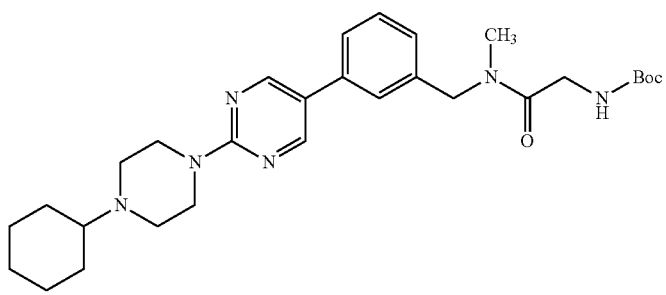 [SMILES: CN(Cc1cccc(-c2cnc(N3CCN(C4CCCCC4)CC3)nc2)c1)C(=O)CNC(=O)OC(C)(C)C] | — |

TABLE 19
| Rf | Syn | Structure | Acid |
|---|---|---|---|
| 80 | R17 | 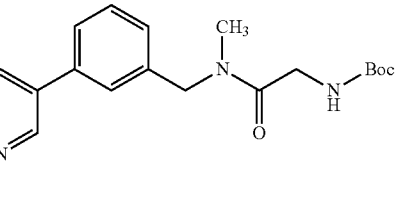 | — |
| 81 | R17 | 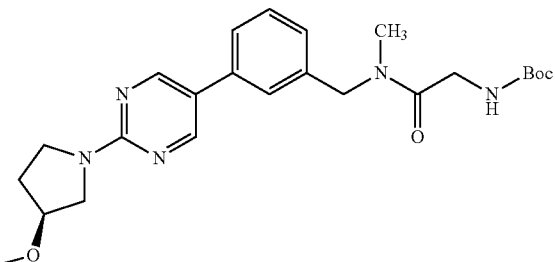 | — |
| 82 | R17 | 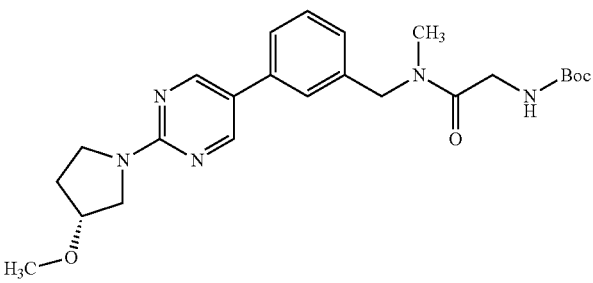 [SMILES: CO[C@@H]1CCN(c2ncc(-c3cccc(CN(C)C(=O)CNC(=O)OC(C)(C)C)c3)cn2)C1] | — |
| 83 | R17 | 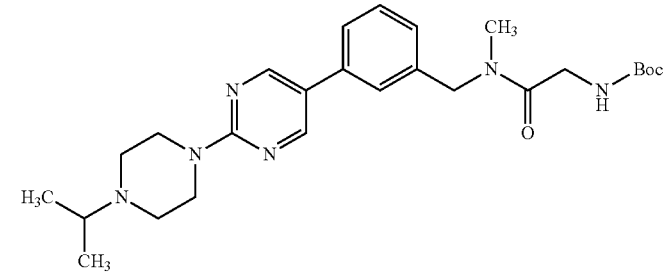 [SMILES: CC(C)N1CCN(c2ncc(-c3cccc(CN(C)C(=O)CNC(=O)OC(C)(C)C)c3)cn2)CC1] | — |
TABLE 20
| Rf | Syn | Structure | Acid |
|---|---|---|---|
| 84 | R17 | 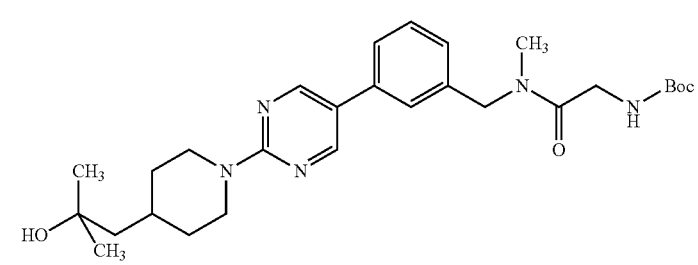 [SMILES: CN(Cc1cccc(-c2cnc(N3CCC(CC(C)(C)O)CC3)nc2)c1)C(=O)CNC(=O)OC(C)(C)C] | — |

TABLE 20-continued

| Rf | Syn | Structure | Acid |
|---|---|---|---|
| 85 | R17 | (structure) | — |
| 86 | R17 | (structure) | — |
| 87 | R17 | (structure) | — |

TABLE 21

| Rf | Syn | Structure | Acid |
|---|---|---|---|
| 88 | R17 | (structure) | — |

TABLE 21-continued

| Rf | Syn | Structure | Acid |
|---|---|---|---|
| 89 | R17 | 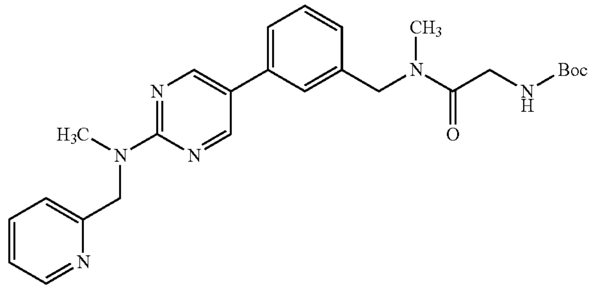 [SMILES: CN(Cc1cccc(-c2cnc(N(C)Cc3ccccn3)nc2)c1)C(=O)CNC(=O)OC(C)(C)C] | — |
| 90 | R17 | 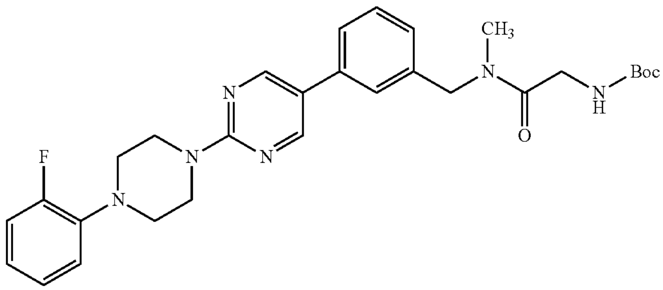 [SMILES: CN(Cc1cccc(-c2cnc(N3CCN(c4ccccc4F)CC3)nc2)c1)C(=O)CNC(=O)OC(C)(C)C] | — |
| 91 | R91 | 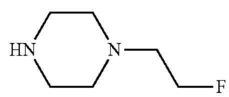 | 2HCl |
| 92 | R92 | 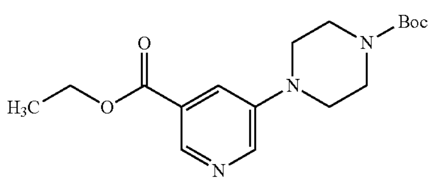 [SMILES: CCOC(=O)c1cncc(N2CCN(C(=O)OC(C)(C)C)CC2)c1] | — |

TABLE 22

| Rf | Syn | Structure | Acid |
|---|---|---|---|
| 93 | R92 | 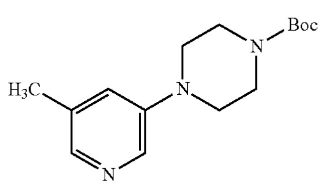 [SMILES: Cc1cncc(N2CCN(C(=O)OC(C)(C)C)CC2)c1] | — |
| 94 | R92 | 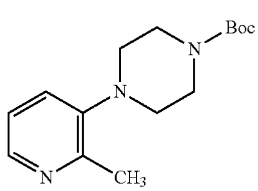 [SMILES: Cc1ncccc1N1CCN(C(=O)OC(C)(C)C)CC1] | — |

TABLE 22-continued

| Rf | Syn | Structure | Acid |
|---|---|---|---|
| 95 | R92 | 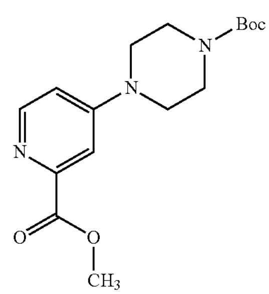 [SMILES: COC(=O)c1cc(N2CCN(C(=O)OC(C)(C)C)CC2)ccn1] | — |
| 96 | R92 | 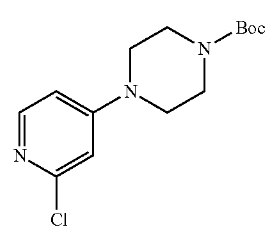 [SMILES: CC(C)(C)OC(=O)N1CCN(c2ccnc(Cl)c2)CC1] | — |

TABLE 22-continued

| Rf | Syn | Structure | Acid |
|---|---|---|---|
| 97 | R92 | trans, pyridin-4-yl with (2S,5S)-2,5-dimethyl-piperazine-N-Boc | — |
| 98 | R92 | trans, pyridin-2-yl with (2S,5S)-2,5-dimethyl-piperazine-N-Boc | — |

TABLE 23

| Rf | Syn | Structure | Acid |
|---|---|---|---|
| 99 | R92 | 3-fluoropyridin-2-yl-piperazine-N-Boc | — |
| 100 | R92 | 5-fluoropyridin-2-yl-piperazine-N-Boc | — |
| 101 | R92 | 3-methoxypyridin-2-yl-piperazine-N-Boc | — |
| 102 | R92 | 4-(dimethylamino)phenyl-piperazine-N-Boc | — |
| 103 | R92 | ethyl 5-(4-Boc-piperazin-1-yl)nicotinate | — |

TABLE 23-continued

| Rf | Syn | Structure | Acid |
|---|---|---|---|
| 104 | R92 | 5-methylpyridin-2-yl-piperazine-N-Boc | — |

TABLE 24

| Rf | Syn | Structure | Acid |
|---|---|---|---|
| 105 | R92 | 4-methylpyridin-2-yl-piperazine-N-Boc | — |
| 106 | R92 | 3-methyl-5-formyl-pyridin-2-yl-piperazine-N-Boc | — |
| 107 | R107 | 3-methylpyridin-2-yl-piperazine | 2HCl |
| 108 | R108 | 3-formyl-pyridin-2-yl-piperazine-N-Boc | — |
| 109 | R108 | 4-nitrophenyl-piperazine-N-Boc | — |
| 110 | R108 | 6-chloro-5-methyl-pyrimidin-4-yl-piperazine-N-Boc | — |
| 111 | R108 | 5-bromopyridin-2-yl-piperazine-N-Boc | — |

TABLE 25
| Rf | Syn | Structure | Acid |
|---|---|---|---|
| 112 | R112 | 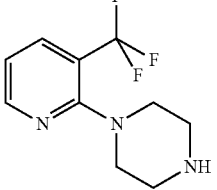 | 2HCl |
| 113 | R112 | 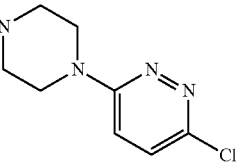 | — |
| 114 | R112 | 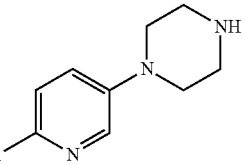 | — |
| 115 | R115 | 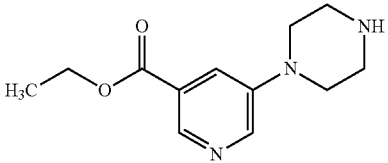 [SMILES: CCOC(=O)c1cncc(N2CCNCC2)c1] | — |
| 116 | R115 | 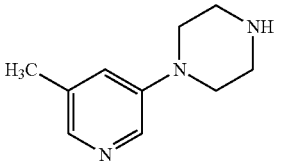 | 3HCl |
| 117 | R115 | 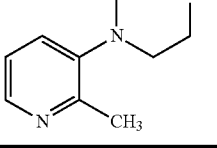 | 3HCl |
TABLE 26
| Rf | Syn | Structure | Acid |
|---|---|---|---|
| 118 | R115 | 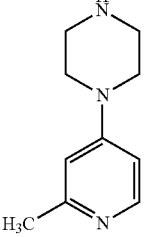 | 2HCl |
| 119 | R115 | 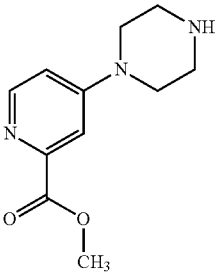 [SMILES: COC(=O)c1cc(N2CCNCC2)ccn1] | 2HCl |
| 120 | R115 | 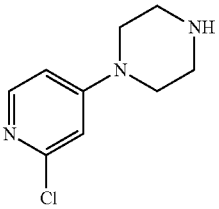 [SMILES: Clc1cc(N2CCNCC2)ccn1] | 2HCl |
| 121 | R115 | 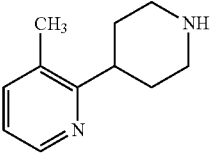 | 2HCl |
| 122 | R115 | 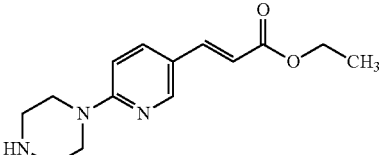 | 2HCl |
TABLE 27
| Rf | Syn | Structure | Acid |
|---|---|---|---|
| 123 | R115 | 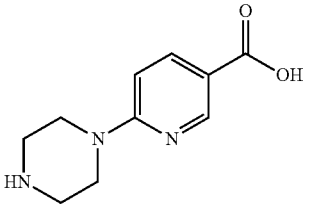 [SMILES: O=C(O)c1ccc(N2CCNCC2)nc1] | 2HCl |

TABLE 27-continued

| Rf | Syn | Structure | Acid |
|----|-----|-----------|------|
| 124 | R124 | trans, structure with 2,5-dimethylpiperazine, 2-pyridyl, pyrimidine, phenyl, N-methyl glycinamide-Boc | — |
| 125 | R124 | trans, structure with 2,5-dimethylpiperazine, 4-pyridyl, pyrimidine, phenyl, N-methyl glycinamide-Boc | — |
| 126 | R124 | structure with 3-methoxy-2-pyridyl piperazine, pyrimidine, phenyl, N-methyl glycinamide-Boc | — |
| 127 | R124 | structure with 5-fluoro-2-pyridyl piperazine, pyrimidine, phenyl, N-methyl glycinamide-Boc | — |

TABLE 28
| Rf | Syn | Structure | Acid |
|---|---|---|---|
| 128 | R124 | 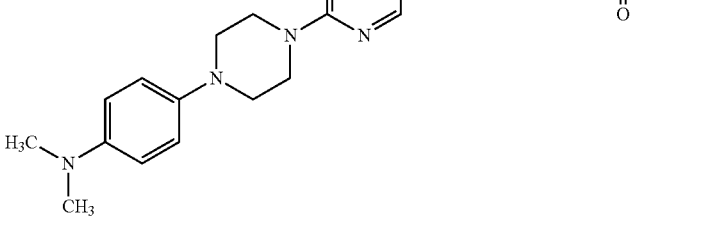 | — |
| 129 | R124 | 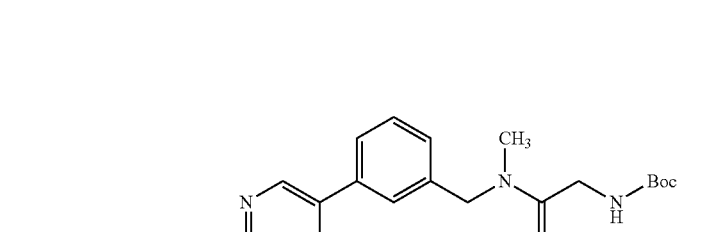 | — |
| 130 | R124 | 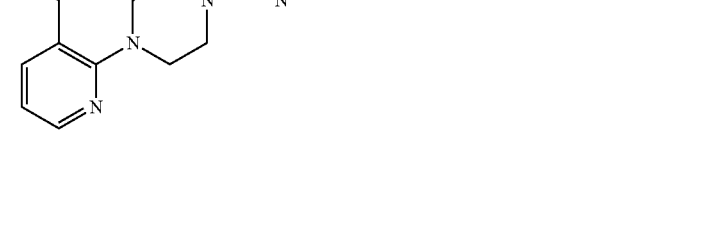 | — |
| 131 | R124 | 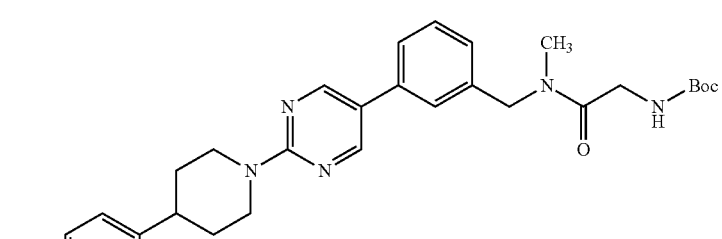 | — |

TABLE 29
| Rf | Syn | Structure | Acid |
|----|-----|-----------|------|
| 132 | R124 | 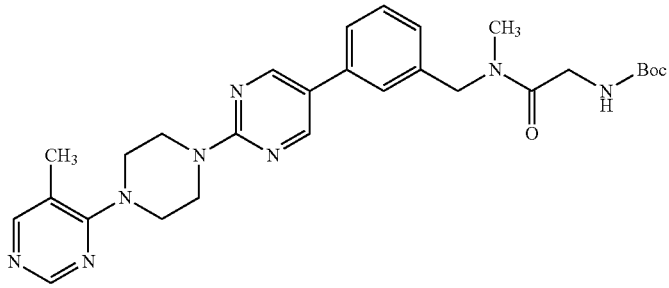 | — |
| 133 | R124 | 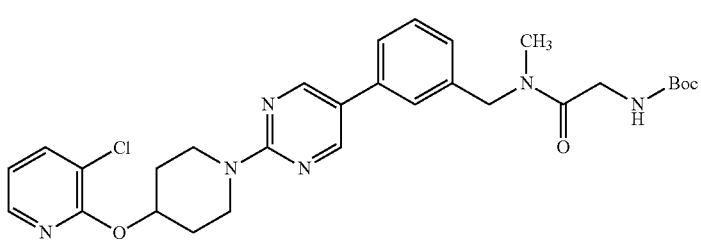 [SMILES: CN(Cc1cccc(-c2cnc(N3CCC(Oc4ncccc4Cl)CC3)nc2)c1)C(=O)CNC(=O)OC(C)(C)C] | — |
| 134 | R124 | 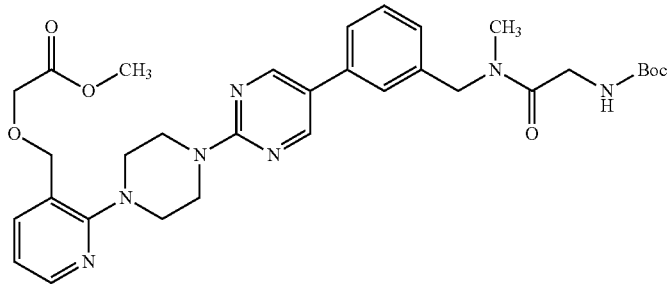 [SMILES: COC(=O)COCc1cccnc1N1CCN(c2ncc(-c3cccc(CN(C)C(=O)CNC(=O)OC(C)(C)C)c3)cn2)CC1] | — |
| 135 | R124 | 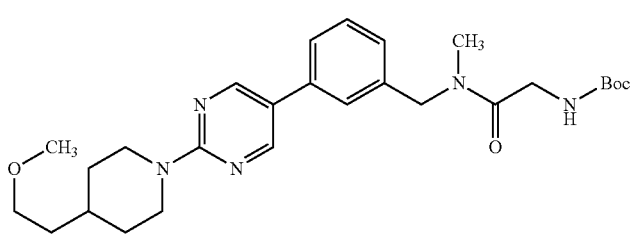 [SMILES: COCCC1CCN(c2ncc(-c3cccc(CN(C)C(=O)CNC(=O)OC(C)(C)C)c3)cn2)CC1] | — |
| 136 | R124 | 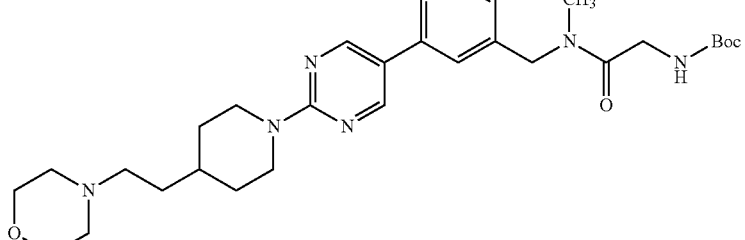 | — |

TABLE 30
| Rf | Syn | Structure | Acid |
|----|-----|-----------|------|
| 137 | R124 | 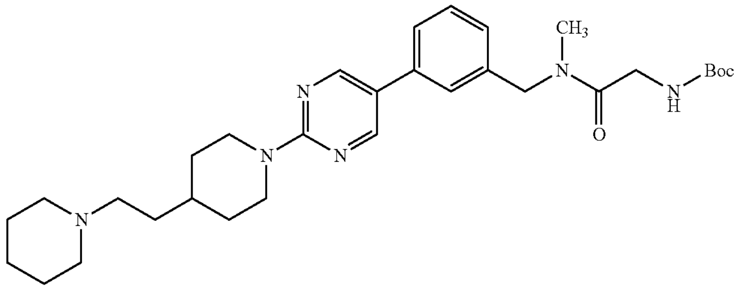 [SMILES: CN(Cc1cccc(-c2cnc(N3CCC(CCN4CCCCC4)CC3)nc2)c1)C(=O)CNC(=O)OC(C)(C)C] | — |
| 138 | R124 | 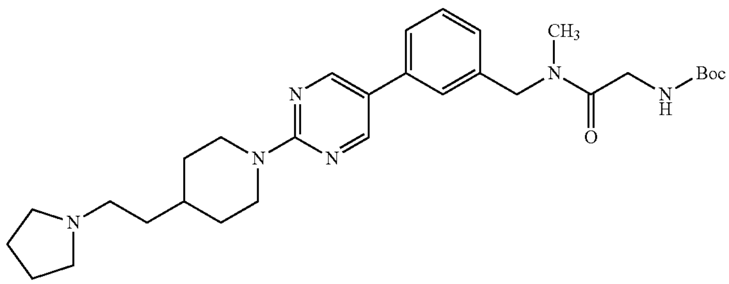 [SMILES: CN(Cc1cccc(-c2cnc(N3CCC(CCN4CCCC4)CC3)nc2)c1)C(=O)CNC(=O)OC(C)(C)C] | — |
| 139 | R124 | 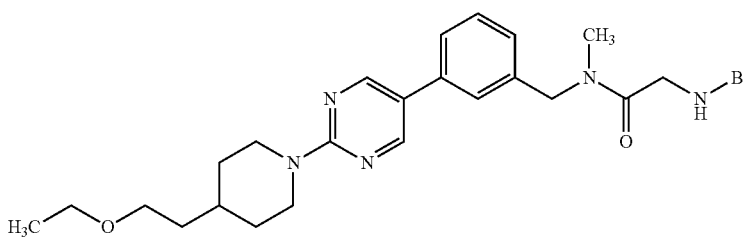 | — |
| 140 | R124 | 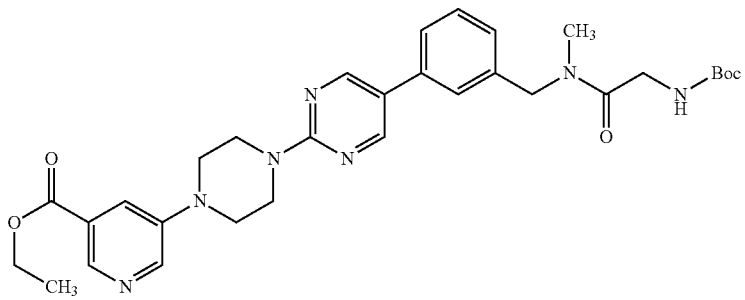 [SMILES: CCOC(=O)c1cncc(N2CCN(c3ncc(-c4cccc(CN(C)C(=O)CNC(=O)OC(C)(C)C)c4)cn3)CC2)c1] | — |
| 141 | R124 | 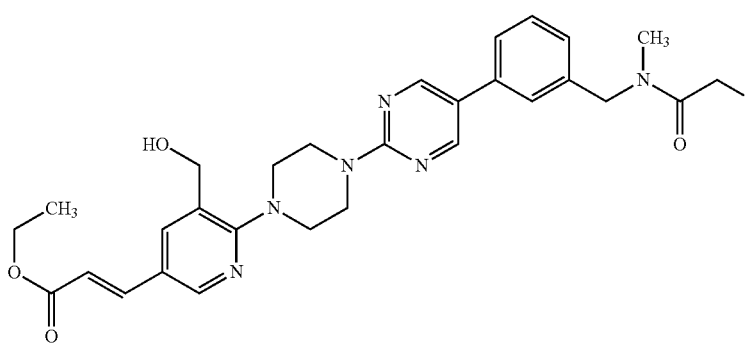 | — |

TABLE 31
| Rf | Syn | Structure | Acid |
|---|---|---|---|
| 142 | R124 | ![structure] | — |
| 143 | R124 | ![structure] | — |
| 144 | R144 | ![structure] | — |
| 145 | R144 | ![structure] | — |
TABLE 32
| Rf | Syn | Structure | Acid |
|---|---|---|---|
| 146 | R146 | ![structure] | — |
TABLE 32-continued
| Rf | Syn | Structure | Acid |
|---|---|---|---|
| 147 | R147 | 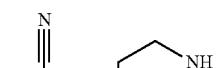 | — |

TABLE 32-continued

| Rf | Syn | Structure | Acid |
|---|---|---|---|
| 148 | R148 | H3C-O-CH2CH2-N(CH3)-(5-bromopyrimidin-2-yl) | — |
| 149 | R148 | cis 4-(5-bromopyrimidin-2-yl)-2,6-dimethylmorpholine | — |
| 150 | R148 | [4-(5-bromopyrimidin-2-yl)morpholin-2-yl]methanol | — |
| 151 | R148 | [1-(5-bromopyrimidin-2-yl)piperidin-4-yl]methanol | — |

TABLE 33

| Rf | Syn | Structure | Acid |
|---|---|---|---|
| 152 | R148 | cis 4-(5-bromopyridin-2-yl)-2,6-dimethylmorpholine | — |

TABLE 33-continued

| Rf | Syn | Structure | Acid |
|---|---|---|---|
| 153 | R148 | 5-bromo-2-[4-(pyridin-4-yl)piperazin-1-yl]pyrimidine | — |
| 154 | R148 | 5-bromo-2-[4-(pyrimidin-2-yl)piperazin-1-yl]pyrimidine | — |
| 155 | R148 | 5-bromo-2-[4-(pyridin-2-yl)piperazin-1-yl]pyridine | — |
| 156 | R148 | 5-bromo-2-[4-(pyridin-4-yl)piperazin-1-yl]pyridine | — |

TABLE 34

| Rf | Syn | Structure | Acid |
|---|---|---|---|
| 157 | R148 | 5-bromo-2-{4-[3-methylpyridin-2-yl]piperazin-1-yl}pyridine | — |

TABLE 34-continued

| Rf | Syn | Structure | Acid |
|---|---|---|---|
| 158 | R148 | 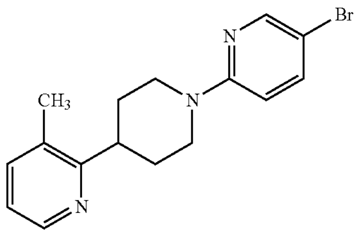 [SMILES: Cc1cccnc1C1CCN(c2ccc(Br)cn2)CC1] | — |
| 159 | R148 | 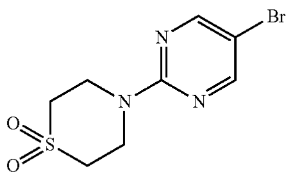 [SMILES: O=S1(=O)CCN(c2ncc(Br)cn2)CC1] | — |
| 160 | R160 | 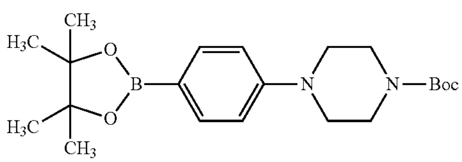 | — |
| 161 | R161 | 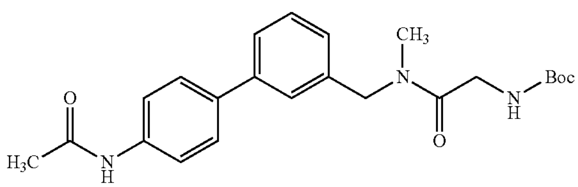 [SMILES: CC(=O)Nc1ccc(-c2cccc(CN(C)C(=O)CNC(=O)OC(C)(C)C)c2)cc1] | — |
| 162 | R161 | 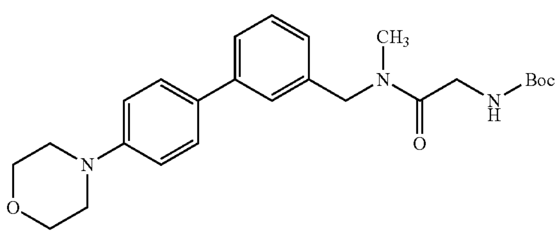 [SMILES: CN(Cc1cccc(-c2ccc(N3CCOCC3)cc2)c1)C(=O)CNC(=O)OC(C)(C)C] | — |

TABLE 35

| Rf | Syn | Structure | Acid |
|---|---|---|---|
| 163 | R161 | 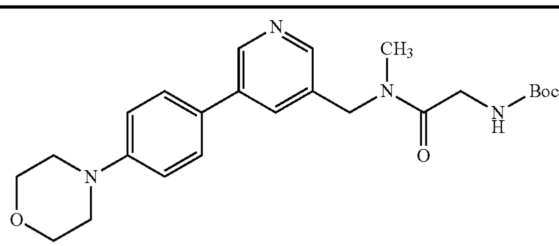 | — |

TABLE 35-continued

| Rf | Syn | Structure | Acid |
|---|---|---|---|
| 164 | R161 | 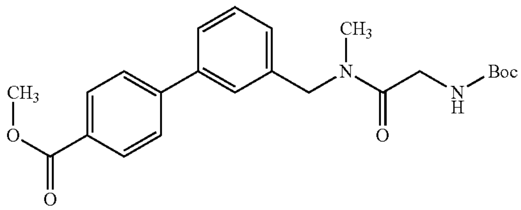 [SMILES: COC(=O)c1ccc(-c2cccc(CN(C)C(=O)CNC(=O)OC(C)(C)C)c2)cc1] | — |
| 165 | R161 | 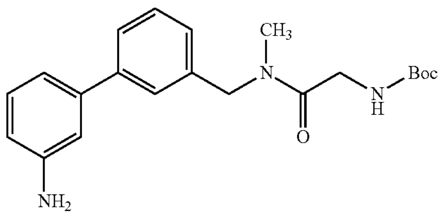 [SMILES: CN(Cc1cccc(-c2cccc(N)c2)c1)C(=O)CNC(=O)OC(C)(C)C] | — |
| 166 | R161 | 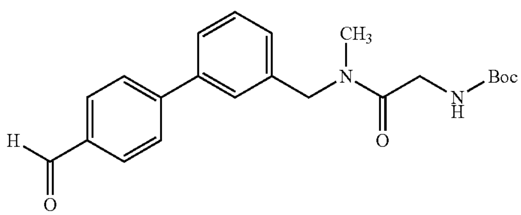 [SMILES: CN(Cc1cccc(-c2ccc(C=O)cc2)c1)C(=O)CNC(=O)OC(C)(C)C] | — |
| 167 | R161 | 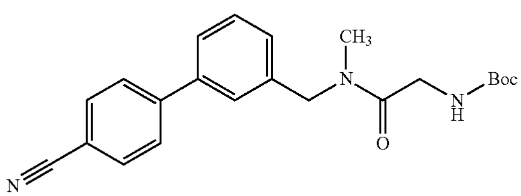 [SMILES: CN(Cc1cccc(-c2ccc(C#N)cc2)c1)C(=O)CNC(=O)OC(C)(C)C] | — |
| 168 | R161 | 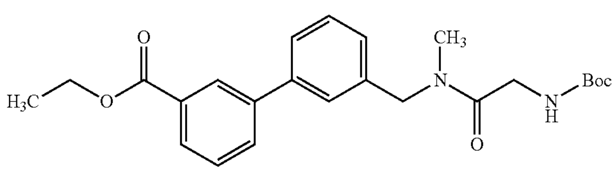 [SMILES: CCOC(=O)c1cccc(-c2cccc(CN(C)C(=O)CNC(=O)OC(C)(C)C)c2)c1] | — |

TABLE 36

| Rf | Syn | Structure | Acid |
|---|---|---|---|
| 169 | R161 | 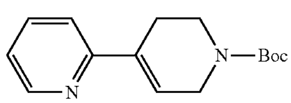 [SMILES: CC(C)(C)OC(=O)N1CC=C(c2ccccn2)CC1] | — |
| 170 | R161 | 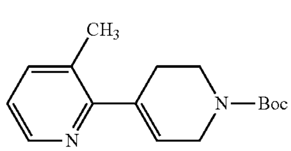 [SMILES: Cc1cccnc1C1=CCN(C(=O)OC(C)(C)C)CC1] | — |

TABLE 36-continued

| Rf | Syn | Structure | Acid |
|---|---|---|---|
| 171 | R171 | cis, (2,6-dimethylmorpholin-4-yl)pyrimidin-5-yl phenyl CH2-N(CH3)-C(O)-CH2-NHBoc | — |
| 172 | R171 | (2-(hydroxymethyl)morpholin-4-yl)pyrimidin-5-yl phenyl CH2-N(CH3)-C(O)-CH2-NHBoc | — |
| 173 | R171 | cis, (2,6-dimethylmorpholin-4-yl)pyridin-5-yl phenyl CH2-N(CH3)-C(O)-CH2-NHBoc | — |
| 174 | R171 | (N-(2-methoxyethyl)-N-methylamino)pyrimidin-5-yl phenyl CH2-N(CH3)-C(O)-CH2-NHBoc | — |

TABLE 37

| Rf | Syn | Structure | Acid |
|---|---|---|---|
| 175 | R171 | (4-(hydroxymethyl)piperidin-1-yl)pyrimidin-5-yl phenyl CH2-N(CH3)-C(O)-CH2-NHBoc | — |

TABLE 37-continued

| Rf | Syn | Structure | Acid |
|----|-----|-----------|------|
| 176 | R171 | (4-hydroxypiperidin-1-yl)-pyrimidin-5-yl phenyl CH2-N(CH3)-C(O)-CH2-NH-Boc | — |
| 177 | R171 | [4-(pyridin-2-yl)piperazin-1-yl]-pyrimidin-5-yl phenyl CH2-N(CH3)-C(O)-CH2-NH-Boc | — |
| 178 | R171 | [4-(pyrimidin-2-yl)piperazin-1-yl]-pyrimidin-5-yl phenyl CH2-N(CH3)-C(O)-CH2-NH-Boc | — |
| 179 | R171 | 2-chloropyrimidin-5-yl phenyl CH2-N(CH2CH3)-C(O)-CH2-NH-Boc | — |
| 180 | R171 | 2-chloropyrimidin-5-yl phenyl CH2-NH-C(O)-CH2-NH-Boc | — |

TABLE 38

| Rf | Syn | Structure | Acid |
|---|---|---|---|
| 181 | R171 | 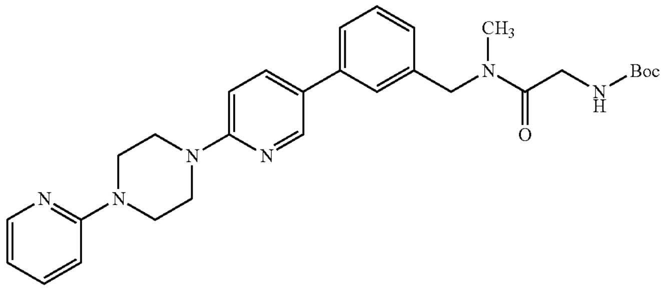 [SMILES: CN(Cc1cccc(-c2cnc(N3CCN(c4ccccn4)CC3)nc2)c1)C(=O)CNC(=O)OC(C)(C)C] | — |
| 182 | R171 | 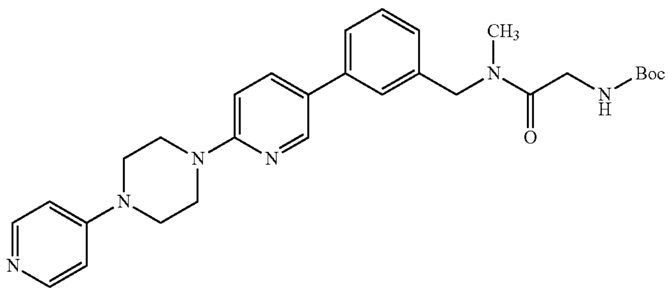 [SMILES: CN(Cc1cccc(-c2ccc(N3CCN(c4ccncc4)CC3)nc2)c1)C(=O)CNC(=O)OC(C)(C)C] | — |
| 183 | R171 | 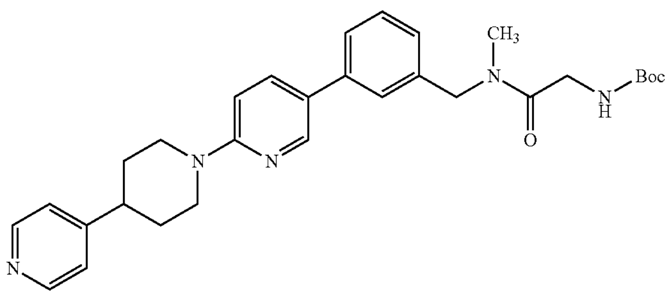 [SMILES: CN(Cc1cccc(-c2ccc(N3CCC(c4ccncc4)CC3)nc2)c1)C(=O)CNC(=O)OC(C)(C)C] | — |
| 184 | R171 | 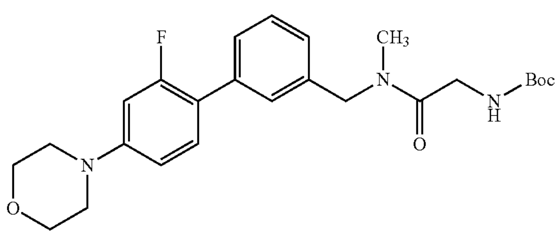 [SMILES: CN(Cc1cccc(-c2ccc(N3CCOCC3)cc2F)c1)C(=O)CNC(=O)OC(C)(C)C] | — |
| 185 | R171 | 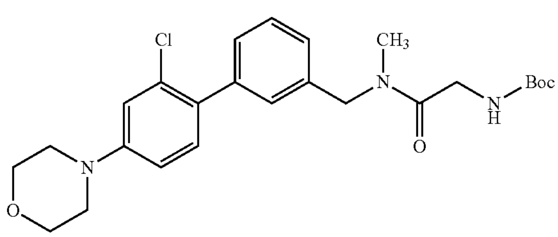 [SMILES: CN(Cc1cccc(-c2ccc(N3CCOCC3)cc2Cl)c1)C(=O)CNC(=O)OC(C)(C)C] | — |

TABLE 39

| Rf | Syn | Structure | Acid |
|---|---|---|---|
| 186 | R171 | 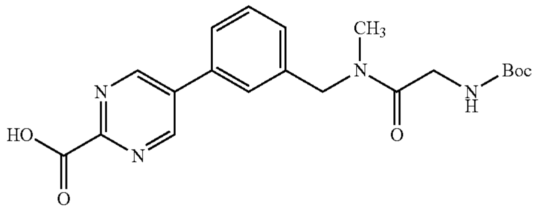 [SMILES: CN(Cc1cccc(-c2cnc(C(=O)O)nc2)c1)C(=O)CNC(=O)OC(C)(C)C] | — |
| 187 | R171 | 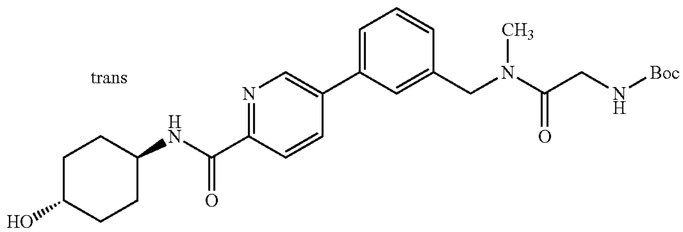 [SMILES: CN(Cc1cccc(-c2ccc(C(=O)N[C@H]3CC[C@H](O)CC3)nc2)c1)C(=O)CNC(=O)OC(C)(C)C] | — |
| 188 | R171 | 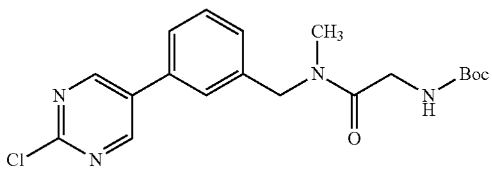 [SMILES: CN(Cc1cccc(-c2cnc(Cl)nc2)c1)C(=O)CNC(=O)OC(C)(C)C] | — |
| 189 | R171 | 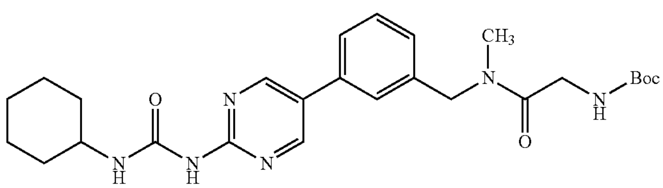 [SMILES: CN(Cc1cccc(-c2cnc(NC(=O)NC3CCCCC3)nc2)c1)C(=O)CNC(=O)OC(C)(C)C] | — |
| 190 | R171 | 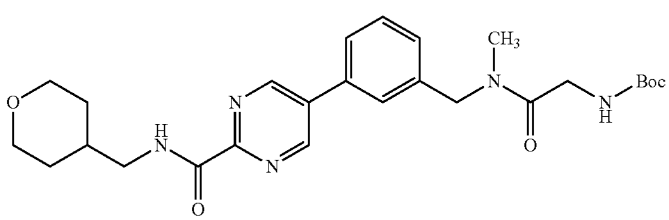 [SMILES: CN(Cc1cccc(-c2cnc(C(=O)NCC3CCOCC3)nc2)c1)C(=O)CNC(=O)OC(C)(C)C] | — |
| 191 | R171 | 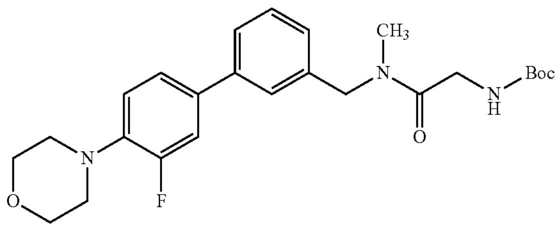 | — |

TABLE 40
| Rf | Syn | Structure | Acid |
|---|---|---|---|
| 192 | R171 | 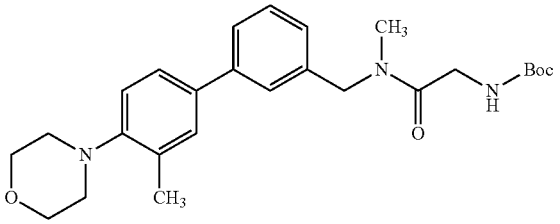 [SMILES: Cc1cc(-c2cccc(CN(C)C(=O)CNC(=O)OC(C)(C)C)c2)ccc1N1CCOCC1] | — |
| 193 | R171 | 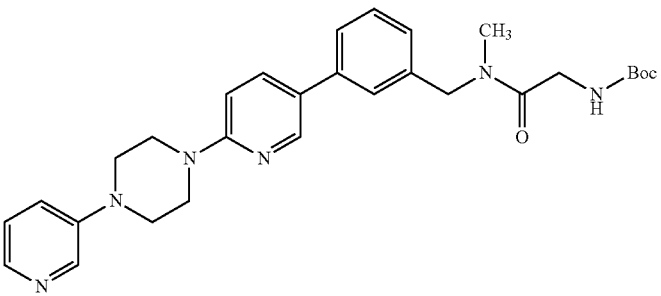 | — |
| 194 | R171 | 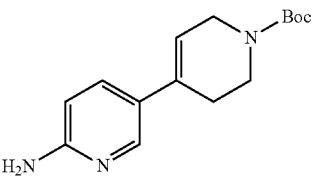 | — |
| 195 | R171 | 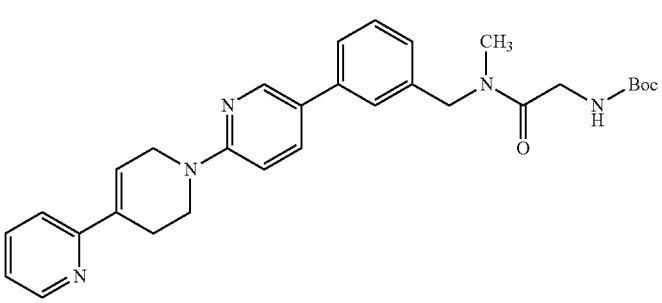 [SMILES: CN(Cc1cccc(-c2ccc(N3CC=C(c4ccccn4)CC3)nc2)c1)C(=O)CNC(=O)OC(C)(C)C] | — |
| 196 | R171 | 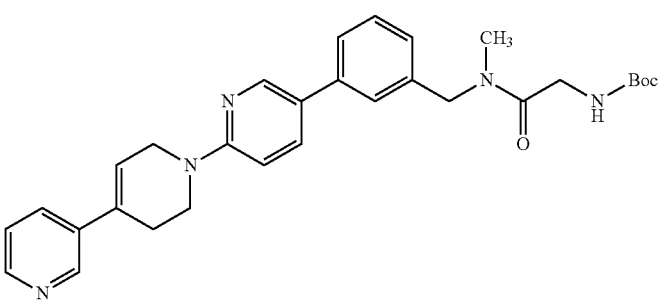 [SMILES: CN(Cc1cccc(-c2ccc(N3CC=C(c4cccnc4)CC3)nc2)c1)C(=O)CNC(=O)OC(C)(C)C] | — |

TABLE 41

| Rf | Syn | Structure | Acid |
|---|---|---|---|
| 197 | R171 | 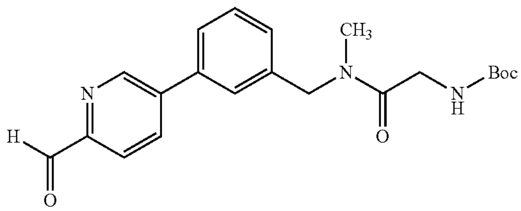 [SMILES: CN(Cc1cccc(-c2ccc(C=O)nc2)c1)C(=O)CNC(=O)OC(C)(C)C] | — |
| 198 | R171 | 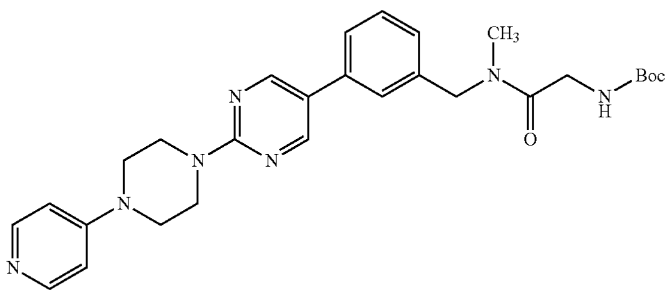 [SMILES: CN(Cc1cccc(-c2cnc(N3CCN(c4ccncc4)CC3)nc2)c1)C(=O)CNC(=O)OC(C)(C)C] | — |
| 199 | R171 | 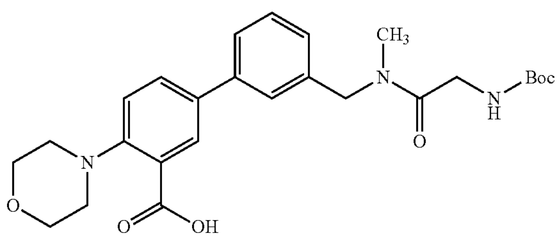 [SMILES: CN(Cc1cccc(-c2ccc(N3CCOCC3)c(C(=O)O)c2)c1)C(=O)CNC(=O)OC(C)(C)C] | — |
| 200 | R200 | 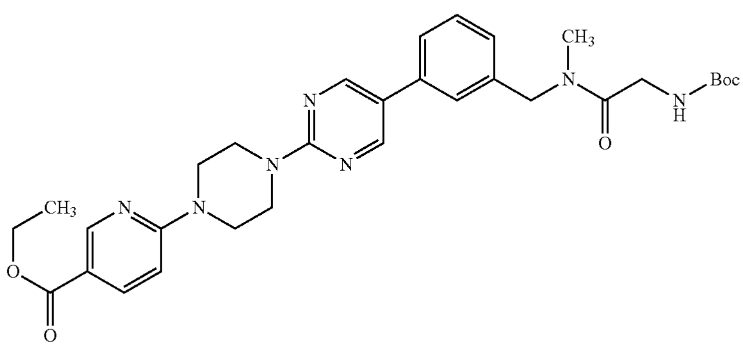 [SMILES: CCOC(=O)c1ccc(N2CCN(c3ncc(-c4cccc(CN(C)C(=O)CNC(=O)OC(C)(C)C)c4)cn3)CC2)nc1] | — |
| 201 | R201 | 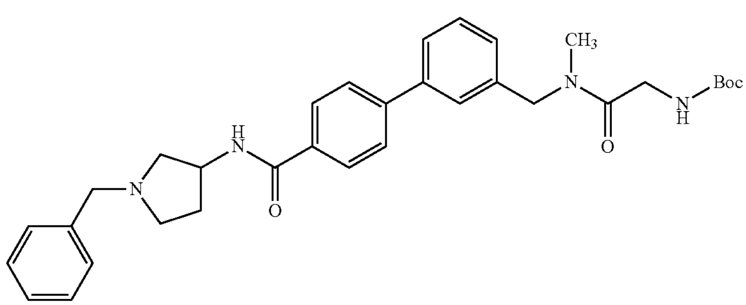 [SMILES: CN(Cc1cccc(-c2ccc(C(=O)NC3CCN(Cc4ccccc4)C3)cc2)c1)C(=O)CNC(=O)OC(C)(C)C] | — |

TABLE 42

| Rf | Syn | Structure | Acid |
|---|---|---|---|
| 202 | R201 | 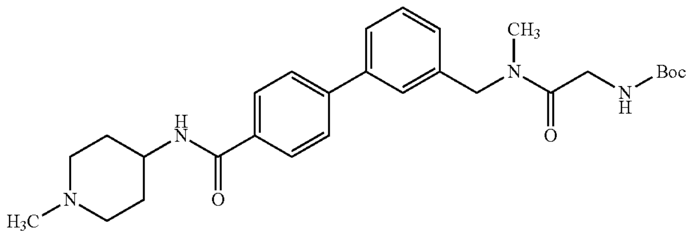 [SMILES: CN1CCC(NC(=O)c2ccc(-c3cccc(CN(C)C(=O)CNC(=O)OC(C)(C)C)c3)cc2)CC1] | — |
| 203 | R201 | 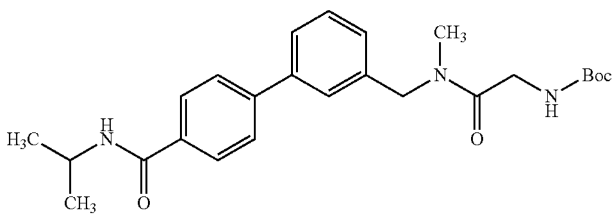 [SMILES: CC(C)NC(=O)c1ccc(-c2cccc(CN(C)C(=O)CNC(=O)OC(C)(C)C)c2)cc1] | — |
| 204 | R201 | 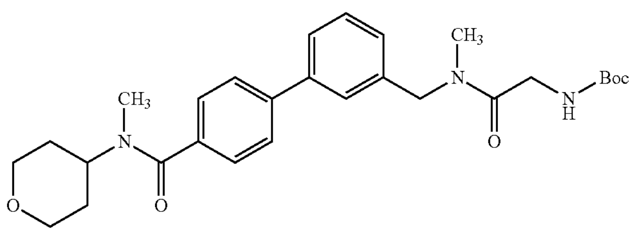 [SMILES: CN(Cc1cccc(-c2ccc(C(=O)N(C)C3CCOCC3)cc2)c1)C(=O)CNC(=O)OC(C)(C)C] | — |
| 205 | R201 | 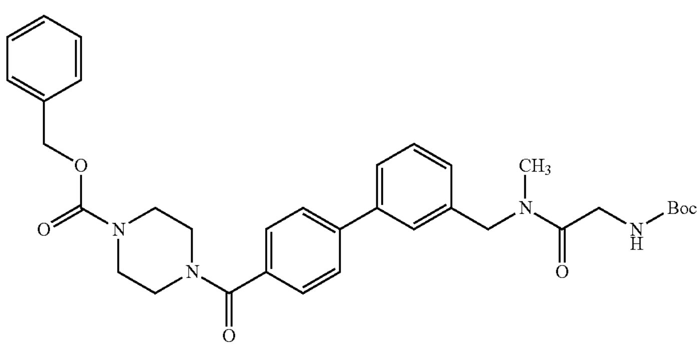 [SMILES: CN(Cc1cccc(-c2ccc(C(=O)N3CCN(C(=O)OCc4ccccc4)CC3)cc2)c1)C(=O)CNC(=O)OC(C)(C)C] | — |
| 206 | R201 | 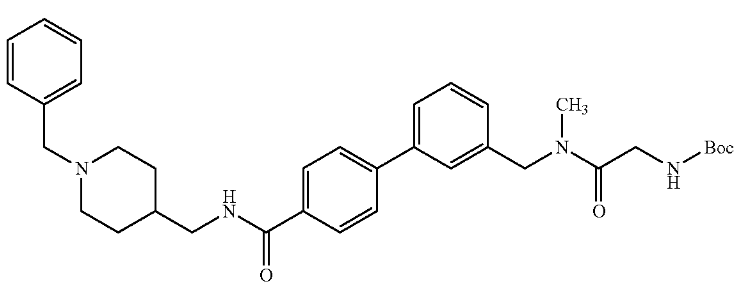 [SMILES: CN(Cc1cccc(-c2ccc(C(=O)NCC3CCN(Cc4ccccc4)CC3)cc2)c1)C(=O)CNC(=O)OC(C)(C)C] | — |

TABLE 43
| Rf | Syn | Structure | Acid |
|---|---|---|---|
| 207 | R201 | 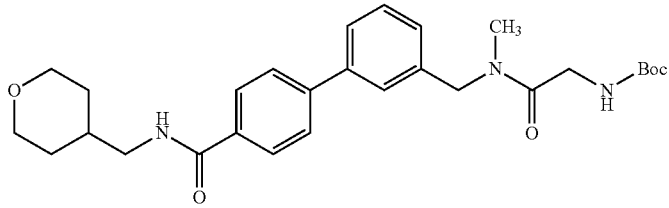 [SMILES: CN(Cc1cccc(-c2ccc(C(=O)NCC3CCOCC3)cc2)c1)C(=O)CNC(=O)OC(C)(C)C] | — |
| 208 | R201 | 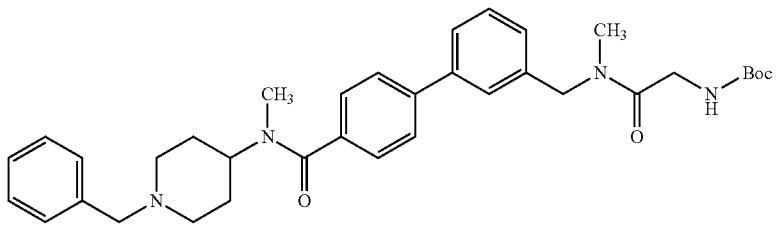 [SMILES: CN(Cc1cccc(-c2ccc(C(=O)N(C)C3CCN(Cc4ccccc4)CC3)cc2)c1)C(=O)CNC(=O)OC(C)(C)C] | — |
| 209 | R201 | 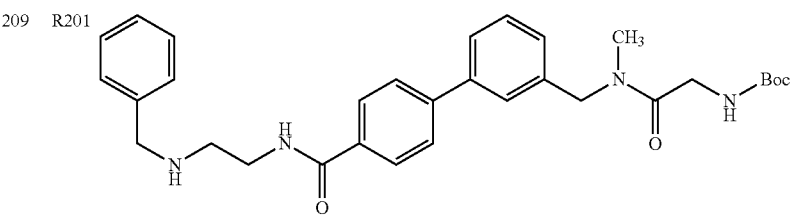 | — |
| 210 | R201 | 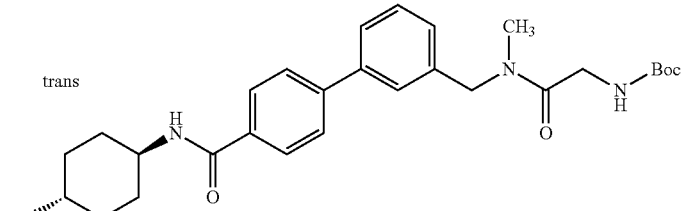 | — |
| 211 | R201 | 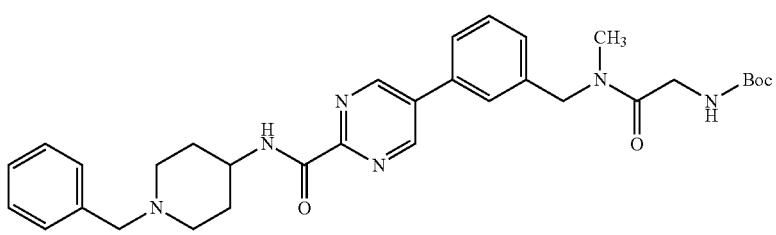 [SMILES: CN(Cc1cccc(-c2cnc(C(=O)NC3CCN(Cc4ccccc4)CC3)nc2)c1)C(=O)CNC(=O)OC(C)(C)C] | — |
| 212 | R201 | 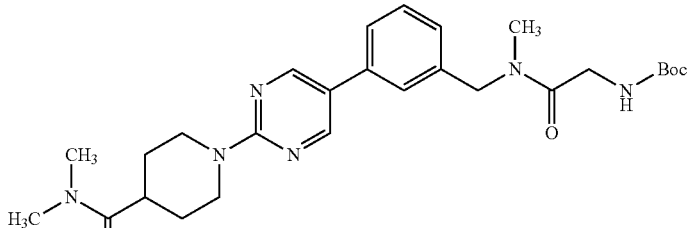 | — |

TABLE 44

| Rf | Syn | Structure | Acid |
|---|---|---|---|
| 213 | R201 | 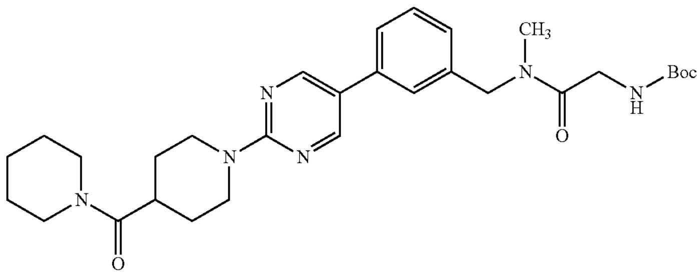 [SMILES: CN(Cc1cccc(-c2cnc(N3CCC(C(=O)N4CCCCC4)CC3)nc2)c1)C(=O)CNC(=O)OC(C)(C)C] | — |
| 214 | R201 | 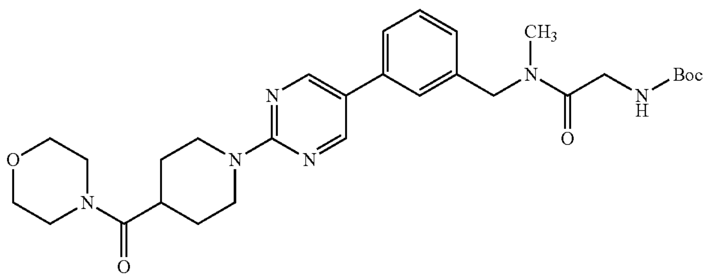 [SMILES: CN(Cc1cccc(-c2cnc(N3CCC(C(=O)N4CCOCC4)CC3)nc2)c1)C(=O)CNC(=O)OC(C)(C)C] | — |
| 215 | R201 | 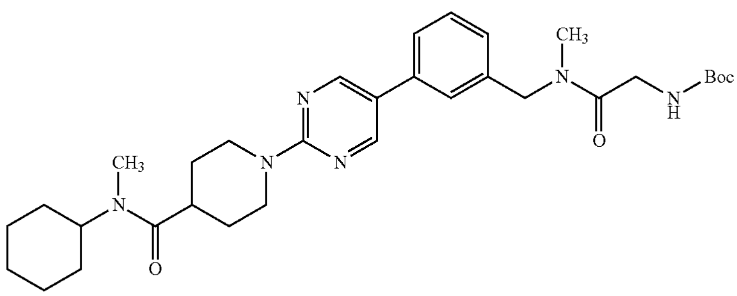 [SMILES: CN(Cc1cccc(-c2cnc(N3CCC(C(=O)N(C)C4CCCCC4)CC3)nc2)c1)C(=O)CNC(=O)OC(C)(C)C] | — |
| 216 | R201 | 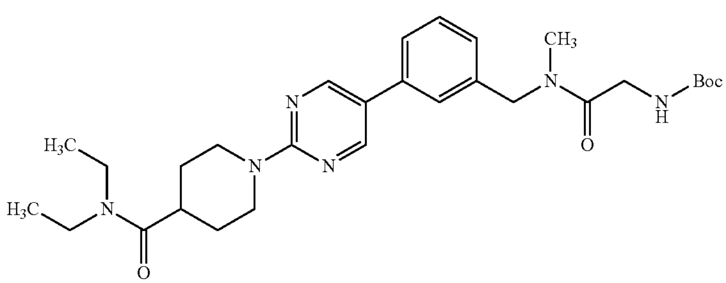 [SMILES: CCN(CC)C(=O)C1CCN(c2ncc(-c3cccc(CN(C)C(=O)CNC(=O)OC(C)(C)C)c3)cn2)CC1] | — |
| 217 | R201 | 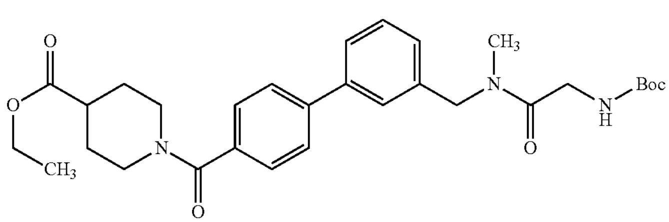 [SMILES: CCOC(=O)C1CCN(C(=O)c2ccc(-c3cccc(CN(C)C(=O)CNC(=O)OC(C)(C)C)c3)cc2)CC1] | — |

TABLE 45

| Rf | Syn | Structure | Acid |
|---|---|---|---|
| 218 | R201 | 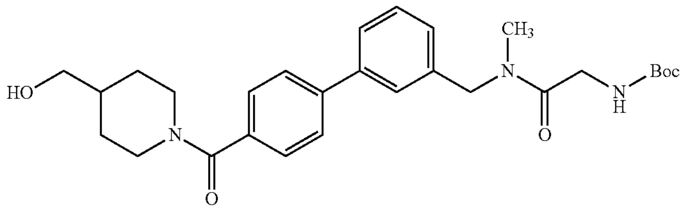 [SMILES: CN(Cc1cccc(-c2ccc(C(=O)N3CCC(CO)CC3)cc2)c1)C(=O)CNC(=O)OC(C)(C)C] | — |
| 219 | R201 | 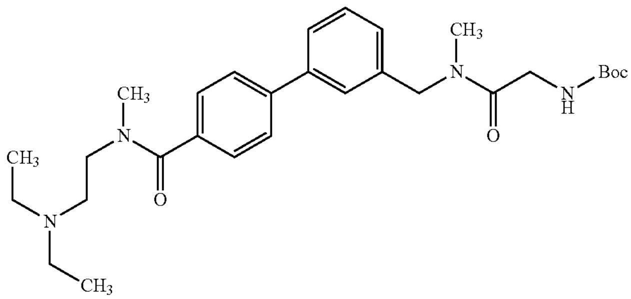 [SMILES: CCN(CC)CCN(C)C(=O)c1ccc(-c2cccc(CN(C)C(=O)CNC(=O)OC(C)(C)C)c2)cc1] | — |
| 220 | R201 | 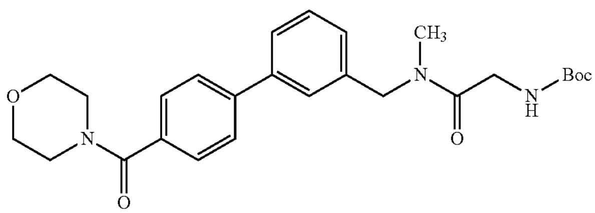 [SMILES: CN(Cc1cccc(-c2ccc(C(=O)N3CCOCC3)cc2)c1)C(=O)CNC(=O)OC(C)(C)C] | — |
| 221 | R201 | 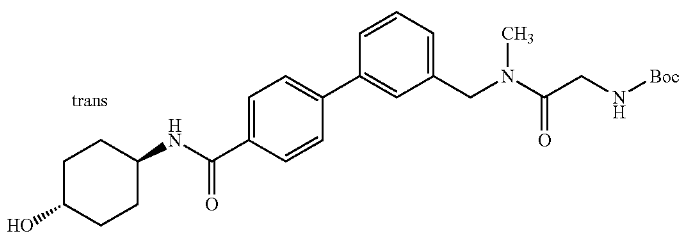 [SMILES: CN(Cc1cccc(-c2ccc(C(=O)N[C@H]3CC[C@H](O)CC3)cc2)c1)C(=O)CNC(=O)OC(C)(C)C] | — |
| 222 | R222 | 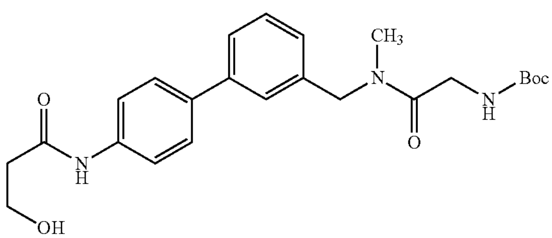 [SMILES: CN(Cc1cccc(-c2ccc(NC(=O)CCO)cc2)c1)C(=O)CNC(=O)OC(C)(C)C] | — |

TABLE 46

| Rf | Syn | Structure | Acid |
|---|---|---|---|
| 223 | R222 | 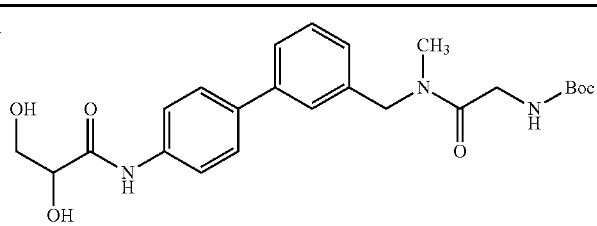 | — |

TABLE 46-continued

| Rf | Syn | Structure | Acid |
|---|---|---|---|
| 224 | R222 | cis-4-hydroxycyclohexanecarboxamide-N-(4'-((N-methyl-N-(2-(Boc-amino)acetyl))aminomethyl)biphenyl-4-yl) | — |
| 225 | R222 | cyclobutanecarboxamide-N-(4'-((N-methyl-N-(2-(Boc-amino)acetyl))aminomethyl)biphenyl-4-yl) | — |
| 226 | R222 | cyclopropanecarboxamide-N-(4'-((N-methyl-N-(2-(Boc-amino)acetyl))aminomethyl)biphenyl-4-yl) | — |
| 227 | R222 | pyridine-2-carboxamide-N-(4'-((N-methyl-N-(2-(Boc-amino)acetyl))aminomethyl)biphenyl-4-yl) | — |

TABLE 47

| Rf | Syn | Structure | Acid |
|---|---|---|---|
| 228 | R222 | pyridine-3-carboxamide-N-(4'-((N-methyl-N-(2-(Boc-amino)acetyl))aminomethyl)biphenyl-4-yl) | — |
| 229 | R222 | 1-methylpiperidine-4-carboxamide-N-(4'-((N-methyl-N-(2-(Boc-amino)acetyl))aminomethyl)biphenyl-4-yl) | — |

TABLE 47-continued

| Rf | Syn | Structure | Acid |
|---|---|---|---|
| 230 | R230 | 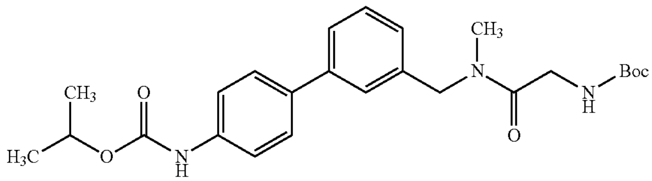 [SMILES: CC(C)OC(=O)Nc1ccc(-c2cccc(CN(C)C(=O)CNC(=O)OC(C)(C)C)c2)cc1] | — |
| 231 | R230 | 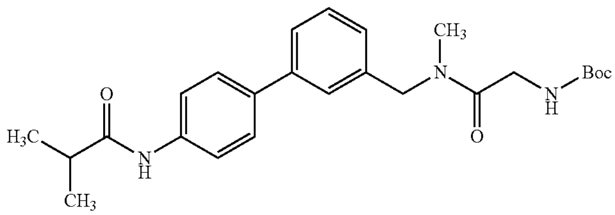 [SMILES: CC(C)C(=O)Nc1ccc(-c2cccc(CN(C)C(=O)CNC(=O)OC(C)(C)C)c2)cc1] | — |
| 232 | R230 | 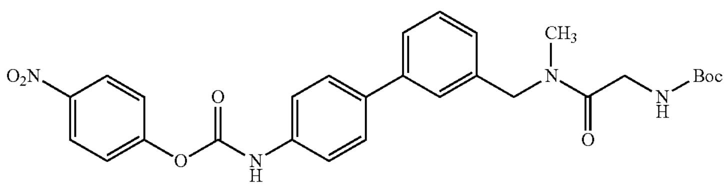 [SMILES: CN(Cc1cccc(-c2ccc(NC(=O)Oc3ccc([N+](=O)[O-])cc3)cc2)c1)C(=O)CNC(=O)OC(C)(C)C] | — |
| 233 | R230 | 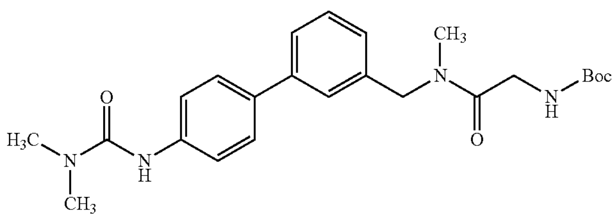 | — |

TABLE 48

| Rf | Syn | Structure | Acid |
|---|---|---|---|
| 234 | R234 | 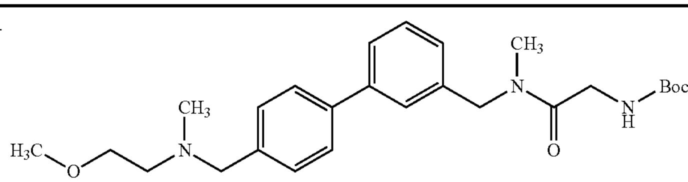 | — |
| 235 | R234 | 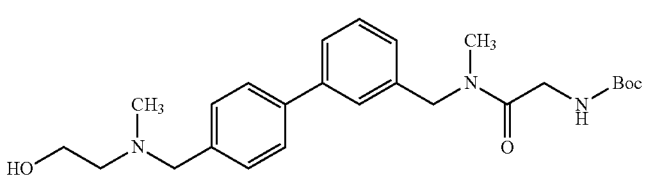 [SMILES: CN(CCO)Cc1ccc(-c2cccc(CN(C)C(=O)CNC(=O)OC(C)(C)C)c2)cc1] | — |
| 236 | R234 | 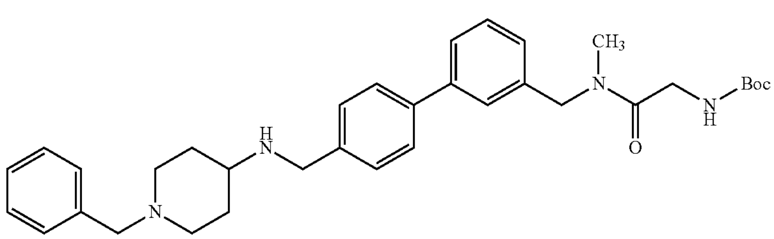 [SMILES: CN(Cc1cccc(-c2ccc(CNC3CCN(Cc4ccccc4)CC3)cc2)c1)C(=O)CNC(=O)OC(C)(C)C] | — |

TABLE 48-continued

| Rf | Syn | Structure | Acid |
|---|---|---|---|
| 237 | R237 | 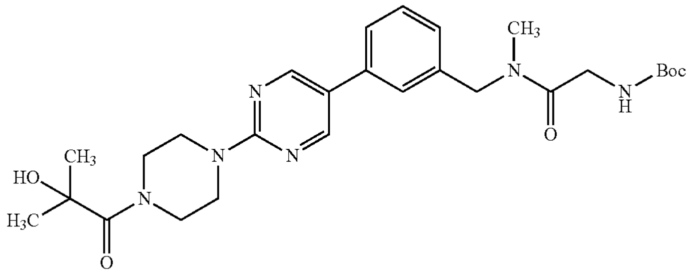 [SMILES: CN(Cc1cccc(-c2cnc(N3CCN(C(=O)C(C)(C)O)CC3)nc2)c1)C(=O)CNC(=O)OC(C)(C)C] | — |
| 238 | R237 | 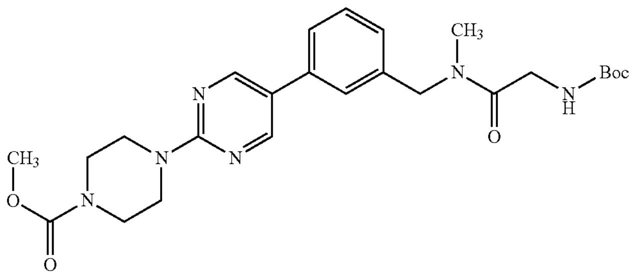 [SMILES: COC(=O)N1CCN(c2ncc(-c3cccc(CN(C)C(=O)CNC(=O)OC(C)(C)C)c3)cn2)CC1] | — |

TABLE 49

| Rf | Syn | Structure | Acid |
|---|---|---|---|
| 239 | R237 | 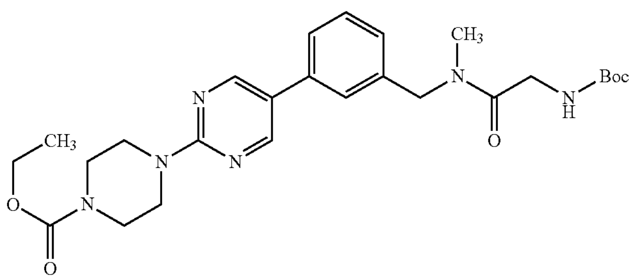 [SMILES: CCOC(=O)N1CCN(c2ncc(-c3cccc(CN(C)C(=O)CNC(=O)OC(C)(C)C)c3)cn2)CC1] | — |
| 240 | R237 | 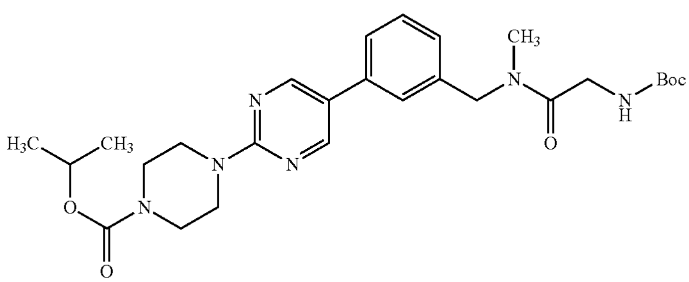 [SMILES: CC(C)OC(=O)N1CCN(c2ncc(-c3cccc(CN(C)C(=O)CNC(=O)OC(C)(C)C)c3)cn2)CC1] | — |
| 241 | R237 | 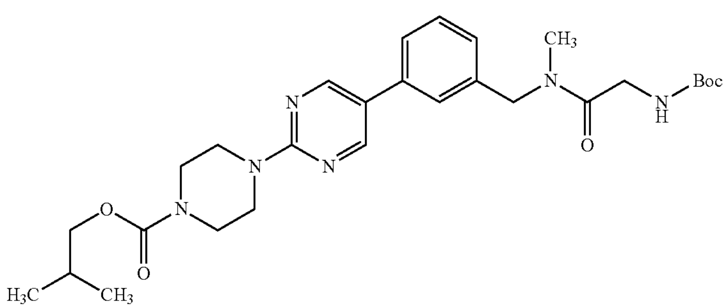 [SMILES: CC(C)COC(=O)N1CCN(c2ncc(-c3cccc(CN(C)C(=O)CNC(=O)OC(C)(C)C)c3)cn2)CC1] | — |

TABLE 49-continued
| Rf | Syn | Structure | Acid |
|---|---|---|---|
| 242 | R237 | 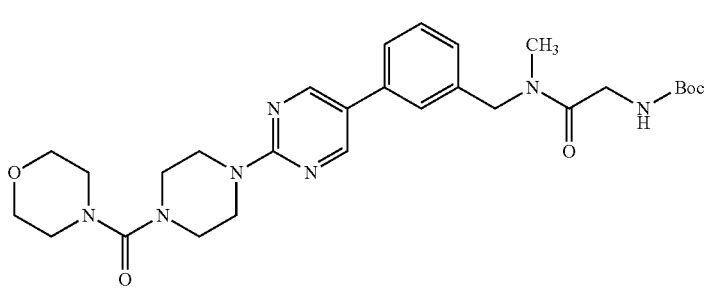 | — |
TABLE 50
| Rf | Syn | Structure | Acid |
|---|---|---|---|
| 243 | R237 | 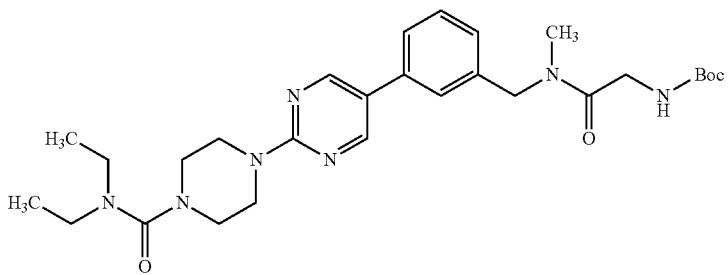 [SMILES: CCN(CC)C(=O)N1CCN(c2ncc(-c3cccc(CN(C)C(=O)CNC(=O)OC(C)(C)C)c3)cn2)CC1] | — |
| 244 | R237 | 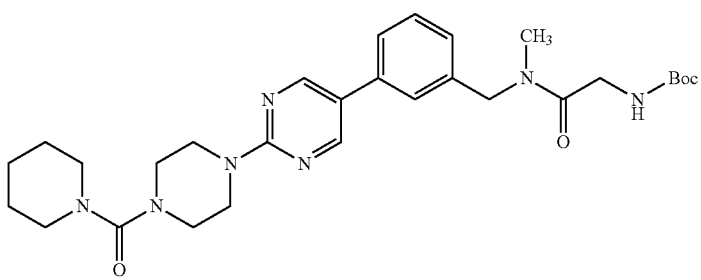 | — |
| 245 | R245 | 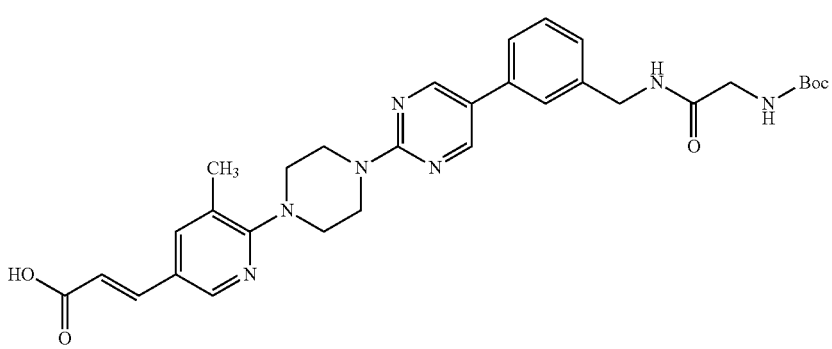 [SMILES: Cc1cc(/C=C/C(=O)O)cnc1N1CCN(c2ncc(-c3cccc(CNC(=O)CNC(=O)OC(C)(C)C)c3)cn2)CC1] | — |

TABLE 50-continued
| Rf | Syn | Structure | Acid |
|---|---|---|---|
| 246 | R245 | 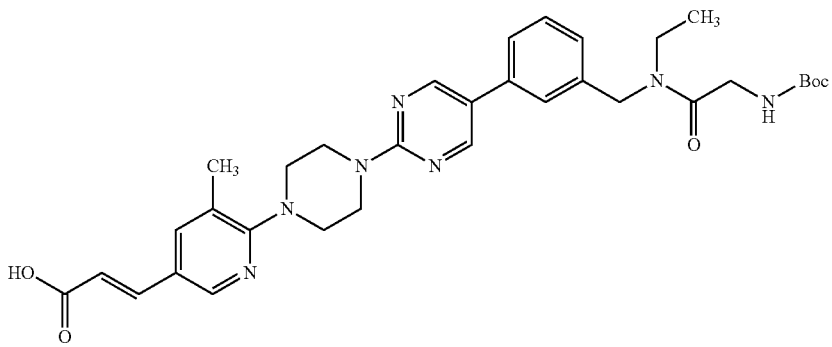 [SMILES: CCN(Cc1cccc(-c2cnc(N3CCN(c4ncc(/C=C/C(=O)O)cc4C)CC3)nc2)c1)C(=O)CNC(=O)OC(C)(C)C] | — |
TABLE 51
| Rf | Syn | Structure | Acid |
|---|---|---|---|
| 247 | R245 | 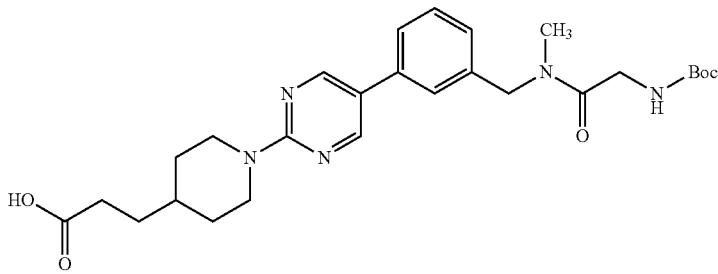 [SMILES: CN(Cc1cccc(-c2cnc(N3CCC(CCC(=O)O)CC3)nc2)c1)C(=O)CNC(=O)OC(C)(C)C] | — |
| 248 | R245 | 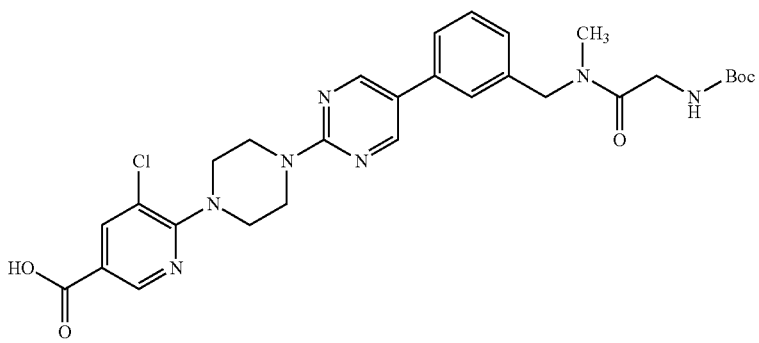 [SMILES: CN(Cc1cccc(-c2cnc(N3CCN(c4ncc(C(=O)O)cc4Cl)CC3)nc2)c1)C(=O)CNC(=O)OC(C)(C)C] | — |
| 249 | R245 | 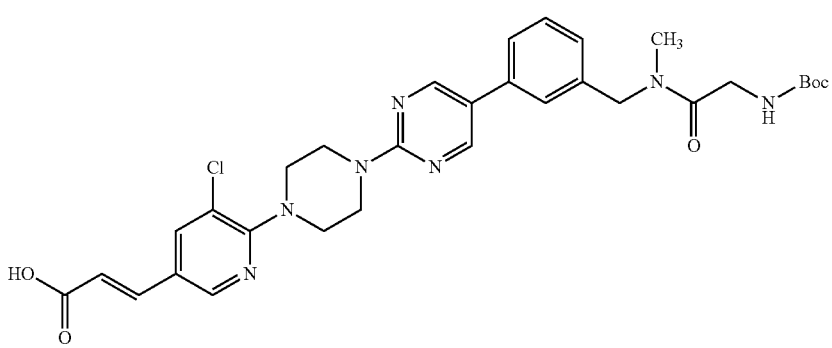 [SMILES: CN(Cc1cccc(-c2cnc(N3CCN(c4ncc(/C=C/C(=O)O)cc4Cl)CC3)nc2)c1)C(=O)CNC(=O)OC(C)(C)C] | — |

TABLE 51-continued

| Rf | Syn | Structure | Acid |
|----|-----|-----------|------|
| 250 | R245 | 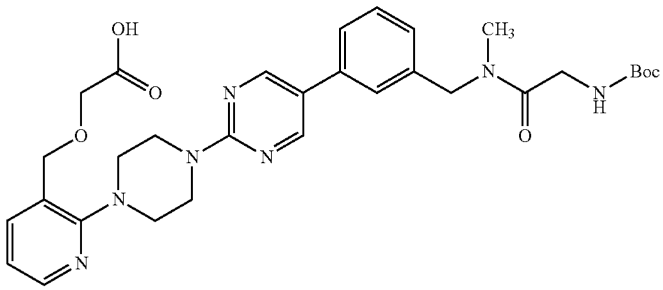 [SMILES: CN(Cc1cccc(-c2cnc(N3CCN(c4ncccc4COCC(=O)O)CC3)nc2)c1)C(=O)CNC(=O)OC(C)(C)C] | — |
| 251 | R245 | 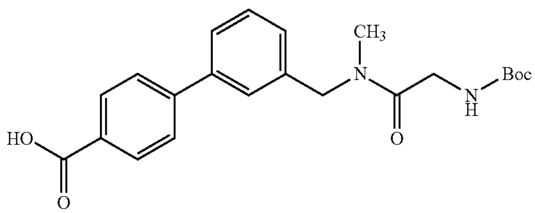 [SMILES: CN(Cc1cccc(-c2ccc(C(=O)O)cc2)c1)C(=O)CNC(=O)OC(C)(C)C] | — |

TABLE 52

| Rf | Syn | Structure | Acid |
|----|-----|-----------|------|
| 252 | R245 | 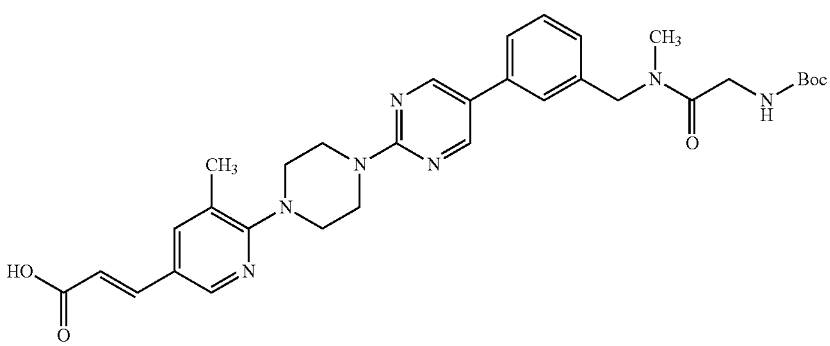 [SMILES: Cc1cc(/C=C/C(=O)O)cnc1N1CCN(c2ncc(-c3cccc(CN(C)C(=O)CNC(=O)OC(C)(C)C)c3)cn2)CC1] | — |
| 253 | R245 | 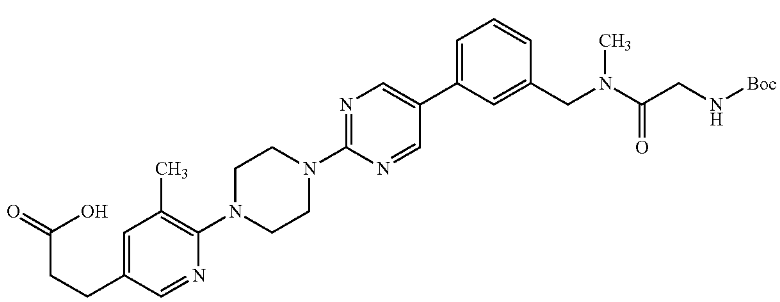 [SMILES: Cc1cc(CCC(=O)O)cnc1N1CCN(c2ncc(-c3cccc(CN(C)C(=O)CNC(=O)OC(C)(C)C)c3)cn2)CC1] | — |

TABLE 52-continued

| Rf | Syn | Structure | Acid |
|---|---|---|---|
| 254 | R245 | (structure) | — |
| 255 | R255 | (structure) | — |
| 256 | R255 | (structure) | — |

TABLE 53

| Rf | Syn | Structure | Acid |
|---|---|---|---|
| 257 | R257 | (structure) | — |
| 258 | R258 | (structure) | — |
| 259 | R259 | (structure) | — |

TABLE 53-continued

| Rf | Syn | Structure | Acid |
|---|---|---|---|
| 260 | R260 | 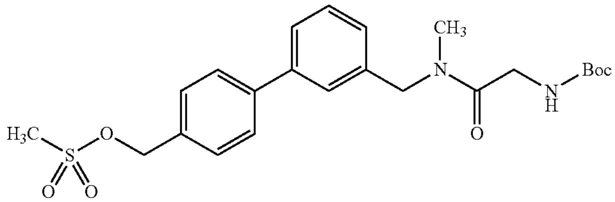 [SMILES: CN(Cc1cccc(-c2ccc(COS(C)(=O)=O)cc2)c1)C(=O)CNC(=O)OC(C)(C)C] | — |
| 261 | R261 | 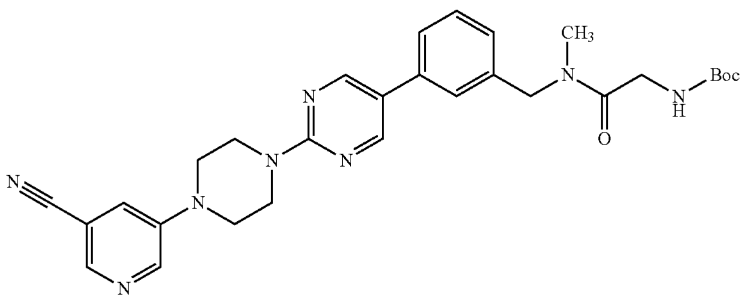 [SMILES: CN(Cc1cccc(-c2cnc(N3CCN(c4cncc(C#N)c4)CC3)nc2)c1)C(=O)CNC(=O)OC(C)(C)C] | — |

TABLE 54

| Rf | Syn | Structure | Acid |
|---|---|---|---|
| 262 | R261 | 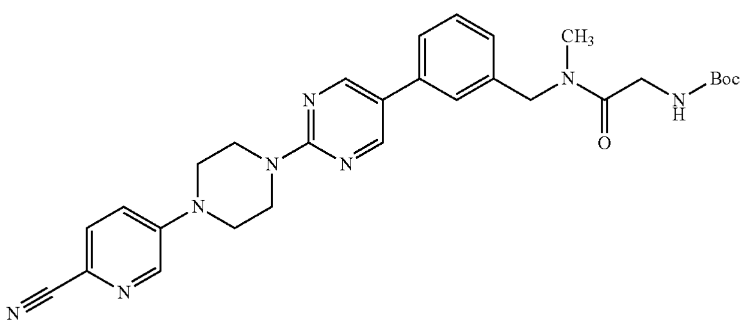 [SMILES: CN(Cc1cccc(-c2cnc(N3CCN(c4ccc(C#N)nc4)CC3)nc2)c1)C(=O)CNC(=O)OC(C)(C)C] | — |
| 263 | R261 | 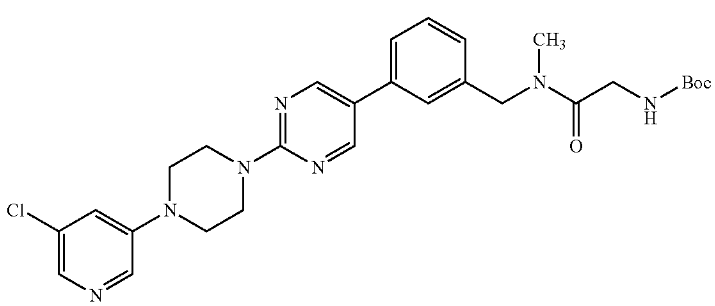 [SMILES: CN(Cc1cccc(-c2cnc(N3CCN(c4cncc(Cl)c4)CC3)nc2)c1)C(=O)CNC(=O)OC(C)(C)C] | — |

TABLE 54-continued

| Rf | Syn | Structure | Acid |
|---|---|---|---|
| 264 | R261 | 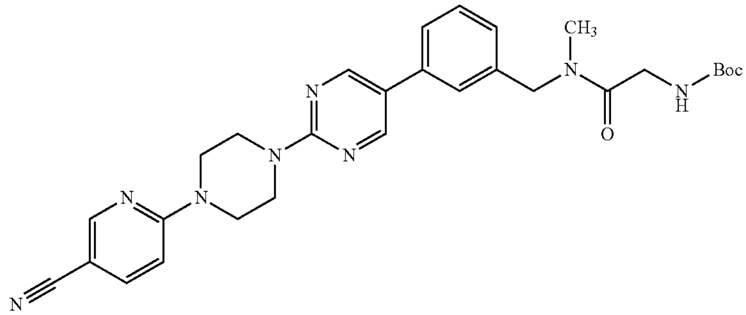 [SMILES: CN(Cc1cccc(-c2cnc(N3CCN(c4ccc(C#N)cn4)CC3)nc2)c1)C(=O)CNC(=O)OC(C)(C)C] | — |
| 265 | R261 | trans | — |

TABLE 55

| Rf | Syn | Structure | Acid |
|---|---|---|---|
| 266 | R266 | 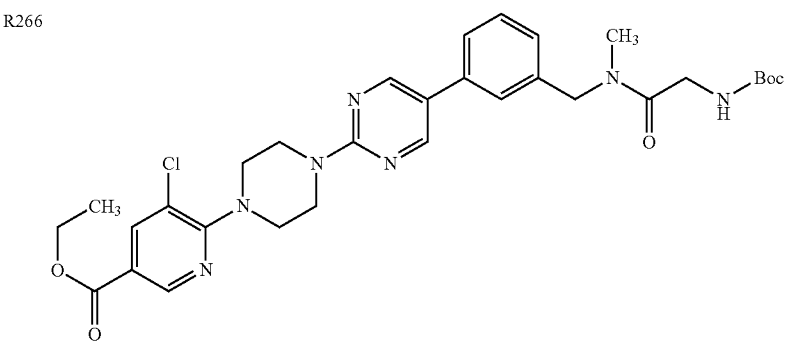 | — |
| 267 | R266 | 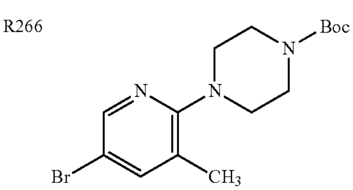 | — |
| 268 | R266 | 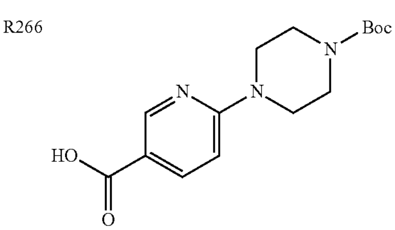 | — |

TABLE 55-continued

| Rf | Syn | Structure | Acid |
|---|---|---|---|
| 269 | R266 | 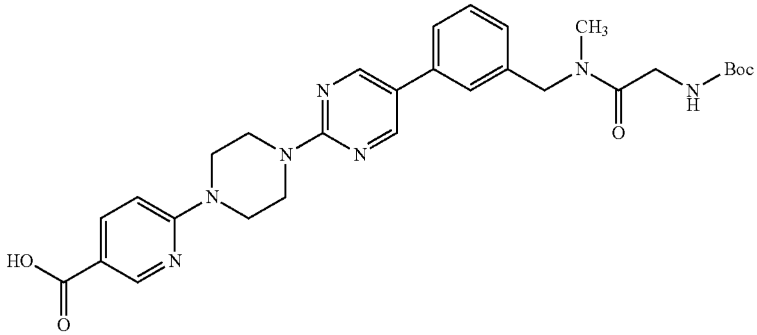 [SMILES: CN(Cc1cccc(-c2cnc(N3CCN(c4ccc(C(=O)O)cn4)CC3)nc2)c1)C(=O)CNC(=O)OC(C)(C)C] | — |
| 270 | R270 | 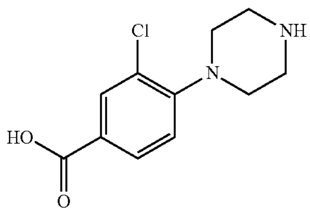 [SMILES: O=C(O)c1ccc(N2CCNCC2)c(Cl)c1] | HCl |

TABLE 56

| Rf | Syn | Structure | Acid |
|---|---|---|---|
| 271 | R271 | 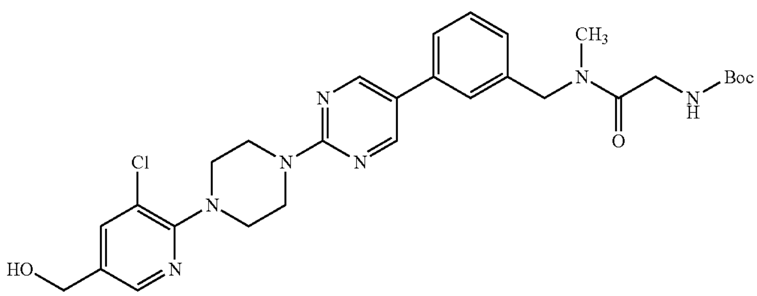 [SMILES: CN(Cc1cccc(-c2cnc(N3CCN(c4ncc(CO)cc4Cl)CC3)nc2)c1)C(=O)CNC(=O)OC(C)(C)C] | — |
| 272 | R272 | 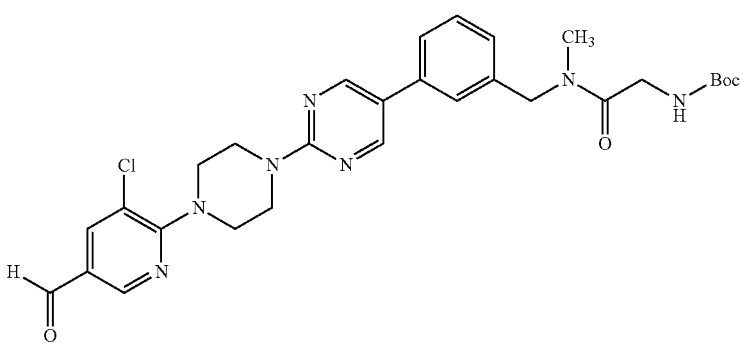 [SMILES: CN(Cc1cccc(-c2cnc(N3CCN(c4ncc(C=O)cc4Cl)CC3)nc2)c1)C(=O)CNC(=O)OC(C)(C)C] | — |
| 273 | R273 | 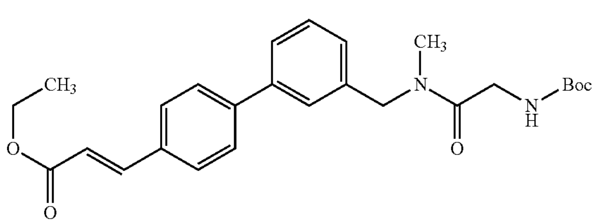 [SMILES: CCOC(=O)/C=C/c1ccc(-c2cccc(CN(C)C(=O)CNC(=O)OC(C)(C)C)c2)cc1] | — |

TABLE 56-continued

| Rf | Syn | Structure | Acid |
|---|---|---|---|
| 274 | R274 | [structure: ethyl (E)-3-[6-[4-[5-[3-[(N-methyl-N-(Boc-glycyl))aminomethyl]phenyl]pyrimidin-2-yl]piperazin-1-yl]-5-chloropyridin-3-yl]acrylate] | — |
| 275 | R274 | [structure: ethyl (E)-3-[6-(4-Boc-piperazin-1-yl)-5-methylpyridin-3-yl]acrylate] | — |

TABLE 57

| Rf | Syn | Structure | Acid |
|---|---|---|---|
| 276 | R276 | [structure: N-Boc-glycyl-N-methyl-N-[3-[2-[4-(4-aminophenyl)piperazin-1-yl]pyrimidin-5-yl]benzyl]amine] | — |
| 277 | R277 | [structure: 7-nitro-1,2,3,4-tetrahydroisoquinoline] | — |
| 278 | R278 | [structure: 2-amino-5-(1-Boc-piperidin-4-yl)pyridine] | — |

TABLE 57-continued
| Rf | Syn | Structure | Acid |
|----|-----|-----------|------|
| 279 | R278 | 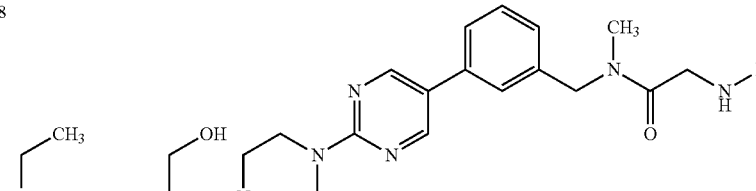 | — |
| 280 | R278 | 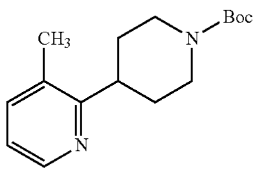 [SMILES: Cc1cccnc1C1CCN(C(=O)OC(C)(C)C)CC1] | — |
| 281 | R278 | 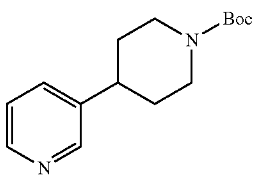 [SMILES: CC(C)(C)OC(=O)N1CCC(c2cccnc2)CC1] | — |
TABLE 58
| Rf | Syn | Structure | Acid |
|----|-----|-----------|------|
| 282 | R278 | 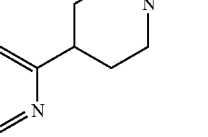 | — |
| 283 | R278 | 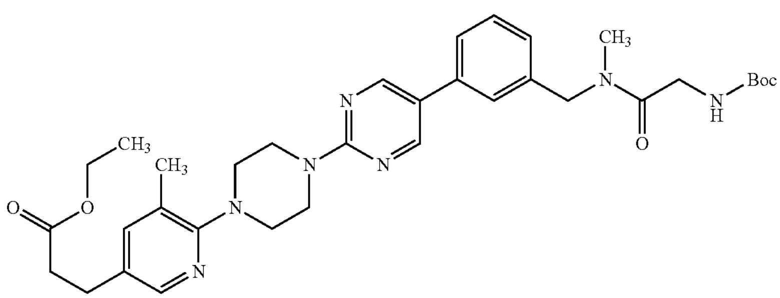 [SMILES: CCOC(=O)CCc1cnc(N2CCN(c3ncc(-c4cccc(CN(C)C(=O)CNC(=O)OC(C)(C)C)c4)cn3)CC2)c(C)c1] | — |
| 284 | R278 | 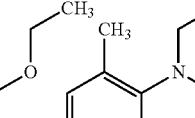 | — |

TABLE 58-continued

| Rf | Syn | Structure | Acid |
|---|---|---|---|
| 285 | R285 | 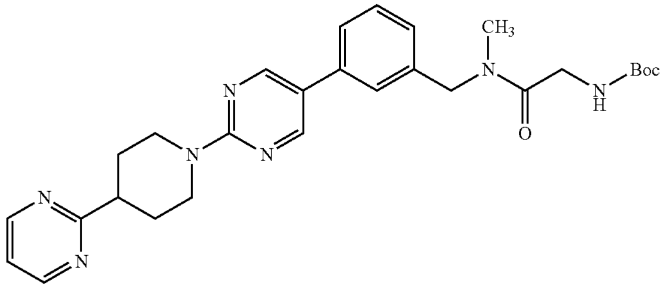 | — |
| 286 | R286 | 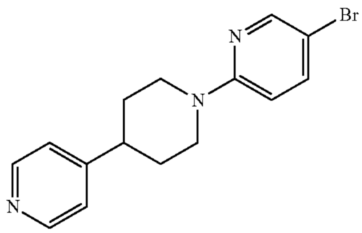 [SMILES: Brc1ccc(N2CCC(c3ccncc3)CC2)nc1] | — |

TABLE 59

| Rf | Syn | Structure | Acid |
|---|---|---|---|
| 287 | R287 | 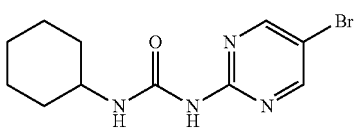 [SMILES: O=C(Nc1ncc(Br)cn1)NC1CCCCC1] | — |
| 288 | R288 | trans | — |
| 289 | R288 | 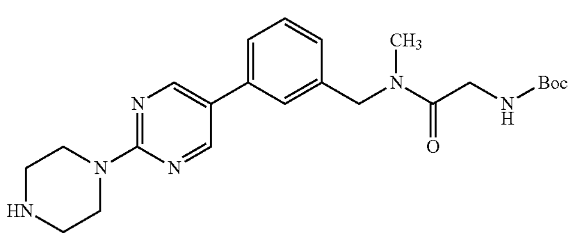 [SMILES: CN(Cc1cccc(-c2cnc(N3CCNCC3)nc2)c1)C(=O)CNC(=O)OC(C)(C)C] | — |
| 290 | R288 | 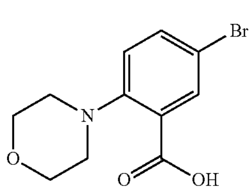 [SMILES: O=C(O)c1cc(Br)ccc1N1CCOCC1] | — |

TABLE 59-continued

| Rf | Syn | Structure | Acid |
|---|---|---|---|
| 291 | R288 | 2-(piperazin-1-yl)nicotinonitrile | — |
| 292 | R288 | 3-chloro-2-(piperazin-1-yl)pyridine | — |

TABLE 60

| Rf | Syn | Structure | Acid |
|---|---|---|---|
| 293 | R288 | 2-(piperazin-1-yl)-5-(trifluoromethyl)pyridine | — |
| 294 | R288 | 5-chloro-2-(piperazin-1-yl)pyridine | — |
| 295 | R288 | 5-bromo-2-(piperazin-1-yl)pyridine | — |
| 296 | R296 | biphenyl cyclohexanecarboxamide with N-methyl-N-Boc-glycinamide substituent | — |
| 297 | R297 | 4-(4-bromo-2-methylphenyl)morpholine | — |

TABLE 60-continued
| Rf | Syn | Structure | Acid |
|---|---|---|---|
| 298 | R297 | 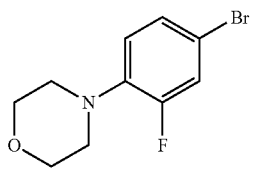 [SMILES: Fc1cc(Br)ccc1N1CCOCC1] | — |
TABLE 61
| Rf | Syn | Structure | Acid |
|---|---|---|---|
| 299 | R297 | 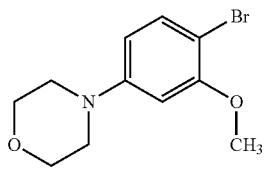 | — |
| 300 | R297 | 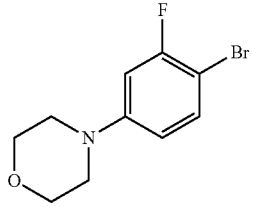 [SMILES: Fc1cc(N2CCOCC2)ccc1Br] | — |
| 301 | R297 | 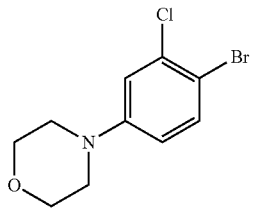 [SMILES: Clc1cc(N2CCOCC2)ccc1Br] | — |
| 302 | R302 | 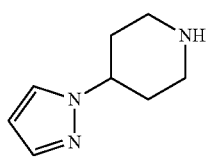 [SMILES: c1cnn(C2CCNCC2)c1] | 2HCl |
| 303 | R303 | 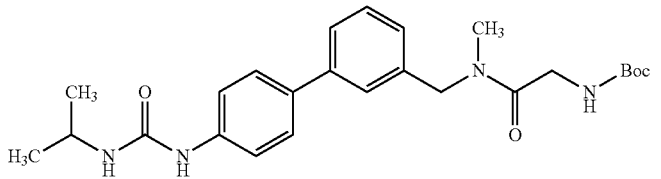 [SMILES: CC(C)NC(=O)Nc1ccc(-c2cccc(CN(C)C(=O)CNC(=O)OC(C)(C)C)c2)cc1] | — |
| 304 | R304 | 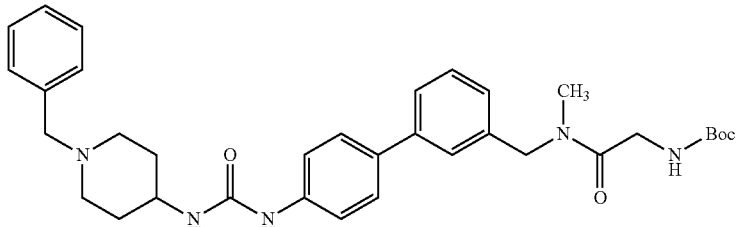 | — |

TABLE 62

| Rf | Syn | Structure | Acid |
|---|---|---|---|
| 305 | R304 | [structure] | — |
| 306 | R306 | [structure] | — |
| 307 | R306 | [structure] | — |
| 308 | R306 | [structure] | — |
| 309 | R309 | [structure] | — |
| 310 | R309 | [structure] | — |
| 311 | R309 | [structure] | — |

TABLE 63

| Rf | Syn | Structure | Acid |
|---|---|---|---|
| 312 | R309 | [structure] | — |

TABLE 63-continued

| Rf | Syn | Structure | Acid |
|---|---|---|---|
| 313 | R313 | 2-(pyridin-3-yl)-4-(4-bromophenyl)thiazole | HBr |
| 314 | R314 | 1-Boc-4-(2-methylpyridin-4-yl)piperazine | — |
| 315 | R315 | 1-Boc-4-(pyridin-4-yl)-1,2,3,6-tetrahydropyridine | — |
| 316 | R316 | 1-Boc-4-(3-(hydroxymethyl)pyridin-2-yl)piperazine | — |
| 317 | R316 | 1-Boc-4-(5-bromo-3-(hydroxymethyl)pyridin-2-yl)piperazine | — |
| 318 | R318 | 1-Boc-4-(5-methylpyrimidin-4-yl)piperazine | — |
| 319 | R318 | tert-butyl (2-(N-methyl-N-(3-(2-(4-(pyridazin-3-yl)piperazin-1-yl)pyrimidin-5-yl)benzyl)amino)-2-oxoethyl)carbamate | — |

TABLE 64

| Rf | Syn | Structure | Acid |
|---|---|---|---|
| 320 | R320 | tert-butyl (2-((4'-(4-acetylpiperazin-1-yl)-[1,1'-biphenyl]-3-yl)methyl(methyl)amino)-2-oxoethyl)carbamate | — |

TABLE 64-continued

| Rf | Syn | Structure | Acid |
|---|---|---|---|
| 321 | R320 | (structure) | — |
| 322 | R320 | (structure) | — |
| 323 | R321 | (structure) | — |
| 324 | R321 | (structure) | — |

TABLE 65

| Rf | Syn | Structure | Acid |
|---|---|---|---|
| 325 | R325 | (structure) | — |
| 326 | R326 | (structure) | — |

TABLE 65-continued
| Rf | Syn | Structure | Acid |
|---|---|---|---|
| 327 | R327 | 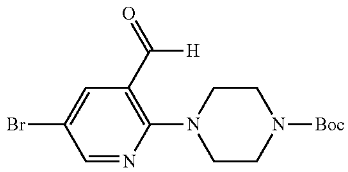 [SMILES: CC(C)(C)OC(=O)N1CCN(c2ncc(Br)cc2C=O)CC1] | — |
| 328 | R328 | 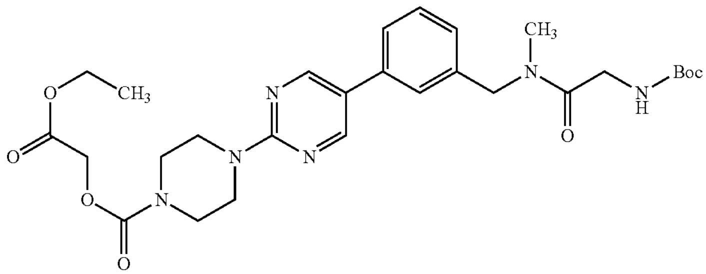 [SMILES: CCOC(=O)COC(=O)N1CCN(c2ncc(-c3cccc(CN(C)C(=O)CNC(=O)OC(C)(C)C)c3)cn2)CC1] | — |
| 329 | R329 | 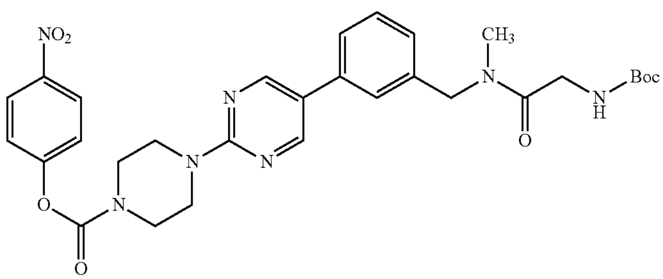 [SMILES: CN(Cc1cccc(-c2cnc(N3CCN(C(=O)Oc4ccc([N+](=O)[O-])cc4)CC3)nc2)c1)C(=O)CNC(=O)OC(C)(C)C] | — |
| 330 | R330 | 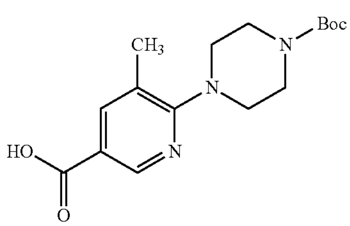 [SMILES: Cc1cc(C(=O)O)cnc1N1CCN(C(=O)OC(C)(C)C)CC1] | — |
TABLE 66
| Rf | Syn | Structure | Acid |
|---|---|---|---|
| 331 | R7 | 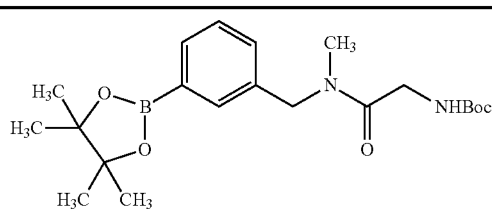 | — |

TABLE 66-continued
| Rf | Syn | Structure | Acid |
|---|---|---|---|
| 332 | R245 | 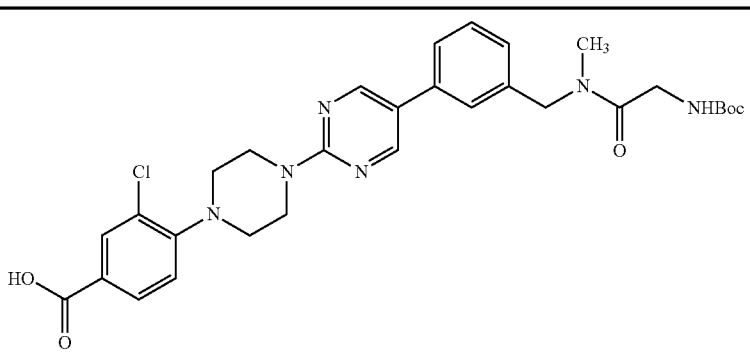 | — |
| 333 | R92 | 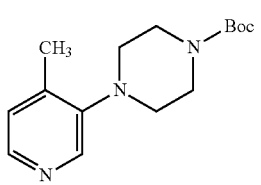 [SMILES: Cc1ccncc1N1CCN(C(=O)OC(C)(C)C)CC1] | — |
| 334 | R115 | 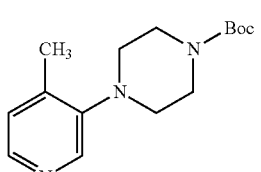 | 3HCl |
| 335 | R296 | 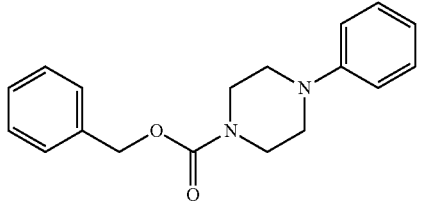 [SMILES: O=C(OCc1ccccc1)N1CCN(c2ccccc2)CC1] | — |
| 336 | R338 | 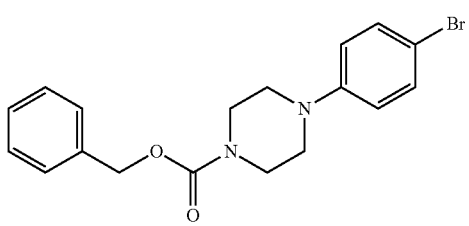 [SMILES: O=C(OCc1ccccc1)N1CCN(c2ccc(Br)cc2)CC1] | — |
TABLE 67
| Rf | Syn | Structure | Acid |
|---|---|---|---|
| 337 | R10 | 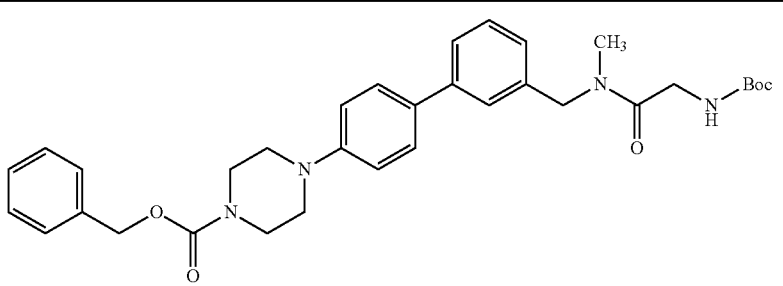 | — |

TABLE 67-continued

| Rf | Syn | Structure | Acid |
|---|---|---|---|
| 338 | R340 | [structure: 4'-(piperazin-1-yl)biphenyl-3-yl)methyl with N-CH3, C(=O)CH2NHBoc] | — |

TABLE 68

| Rf | Data |
|---|---|
| 1 | ESI+: 214 |
| 2 | FAB+: 357 |
| 3 | ESI+: 371 |
| 4 | ESI+: 301 |
| 5 | ESI+: 302 |
| 6 | ESI+: 301 |
| 7 | ESI+: 391 |
| 8 | ESI+: 419 |
| 9 | ESI+: 442 |
| 10 | ESI+: 426 |
| 11 | ESI+: 441 |
| 12 | ESI+: 468 |
| 13 | ESI+: 453 |
| 14 | ESI+: 370 |
| 15 | ESI+: 515 |
| 16 | ESI+: 385 |
| 17 | ESI+: 532 |
| 18 | ESI+: 590 |
| 19 | ESI+: 532 |
| 20 | ESI+: 532 |
| 21 | ESI+: 524 |
| 22 | ESI+: 484 |
| 23 | ESI+: 509 |
| 24 | ESI+: 533 |
| 25 | ESI+: 475 |
| 26 | ESI+: 512 |
| 27 | ESI+: 497 |
| 28 | ESI+: 470 |
| 29 | ESI+: 484 |
| 30 | ESI+: 502 |
| 31 | ESI+: 547 |
| 32 | ESI+: 616 |
| 33 | ESI+: 644 |
| 34 | ESI+: 526 |

TABLE 69

| Rf | Data |
|---|---|
| 35 | ESI+: 456 |
| 36 | ESI+: 470 |
| 37 | ESI+: 456 |
| 38 | ESI+: 470 |
| 39 | ESI+: 454 |
| 40 | ESI+: 517 |
| 41 | ESI+: 483 |
| 42 | ESI+: 477 |
| 43 | ESI+: 491 |
| 44 | ESI+: 547 |
| 45 | ESI+: 561 |
| 46 | ESI+: 518 |
| 47 | ESI+: 477 |
| 48 | ESI+: 463 |
| 49 | ESI+: 538 |
| 50 | ESI+: 525 |
| 51 | ESI+: 519 |
| 52 | ESI+: 517 |
| 53 | ESI+: 531 |
| 54 | ESI+: 535 |
| 55 | ESI+: 551 |
| 56 | ESI+: 532 |
| 57 | ESI+: 485 |
| 58 | ESI+: 554 |
| 59 | ESI+: 513 |
| 60 | ESI+: 488 |
| 61 | ESI+: 469 |
| 62 | ESI+: 477 |
| 63 | ESI+: 532 |
| 64 | ESI+: 576 |
| 65 | ESI+: 552 |
| 66 | ESI+: 532 |
| 67 | ESI+: 543 |
| 68 | ESI+: 552 |

TABLE 70

| Rf | Data |
|---|---|
| 69 | ESI+: 586 |
| 70 | ESI+: 531 |
| 71 | ESI+: 536 |
| 72 | ESI+: 553 |
| 73 | ESI+: 546 |
| 74 | ESI+: 552 |
| 75 | ESI+: 598 |
| 76 | ESI+: 484 |
| 77 | ESI+: 497 |
| 78 | ESI+: 483 |
| 79 | ESI+: 523 |
| 80 | ESI+: 482 |
| 81 | ESI+: 456 |
| 82 | ESI+: 456 |
| 83 | ESI+: 483 |
| 84 | ESI+: 512 |
| 85 | ESI+: 498 |
| 86 | ESI+: 554 |
| 87 | ESI+: 616 |
| 88 | ESI+: 589 |
| 89 | ESI+: 477 |
| 90 | ESI+: 536 |
| 91 | ESI+: 133 |
| 92 | ESI+: 336 |
| 93 | ESI+: 278 |
| 94 | ESI+: 278 |
| 95 | ESI+: 322 |
| 96 | ESI+: 298 |
| 97 | ESI+: 292 |
| 98 | ESI+: 292 |
| 99 | ESI+: 282 |
| 100 | ESI+: 282 |
| 101 | ESI+: 294 |
| 102 | ESI+: 306 |

TABLE 71

| Rf | Data |
|---|---|
| 103 | ESI+: 336 |
| 104 | ESI+: 278 |
| 105 | ESI+: 278 |
| 106 | NMR-CDCl₃: 1.45-1.55 (9H, m), 2.33 (3H, s), 3.32-3.42 (4H, m), 3.50-3.64 (4H, m), 7.82-7.87 (1H, m), 8.51-8.56 (1H, m), 9.91 (1H, s) |
| 107 | ESI+: 178 |
| 108 | ESI+: 236 ([M − tBu + H]+) |
| 109 | ESI+: 308 |
| 110 | ESI+: 313 |
| 111 | ESI+: 342, 344 |
| 112 | APCI+: 232 |
| 113 | ESI+: 199. 201 |
| 114 | ESI+: 198, 200 |
| 115 | ESI+: 236 |
| 116 | ESI+: 178 |
| 117 | ESI+: 178 |
| 118 | ESI+: 178 |
| 119 | ESI+: 222 |
| 120 | ESI+: 198 |
| 121 | ESI+: 177 |
| 122 | ESI+: 262 |
| 123 | ESI+: 208 |
| 124 | ESI+: 546 |
| 125 | ESI+: 546 |
| 126 | ESI+: 548 |
| 127 | ESI+: 536 |
| 128 | ESI+: 561 |
| 129 | ESI+: 548 |
| 130 | ESI+: 533 |
| 131 | ESI+: 568 |
| 132 | ESI+: 534 |
| 133 | ESI+: 567 |
| 134 | ESI+: 620 |

TABLE 72

| Rf | Data |
|---|---|
| 135 | ESI+: 498 |
| 136 | ESI+: 553 |
| 137 | ESI+: 551 |
| 138 | ESI+: 537 |
| 139 | ESI+: 512 |
| 140 | ESI+: 590 |
| 141 | ESI+: 646 |
| 142 | ESI+: 517 |
| 143 | ESI+: 630 |
| 144 | ESI+: 316, 318 |
| 145 | ESI+: 316, 318 |
| 146 | ESI+: 321 |
| 147 | APCI+: 203 |
| 148 | ESI+: 245 |
| 149 | ESI+: 271 |
| 150 | ESI+: 274 |
| 151 | ESI+: 279 |
| 152 | ESI+: 271 |
| 153 | ESI+: 320 |
| 154 | ESI+: 321 |
| 155 | ESI+: 319 |
| 156 | ESI+: 319 |
| 157 | ESI+: 333, 335 |
| 158 | ESI+: 332, 334 |
| 159 | ESI+: 293 |
| 160 | ESI+: 389 |
| 161 | ESI+: 412 |
| 162 | ESI+: 440 |
| 163 | ESI+: 441 |
| 164 | ESI+: 412 |
| 165 | ESI+: 370 |
| 166 | FAB+: 383 |
| 167 | FAB+: 380 |
| 168 | ESI+: 427 |

TABLE 73

| Rf | Data |
|---|---|
| 169 | ESI+: 261 |
| 170 | ESI+: 275 |
| 171 | ESI+: 470 |
| 172 | ESI+: 472 |
| 173 | ESI+: 469 |
| 174 | ESI+: 444 |
| 175 | ESI+: 470 |
| 176 | ESI+: 456 |
| 177 | ESI+: 518 |
| 178 | ESI+: 519 |
| 179 | ESI+: 405 |
| 180 | ESI+: 377 |
| 181 | ESI+: 518 |
| 182 | ESI+: 518 |
| 183 | ESI+: 517 |
| 184 | APCI+: 458 |
| 185 | ESI+: 374 ([M − Boc]+) |
| 186 | ESI−: 399 |
| 187 | ESI+: 497 |
| 188 | ESI+: 391 |
| 189 | ESI+: 497 |
| 190 | ESI+: 498 |
| 191 | ESI+: 358 ([M − Boc]+) |
| 192 | ESI+: 454 |
| 193 | ESI+: 517 |
| 194 | ESI+: 276 |
| 195 | NMR-CDCl₃: 1.44 (2.7H, s), 1.47 (6.3H, s), 2.79-2.87 (2H, m), 2.92 (2.1H, s), 3.02 (0.9H, s), 3.92-4.11 (4H, m), 4.24-4.31 (2H, m), 4.52 (0.6H, s), 4.66 (1.4H, s), 5.50-5.63 (1H, m), 6.73-6.82 (2H, m), 7.05-7.20 (2H, m), 7.22-7.31 (1H, m), 7.35-7.51 (3H, m), 7.64-7.76 (2H, m), 8.43-8.48 (1H, m), 8.57-8.62 (1H, m) |

TABLE 74

| Rf | Data |
|---|---|
| 196 | NMR-CDCl₃: 1.44 (2.7H, s), 1.47 (6.3H, s), 2.66-2.73 (2H, m), 2.92 (2.1H, s), 3.02 (0.9H, s), 3.92-4.11 (4H, m), 4.18-4.27 (2H, m), 4.52 (0.6H, s), 4.66 (1.4H, s), 5.50-5.63 (1H, m), 6.24-6.32 (1H, m), 6.75 (1H, d, J = 8.8 Hz), 7.05-7.20 (1H, m), 7.23-7.32 (1H, m), 7.35-7.51 (3H, m), 7.67-7.78 (2H, m), 8.43-8.48 (1H, m), 8.49-8.54 (1H, m), 8.69-8.74 (1H, m) |
| 197 | API−: 382 |
| 198 | ESI+: 518 |
| 199 | ESI−: 482 |
| 200 | ESI+: 590 |
| 201 | ESI+: 557 |
| 202 | ESI+: 495 |
| 203 | ESI+: 440 |
| 204 | ESI+: 496 |
| 205 | ESI+: 601 |
| 206 | ESI+: 585 |
| 207 | ESI+: 496 |
| 208 | ESI+: 585 |
| 209 | ESI+: 531 |
| 210 | ESI+: 496 |
| 211 | ESI+: 573 |
| 212 | ESI+: 511 |
| 213 | ESI+: 551 |
| 214 | ESI+: 553 |
| 215 | ESI+: 579 |
| 216 | ESI+: 539 |
| 217 | ESI−: 582 |
| 218 | API+: 496 |
| 219 | ESI+: 511 |
| 220 | ESI+: 468 |
| 221 | ESI+: 496 |
| 222 | FAB−: 440 |
| 223 | ESI+: 458 |
| 224 | ESI−: 494 |
| 225 | FAB−: 450 |

TABLE 75

| Rf | Data |
|---|---|
| 226 | ESI−: 436 |
| 227 | FAB+: 475 |
| 228 | ESI−: 473 |
| 229 | ESI+: 495 |
| 230 | ESI+: 456 |
| 231 | ESI+: 440 |
| 232 | ESI+: 535 |
| 233 | NMR-CDCl$_3$: 1.44 (3.6H, s), 1.46 (5.4H, s), 2.80 (1.2H, s), 2.90 (1.8H, s), 3.0-3.1 (6H, m), 3.99-4.09 (2H, m), 4.51 (0.8H, s), 4.66 (1.2H, s), 5.52-5.62 (1H, br), 7.05-7.55 (8H, m) |
| 234 | ESI+: 456 |
| 235 | NMR-CDCl$_3$: 1.44 (3.6H, s), 1.46 (5.4H, s), 2.27 (3H, s), 2.64 (2H, t, J = 6 Hz), 2.91 (1.8H, s), 3.02 (1.2H, s), 3.59-3.69 (4H, m), 3.99-4.09 (2H, m), 4.53 (0.8H, s), 4.67 (1.2H, s), 5.52-5.63 (1H, br), 7.10-7.23 (1H, m), 7.32-7.57 (7H, m) |
| 236 | ESI+: 557 |
| 237 | ESI+: 527 |
| 238 | ESI+: 499 |
| 239 | ESI+: 527 |
| 240 | ESI+: 527 |
| 241 | ESI+: 541 |
| 242 | ESI+: 554 |
| 243 | ESI+: 540 |
| 244 | ESI+: 552 |
| 245 | ESI+: 588 |
| 246 | ESI+: 616 |
| 247 | ESI+: 512 |
| 248 | ESI+: 596, 598 |
| 249 | ESI+: 622, 624 |
| 250 | ESI+: 606 |
| 251 | ESI−: 397 |
| 252 | ESI+: 602 |
| 253 | ESI+: 604 |
| 254 | ESI+: 561 |

TABLE 76

| Rf | Data |
|---|---|
| 255 | ESI+: 392 |
| 256 | ESI+: 362 |
| 257 | FAB+: 384 |
| 258 | ESI+: 220 |
| 259 | ESI+: 302 |
| 260 | ESI+: 463 |
| 261 | ESI+: 543 |
| 262 | ESI+: 543 |
| 263 | ESI+: 552, 554 |
| 264 | ESI+: 543 |
| 265 | ESI+: 546 |
| 266 | ESI+: 624, 626 |
| 267 | ESI+: 356, 358 |
| 268 | ESI+: 308 |
| 269 | ESI+: 562 |
| 270 | ESI+: 241 |
| 271 | ESI+: 582, 584 |
| 272 | ESI+: 580, 582 |
| 273 | ESI+: 453 |
| 274 | ESI+: 650, 652 |
| 275 | ESI+: 376 |
| 276 | ESI+: 533 |
| 277 | APCI+: 261 |
| 278 | ESI+: 278 |
| 279 | ESI+: 648 |
| 280 | ESI+: 277 |
| 281 | ESI+: 263 |
| 282 | ESI+: 263 |
| 283 | ESI+: 632 |
| 284 | ESI+: 618 |
| 285 | ESI+: 518 |
| 286 | ESI+: 320 |
| 287 | ESI+: 301 |
| 288 | ESI+: 469 |

TABLE 77

| Rf | Data |
|---|---|
| 289 | ESI+: 441 |
| 290 | ESI+: 286 |
| 291 | ESI+: 189 |
| 292 | ESI+: 198 |
| 293 | ESI+: 232 |
| 294 | ESI+: 198 |
| 295 | ESI+: 242 |
| 296 | ESI−: 478 |
| 297 | ESI+: 258 |
| 298 | ES+: 262 |
| 299 | ESI+: 274 |
| 300 | ESI+: 262 |
| 301 | ESI+: 278 |
| 302 | ESI+: 152 |
| 303 | ESI+: 455 |
| 304 | NMR-CDCl$_3$: 1.39-1.55 (11H, m), 1.92-2.03 (2H, m), 2.08-2.20 (2H, m), 2.77-2.87 (2H, m), 2.90 (1.8H, s), 3.01 (1.2H, s), 3.50 (2H, s), 3.67-3.80 (1H, m), 3.99-4.08 (2H, m), 4.50 (0.8H, s), 4.65 (1.2H, s), 4.65-4.72 (1H, m), 5.52-5.61 (1H, m), 6.39-6.46 (1H, m), 7.06-7.52 (13H, m) |
| 305 | ESI+: 496 |
| 306 | ESI+: 464 |
| 307 | ESI+: 533 |
| 308 | ESI+: 486 |
| 309 | ESI+: 233 |
| 310 | ESI+: 299 |
| 311 | ESI+: 297 |
| 312 | ESI+: 283 |
| 313 | ESI+: 316 |
| 314 | ESI+: 278 |
| 315 | ESI+: 261 |
| 316 | ESI+: 294 |
| 317 | ESI+: 375 |
| 318 | ESI+: 279 |
| 319 | ESI+: 519 |

TABLE 78

| Rf | Data |
|---|---|
| 320 | ESI+: 481 |
| 321 | ESI+: 495 |
| 322 | ESI+: 541 |
| 323 | ESI+: 380 |
| 324 | EI: 257 |
| 325 | ESI+: 467 |
| 326 | ESI+: 201 |
| 327 | ESI+: 370 |
| 328 | ESI+: 571 |
| 329 | ESI+: 606 |
| 330 | ESI+: 322 |
| 331 | ESI+: 405 |
| 332 | ESI+: 595 |
| 333 | ESI+: 278 |
| 334 | ESI+: 178 |
| 335 | ESI+: 297 |
| 336 | ESI+: 376 |
| 337 | ESI+: 573 |
| 338 | ESI+: 439 |

Example 1 tert-Butyl {2-[(3-bromobenzyl)amino]-2-oxoethyl} carbamate (350 mg) was dissolved in DME (3 ml) and water (1.5 ml), and 1,4-benzodioxane-6-boronic acid (194 mg), sodium carbonate (313 mg), and tetrakis(triphenylphosphine)palladium (34 mg) were added thereto, followed by stirring at 80° C. for 1 day. The reaction mixture was concentrated under reduced pressure, and a saturated aqueous sodium hydrogen carbonate solution was added thereto, followed by extraction with $CHCl_3$. The organic layer was dried over $Na_2SO_4$ and concentrated under reduced pressure. The obtained residue was purified by silica gel column chromatography ($CHCl_3$/MeOH). The product was dissolved in MeOH (3.5 ml), and 4 M hydrogen chloride/EtOAc (2.0 ml) was added thereto, followed by stirring at room temperature for one day. The reaction mixture was concentrated under reduced pressure, and a saturated aqueous sodium hydrogen carbonate solution was added thereto, followed by extraction with $CHCl_3$. The organic layer was dried over $Na_2SO_4$ and concentrated under reduced pressure. The obtained residue was purified by silica gel column chromatography ($CHCl_3$/MeOH). The product was dissolved in EtOH (3 ml), and L-tartaric acid (126 mg) was added thereto, followed by stirring at room temperature for 2 hours. The precipitated solid was collected by filtration to obtain N-[3-(2,3-dihydro-1,4-benzodioxin-6-yl)benzyl]-N-methylglycinamide L-tartrate (453 mg).

Example 2

Azetidine hydrochloride (287 mg) was suspended in DMF (5 ml), and tert-butyl (2-{[3-(2-chloropyrimidin-5-yl)benzyl](methyl)amino}-2-oxoethyl)carbamate (300 mg) and $K_2CO_3$ (849 mg) were added thereto, followed by stirring at 80° C. overnight. The reaction mixture was concentrated under reduced pressure, and then a saturated aqueous sodium hydrogen carbonate solution was added thereto, followed by extraction with $CHCl_3$. The organic layer was dried over $Na_2SO_4$ and the solvent was concentrated under reduced pressure. The obtained residue was purified by silica gel column chromatography (hexane/EtOAc). The product was dissolved in EtOH (4 ml), and 4 M hydrogen chloride/EtOAc (2 ml) was added thereto, followed by stirring at room temperature overnight. The precipitated solid was collected by filtration to obtain N-[3-(2-azetidin-1-ylpyrimidin-5-yl)benzyl]-N-methylglycinamide dihydrochloride (295 mg).

Example 3

1-(3-Methylpyridin-2-yl)piperazine dihydrochloride (3.0 g) and $K_2CO_3$ (8.5 g) were suspended in DMF (100 ml), followed by stirring at 60° C. for 30 minutes. tert-Butyl (2-{[3-(2-chloropyrimidin-5-yl)benzyl](methyl)amino}-2-oxoethyl)carbamate (4.0 g) was added thereto, followed by stirring at 60° C. overnight. The reaction mixture was concentrated under reduced pressure, and a saturated aqueous sodium hydrogen carbonate solution was added thereto, followed by extraction with $CHCl_3$. The organic layer was dried over $Na_2SO_4$, the solvent was concentrated under reduced pressure, and the obtained residue was purified by silica gel column chromatography ($CHCl_3$/MeOH). The product was dissolved in EtOH (40 ml), and 4 M hydrogen chloride/EtOAc (20 ml) was added thereto, followed by stirring at room temperature overnight. The reaction mixture was concentrated under reduced pressure, and then a saturated aqueous sodium hydrogen carbonate solution was added thereto, followed by extraction with $CHCl_3$. The organic layer was dried over $Na_2SO_4$ and the solvent was concentrated under reduced pressure. The obtained residue was purified by silica gel column chromatography ($CHCl_3$/MeOH). The product was dissolved in EtOH (40 ml), and L-tartaric acid (960 mg) was added thereto, followed by stirring at room temperature overnight. The precipitated solid was collected by filtration to obtain N-methyl-N-(3-{2-[4-(3-methylpyridin-2-yl)piperazin-1-yl]pyrimidin-5-yl}benzyl)glycinamide L-tartrate (2.9 g).

Example 19

(2E)-3-[6-(4-{5-[3-({[N-(tert-Butoxycarbonyl)glycyl](methyl)amino}methyl)phenyl]pyrimidin-2-yl}piperazin-1-yl)-5-methylpyridin-3-yl]acrylic acid (147 mg) was dissolved in dioxane (3 ml), and $CHCl_3$ (1 ml) and 4 M hydrogen chloride/dioxane (1 ml) was added thereto, followed by stirring at room temperature overnight. The precipitated solid was collected by filtration to obtain (2E)-3-(6-{-4-[5-(3-{[glycyl(methyl)amino]methyl}phenyl)pyrimidin-2-yl]piperazin-1-yl}-5-methylpyridin-3-yl)acrylic acid dihydrochloride (130 mg).

Example 69

To a solution of tert-butyl (2-{methyl[3-(2-morpholin-4-ylpyrimidin-5-yl)benzyl]amino}-2-oxoethyl)carbamate (230 mg) in MeOH (2.3 ml) was added 4 M hydrogen chloride/EtOAc (1 ml), followed by stirring at room temperature for 4 hours. The reaction mixture was concentrated under reduced pressure, and the obtained residue was subjected to liquid separation with $CHCl_3$ and a saturated aqueous sodium hydrogen carbonate solution. The organic layer was separated, and then the aqueous layer was extracted with $CHCl_3$ again. These organic layers were combined, dried over $Na_2SO_4$, and then concentrated under reduced pressure. The obtained residue was purified by flash column chromatography (NH silica 20 ml, 2% MeOH/$CHCl_3$). The product was dissolved in EtOH (5 ml), and L-tartaric acid was added thereto, followed by stirring for 3 hours. The precipitated solid was collected and washed with EtOH to obtain N-methyl-N-[3-(2-morpholin-4-ylpyrimidin-5-yl)benzyl]glycinamide L-tartrate (191 mg) as a colorless solid.

Example 208

To N-methyl-N-{3-[2-(4-pyridin-3-ylpiperazin-1-yl)pyrimidin-5-yl]benzyl}glycinamide trihydrochloride (140 mg) were added a saturated aqueous sodium hydrogen carbonate solution and $CHCl_3$, and the organic layer was dried over $MgSO_4$ and concentrated under reduced pressure. The mixture was dissolved in EtOH, and L-tartaric acid (40 mg) was added thereto. After stirring at room temperature for 2 hours, the precipitated solid was collected by filtration to obtain N-methyl-N-{3-[2-(4-pyridin-3-ylpiperazin-1-yl)pyrimidin-5-yl]benzyl}glycinamide L-tartrate (151 mg).

Example 209 tert-Butyl 4-(5-methylpyridin-2-yl)piperazine-1-carboxylate (200 mg) was dissolved in MeOH (4 ml), and 4 M hydrogen chloride/EtOAc (2 ml) was added thereto, followed by stirring at room temperature for 5 hours. The reaction mixture was concentrated under reduced pressure and then suspended in DMF (4 ml), and $K_2CO_3$ (500 mg) was added thereto, followed by stirring at 80° C. for 10 minutes. tert-Butyl (2-{[3-(2-chloropyrimidin-5-yl)benzyl](methyl)amino}-2-oxoethyl)carbamate (200 mg) was added thereto, followed by stirring at 80° C. overnight. The reaction mixture was concentrated under reduced pressure, and then a saturated aqueous sodium hydrogen carbonate solution was added thereto, followed by extraction with CHCl₃. The organic layer was dried over Na₂SO₄ and the solvent was concentrated under reduced pressure. The obtained residue was purified by silica gel column chromatography (CHCl₃/MeOH). The product was dissolved in MeOH (3 ml), and 4 M hydrogen chloride/EtOAc (1.5 ml) was added thereto, followed by stirring at room temperature overnight. The reaction mixture was concentrated under reduced pressure, and then a saturated aqueous sodium hydrogen carbonate solution was added thereto, followed by extraction with CHCl₃. The organic layer was dried over Na₂SO₄ and the solvent was concentrated under reduced pressure. The obtained residue was purified by silica gel column chromatography (CHCl₃/MeOH). The product was dissolved in EtOH (3 ml), and L-tartaric acid (35 mg) was added thereto, followed by stirring at room temperature overnight. The precipitated solid was collected by filtration to obtain N-methyl-N-(3-{2-[4-(5-methylpyridin-2-yl)piperazin-1-yl]pyrimidin-5-yl}benzyl)glycinamide L-tartrate (63 mg).

Example 212

6-[4-(tert-Butoxycarbonyl)piperazin-1-yl]-5-methylnicotinic acid (169 mg) was dissolved in dioxane (3.6 ml), and 4 M hydrogen chloride/EtOAc (1.5 ml) was added thereto, followed by stirring at room temperature overnight. The reaction mixture was concentrated under reduced pressure and then suspended in DMF (3 ml), and tert-butyl (2-{[3-(2-chloropyrimidin-5-yl)benzyl](methyl)amino}-2-oxoethyl)carbamate (200 mg) and DIPEA (371 mg) were added thereto, followed by stirring at 130° C. overnight. The reaction mixture was concentrated under reduced pressure, and then a saturated aqueous sodium hydrogen carbonate solution was added thereto, followed by extraction with CHCl₃. The organic layer was dried over Na₂SO₄ and the solvent was concentrated under reduced pressure. The obtained residue was purified by silica gel column chromatography (CHCl₃/MeOH). The product was dissolved in dioxane, and 4 M hydrogen chloride/EtOAc (1.5 ml) was added thereto, followed by stirring at room temperature overnight. The precipitated solid was collected by filtration to obtain 6-{4-[5-(3-{[glycyl(methyl)amino]methyl}phenyl)pyrimidin-2-yl]piperazin-1-yl}-5-methylnicotinic acid dihydrochloride (60 mg).

Example 213

To a suspension of tert-butyl {2-[(3-bromobenzyl)(methyl)amino]-2-oxoethyl}carbamate (293 mg) in toluene (4 ml) were added water (2 ml), (4-chlorophenyl)boronic acid (192 mg), sodium carbonate (173 mg), and tetrakis(triphenylphosphine)palladium (28 mg), followed by stirring at 80° C. overnight. The reaction mixture was cooled to room temperature, and then water was added thereto, followed by extraction with EtOAc. The organic layer was concentrated under reduced pressure, and then the residue was purified by silica gel column chromatography (hexane/EtOAc=10/0 to ½). The purified product was dissolved in EtOAc (5 ml), and then 4 M hydrogen chloride/EtOAc (10 ml) was added thereto, followed by stirring at room temperature for 2 hours. The reaction mixture was concentrated under reduced pressure, and then MeCN was added thereto. The precipitated solid was collected and washed with MeCN to obtain N-[(4'-chlorobiphenyl-3-yl)methyl]-N-methylglycinamide hydrochloride (267 mg).

Example 215 tert-Butyl {2-[(3-bromobenzyl)amino]-2-oxoethyl}carbamate (200 mg) was dissolved in DME (10 ml), and water (5 ml), 4-[4-(4,4,5,5-tetramethyl-1,3,2-dioxabolan-2-yl)phenyl]morpholine (219 mg), sodium carbonate (216 mg), and tetrakis(triphenylphosphine)palladium (20 mg) were added thereto, followed by stirring at 80° C. overnight. The reaction mixture was cooled to room temperature, and then water was added thereto, followed by extraction with EtOAc. The organic layer was dried over MgSO₄ and concentrated under reduced pressure. The obtained residue was purified by silica gel column chromatography (hexane/EtOAc=2/1). The obtained solid was dissolved in 4 M hydrogen chloride/EtOAc, followed by stirring at room temperature for 1 hour. The solvent was evaporated under reduced pressure, and to the residue was added a 1 M aqueous sodium hydrogen carbonate solution, followed by extraction with CHCl₃. The organic layer was dried over MgSO₄, and then the solvent was evaporated under reduced pressure. The obtained residue was dissolved in EtOH, and oxalic acid (52 mg) was added thereto. The precipitated solid was collected by filtration to obtain N-[(4'-morpholin-4-ylbiphenyl-3-yl)methyl]glycinamide oxalate (126 mg).

Example 217

1-(5-bromopyridin-2-yl)-4-(3-methylpyridin-2-yl)piperazine (280 mg) and tert-butyl (2-{methyl[3-(4,4,5,5-tetramethyl-1,3,2-dioxaborolan-2-yl)benzyl]amino}-2-oxoethyb-carbamate (292 mg) was dissolved in DME (4 ml) and water (2 ml), and tetrakis(triphenylphosphine)palladium (41 mg) and sodium carbonate (230 mg) were added thereto, followed by stirring at 80° C. overnight. To the reaction mixture was added a saturated aqueous sodium hydrogen carbonate solution, followed by extraction with CHCl₃. The organic layer was dried over Na₂SO₄, and then the solvent was concentrated under reduced pressure. The obtained residue was purified by silica gel column chromatography (hexane/EtOAc). The product was dissolved in EtOH (4 ml), and 4 M hydrogen chloride/EtOAc (2 ml) was added thereto, followed by stirring at room temperature overnight. The precipitated solid was collected by filtration to obtain N-methyl-N-(3-{6-[4-(3-methylpyridin-2-yl)piperazin-1-yl]pyridin-3-yl}benzyl)glycinamide trihydrochloride (164 mg).

Example 218

Under an argon atmosphere, tert-butyl (2-{methyl[3-(2-piperazin-1-ylpyrimidin-5-yl)benzyl]amino}-2-oxoethyl)carbamate (200 mg) and 2-bromo-6-methylpyridine (94 mg) were dissolved in toluene (3 ml), and tris(dibenzylideneacetone)dipalladium (12 mg), 1,1'-binaphthalene-2,2'-diylbis(diphenylphosphine) (25 mg), and cesium carbonate (444 mg) were added thereto, followed by stirring at 100° C. for 5 hours. The reaction mixture was concentrated under reduced pressure, and the obtained residue was purified by silica gel column chromatography (CHCl₃/MeOH). The product was dissolved in MeOH (3 ml), and 4 M hydrogen chloride/EtOAc was added thereto, followed by stirring at room temperature overnight. To the reaction mixture was added a saturated aqueous sodium hydrogen carbonate solution, followed by extraction with CHCl₃. The organic layer was dried over Na₂SO₄, and concentrated under reduced pressure. The obtained residue was purified by silica gel column chromatography (CHCl₃/MeOH). The product was dissolved in EtOH (2 ml), and L-tartaric acid (15 mg) was added thereto, followed by stirring at room temperature for 1 hour. The precipitated solid was collected by filtration to obtain N-methyl-N-(3-{2-[4-(6-methylpyridin-2-yl)piperazin-1-yl]pyrimidin-5-yl}benzyl)glycinamide L-tartrate (50 mg).

Example 219

3'-({[N-(tert-Butoxycarbonyl)glycyl](methyl)amino}methyl)biphenyl-4-carboxylic acid (400 mg) and 1-benzylpiperidin-4-amine (210 mg) were suspended in methylene chloride (4 ml), and WSC hydrochloride (231 mg) and HOBt (163 mg) were added thereto, followed by stirring at room temperature for 3 hours. The reaction mixture was subjected to liquid separation with $CHCl_3$ and water. The organic layer was separated, and then the aqueous layer was extracted with $CHCl_3$ again. These organic layers were combined and dried over $Na_2SO_4$, and then the solvent was evaporated under reduced pressure. The obtained residue was purified by silica gel column chromatography (2% MeOH/$CHCl_3$). The product was dissolved in MeOH (4 ml), and 4 N hydrogen chloride/EtOAc (1 ml) was added thereto, followed by stirring at room temperature for 4 hours. The reaction mixture was concentrated under reduced pressure. To the obtained residue were added $CHCl_3$ and an aqueous sodium hydrogen carbonate solution, and the organic layer was dried over $Na_2SO_4$ and then concentrated under reduced pressure. The obtained residue was dissolved in EtOH (3 ml), and oxalic acid (90 mg) was added thereto. The precipitated solid was collected by filtration to obtain N-(1-benzylpiperidin-4-yl)-3'-{[glycyl(methyl)amino]methyl}biphenyl-4-carboxamide oxalate (198 mg) as a colorless solid.

Example 222 tert-Butyl (2-{methyl[3-(2-piperazin-1-ylpyrimidin-5-yl)benzyl]amino}-2-oxoethyl)carbamate (250 mg) was dissolved in dichloroethane (3 ml), and 3-hydroxy-2,2-dimethylpropionic acid (74 mg), WSC hydrochloride (131 mg), and HOBt (92 mg) were added thereto, followed by stirring at 60° C. for 6 hours. To the reaction mixture was added water, followed by extraction with $CHCl_3$. After drying over $Na_2SO_4$, the solvent was concentrated under reduced pressure. The obtained residue was purified by silica gel column chromatography ($CHCl_3$/MeOH). The product was dissolved in EtOH (3 ml), and 4 M hydrogen chloride/EtOAc (1 ml) was added thereto, followed by stirring at room temperature overnight. The reaction mixture was concentrated under reduced pressure, and then a saturated aqueous sodium hydrogen carbonate solution was added thereto, followed by extraction with $CHCl_3$. The organic layer was dried over $Na_2SO_4$ and the solvent was concentrated under reduced pressure. The obtained residue was purified by silica gel column chromatography ($CHCl_3$/MeOH). The product was dissolved in EtOH (3 ml), and L-tartaric acid (27 mg) was added thereto, followed by stirring at room temperature overnight. The precipitated solid was collected by filtration to obtain N-(3-{2-[4-(3-hydroxy-2,2-dimethylpropanoyl)piperazin-1-yl]pyrimidin-5-yl}benzyl)-N-methylglycinamide L-tartrate (62 mg).

Example 226 tert-Butyl {2-[{[4'-(aminomethyl)biphenyl-3-yl]methyl}(methyl)amino]-2-oxoethyl}carbamate (269 mg) was dissolved in THF (4.8 ml), and TEA (85 mg) was added thereto. Acetyl chloride (61 mg) was added thereto, followed by stirring at room temperature for 1 hour. To the reaction mixture was added water, followed by extraction with EtOAc. The organic layer was concentrated under reduced pressure, and then the residue was purified by silica gel column chromatography (NH-silica, hexane/EtOAc=10/0 to ⅖). The purified product was dissolved in EtOAc (5 ml), and then 4 M hydrogen chloride/EtOAc (10 ml) was added thereto, followed by stirring at room temperature for 1 hour. The reaction mixture was concentrated under reduced pressure. The obtained residue was dissolved in EtOH (3 ml), and then added to and suspended in EtOAc (30 ml). The precipitated insoluble material was collected and dried at room temperature under reduced pressure to obtain N-{[4'-(acetamidemethyl)biphenyl-3-yl]methyl}-N-methylglycinamide hydrochloride (146 mg).

Example 228 tert-Butyl (2-{[(4'-aminobiphenyl-3-yl)methyl](methyl)amino]-2-oxoethyl}carbamate (200 mg) was dissolved in $CHCl_3$ (2 ml), and TEA (60 mg) was added thereto. 2,2-Dimethylpropanoyl chloride (73 mg) was added thereto, followed by stirring at room temperature overnight. The reaction mixture was concentrated under reduced pressure, and to the residue was added EtOAc. The mixture was washed with 0.5 M hydrochloric acid, a 1 M aqueous sodium hydrogen carbonate solution, and saturated brine in this order, dried over $MgSO_4$, concentrated under reduced pressure, and then dissolved in EtOAc (5 ml). 4 M hydrogen chloride/EtOAc (10 ml) was added thereto, followed by stirring at room temperature for 1 hour. The reaction mixture was concentrated under reduced pressure. To the obtained residue was added a saturated aqueous sodium hydrogen carbonate solution, followed by extraction with $CHCl_3$. The organic layer was dried over $Na_2SO_4$ and concentrated under reduced pressure. To the obtained residue was added EtOH, and subsequently, oxalic acid (49 mg) was added thereto. The precipitated solid was collected by filtration to obtain N-(3'-{[glycyl(methyl)amino]methyl}biphenyl-4-yl)-2,2-dimethylpropaneamide oxalate (205 mg).

Example 239 tert-Butyl (2-{[3-(6-formylpyridin-3-yl)benzyl](methyl)amino}-2-oxoethyl)carbamate (150 mg) and (2R)-pyrrolidin-2-ylmethanol (59 mg) was dissolved in dichloroethane (1 ml) and acetic acid (1 ml), followed by stirring at 60° C. for 30 minutes. Sodium triacetoxyborohydride (166 mg) was added thereto, followed by stirring at 60° C. for 3 hours. The reaction mixture was concentrated under reduced pressure, and to the obtained residue was added a saturated aqueous sodium hydrogen carbonate solution, followed by extraction with $CHCl_3$. The organic layer was dried over $Na_2SO_4$ and concentrated under reduced pressure. The obtained residue was purified by silica gel column chromatography ($CHCl_3$/MeOH). The product was dissolved in MeOH (3 ml), and 4 M hydrogen chloride/EtOAc (1 ml) was added thereto, followed by stirring at room temperature overnight and concentrating under reduced pressure. Then, EtOH was added thereto, and then the precipitated solid was collected by filtration to obtain N-[3-(6-{[(2S)-2-(hydroxymethyl)pyrrolidin-1-yl]methyl}pyridin-3-yl)benzyl]-N-methylglycinamide trihydrochloride (43 mg).

Example 244 tert-Butyl (2-{[3-(6-formylpyridin-3-yl)benzyl](methyl)amino}-2-oxoethyl)carbamate (300 mg) and 2-piperazin-1- ylpyrimidine (154 mg) was dissolved in dichloroethane (2 ml) and acetic acid (2 ml), followed by stirring at 60° C. for 30 minutes. Sodium triacetoxyborohydride (332 mg) was added thereto, followed by stirring at 60° C. for 3 hours. The reaction mixture was concentrated under reduced pressure, and a saturated aqueous sodium hydrogen carbonate solution was added thereto, followed by extraction with CHCl$_3$. The organic layer was dried over Na$_2$SO$_4$ and concentrated under reduced pressure. The obtained residue was purified by silica gel column chromatography (CHCl$_3$/MeOH). The product was dissolved in MeOH (5 ml), and 4 M hydrogen chloride/EtOAc (2 ml) was added thereto, followed by stirring at room temperature overnight. The reaction mixture was concentrated under reduced pressure, and then a saturated aqueous sodium hydrogen carbonate solution was added thereto, followed by extraction with CHCl$_3$. The organic layer was dried over Na$_2$SO$_4$ and then concentrated under reduced pressure. The obtained residue was purified by silica gel column chromatography (CHCl$_3$/MeOH). The product was dissolved in EtOH (5 ml), and L-tartaric acid (117 mg) was added thereto, followed by stirring at room temperature for 1 hour. The reaction mixture was concentrated under reduced pressure, and then EtOAc was added thereto. The precipitated solid was collected by filtration to obtain N-methyl-N-(3-{6-[(4-pyrimidin-2-ylpiperazin-1-yl)methyl]pyridin-3-yl}benzyl)glycinamide L-tartrate (34 mg).

Example 248

Ethyl 3-[6-(4-{5-[3-({[N-(tert-butoxycarbonyl)glycyl](methyl)amino}methyl)phenyl]pyrimidin-2-yl}piperazin-1-yl)-5-(hydroxymethyl)pyridin-3-yl]propanoate (222 mg) was dissolved in EtOH (1 ml) and THF (2 ml), and a 1 M aqueous NaOH solution (1 ml) was added thereto, followed by stirring at room temperature for 5 hours. To the reaction mixture was added 1 M hydrochloric acid (1 ml), and the solvent was evaporated under reduced pressure. To the obtained residue was added water, followed by extraction with CHCl$_3$. The organic layer was dried over MgSO$_4$, and then the solvent was evaporated under reduced pressure. The obtained residue was purified by silica gel column chromatography (CHCl$_3$/MeOH). The product was dissolved in dioxane (2 ml), and 4 M hydrogen chloride/dioxane (0.8 ml) was added thereto. After stirring at room temperature overnight, the precipitated solid was collected by filtration to obtain 3-[6-{4-[5-(3-{[glycyl(methyl)amino]methyl}phenyl)pyrimidin-2-yl]piperazin-1-yl}-5-(hydroxymethyl)pyridin-3-yl]propionic acid dihydrochloride (203 mg).

Example 254

To a solution of [3'-({[N-(tert-butoxycarbonyl)glycyl](methyl)amino}methyl)biphenyl-4-yl]methylmethanesulfonate (163 mg) in DMF (1.6 ml) was added 1-methyl-1,4-diazepane (80 mg), followed by stirring at room temperature overnight. The reaction mixture was concentrated under reduced pressure, and then purified by silica gel column chromatography (CHCl$_3$/MeOH). The product was dissolved in MeOH (1.6 ml), and 4 M hydrogen chloride/EtOAc (0.8 ml) was added thereto, followed by stirring at room temperature overnight. The reaction mixture was concentrated under reduced pressure, and then a saturated aqueous sodium hydrogen carbonate solution was added thereto, followed by extraction with CHCl$_3$. The organic layer was dried over Na$_2$SO$_4$ and concentrated under reduced pressure. The obtained residue was purified by silica gel column chromatography (CHCl$_3$/MeOH). The product was dissolved in EtOH (2 ml), and L-tartaric acid (9 mg) was added thereto, followed by stirring at room temperature for 1 hour. The reaction mixture was concentrated under reduced pressure, and then EtOAc was added thereto. The precipitated solid was collected by filtration to obtain N-methyl-N-({4'-[(4-methyl-1,4-diazepan-1-yl)methyl]biphenyl-3-yl}methyl)glycinamide L-tartrate (16 mg).

Example 255

To a solution of [3'-({[N-(tert-butoxycarbonyl)glycyl](methyl)amino}methyl)biphenyl-4-yl]methylmethanesulfonate (163 mg) in DMF (1.6 ml) was added 1-methylpiperazine (70 mg), followed by stirring at room temperature overnight. The reaction mixture was concentrated under reduced pressure, and then purified by silica gel column chromatography (CHCl$_3$/MeOH). The product was dissolved in MeOH (3 ml), and 4 M hydrogen chloride/EtOAc (1 ml) was added thereto, followed by stirring at room temperature overnight. The reaction mixture was concentrated under reduced pressure, and then EtOH was added thereto. The precipitated solid was collected by filtration to obtain N-methyl-N-({4'-[(4-methylpiperazin-1-yl)methyl]biphenyl-3-yl}methyl)glycinamide trihydrochloride (168 mg).

Example 261 tert-Butyl {2-[(3-{2-[4-(6-cyanopyridin-3-yl)piperazin-1-yl]pyrimidin-5-yl}benzyl)(methyl)amino]-2-oxoethyl}carbamate (248 mg) was dissolved in dichloromethane (4 ml), and TFA (4.52 g) was added thereto, followed by stirring at room temperature for 3 hours and concentrating under reduced pressure. A saturated aqueous sodium hydrogen carbonate solution was added thereto, followed by extraction with CHCl$_3$. The organic layer was purified by silica gel column chromatography (NH silica, CHCl$_3$/MeOH=100/0 to 96/4). The purified product was dissolved in EtOH (1 ml), and L-tartaric acid (17 mg) was added thereto, followed by stirring at 75° C. for 10 minutes. The precipitated solid was collected by filtration to obtain N-(3-{2-[4-(6-cyanopyridin-3-yl)piperazin-1-yl]pyrimidin-5-yl}benzyl)-N-methylglycinamide L-tartrate (34 mg).

Example 263

3 chloro-4-(piperazin-1-yl)benzoic acid hydrochloride (142 mg) was suspended in DMF (3 ml), and tert-butyl (2-{[3-(2-chloropyrimidin-5-yl)benzyl](methyl)amino}-2-oxoethyl)carbamate (190 mg) and DIPEA (371 mg) were added thereto, followed by stirring at 130° C. overnight. The reaction mixture was concentrated under reduced pressure, and then a saturated aqueous sodium hydrogen carbonate solution was added thereto, followed by extraction with CHCl$_3$. The organic layer was dried over Na$_2$SO$_4$ and the solvent was concentrated under reduced pressure. The obtained residue was purified by silica gel column chromatography (CHCl$_3$/MeOH). The product was dissolved in dioxane, and 4 M hydrogen chloride/dioxane (1 ml) was added thereto, followed by stirring at room temperature overnight. The precipitated solid was collected by filtration to obtain 3-chloro-4-{4-[5-(3-{[glycyl(methyl)amino)methyl}phenyl)pyrimidin-2-yl]piperazin-1-yl}benzoic acid dihydrochloride (72 mg).

Example 264

To a solution of tert-butyl {2-[{([4'-(chloromethyl)biphenyl-3-yl]methyl}(methyl)amino]-2-oxoethyl}carbamate (150 mg) in DMF (2 ml) was added N,N-dimethylpiperidin-4-amine (105 mg), followed by stirring at room temperature overnight. The reaction mixture was concentrated under reduced pressure, and then a saturated aqueous sodium hydrogen carbonate solution was added thereto, followed by extraction with CHCl₃. The organic layer was dried over Na₂SO₄ and concentrated under reduced pressure. The obtained residue was purified by silica gel column chromatography (CHCl₃/MeOH). The product was dissolved in MeOH, and 4 M hydrogen chloride/EtOAc (1 ml) was added thereto, followed by stirring at room temperature overnight. The reaction mixture was concentrated under reduced pressure, and then EtOH was added thereto. The precipitated solid was collected by filtration to obtain N-[(4'-{[4-(dimethylamino)piperidin-1-yl]methyl}biphenyl-3-yl)methyl]-N-methylglycinamide trihydrochloride (188 mg).

Example 265

To a solution of tert-butyl {2-[{[4'-(chloromethyl)biphenyl-3-yl]methyl}(methyl)amino]-2-oxoethyl}carbamate (150 mg) in DMF (1.4 ml) was added piperidin-4-ylmethanol (81 mg), followed by stirring at room temperature overnight. The reaction mixture was concentrated under reduced pressure, and then a saturated aqueous sodium hydrogen carbonate solution was added thereto, followed by extraction with CHCl₃. The organic layer was dried over Na₂SO₄ and concentrated under reduced pressure. The obtained residue was purified by silica gel column chromatography (CHCl₃/MeOH). The product was dissolved in MeOH (1.4 ml), and 4 M hydrogen chloride/EtOAc (1 ml) was added thereto, followed by stirring at room temperature overnight. The reaction mixture was concentrated under reduced pressure, and then a saturated aqueous sodium hydrogen carbonate solution was added thereto, followed by extraction with CHCl₃. The organic layer was dried over Na₂SO₄ and then concentrated under reduced pressure. The obtained residue was purified by silica gel column chromatography (CHCl₃/MeOH). The product was dissolved in EtOH (1.4 ml), and L-tartaric acid (32 mg) was added thereto, followed by stirring at room temperature for 1 hour. The reaction mixture was concentrated under reduced pressure, and then EtOAc was added thereto. The precipitated solid was collected by filtration to obtain N-[(4'-{[4-(hydroxymethyl)piperidin-1-yl]methyl}biphenyl-3-yl)methyl]-N-methylglycinamide L-tartrate (69 mg).

Example 270 tert-Butyl (2-{[3-(3',6'-dihydro-2'H-2,1':4',2''-terpyridin-5-yl)benzyl](methyl)amino}-2-oxoethyl)carbamate (120 mg) was dissolved in EtOH (3 ml), and 10% Pd/C (40 mg) was added thereto, followed by stirring at room temperature for 5 hours under a hydrogen atmosphere at 1 atm. The catalyst was removed by filtration using Celite as a filtration assistant, and then reaction mixture was concentrated under reduced pressure. The obtained residue was purified by silica gel column chromatography (hexane/EtOAc). The product was dissolved in MeOH, and 4 M hydrogen chloride/EtOAc (1 ml) was added thereto, followed by stirring at room temperature overnight. The reaction mixture was concentrated under reduced pressure, and then a saturated aqueous sodium hydrogen carbonate solution was added thereto, followed by extraction with CHCl₃. The organic layer was dried over Na₂SO₄ and the solvent was concentrated under reduced pressure. The obtained residue was dissolved in EtOH, and L-tartaric acid (13 mg) was added thereto, followed by stirring at room temperature for 5 hours. The precipitated solid was collected by filtration to obtain N-methyl-N-{3-[6-(4-pyridin-2-ylpiperidin-1-yl)pyridin-3-yl]benzyl}glycinamide L-tartrate (24 mg).

Example 272

3-Methoxypropan-1-ol (88 mg) was dissolved in THF (3 ml), and NaH (60 mg) was added thereto, followed by stirring at room temperature for 10 minutes. 4-Nitrophenyl 4-{5-[3-({[N-(tert-butoxycarbonyl)glycyl](methyl)amino}methyl)phenyl]pyrimidin-2-yl}piperazine-1-carboxylate (250 mg) was added thereto, followed by stirring at room temperature for 1 hour. To the reaction mixture was added water, followed by extraction with EtOAc. The organic layer was dried over Na₂SO₄ and the solvent was concentrated under reduced pressure. The obtained residue was purified by silica gel column chromatography (hexane/EtOAc). The product was dissolved in EtOH, and 4 M hydrogen chloride/EtOAc was added thereto, followed by stirring at room temperature overnight. The reaction mixture was concentrated under reduced pressure, and then a saturated aqueous sodium hydrogen carbonate solution was added thereto, followed by extraction with CHCl₃. The organic layer was dried over Na₂SO₄ and the solvent was concentrated under reduced pressure. The residue was purified by silica gel column chromatography (CHCl₃/MeOH). The obtained residue was dissolved in EtOH, and L-tartaric acid (26 mg) was added thereto, followed by stirring at room temperature overnight. The precipitated solid was collected by filtration to obtain 3-methoxypropyl 4-[5-(3-{[glycyl(methyl)amino]methyl}phenyl)pyrimidin-2-yl]piperazine-1-carboxylate L-tartrate (60 mg).

Example 281

To a solution of 3'-({[N-(tert-butoxycarbonyl)glycyl](methyl)amino}methyl)biphenyl-4-carboxylic acid (9 mg) in DMF (1 ml) was added HOBt (2 mg) and ethylamine (2 mg), and PS-Carbodiimide (manufactured by Biotage AB) (100 mg) was added thereto, followed by shaking overnight. Thereafter, PS-Isocyanate (manufactured by Biotage AB) and MP-Carbonate (manufactured by Biotage AB) were added in an amount of 50 mg, and DMF (0.5 ml) was further added thereto, followed by shaking for 2 hours. The insoluble material was filtered and the filtrate was concentrated. To the obtained residue was added MeOH (0.5 ml), and a 4 M hydrogen chloride/EtOAc solution (0.5 ml) was added thereto, followed by shaking for 1 hour. Thereafter, the reaction mixture was concentrated to obtain N-ethyl-3'-{[glycyl(methyl)amino]methyl}biphenyl-4-carboxamide (15.4 mg).

Example 374

To a mixture of 2-(piperidin-1-yl)-5-(4,4,5,5-tetramethyl-1,3,2-dioxaborolan-2-yl)pyrimidine (14 mg), tert-butyl {2-[(3-bromobenzyl)(methyl)amino]-2-oxoethyl}carbamate (9 mg), and DMF (0.2 ml) were added tetrakis(triphenylphosphine)palladium (3 mg), sodium carbonate (5 mg), and water (0.1 ml), followed by stirring at 60° C. overnight. After cooling to room temperature, to the reaction mixture was added CHCl₃ (2 ml), and the reaction mixture was filtered in a column preconditioned by the addition of 0.8 ml of water to a diatomaceous earth column (manufactured by Varian Inc., ChemElute 1 ml). The obtained filtrate was concentrated, and then to the residue were added MeOH (0.5 ml) and a 4 M hydrogen chloride/EtOAc solution (0.5 ml), followed by leaving to stand for 30 minutes. Thereafter, the reaction mixture was concentrated and the compound was purified by preparative liquid chromatography (MeOH/0.1% aqueous formic acid solution) to obtain N-methyl-N-{3-[2-(piperidin-1-yl)pyrimidin-5-yl]benzyl}glycinamide (3.8 mg).

Example 417

To 3-chloro-4-{4-[5-(3-{[glycyl(methyl)amino]methyl}phenyl)pyrimidin-2-yl]piperazin-1-yl}benzoic acid dihydrochloride (3.0 g) were added THF (30 ml) and H₂O (15 ml). To this mixture was added 1 N sodium hydroxide (10.6 ml), followed by stirring for 30 minutes. The precipitated solid was filtered and washed with water. The obtained product was dried at 50° C. under reduced pressure to obtain 3-chloro-4-{4-[5-(3-{[glycyl(methyl)amino]methyl}phenyl)pyrimidin-2-yl]piperazin-1-yl}benzoic acid (2.1 g) as a colorless solid.

Next, 3-chloro-4-{4-[5-(3-{[glycyl(methyl)amino]methyl}phenyl)pyrimidin-2-yl]piperazin-1-yl}benzoic acid (2 g) was suspended in THF (40 ml)-H₂O (40 ml), and fumaric acid (938 mg) was added thereto, followed by stirring at 90° C. for 1 hour. The reaction mixture was cooled to room temperature and the solvent was evaporated under reduced pressure. To the residue was added THF (20 ml)-H₂O (20 ml), followed by stirring at 90° C. for 1 hour as it was suspended. The mixture was cooled to room temperature, followed by stirring overnight. After the mixture was filtered, washed with THF—H₂O (1:1), and then dried at 50° C. for 5 hours under reduced pressure to obtain 3-chloro-4-{4-[5-(3-{[glycyl(methyl)amino]methyl}phenyl)pyrimidin-2-yl]piperazin-1-yl}benzoic acid hemifumarate (1.7 g) as a colorless crystal.

Example 418

To N-methyl-N-{[4'-(morpholin-4-yl)biphenyl-3-yl]methyl}glycinamide oxalate (100 mg) were added CHCl₃ (10 ml) and a saturated aqueous sodium hydrogen carbonate solution (10 ml), followed by stirring for 10 minutes. The aqueous layer was extracted with chloroform (10 ml). The combined organic layer was dried over anhydrous sodium sulfate, and then concentrated under reduced pressure. The residue was dissolved in EtOH (2 ml), and succinic acid was added thereto, followed by stirring for 3 hours. The resulting crystal was filtered and washed with EtOH. The product residue was dried under reduced pressure and dried to obtain N-methyl-N-{[4'-(morpholin-4-yl)biphenyl-3-yl]methyl}glycinamide hemisuccinate (85 mg) as a colorless crystal.

The Example Compounds as shown in Tables below were prepared in the same manner as the methods of Examples above, using each of the corresponding starting materials. The structures, the preparation methods, and the physicochemical data of Example Compounds are shown in Tables below.

TABLE 79

| Ex | Syn | Structure | Acid |
|---|---|---|---|
| 1 | 1 | 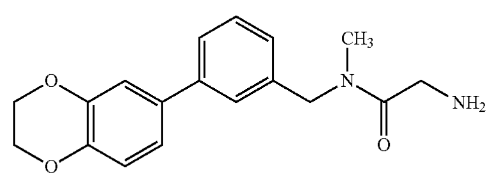 [SMILES: CN(Cc1cccc(-c2ccc3c(c2)OCCO3)c1)C(=O)CN] | L-TA |
| 2 | 2 | 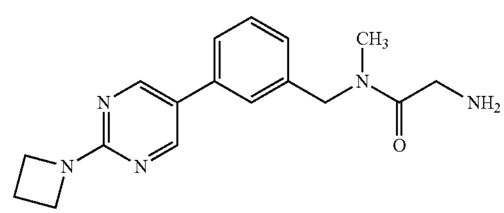 [SMILES: CN(Cc1cccc(-c2cnc(N3CCC3)nc2)c1)C(=O)CN] | 2HCl |
| 3 | 3 | 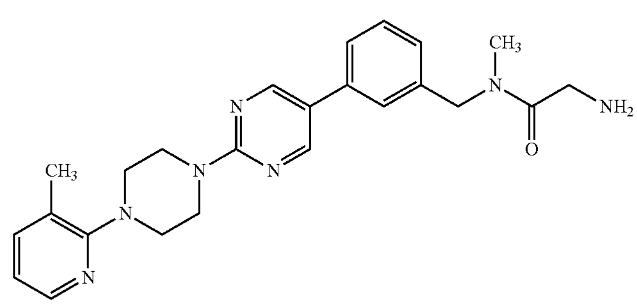 [SMILES: Cc1cccnc1N1CCN(c2ncc(-c3cccc(CN(C)C(=O)CN)c3)cn2)CC1] | L-TA |

TABLE 79-continued

| Ex | Syn | Structure | Acid |
|---|---|---|---|
| 4 | 3 | 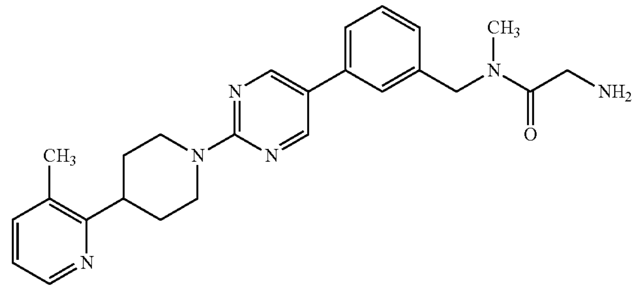 [SMILES: Cc1cccnc1C1CCN(c2ncc(-c3cccc(CN(C)C(=O)CN)c3)cn2)CC1] | 3HCl |
| 5 | 3 | 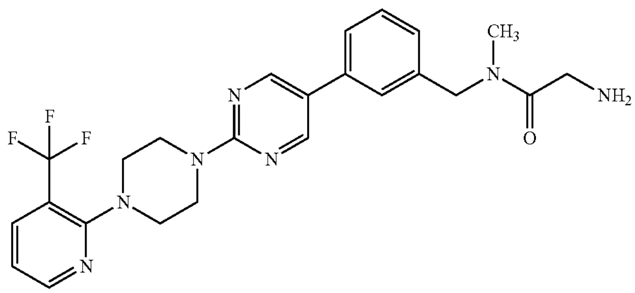 [SMILES: CN(Cc1cccc(-c2cnc(N3CCN(c4ncccc4C(F)(F)F)CC3)nc2)c1)C(=O)CN] | L-TA |

TABLE 80

| Ex | Syn | Structure | Acid |
|---|---|---|---|
| 6 | 3 | 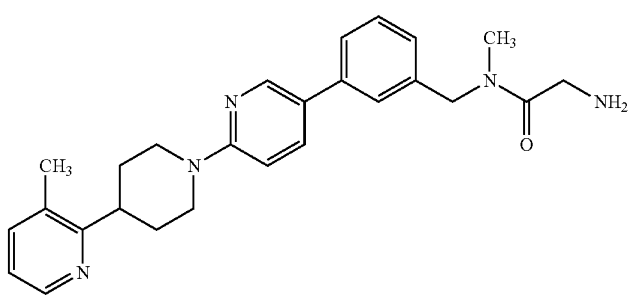 [SMILES: Cc1cccnc1C1CCN(c2ccc(-c3cccc(CN(C)C(=O)CN)c3)cn2)CC1] | 3HCl |
| 7 | 3 | 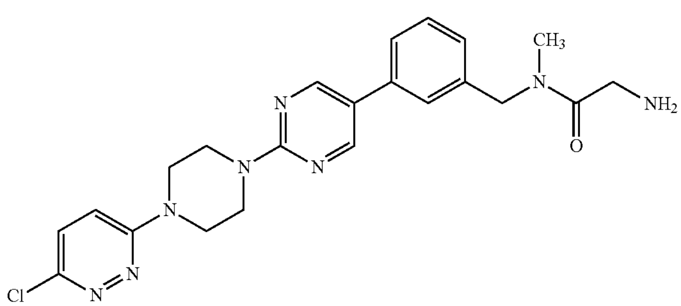 [SMILES: CN(Cc1cccc(-c2cnc(N3CCN(c4ccc(Cl)nn4)CC3)nc2)c1)C(=O)CN] | L-TA |

TABLE 80-continued

| Ex | Syn | Structure | Acid |
|---|---|---|---|
| 8 | 3 | 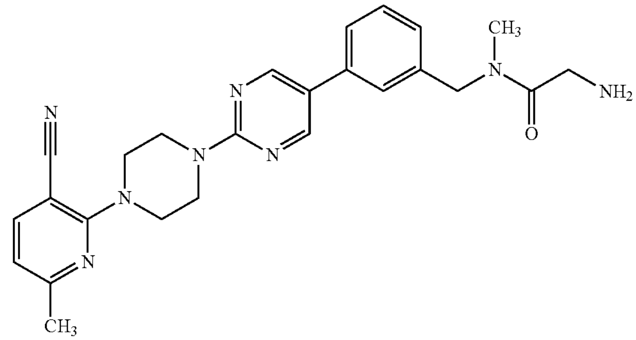 [SMILES: Cc1ccc(C#N)c(N2CCN(c3ncc(-c4cccc(CN(C)C(=O)CN)c4)cn3)CC2)n1] | L-TA |
| 9 | 3 | 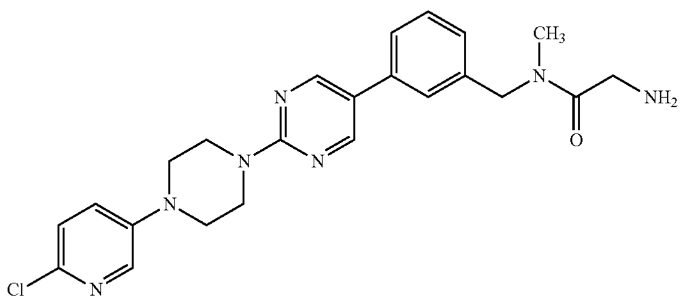 [SMILES: CN(Cc1cccc(-c2cnc(N3CCN(c4ccc(Cl)nc4)CC3)nc2)c1)C(=O)CN] | L-TA |
| 10 | 3 | 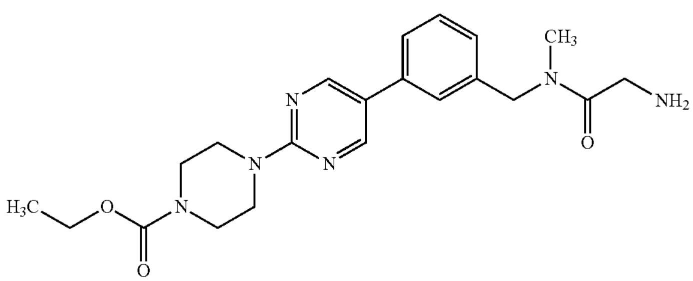 [SMILES: CCOC(=O)N1CCN(c2ncc(-c3cccc(CN(C)C(=O)CN)c3)cn2)CC1] | L-TA |

TABLE 81

| Ex | Syn | Structure | Acid |
|---|---|---|---|
| 11 | 3 | 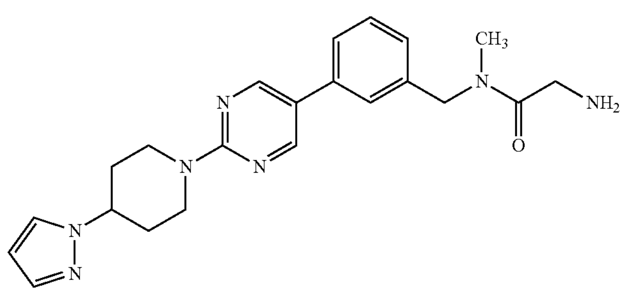 [SMILES: CN(Cc1cccc(-c2cnc(N3CCC(n4cccn4)CC3)nc2)c1)C(=O)CN] | L-TA |

TABLE 81-continued
| Ex | Syn | Structure | Acid |
|----|-----|-----------|------|
| 12 | 3 | 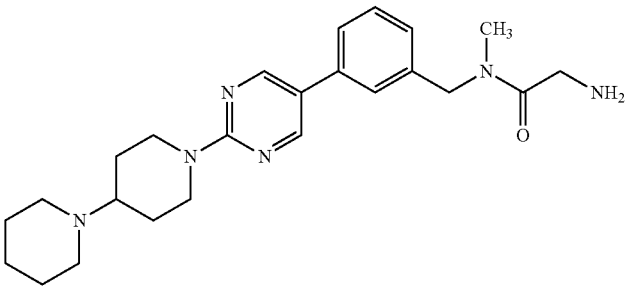 [SMILES: CN(Cc1cccc(-c2cnc(N3CCC(N4CCCCC4)CC3)nc2)c1)C(=O)CN] | L-TA |
| 13 | 3 | 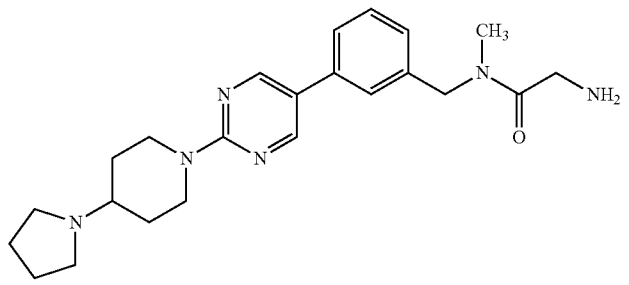 [SMILES: CN(Cc1cccc(-c2cnc(N3CCC(N4CCCC4)CC3)nc2)c1)C(=O)CN] | L-TA |
| 14 | 3 | 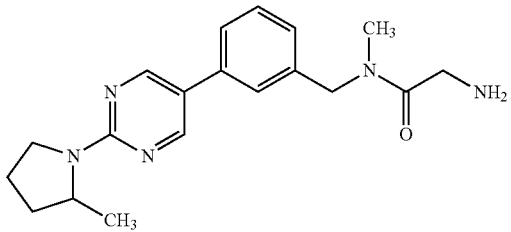 [SMILES: CC1CCCN1c1ncc(-c2cccc(CN(C)C(=O)CN)c2)cn1] | L-TA |
| 15 | 3 | 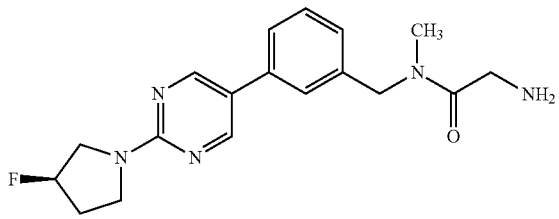 [SMILES: CN(Cc1cccc(-c2cnc(N3CC[C@@H](F)C3)nc2)c1)C(=O)CN] | L-TA |
| 16 | 3 | 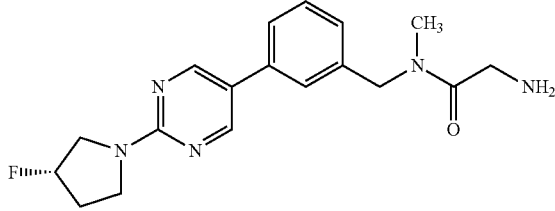 [SMILES: CN(Cc1cccc(-c2cnc(N3CC[C@H](F)C3)nc2)c1)C(=O)CN] | L-TA |

TABLE 82

| Ex | Syn | Structure | Acid |
|----|-----|-----------|------|
| 17 | 3 | 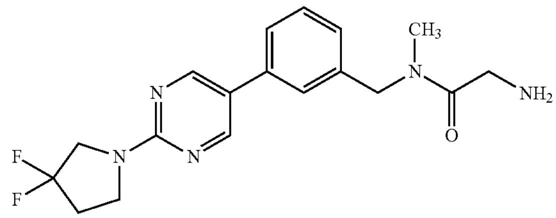 [SMILES: CN(Cc1cccc(-c2cnc(N3CCC(F)(F)C3)nc2)c1)C(=O)CN] | L-TA |
| 18 | 3 | 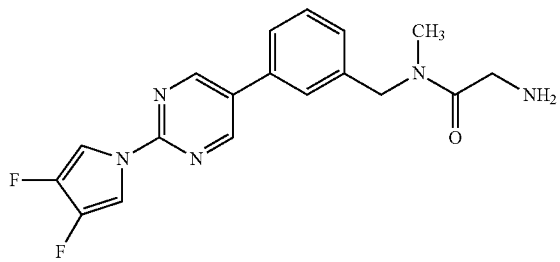 [SMILES: CN(Cc1cccc(-c2cnc(-n3cc(F)c(F)c3)nc2)c1)C(=O)CN] | HCl |
| 19 | 19 | 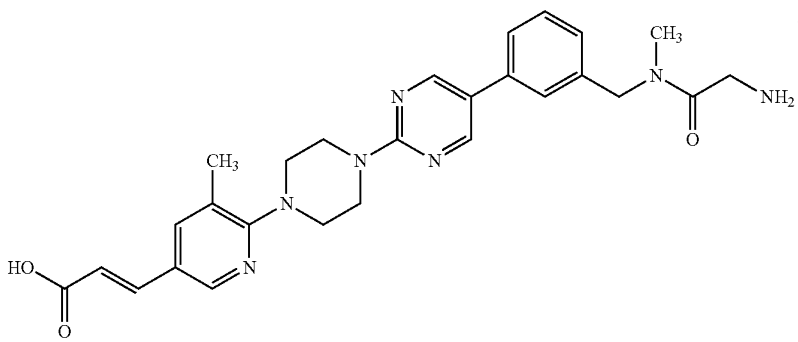 [SMILES: Cc1cc(/C=C/C(=O)O)cnc1N1CCN(c2ncc(-c3cccc(CN(C)C(=O)CN)c3)cn2)CC1] | 2HCl |
| 20 | 19 | 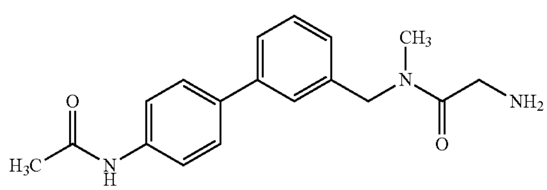 [SMILES: CC(=O)Nc1ccc(-c2cccc(CN(C)C(=O)CN)c2)cc1] | HCl |
| 21 | 19 | 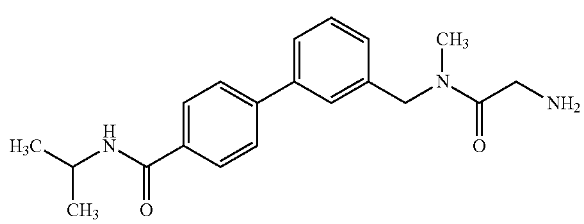 [SMILES: CC(C)NC(=O)c1ccc(-c2cccc(CN(C)C(=O)CN)c2)cc1] | HCl |
| 22 | 19 | 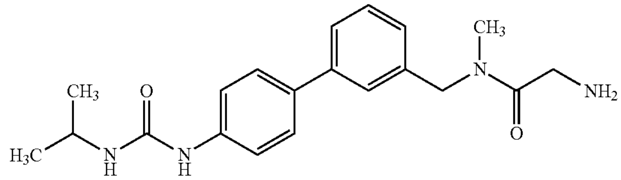 [SMILES: CC(C)NC(=O)Nc1ccc(-c2cccc(CN(C)C(=O)CN)c2)cc1] | HCl |

TABLE 83

| Ex | Syn | Structure | Acid |
|----|-----|-----------|------|
| 23 | 19 | 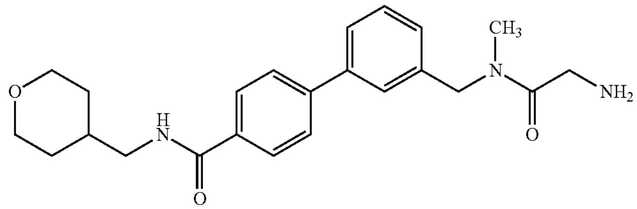 [SMILES: CN(Cc1cccc(-c2ccc(C(=O)NCC3CCOCC3)cc2)c1)C(=O)CN] | HCl |
| 24 | 19 | 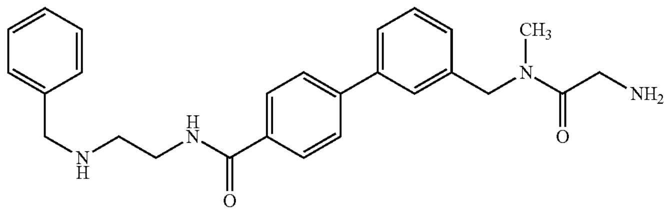 [SMILES: CN(Cc1cccc(-c2ccc(C(=O)NCCNCc3ccccc3)cc2)c1)C(=O)CN] | 2HCl |
| 25 | 19 | 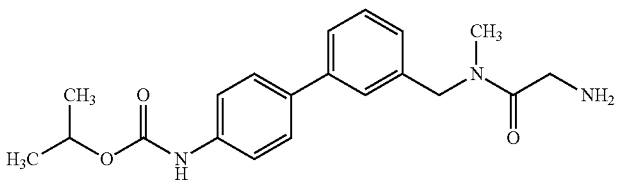 [SMILES: CC(C)OC(=O)Nc1ccc(-c2cccc(CN(C)C(=O)CN)c2)cc1] | HCl |
| 26 | 19 | 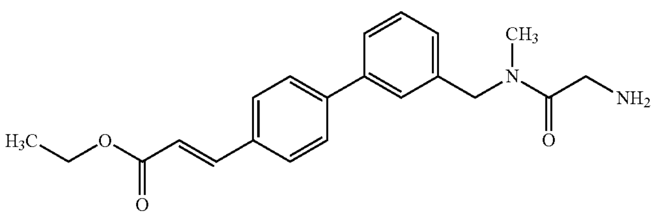 [SMILES: CCOC(=O)/C=C/c1ccc(-c2cccc(CN(C)C(=O)CN)c2)cc1] | HCl |
| 27 | 19 | 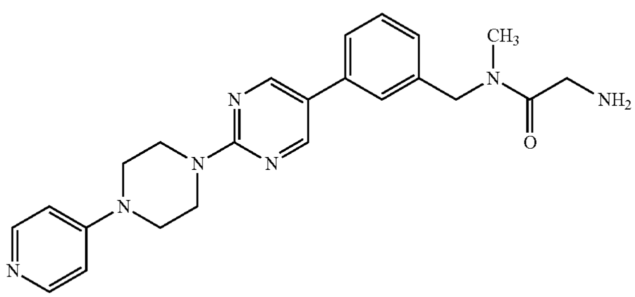 | 4HCl |
| 28 | 19 | 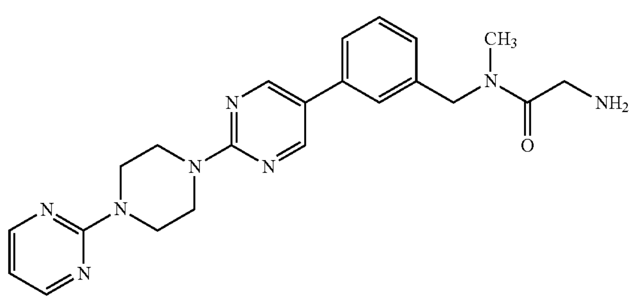 [SMILES: CN(Cc1cccc(-c2cnc(N3CCN(c4ncccn4)CC3)nc2)c1)C(=O)CN] | 4HCl |

TABLE 84
| Ex | Syn | Structure | Acid |
|---|---|---|---|
| 29 | 19 | 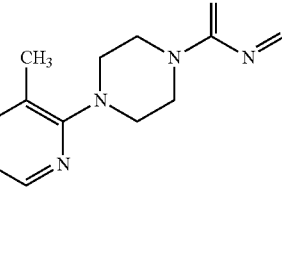 | 3HCl |
| 30 | 19 | 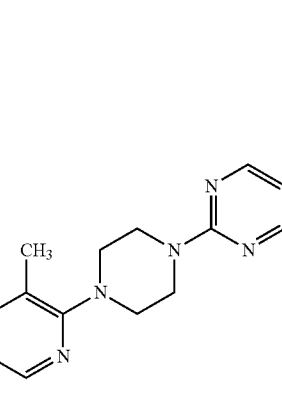 | 2HCl |
| 31 | 19 | 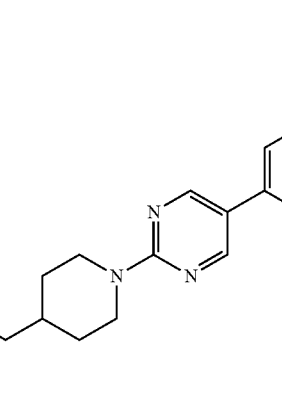 | 2HCl |
| 32 | 19 | 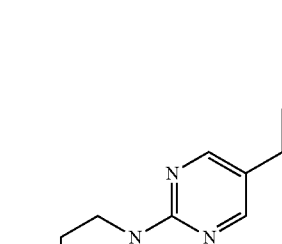 | 2HCl |

TABLE 84-continued

| Ex | Syn | Structure | Acid |
|----|-----|-----------|------|
| 33 | 19 | 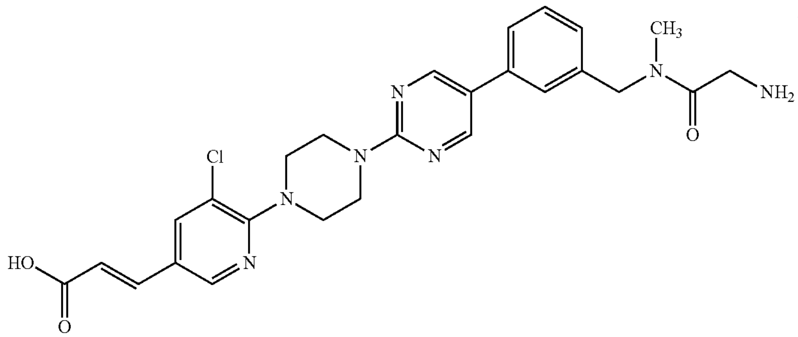 [SMILES: CN(Cc1cccc(-c2cnc(N3CCN(c4ncc(/C=C/C(=O)O)cc4Cl)CC3)nc2)c1)C(=O)CN] | 2HCl |

TABLE 85

| Ex | Syn | Structure | Acid |
|----|-----|-----------|------|
| 34 | 19 | 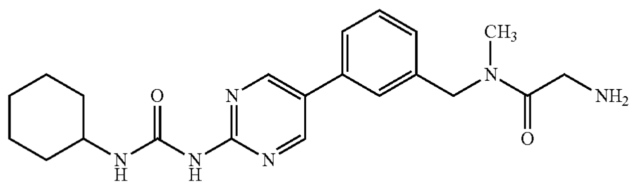 [SMILES: CN(Cc1cccc(-c2cnc(NC(=O)NC3CCCCC3)nc2)c1)C(=O)CN] | HCl |
| 35 | 19 | 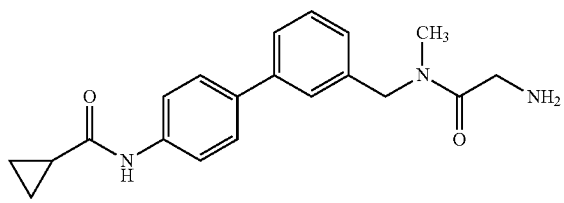 [SMILES: CN(Cc1cccc(-c2ccc(NC(=O)C3CC3)cc2)c1)C(=O)CN] | HCl |
| 36 | 19 | 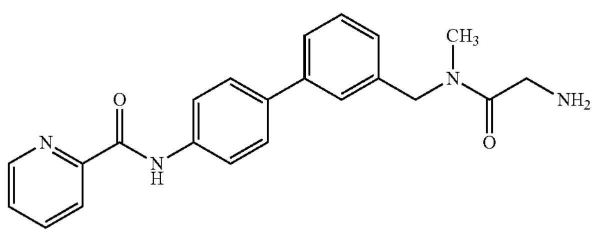 [SMILES: CN(Cc1cccc(-c2ccc(NC(=O)c3ccccn3)cc2)c1)C(=O)CN] | 2HCl |
| 37 | 19 | 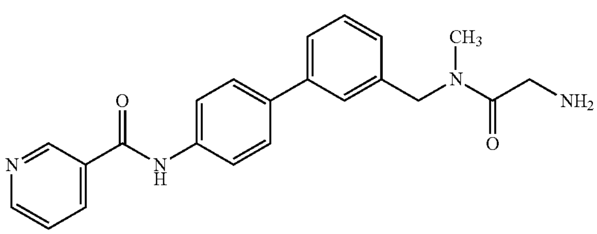 [SMILES: CN(Cc1cccc(-c2ccc(NC(=O)c3cccnc3)cc2)c1)C(=O)CN] | 2HCl |
| 38 | 19 | 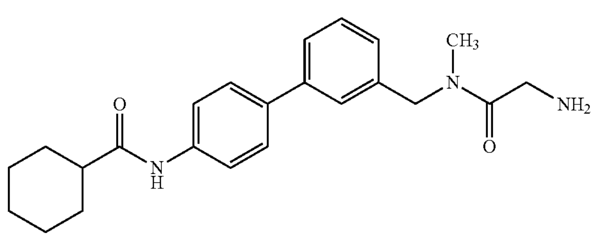 [SMILES: CN(Cc1cccc(-c2ccc(NC(=O)C3CCCCC3)cc2)c1)C(=O)CN] | HCl |

TABLE 85-continued

| Ex | Syn | Structure | Acid |
|---|---|---|---|
| 39 | 19 | 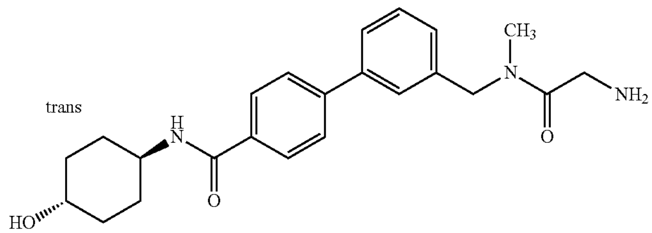 [SMILES: CN(Cc1cccc(-c2ccc(C(=O)N[C@H]3CC[C@H](O)CC3)cc2)c1)C(=O)CN] | HCl |

TABLE 86

| Ex | Syn | Structure | Acid |
|---|---|---|---|
| 40 | 19 | 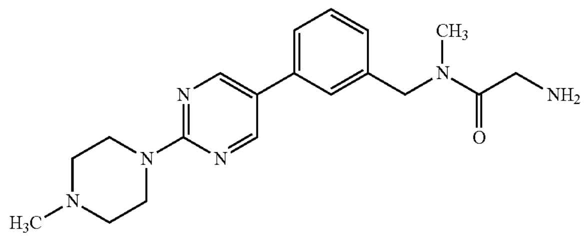 [SMILES: CN1CCN(c2ncc(-c3cccc(CN(C)C(=O)CN)c3)cn2)CC1] | 3HCl |
| 41 | 19 | 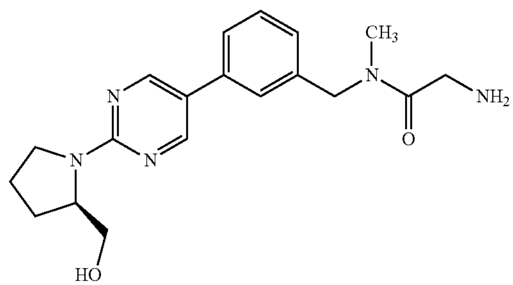 [SMILES: CN(Cc1cccc(-c2cnc(N3CCC[C@@H]3CO)nc2)c1)C(=O)CN] | 2HCl |
| 42 | 19 | 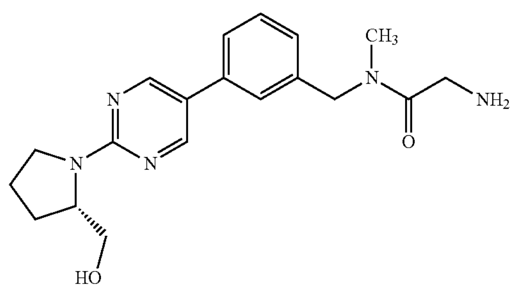 [SMILES: CN(Cc1cccc(-c2cnc(N3CCC[C@H]3CO)nc2)c1)C(=O)CN] | 2HCl |
| 43 | 19 | 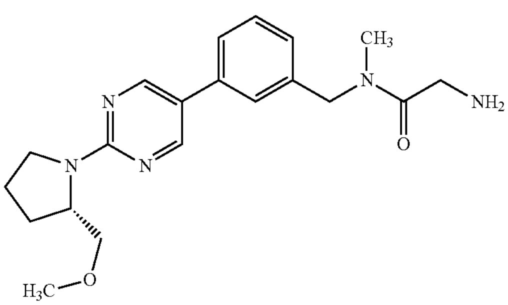 [SMILES: COC[C@@H]1CCCN1c1ncc(-c2cccc(CN(C)C(=O)CN)c2)cn1] | 2HCl |

TABLE 86-continued
| Ex | Syn | Structure | Acid |
|---|---|---|---|
| 44 | 19 | 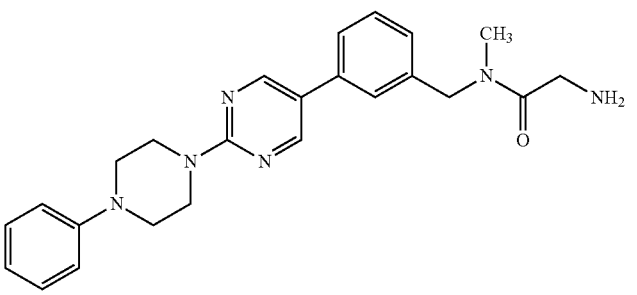 [SMILES: CN(Cc1cccc(-c2cnc(N3CCN(c4ccccc4)CC3)nc2)c1)C(=O)CN] | 3HCl |
TABLE 87
| Ex | Syn | Structure | Acid |
|---|---|---|---|
| 45 | 19 | 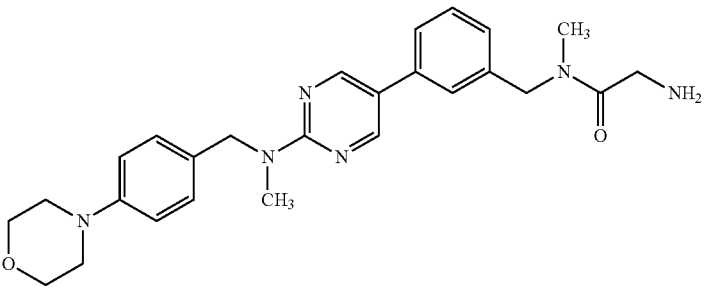 [SMILES: CN(Cc1cccc(-c2cnc(N(C)Cc3ccc(N4CCOCC4)cc3)nc2)c1)C(=O)CN] | 3HCl |
| 46 | 19 | 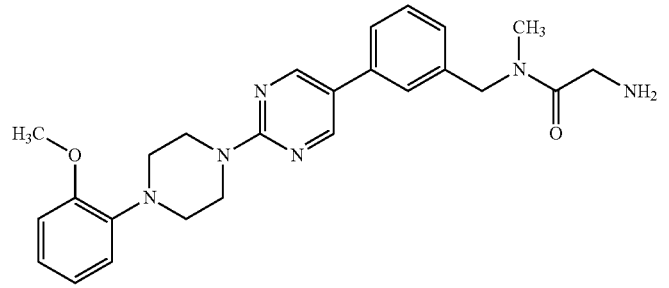 [SMILES: COc1ccccc1N1CCN(c2ncc(-c3cccc(CN(C)C(=O)CN)c3)cn2)CC1] | 3HCl |
| 47 | 19 | 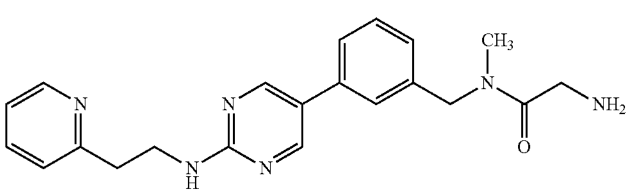 [SMILES: CN(Cc1cccc(-c2cnc(NCCc3ccccn3)nc2)c1)C(=O)CN] | 3HCl |
| 48 | 19 | 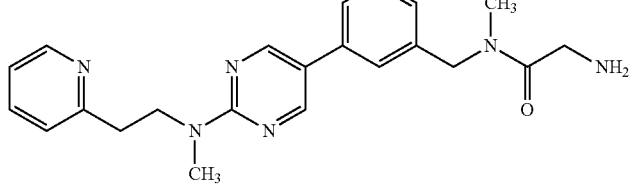 | 3HCl |

TABLE 87-continued

| Ex | Syn | Structure | Acid |
|---|---|---|---|
| 49 | 19 | 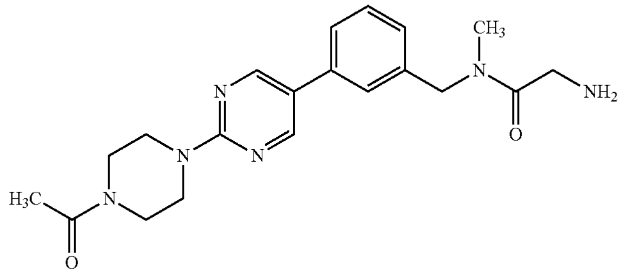 [SMILES: CC(=O)N1CCN(c2ncc(-c3cccc(CN(C)C(=O)CN)c3)cn2)CC1] | 2HCl |
| 50 | 19 | 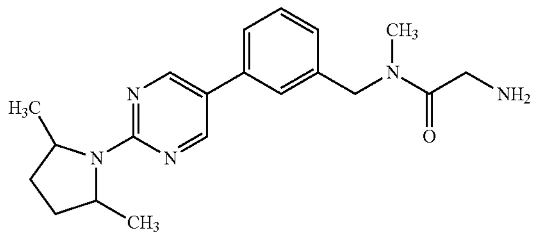 [SMILES: CC1CCC(C)N1c1ncc(-c2cccc(CN(C)C(=O)CN)c2)cn1] | 2HCl |

TABLE 88

| Ex | Syn | Structure | Acid |
|---|---|---|---|
| 51 | 19 | 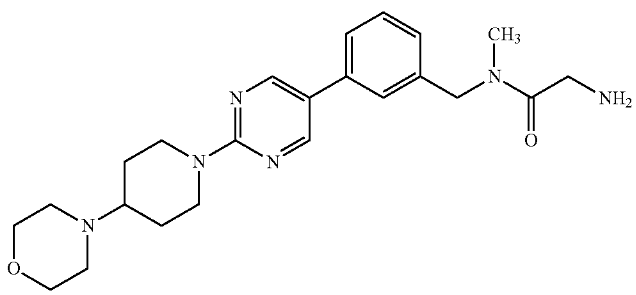 [SMILES: CN(Cc1cccc(-c2cnc(N3CCC(N4CCOCC4)CC3)nc2)c1)C(=O)CN] | 3HCl |
| 52 | 19 | 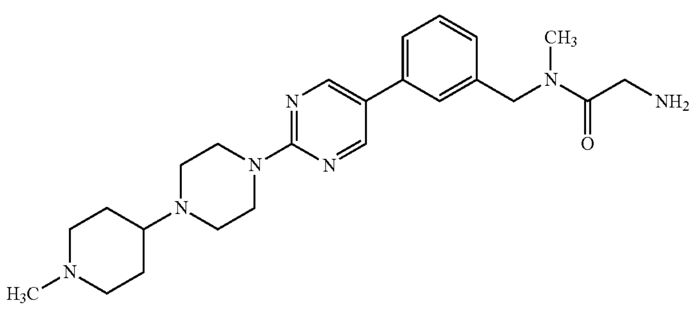 [SMILES: CN1CCC(N2CCN(c3ncc(-c4cccc(CN(C)C(=O)CN)c4)cn3)CC2)CC1] | 4HCl |
| 53 | 19 | 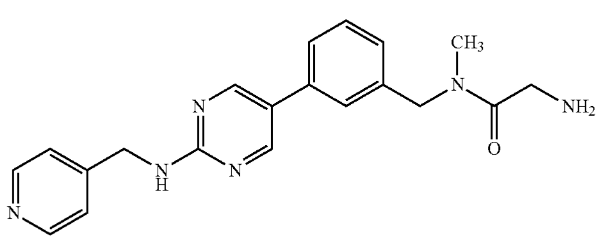 [SMILES: CN(Cc1cccc(-c2cnc(NCc3ccncc3)nc2)c1)C(=O)CN] | 3HCl |

TABLE 88-continued
| Ex | Syn | Structure | Acid |
|----|-----|-----------|------|
| 54 | 19 | 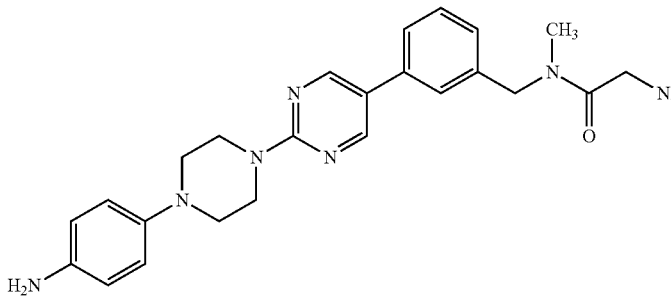 | 3HCl |
| 55 | 19 | 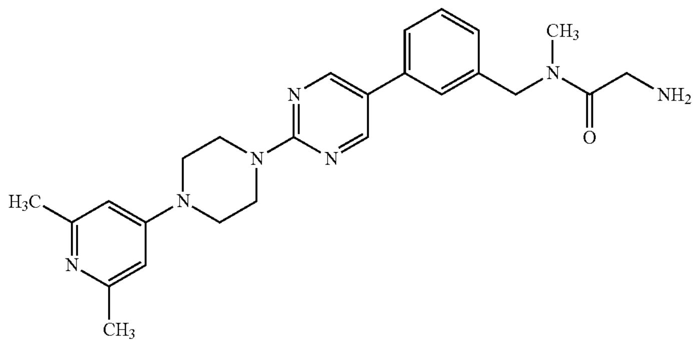 [SMILES: Cc1cc(N2CCN(c3ncc(-c4cccc(CN(C)C(=O)CN)c4)cn3)CC2)cc(C)n1] | 3HCl |
TABLE 89
| Ex | Syn | Structure | Acid |
|----|-----|-----------|------|
| 56 | 19 | 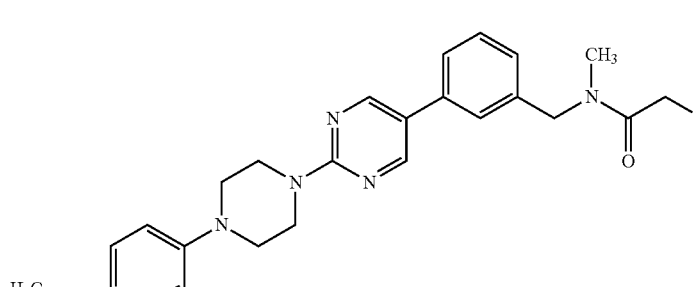 | 3HCl |
| 57 | 19 | 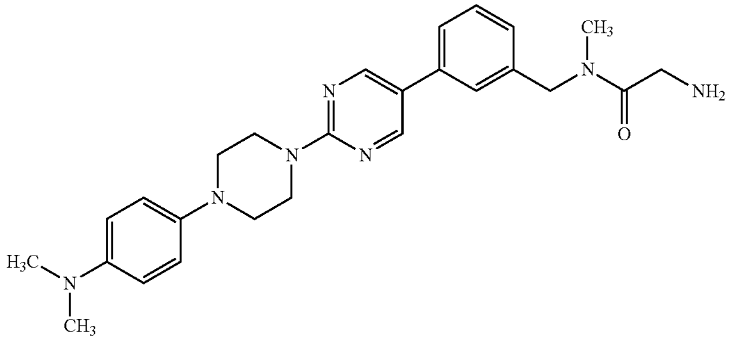 [SMILES: CN(Cc1cccc(-c2cnc(N3CCN(c4ccc(N(C)C)cc4)CC3)nc2)c1)C(=O)CN] | 3HCl |

TABLE 89-continued

| Ex | Syn | Structure | Acid |
|---|---|---|---|
| 58 | 19 | 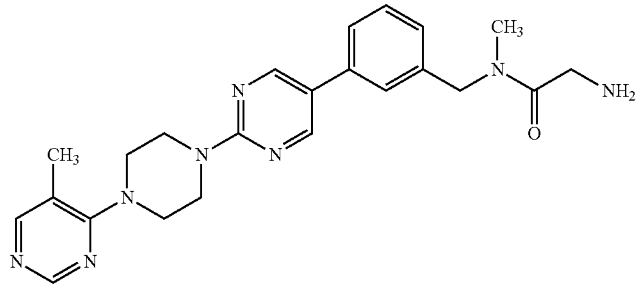 [SMILES: Cc1cncnc1N1CCN(c2ncc(-c3cccc(CN(C)C(=O)CN)c3)cn2)CC1] | 3HCl |
| 59 | 19 | 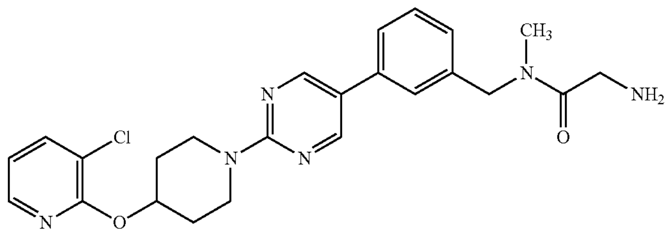 [SMILES: CN(Cc1cccc(-c2cnc(N3CCC(Oc4ncccc4Cl)CC3)nc2)c1)C(=O)CN] | 3HCl |
| 60 | 19 | 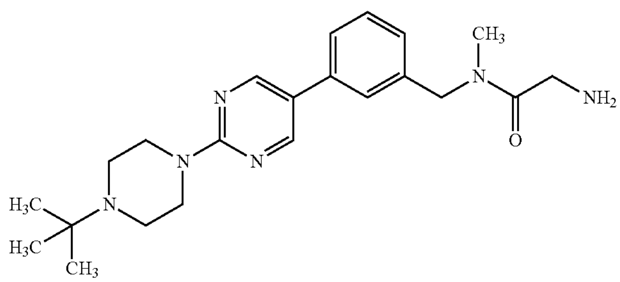 [SMILES: CN(Cc1cccc(-c2cnc(N3CCN(C(C)(C)C)CC3)nc2)c1)C(=O)CN] | 2HCl |

TABLE 90

| Ex | Syn | Structure | Acid |
|---|---|---|---|
| 61 | 19 | 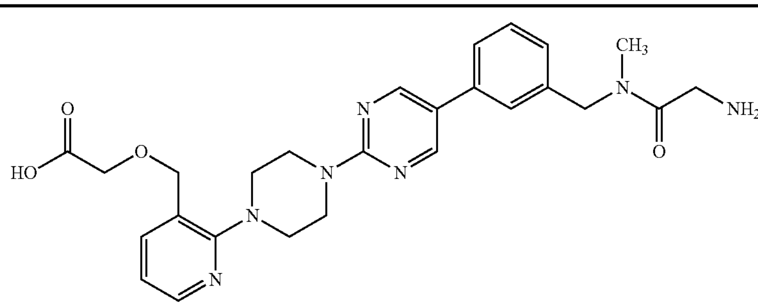 | 2HCl |
| 62 | 19 | 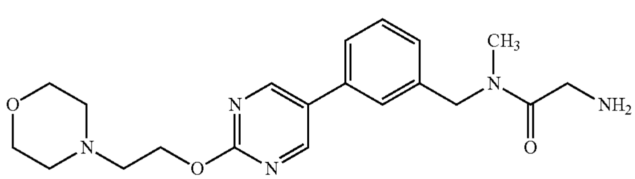 [SMILES: CN(Cc1cccc(-c2cnc(OCCN3CCOCC3)nc2)c1)C(=O)CN] | 2HCl |

TABLE 90-continued

| Ex | Syn | Structure | Acid |
|----|-----|-----------|------|
| 63 | 19 | 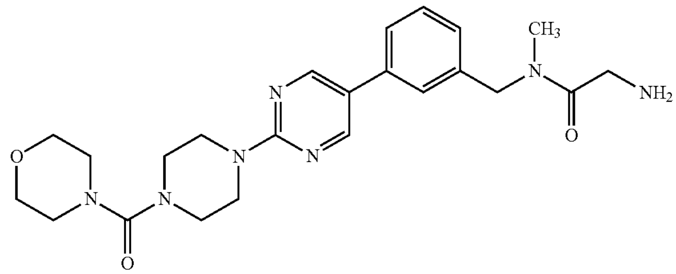 [SMILES: CN(Cc1cccc(-c2cnc(N3CCN(C(=O)N4CCOCC4)CC3)nc2)c1)C(=O)CN] | 2HCl |
| 64 | 19 | 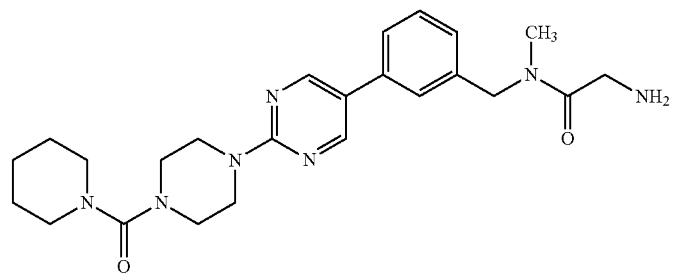 [SMILES: CN(Cc1cccc(-c2cnc(N3CCN(C(=O)N4CCCCC4)CC3)nc2)c1)C(=O)CN] | 2HCl |
| 65 | 19 | 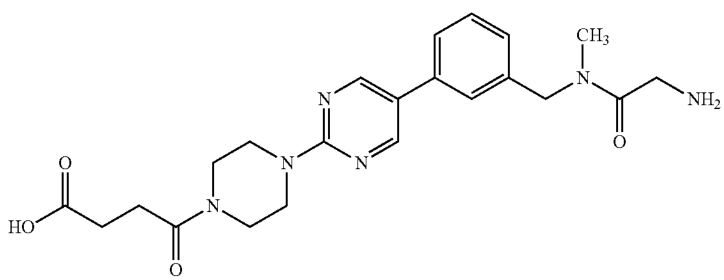 [SMILES: CN(Cc1cccc(-c2cnc(N3CCN(C(=O)CCC(=O)O)CC3)nc2)c1)C(=O)CN] | 2HCl |
| 66 | 19 | 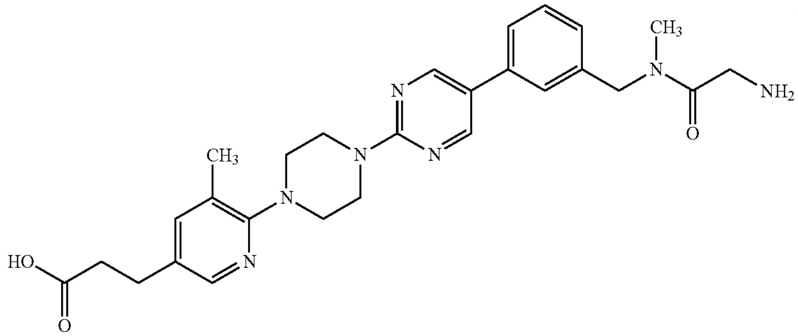 [SMILES: Cc1cc(CCC(=O)O)cnc1N1CCN(c2ncc(-c3cccc(CN(C)C(=O)CN)c3)cn2)CC1] | 2HCl |

TABLE 91

| Ex | Syn | Structure | Acid |
|---|---|---|---|
| 67 | 19 | 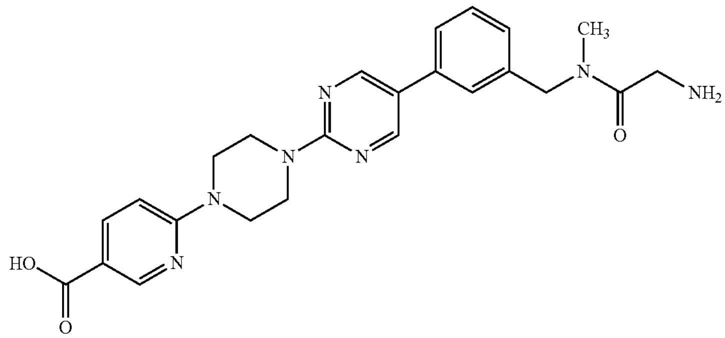 [SMILES: CN(Cc1cccc(-c2cnc(N3CCN(c4ccc(C(=O)O)cn4)CC3)nc2)c1)C(=O)CN] | 3HCl |
| 68 | 19 | 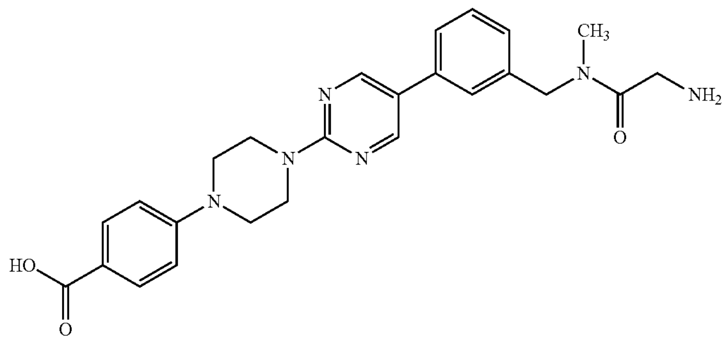 [SMILES: CN(Cc1cccc(-c2cnc(N3CCN(c4ccc(C(=O)O)cc4)CC3)nc2)c1)C(=O)CN] | 2HCl |
| 69 | 69 | 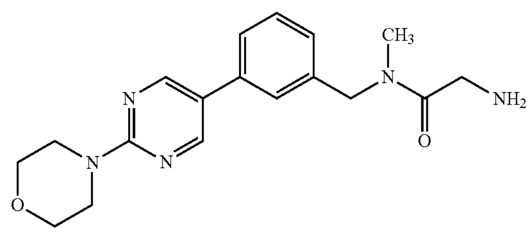 [SMILES: CN(Cc1cccc(-c2cnc(N3CCOCC3)nc2)c1)C(=O)CN] | L-TA |
| 70 | 69 | 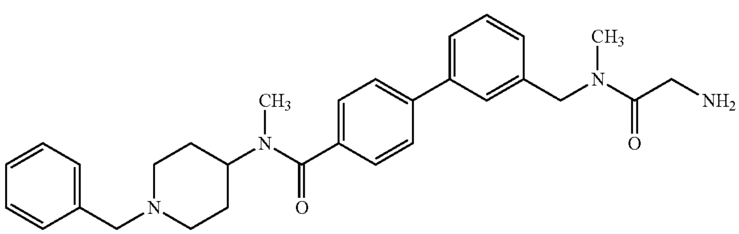 [SMILES: CN(Cc1cccc(-c2ccc(C(=O)N(C)C3CCN(Cc4ccccc4)CC3)cc2)c1)C(=O)CN] | OA |
| 71 | 69 | 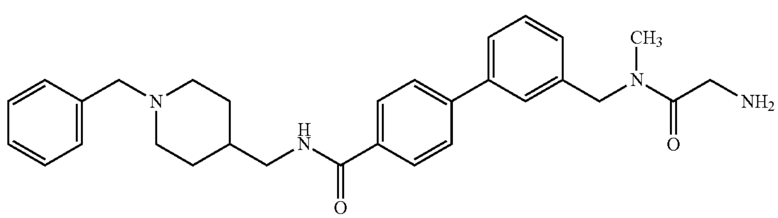 [SMILES: CN(Cc1cccc(-c2ccc(C(=O)NCC3CCN(Cc4ccccc4)CC3)cc2)c1)C(=O)CN] | OA |
| 72 | 69 | 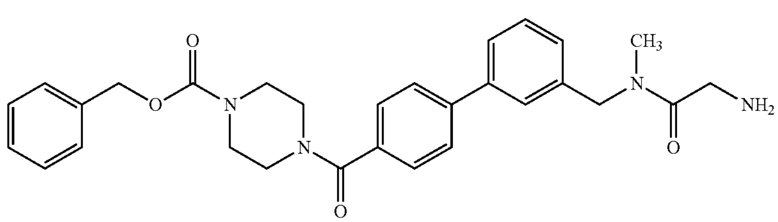 [SMILES: CN(Cc1cccc(-c2ccc(C(=O)N3CCN(C(=O)OCc4ccccc4)CC3)cc2)c1)C(=O)CN] | OA |

TABLE 92

| Ex | Syn | Structure | Acid |
|---|---|---|---|
| 73 | 69 | 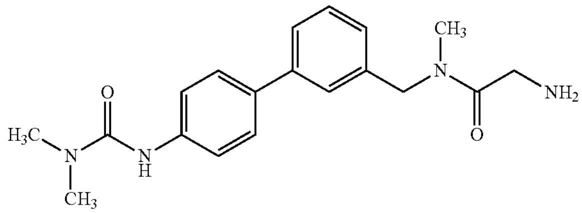 [SMILES: CN(C)C(=O)Nc1ccc(-c2cccc(CN(C)C(=O)CN)c2)cc1] | OA |
| 74 | 69 | 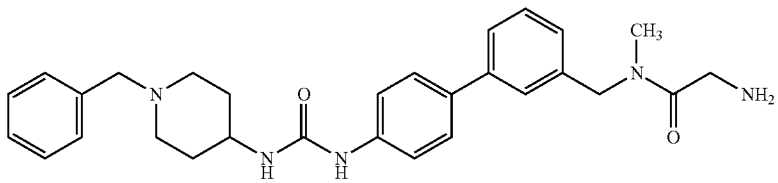 [SMILES: CN(Cc1cccc(-c2ccc(NC(=O)NC3CCN(Cc4ccccc4)CC3)cc2)c1)C(=O)CN] | OA |
| 75 | 69 | 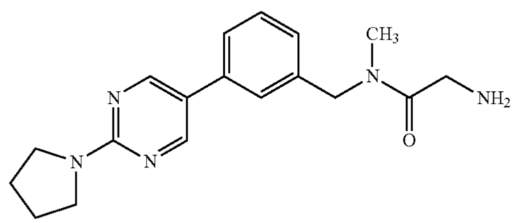 [SMILES: CN(Cc1cccc(-c2cnc(N3CCCC3)nc2)c1)C(=O)CN] | L-TA |
| 76 | 69 | 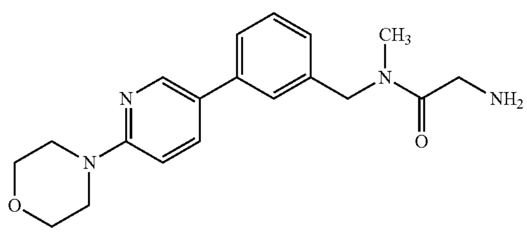 [SMILES: CN(Cc1cccc(-c2ccc(N3CCOCC3)nc2)c1)C(=O)CN] | L-TA |
| 77 | 69 | cis | L-TA |
| 78 | 69 | cis | L-TA |

TABLE 93

| Ex | Syn | Structure | Acid |
|---|---|---|---|
| 79 | 69 | (structure) | L-TA |
| 80 | 69 | (structure, cis) | L-TA |
| 81 | 69 | (structure) | L-TA |
| 82 | 69 | (structure) | L-TA |
| 83 | 69 | (structure) | L-TA |
| 84 | 69 | (structure) | L-TA |

TABLE 94

| Ex | Syn | Structure | Acid |
|----|-----|-----------|------|
| 85 | 69 | 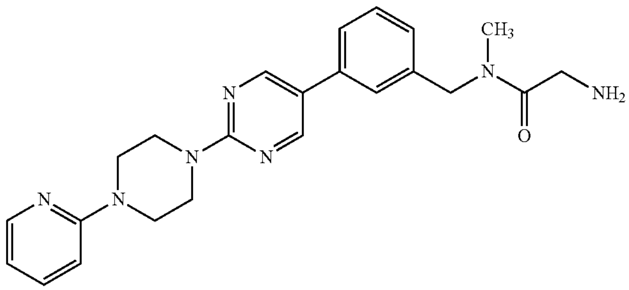 [SMILES: CN(Cc1cccc(-c2cnc(N3CCN(c4ccccn4)CC3)nc2)c1)C(=O)CN] | L-TA |
| 86 | 69 | 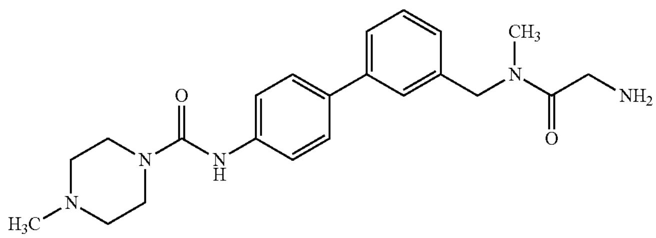 [SMILES: CN1CCN(C(=O)Nc2ccc(-c3cccc(CN(C)C(=O)CN)c3)cc2)CC1] | L-TA |
| 87 | 69 | 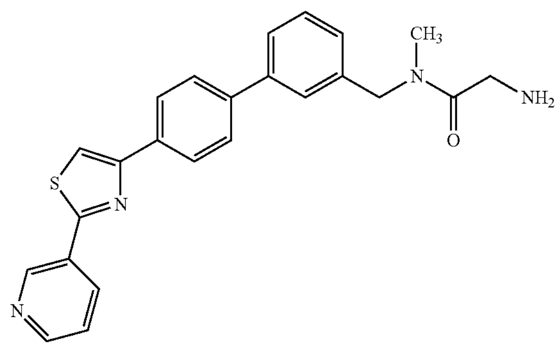 [SMILES: CN(Cc1cccc(-c2ccc(-c3csc(-c4cccnc4)n3)cc2)c1)C(=O)CN] | L-TA |
| 88 | 69 | 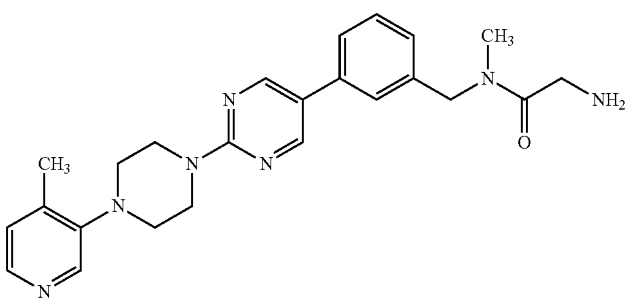 [SMILES: Cc1ccncc1N1CCN(c2ncc(-c3cccc(CN(C)C(=O)CN)c3)cn2)CC1] | L-TA |
| 89 | 69 | 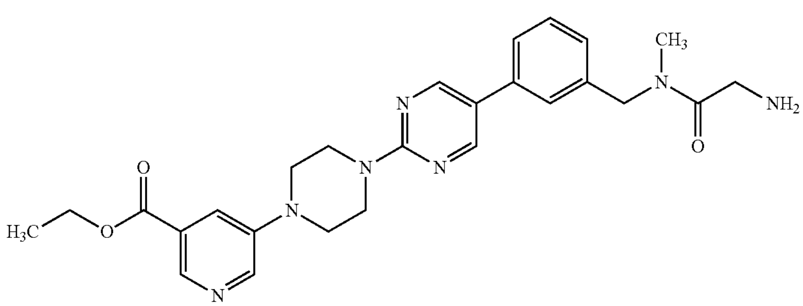 [SMILES: CCOC(=O)c1cncc(N2CCN(c3ncc(-c4cccc(CN(C)C(=O)CN)c4)cn3)CC2)c1] | L-TA |

TABLE 95
| Ex | Syn | Structure | Acid |
|----|-----|-----------|------|
| 90 | 69 | 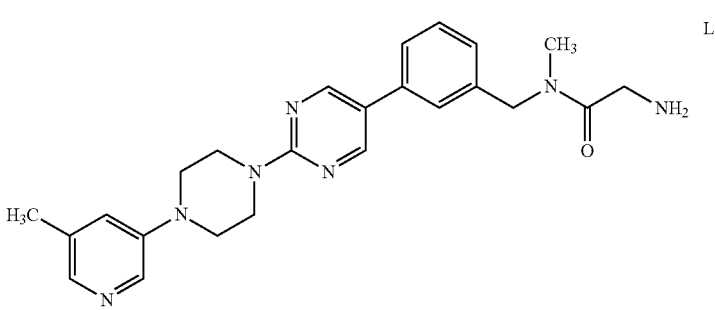 | L-TA |
| 91 | 69 | 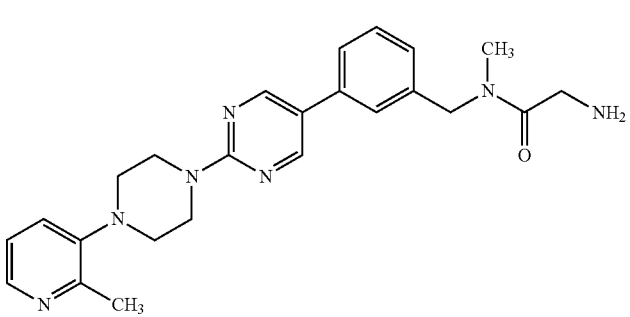 [SMILES: Cc1ncccc1N1CCN(c2ncc(-c3cccc(CN(C)C(=O)CN)c3)cn2)CC1] | L-TA |
| 92 | 69 | 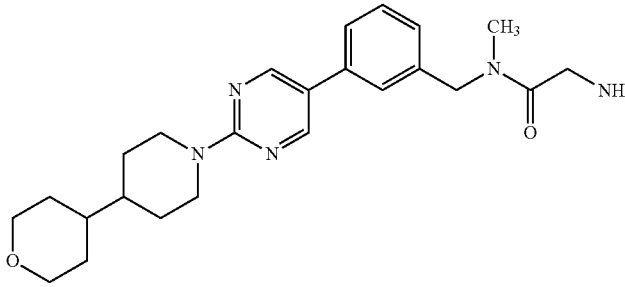 | L-TA |
| 93 | 69 | 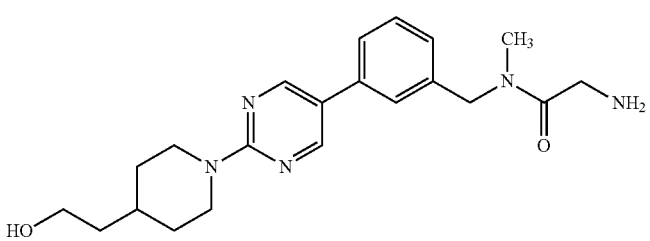 [SMILES: CN(Cc1cccc(-c2cnc(N3CCC(CCO)CC3)nc2)c1)C(=O)CN] | L-TA |
| 94 | 69 | 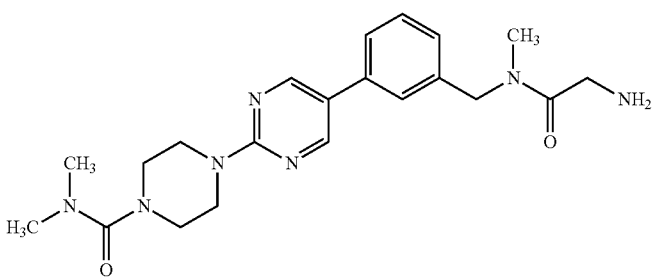 [SMILES: CN(C)C(=O)N1CCN(c2ncc(-c3cccc(CN(C)C(=O)CN)c3)cn2)CC1] | L-TA |

TABLE 96

| Ex | Syn | Structure | Acid |
|----|-----|-----------|------|
| 95 | 69 | 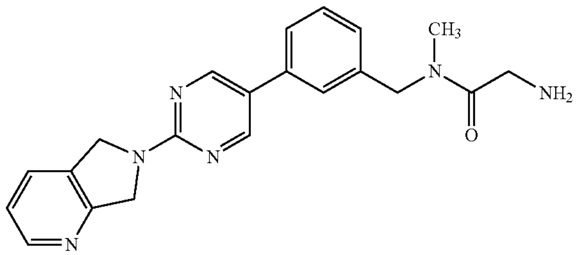 [SMILES: CN(Cc1cccc(-c2cnc(N3Cc4cccnc4C3)nc2)c1)C(=O)CN] | 3HCl |
| 96 | 69 | 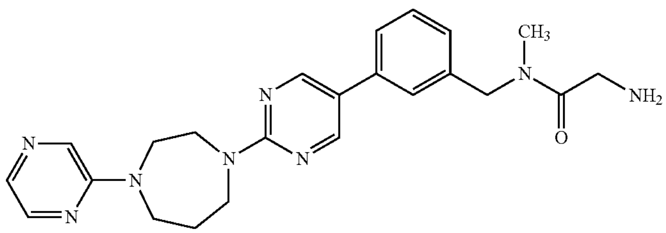 [SMILES: CN(Cc1cccc(-c2cnc(N3CCCN(c4cnccn4)CC3)nc2)c1)C(=O)CN] | L-TA |
| 97 | 69 | 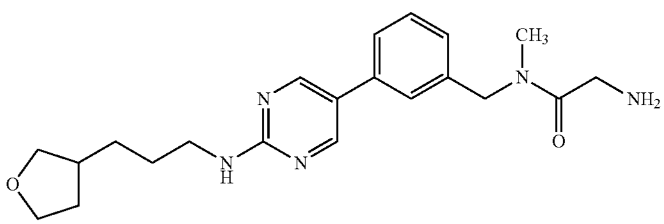 [SMILES: CN(Cc1cccc(-c2cnc(NCCCC3CCOC3)nc2)c1)C(=O)CN] | L-TA |
| 98 | 69 | 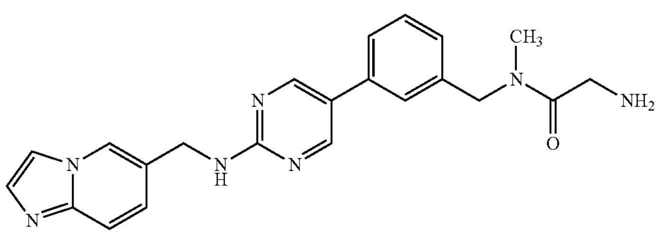 [SMILES: CN(Cc1cccc(-c2cnc(NCc3ccc4nccn4c3)nc2)c1)C(=O)CN] | L-TA |
| 99 | 69 | 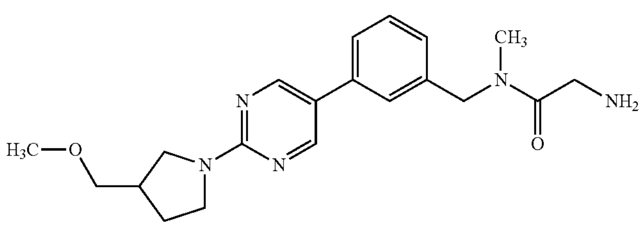 [SMILES: COCC1CCN(c2ncc(-c3cccc(CN(C)C(=O)CN)c3)cn2)C1] | L-TA |
| 100 | 69 | 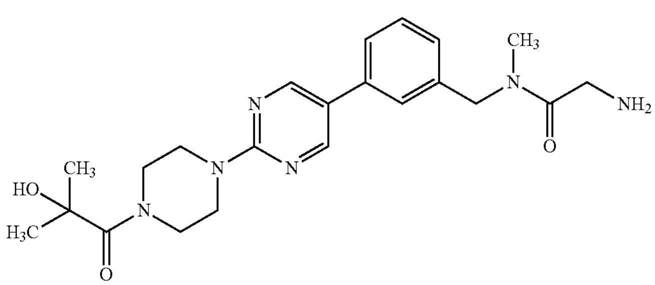 [SMILES: CN(Cc1cccc(-c2cnc(N3CCN(C(=O)C(C)(C)O)CC3)nc2)c1)C(=O)CN] | L-TA |

TABLE 97
| Ex | Syn | Structure | Acid |
|---|---|---|---|
| 101 | 69 | 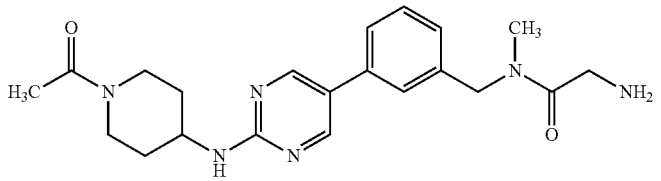 [SMILES: CC(=O)N1CCC(Nc2ncc(-c3cccc(CN(C)C(=O)CN)c3)cn2)CC1] | L-TA |
| 102 | 69 | 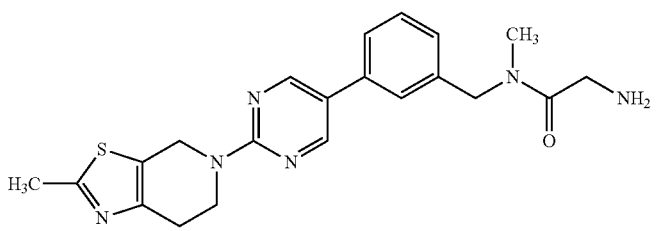 [SMILES: Cc1nc2c(s1)CN(c1ncc(-c3cccc(CN(C)C(=O)CN)c3)cn1)CC2] | L-TA |
| 103 | 69 | 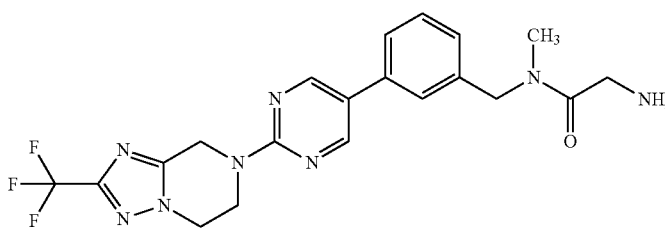 | L-TA |
| 104 | 69 | 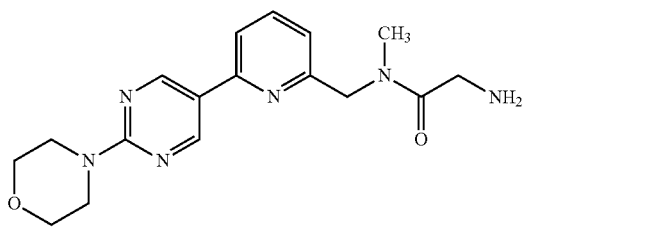 [SMILES: CN(Cc1cccc(-c2cnc(N3CCOCC3)nc2)n1)C(=O)CN] | L-TA |
| 105 | 69 | 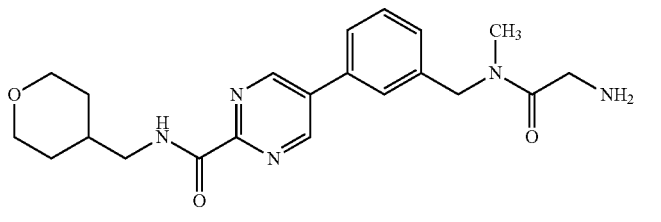 [SMILES: CN(Cc1cccc(-c2cnc(C(=O)NCC3CCOCC3)nc2)c1)C(=O)CN] | L-TA |
| 106 | 69 | 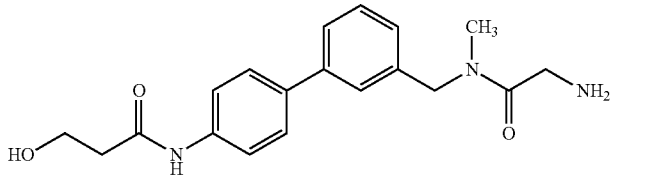 [SMILES: CN(Cc1cccc(-c2ccc(NC(=O)CCO)cc2)c1)C(=O)CN] | L-TA |
| 107 | 69 | 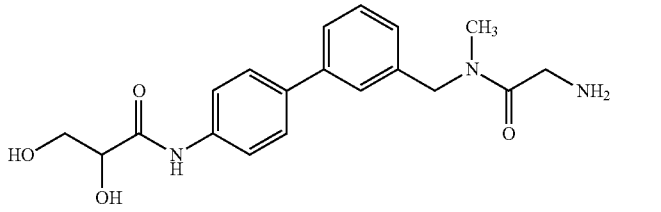 [SMILES: CN(Cc1cccc(-c2ccc(NC(=O)C(O)CO)cc2)c1)C(=O)CN] | L-TA |

TABLE 98

| Ex | Syn | Structure | Acid |
|---|---|---|---|
| 108 | 69 | 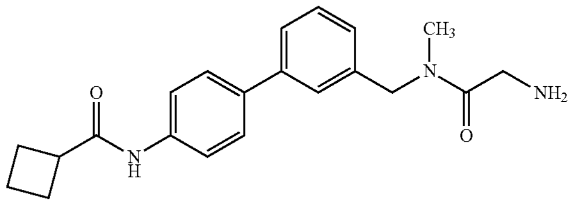 [SMILES: CN(Cc1cccc(-c2ccc(NC(=O)C3CCC3)cc2)c1)C(=O)CN] | L-TA |
| 109 | 69 | cis | L-TA |
| 110 | 69 | trans | L-TA |
| 111 | 69 | 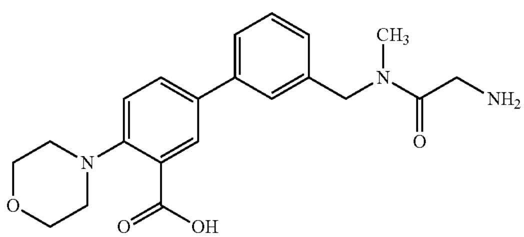 [SMILES: CN(Cc1cccc(-c2ccc(N3CCOCC3)c(C(=O)O)c2)c1)C(=O)CN] | L-TA |
| 112 | 69 | 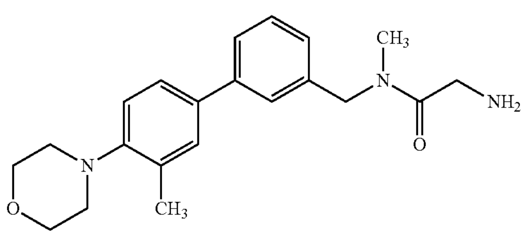 [SMILES: Cc1cc(-c2cccc(CN(C)C(=O)CN)c2)ccc1N1CCOCC1] | L-TA |
| 113 | 69 | 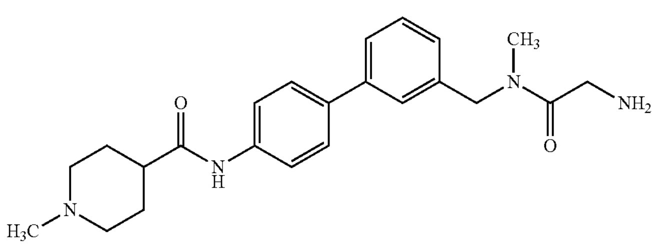 | L-TA |

TABLE 99
| Ex | Syn | Structure | Acid |
|----|-----|-----------|------|
| 114 | 69 | 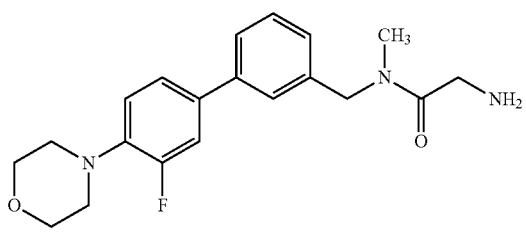 [SMILES: CN(Cc1cccc(-c2ccc(N3CCOCC3)c(F)c2)c1)C(=O)CN] | L-TA |
| 115 | 69 | 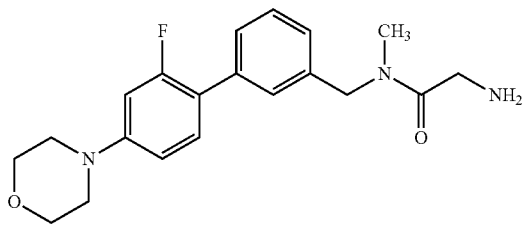 [SMILES: CN(Cc1cccc(-c2ccc(N3CCOCC3)cc2F)c1)C(=O)CN] | L-TA |
| 116 | 69 | 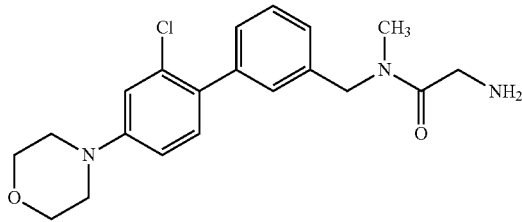 [SMILES: CN(Cc1cccc(-c2ccc(N3CCOCC3)cc2Cl)c1)C(=O)CN] | L-TA |
| 117 | 69 | 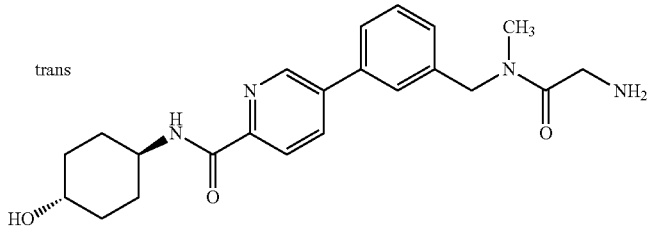 [SMILES: CN(Cc1cccc(-c2ccc(C(=O)N[C@H]3CC[C@H](O)CC3)nc2)c1)C(=O)CN] | L-TA |
| 118 | 69 | 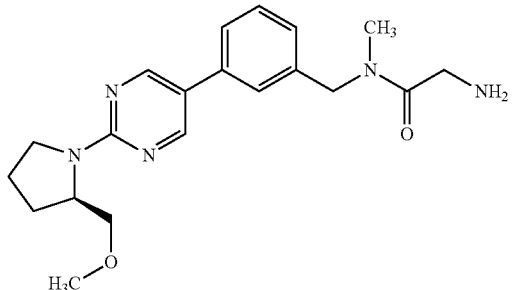 | L-TA |
| 119 | 69 | 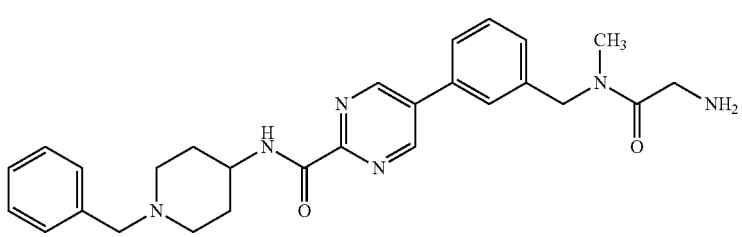 [SMILES: CN(Cc1cccc(-c2cnc(C(=O)NC3CCN(Cc4ccccc4)CC3)nc2)c1)C(=O)CN] | L-TA |

TABLE 100

| Ex | Syn | Structure | Acid |
|----|-----|-----------|------|
| 120 | 69 | 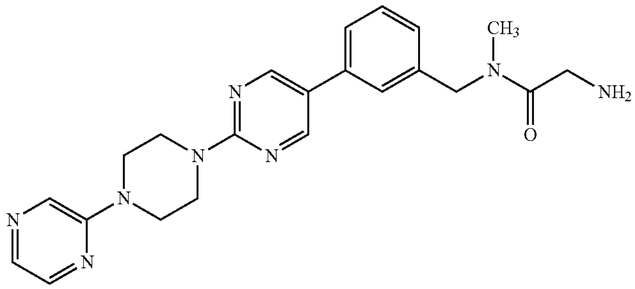 [SMILES: CN(Cc1cccc(-c2cnc(N3CCN(c4cnccn4)CC3)nc2)c1)C(=O)CN] | L-TA |
| 121 | 69 | 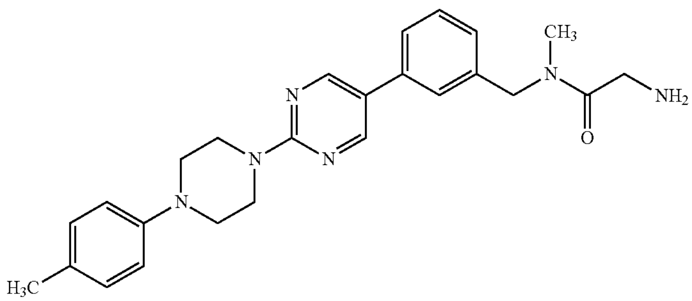 [SMILES: Cc1ccc(N2CCN(c3ncc(-c4cccc(CN(C)C(=O)CN)c4)cn3)CC2)cc1] | L-TA |
| 122 | 69 | 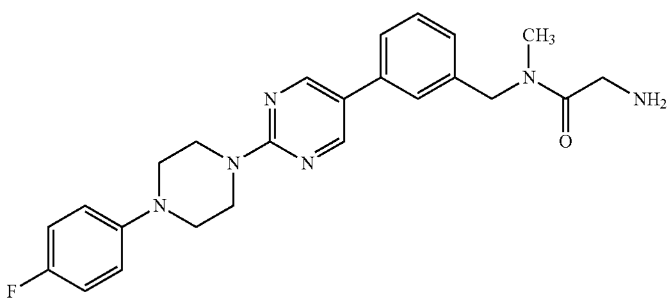 [SMILES: CN(Cc1cccc(-c2cnc(N3CCN(c4ccc(F)cc4)CC3)nc2)c1)C(=O)CN] | L-TA |
| 123 | 69 | 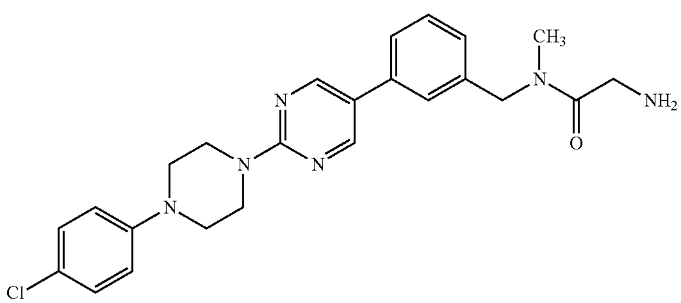 [SMILES: CN(Cc1cccc(-c2cnc(N3CCN(c4ccc(Cl)cc4)CC3)nc2)c1)C(=O)CN] | L-TA |
| 124 | 69 | 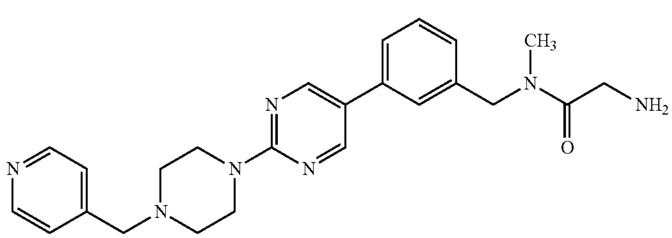 [SMILES: CN(Cc1cccc(-c2cnc(N3CCN(Cc4ccncc4)CC3)nc2)c1)C(=O)CN] | L-TA |

TABLE 101

| Ex | Syn | Structure | Acid |
|----|-----|-----------|------|
| 125 | 69 | 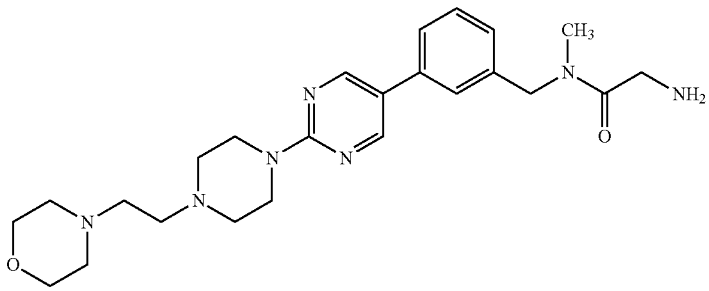 | L-TA |
| 126 | 69 | 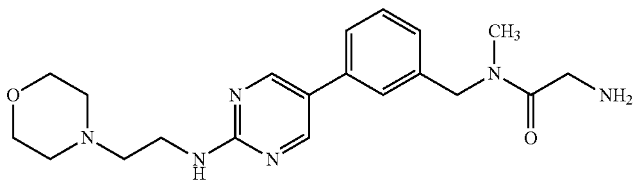 [SMILES: CN(Cc1cccc(-c2cnc(NCCN3CCOCC3)nc2)c1)C(=O)CN] | L-TA |
| 127 | 69 | cis | L-TA |
| 128 | 69 | 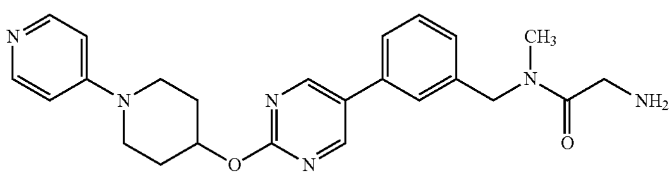 [SMILES: CN(Cc1cccc(-c2cnc(OC3CCN(c4ccncc4)CC3)nc2)c1)C(=O)CN] | L-TA |
| 129 | 69 | 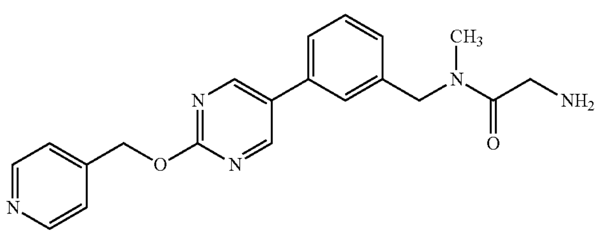 [SMILES: CN(Cc1cccc(-c2cnc(OCc3ccncc3)nc2)c1)C(=O)CN] | L-TA |
| 130 | 69 | 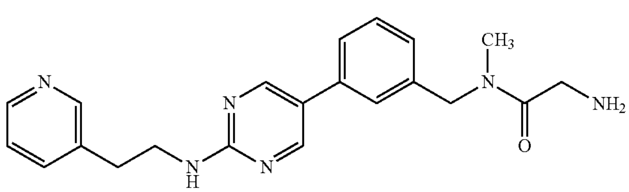 [SMILES: CN(Cc1cccc(-c2cnc(NCCc3cccnc3)nc2)c1)C(=O)CN] | L-TA |
| 131 | 69 | 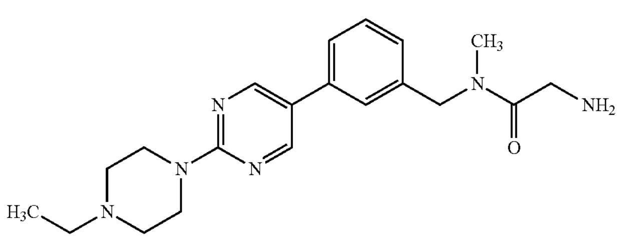 [SMILES: CCN1CCN(c2ncc(-c3cccc(CN(C)C(=O)CN)c3)cn2)CC1] | L-TA |

TABLE 102

| Ex | Syn | Structure | Acid |
|----|-----|-----------|------|
| 132 | 69 | 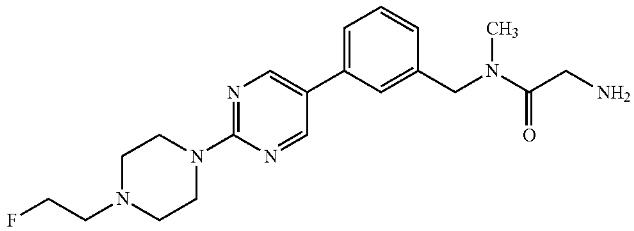 [SMILES: CN(Cc1cccc(-c2cnc(N3CCN(CCF)CC3)nc2)c1)C(=O)CN] | L-TA |
| 133 | 69 | 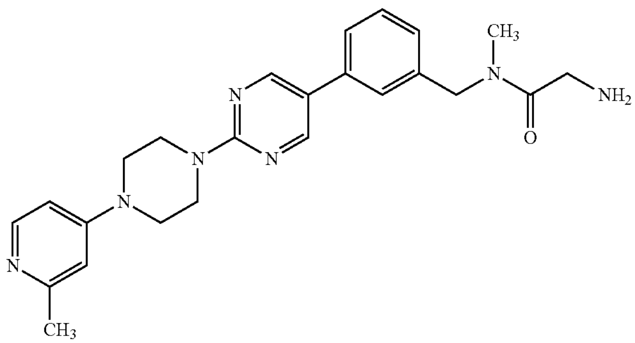 [SMILES: Cc1cc(N2CCN(c3ncc(-c4cccc(CN(C)C(=O)CN)c4)cn3)CC2)ccn1] | L-TA |
| 134 | 69 | 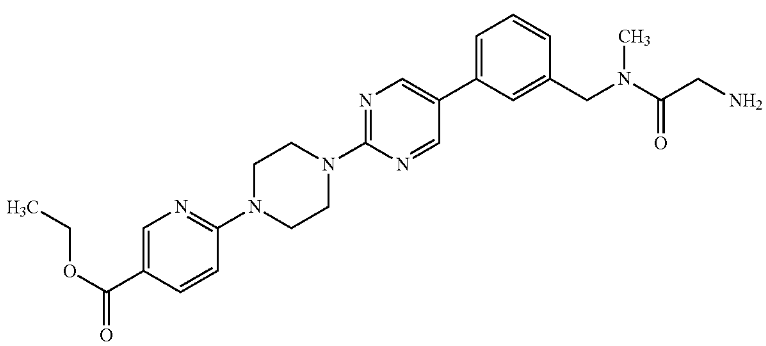 [SMILES: CCOC(=O)c1ccc(N2CCN(c3ncc(-c4cccc(CN(C)C(=O)CN)c4)cn3)CC2)nc1] | L-TA |
| 135 | 69 | 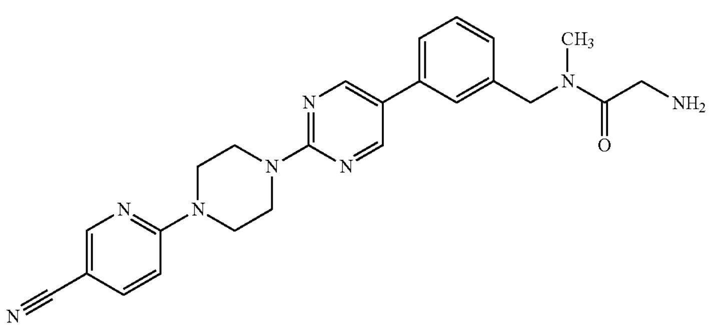 [SMILES: CN(Cc1cccc(-c2cnc(N3CCN(c4ccc(C#N)cn4)CC3)nc2)c1)C(=O)CN] | L-TA |
| 136 | 69 | 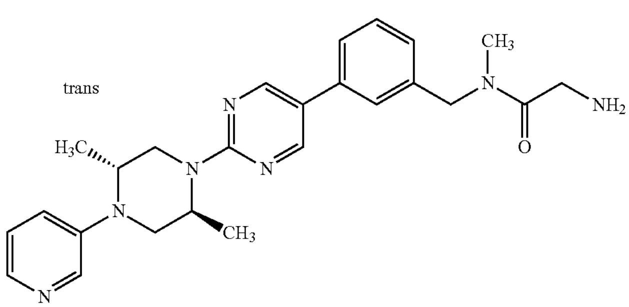 [SMILES: C[C@@H]1CN(c2ncc(-c3cccc(CN(C)C(=O)CN)c3)cn2)[C@@H](C)CN1c1cccnc1] | L-TA |

TABLE 103

| Ex | Syn | Structure | Acid |
|---|---|---|---|
| 137 | 69 | (structure) | L-TA |
| 138 | 69 | (structure) | L-TA |
| 139 | 69 | (structure) | L-TA |
| 140 | 69 | (structure, trans) | L-TA |

TABLE 104

| Ex | Syn | Structure | Acid |
|---|---|---|---|
| 141 | 69 | trans isomer; 2,5-dimethylpiperazine with N-(2-pyridyl) and N'-[5-(3-{[N-methyl-N-(glycylamide)methyl]}phenyl)pyrimidin-2-yl] substituents | L-TA |
| 142 | 69 | 4-(2-pyridyl)piperazin-1-yl-pyridin-2-yl linked to 3-{[N-methyl-N-(glycylamide)methyl]}phenyl | L-TA |
| 143 | 69 | 4-(4-pyridyl)piperazin-1-yl-pyridin-2-yl linked to 3-{[N-methyl-N-(glycylamide)methyl]}phenyl | L-TA |
| 144 | 69 | 4-(4-pyridyl)piperidin-1-yl-pyridin-2-yl linked to 3-{[N-methyl-N-(glycylamide)methyl]}phenyl | L-TA |
| 145 | 69 | 4-(2-pyrimidinyl)piperidin-1-yl-pyrimidin-2-yl linked to 3-{[N-methyl-N-(glycylamide)methyl]}phenyl | L-TA |

TABLE 105

| Ex | Syn | Structure | Acid |
|----|-----|-----------|------|
| 146 | 69 | 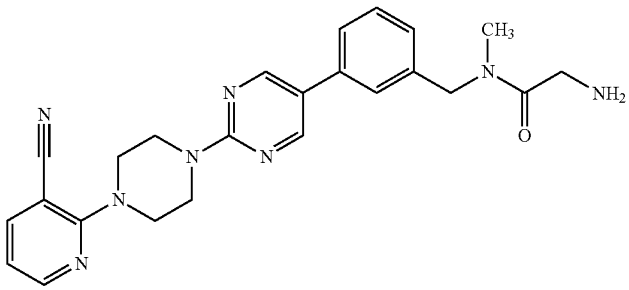 [SMILES: CN(Cc1cccc(-c2cnc(N3CCN(c4ncccc4C#N)CC3)nc2)c1)C(=O)CN] | L-TA |
| 147 | 69 | 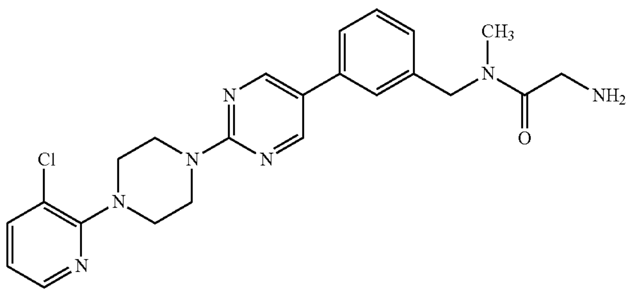 [SMILES: CN(Cc1cccc(-c2cnc(N3CCN(c4ncccc4Cl)CC3)nc2)c1)C(=O)CN] | L-TA |
| 148 | 69 | 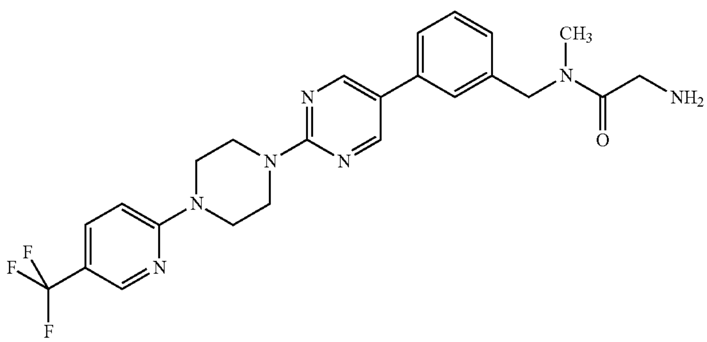 [SMILES: CN(Cc1cccc(-c2cnc(N3CCN(c4ccc(C(F)(F)F)cn4)CC3)nc2)c1)C(=O)CN] | L-TA |
| 149 | 69 | 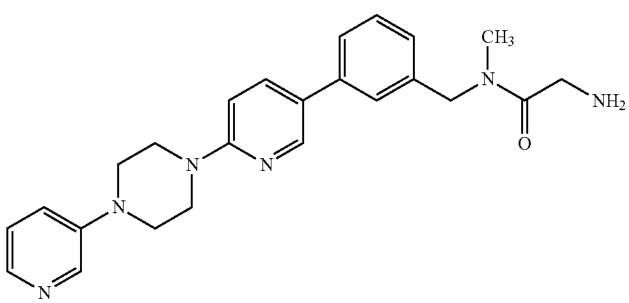 | L-TA |
| 150 | 69 | 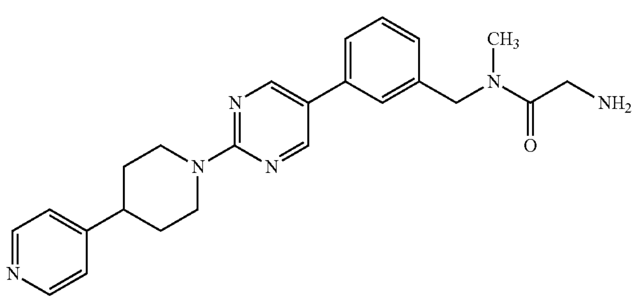 [SMILES: CN(Cc1cccc(-c2cnc(N3CCC(c4ccncc4)CC3)nc2)c1)C(=O)CN] | L-TA |

TABLE 106
| Ex | Syn | Structure | Acid |
|---|---|---|---|
| 151 | 69 | 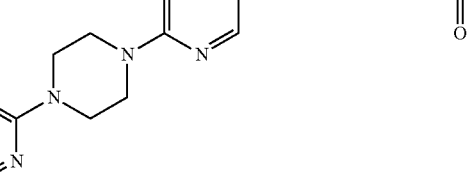 | L-TA |
| 152 | 69 | 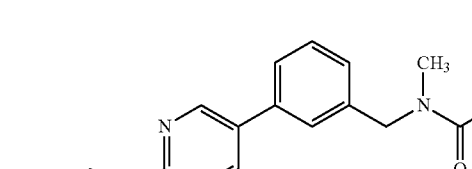 | L-TA |
| 153 | 69 | 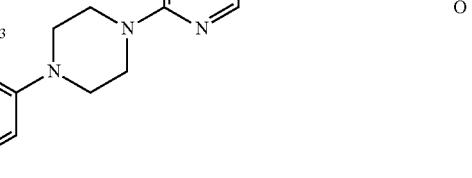 | L-TA |
| 154 | 69 | 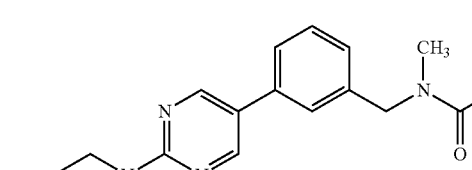 | L-TA |
| 155 | 69 | 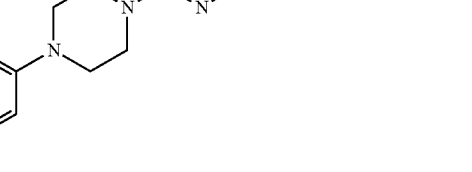 | L-TA |

TABLE 107
| Ex | Syn | Structure | Acid |
|---|---|---|---|
| 156 | 69 | 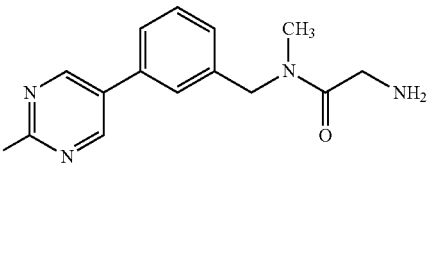 | L-TA |
| 157 | 69 | 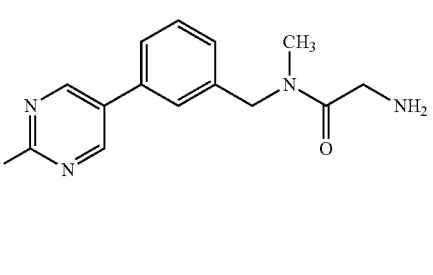 | L-TA |
| 158 | 69 | 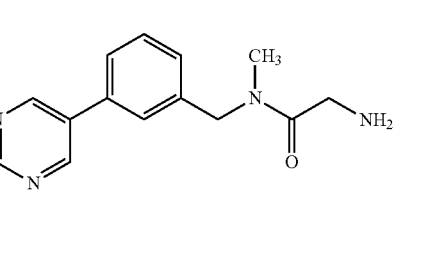 | L-TA |
| 159 | 69 | 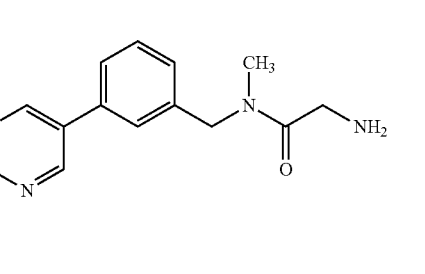 | L-TA |
| 160 | 69 | 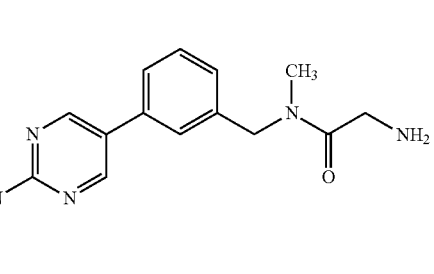 | L-TA |

TABLE 108
| Ex | Syn | Structure | Acid |
|---|---|---|---|
| 161 | 69 | 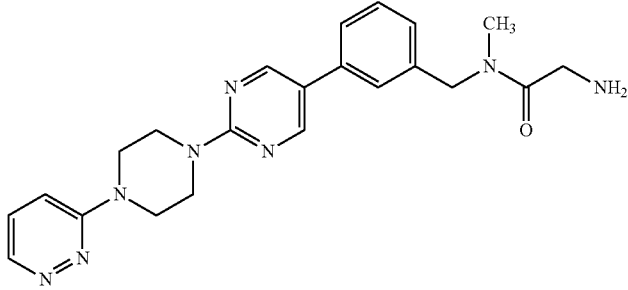 [SMILES: CN(Cc1cccc(-c2cnc(N3CCN(c4cccnn4)CC3)nc2)c1)C(=O)CN] | L-TA |
| 162 | 69 | 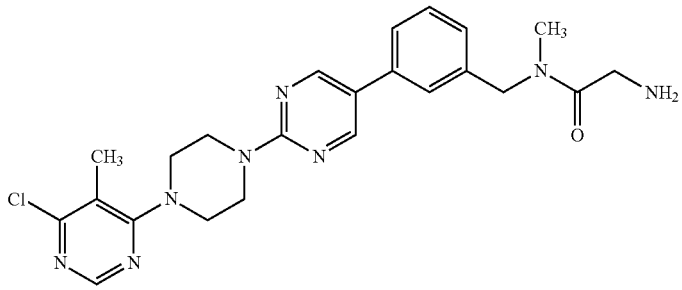 [SMILES: Cc1c(Cl)ncnc1N1CCN(c2ncc(-c3cccc(CN(C)C(=O)CN)c3)cn2)CC1] | L-TA |
| 163 | 69 | 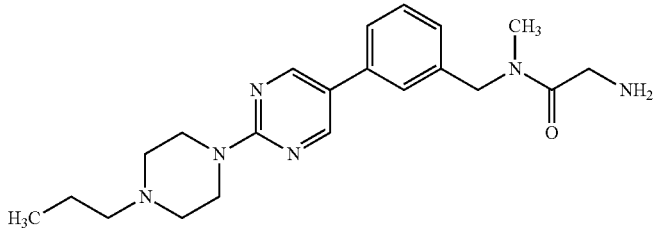 [SMILES: CCCN1CCN(c2ncc(-c3cccc(CN(C)C(=O)CN)c3)cn2)CC1] | L-TA |
| 164 | 69 | 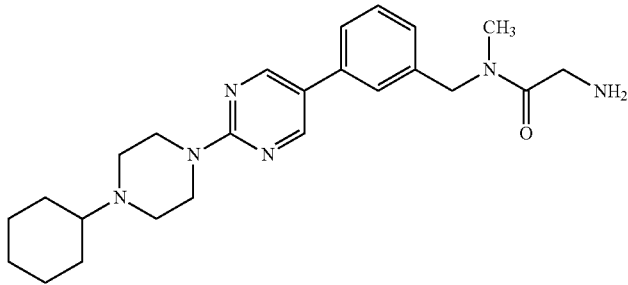 [SMILES: CN(Cc1cccc(-c2cnc(N3CCN(C4CCCCC4)CC3)nc2)c1)C(=O)CN] | L-TA |
| 165 | 69 | 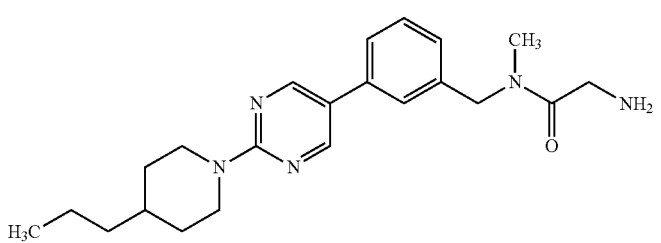 | L-TA |

TABLE 109

| Ex | Syn | Structure | Acid |
|---|---|---|---|
| 166 | 69 | 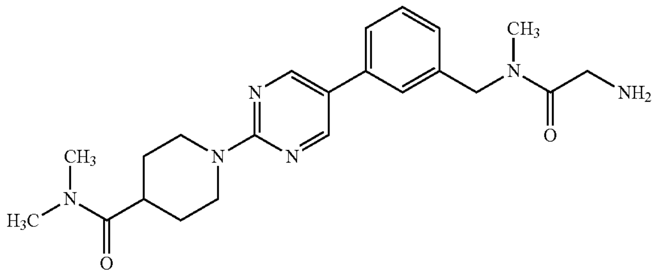 [SMILES: CN(C)C(=O)C1CCN(c2ncc(-c3cccc(CN(C)C(=O)CN)c3)cn2)CC1] | L-TA |
| 167 | 69 | 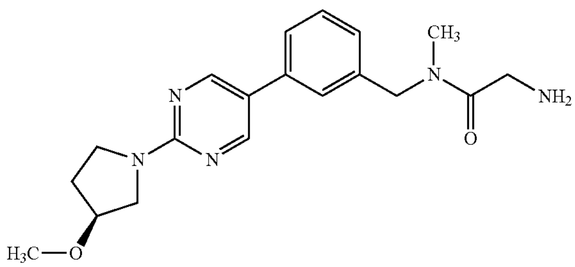 [SMILES: CO[C@H]1CCN(c2ncc(-c3cccc(CN(C)C(=O)CN)c3)cn2)C1] | L-TA |
| 168 | 69 | 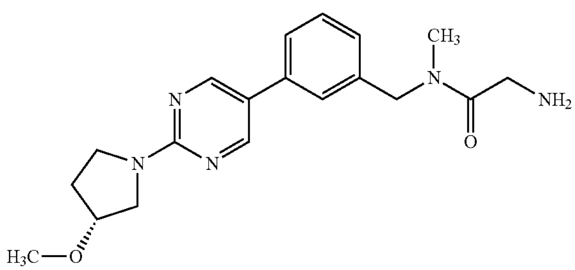 [SMILES: CO[C@@H]1CCN(c2ncc(-c3cccc(CN(C)C(=O)CN)c3)cn2)C1] | L-TA |
| 169 | 69 | 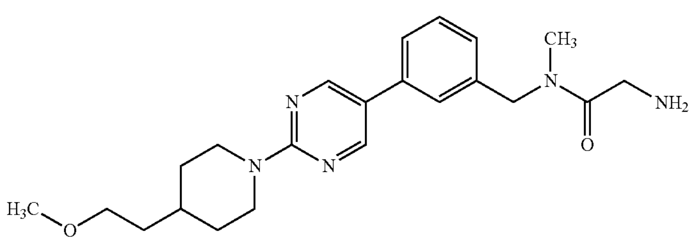 [SMILES: COCCC1CCN(c2ncc(-c3cccc(CN(C)C(=O)CN)c3)cn2)CC1] | L-TA |
| 170 | 69 | 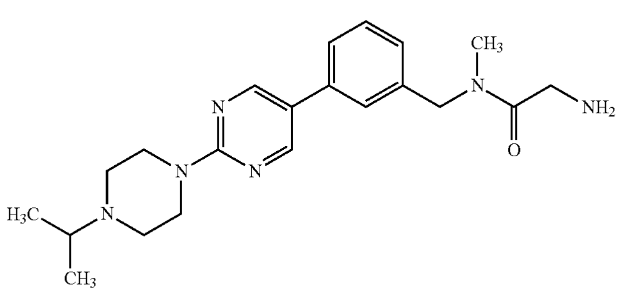 [SMILES: CC(C)N1CCN(c2ncc(-c3cccc(CN(C)C(=O)CN)c3)cn2)CC1] | L-TA |

TABLE 110

| Ex | Syn | Structure | Acid |
|----|-----|-----------|------|
| 171 | 69 | (chemical structure) | L—TA |
| 172 | 69 | (chemical structure) | L—TA |
| 173 | 69 | (chemical structure) | L—TA |
| 174 | 69 | (chemical structure) | L—TA |
| 175 | 69 | (chemical structure) | L—TA |

TABLE 111
| Ex | Syn | Structure | Acid |
|---|---|---|---|
| 176 | 69 | 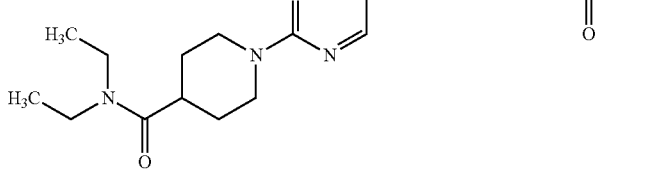 | L—TA |
| 177 | 69 | 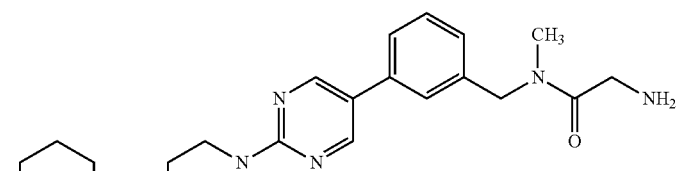 | L—TA |
| 178 | 69 | 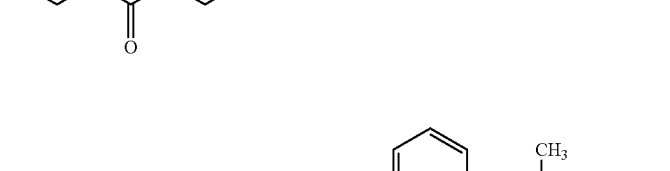 | L—TA |
| 179 | 69 | 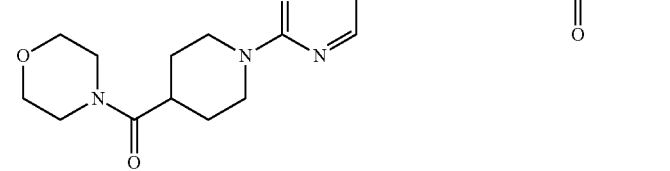 | L—TA |
| 180 | 69 | 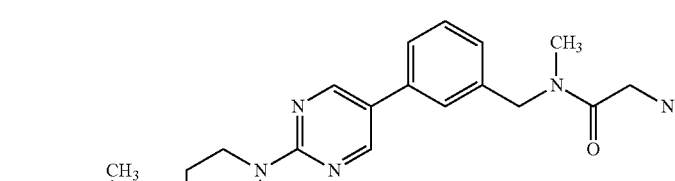 | L—TA |

TABLE 112
| Ex | Syn | Structure | Acid |
|---|---|---|---|
| 181 | 69 | 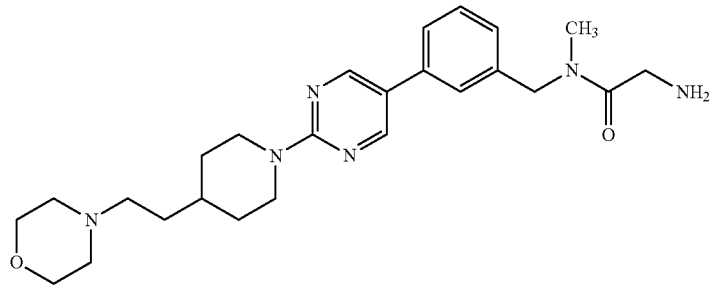 [SMILES: CN(Cc1cccc(-c2cnc(N3CCC(CCN4CCOCC4)CC3)nc2)c1)C(=O)CN] | L—TA |
| 182 | 69 | 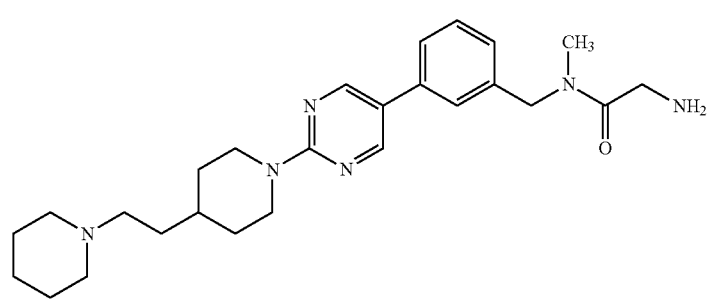 [SMILES: CN(Cc1cccc(-c2cnc(N3CCC(CCN4CCCCC4)CC3)nc2)c1)C(=O)CN] | L—TA |
| 183 | 69 | 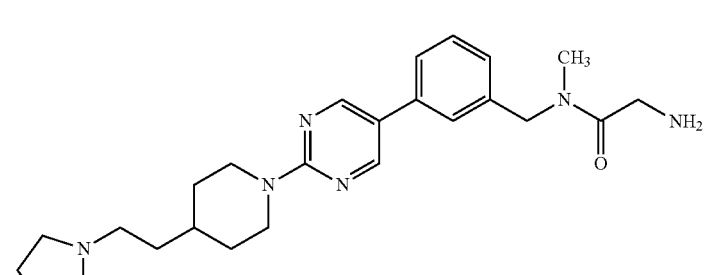 | L—TA |
| 184 | 69 | 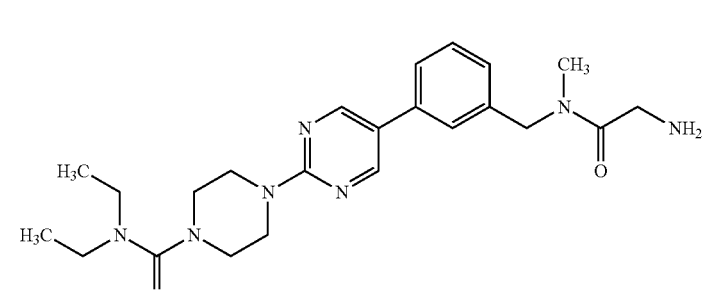 | L—TA |
| 185 | 69 | 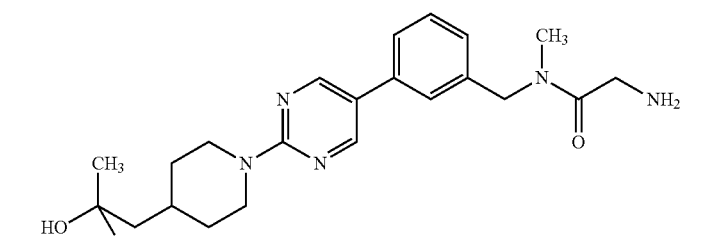 | L—TA |

TABLE 113
| Ex | Syn | Structure | Acid |
|---|---|---|---|
| 186 | 69 | 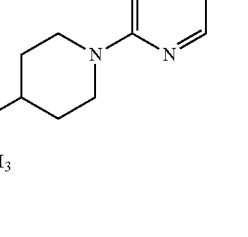 | L—TA |
| 187 | 69 | 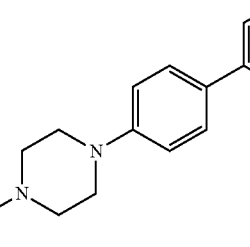 | L—TA |
| 188 | 69 | 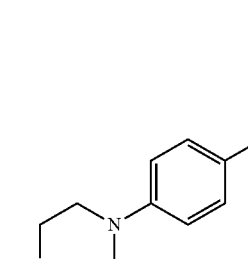 | L—TA |
| 189 | 69 | 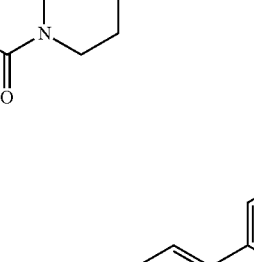 | L—TA |
| 190 | 69 | 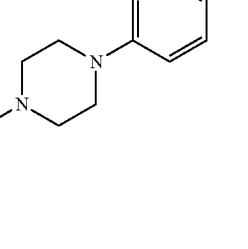 | L—TA |

TABLE 114

| Ex | Syn | Structure | Acid |
|----|-----|-----------|------|
| 191 | 69 | 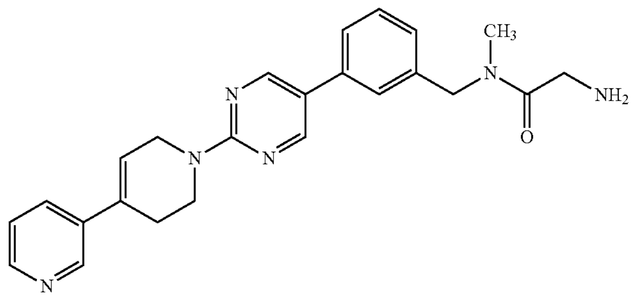 [SMILES: CN(Cc1cccc(-c2cnc(N3CC=C(c4cccnc4)CC3)nc2)c1)C(=O)CN] | L—TA |
| 192 | 69 | 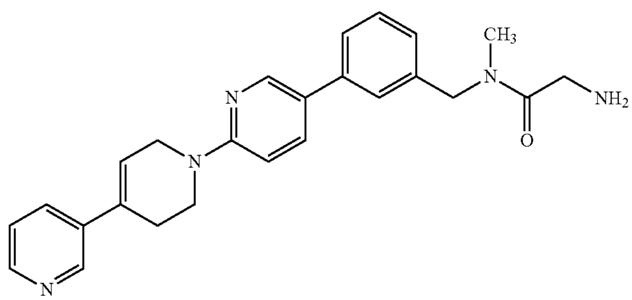 [SMILES: CN(Cc1cccc(-c2ccc(N3CC=C(c4cccnc4)CC3)nc2)c1)C(=O)CN] | L—TA |
| 193 | 69 | 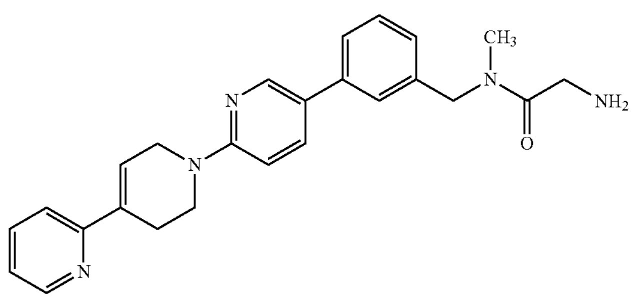 [SMILES: CN(Cc1cccc(-c2ccc(N3CC=C(c4ccccn4)CC3)nc2)c1)C(=O)CN] | L—TA |
| 194 | 69 | 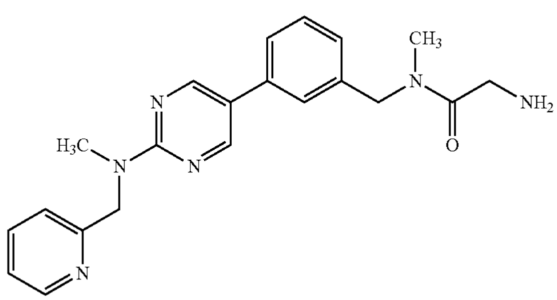 [SMILES: CN(Cc1cccc(-c2cnc(N(C)Cc3ccccn3)nc2)c1)C(=O)CN] | L—TA |
| 195 | 69 | 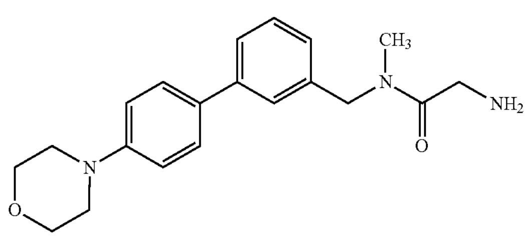 [SMILES: CN(Cc1cccc(-c2ccc(N3CCOCC3)cc2)c1)C(=O)CN] | OA |

TABLE 115

| Ex | Syn | Structure | Acid |
|---|---|---|---|
| 196 | 69 | 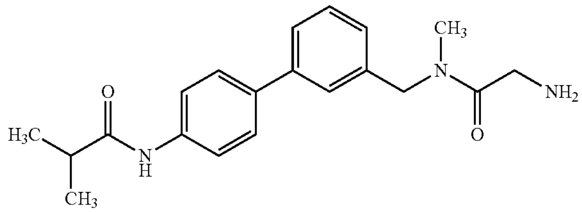 | HCl |
| 197 | 69 | 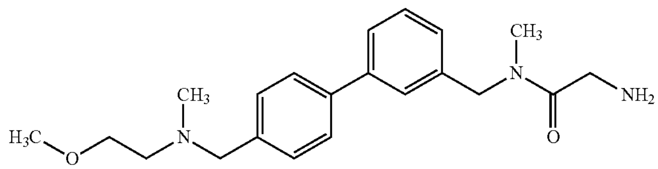 [SMILES: COCCN(C)Cc1ccc(-c2cccc(CN(C)C(=O)CN)c2)cc1] | OA |
| 198 | 69 | 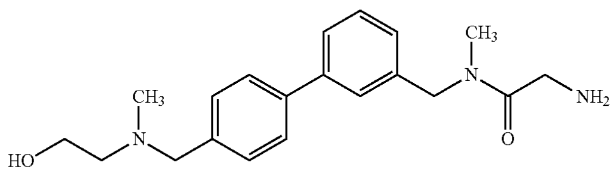 [SMILES: CN(CCO)Cc1ccc(-c2cccc(CN(C)C(=O)CN)c2)cc1] | OA |
| 199 | 69 | 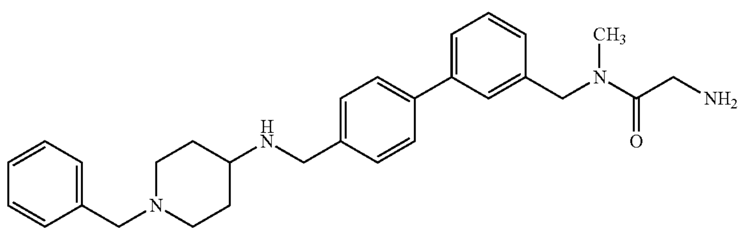 [SMILES: CN(Cc1cccc(-c2ccc(CNC3CCN(Cc4ccccc4)CC3)cc2)c1)C(=O)CN] | 3HCl |
| 200 | 69 | 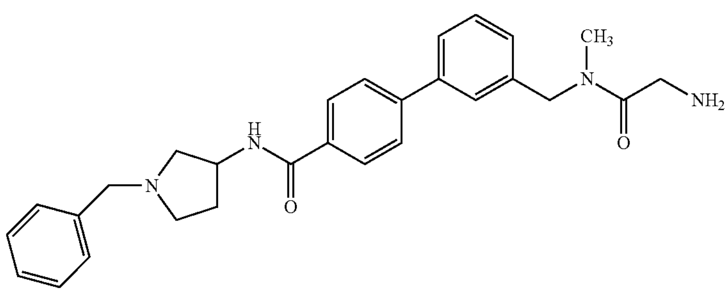 [SMILES: CN(Cc1cccc(-c2ccc(C(=O)NC3CCN(Cc4ccccc4)C3)cc2)c1)C(=O)CN] | OA |
| 201 | 69 | 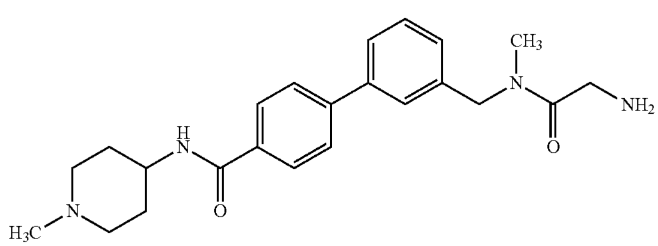 [SMILES: CN1CCC(NC(=O)c2ccc(-c3cccc(CN(C)C(=O)CN)c3)cc2)CC1] | OA |

TABLE 116

| Ex | Syn | Structure | Acid |
|---|---|---|---|
| 202 | 69 | 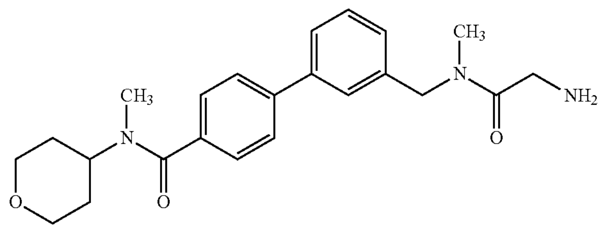 [SMILES: CN(Cc1cccc(-c2ccc(C(=O)N(C)C3CCOCC3)cc2)c1)C(=O)CN] | OA |
| 203 | 69 | 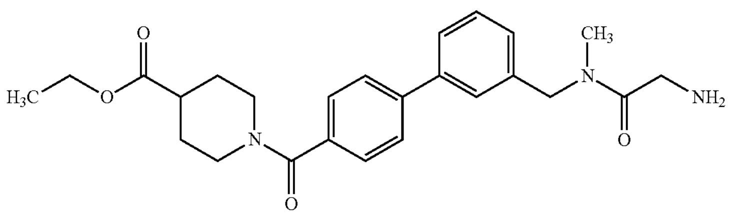 [SMILES: CCOC(=O)C1CCN(C(=O)c2ccc(-c3cccc(CN(C)C(=O)CN)c3)cc2)CC1] | L—TA |
| 204 | 69 | 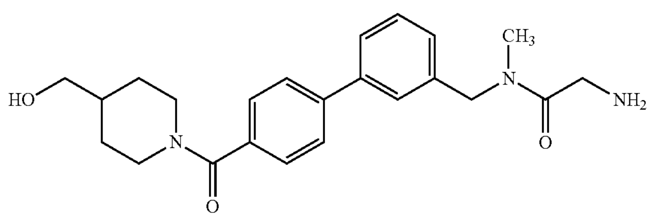 [SMILES: CN(Cc1cccc(-c2ccc(C(=O)N3CCC(CO)CC3)cc2)c1)C(=O)CN] | L—TA |
| 205 | 69 | 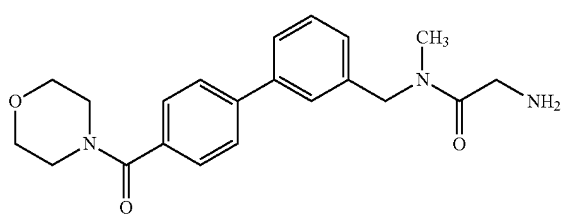 [SMILES: CN(Cc1cccc(-c2ccc(C(=O)N3CCOCC3)cc2)c1)C(=O)CN] | L—TA |
| 206 | 69 | 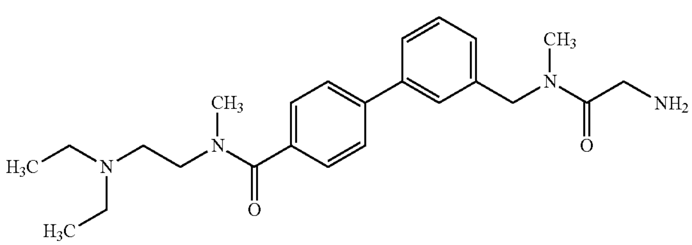 [SMILES: CCN(CC)CCN(C)C(=O)c1ccc(-c2cccc(CN(C)C(=O)CN)c2)cc1] | L—TA |
| 207 | 69 | 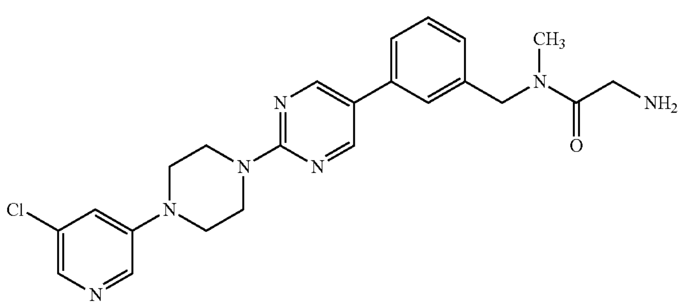 [SMILES: CN(Cc1cccc(-c2cnc(N3CCN(c4cncc(Cl)c4)CC3)nc2)c1)C(=O)CN] | L—TA |

TABLE 117

| Ex | Syn | Structure | Acid |
|---|---|---|---|
| 208 | 208 | 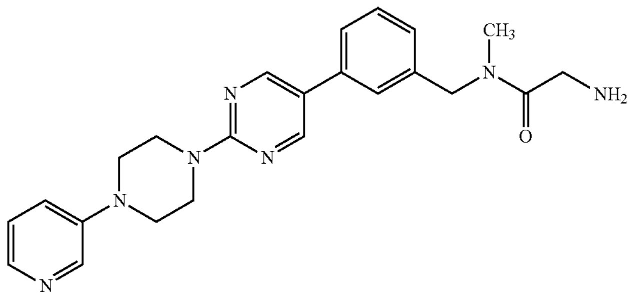 | L—TA |
| 209 | 209 | 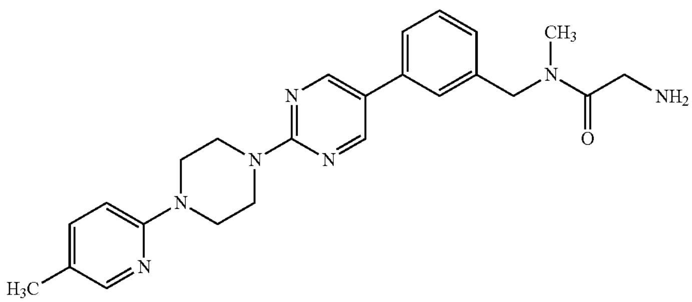 | L—TA |
| 210 | 209 | 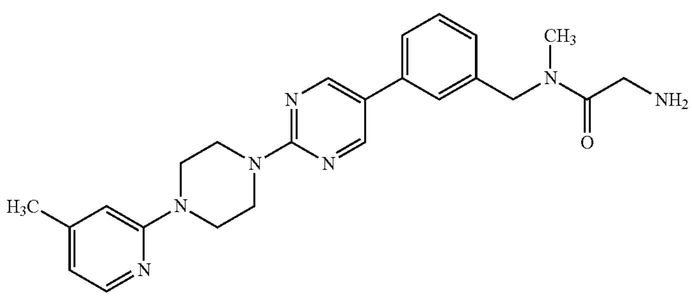 [SMILES: Cc1ccnc(N2CCN(c3ncc(-c4cccc(CN(C)C(=O)CN)c4)cn3)CC2)c1] | L—TA |
| 211 | 209 | 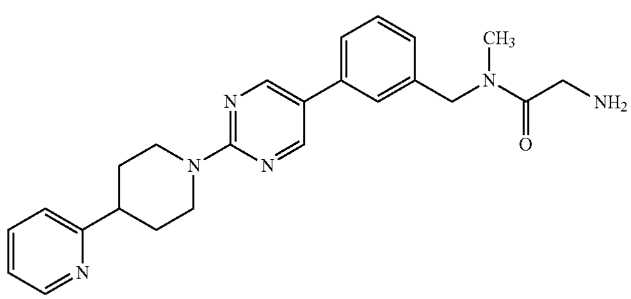 [SMILES: CN(Cc1cccc(-c2cnc(N3CCC(c4ccccn4)CC3)nc2)c1)C(=O)CN] | L—TA |
| 212 | 212 | 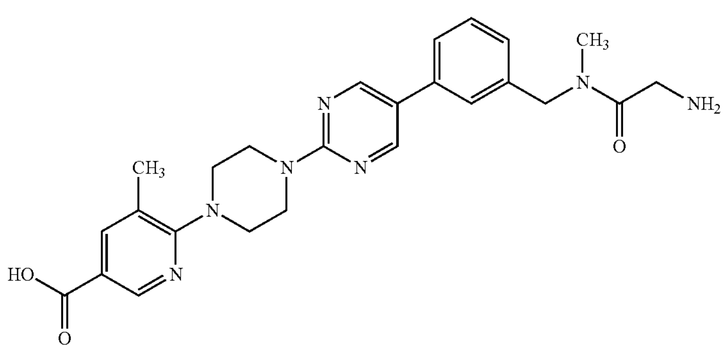 | 2HCl |

TABLE 118

| Ex | Syn | Structure | Acid |
|---|---|---|---|
| 213 | 213 | 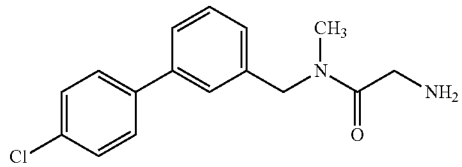 [SMILES: CN(Cc1cccc(-c2ccc(Cl)cc2)c1)C(=O)CN] | HCl |
| 214 | 213 | 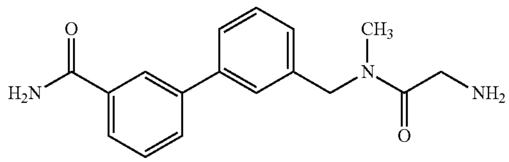 [SMILES: CN(Cc1cccc(-c2cccc(C(N)=O)c2)c1)C(=O)CN] | HCl |
| 215 | 215 | 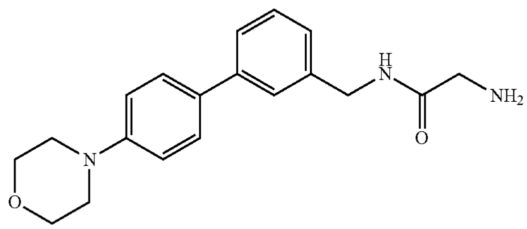 [SMILES: NCC(=O)NCc1cccc(-c2ccc(N3CCOCC3)cc2)c1] | OA |
| 216 | 11 | 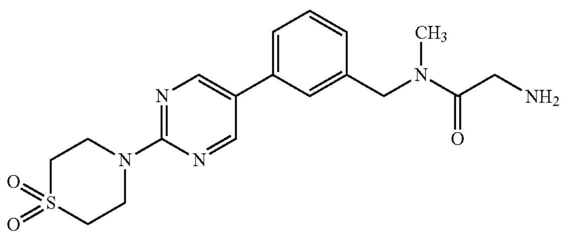 [SMILES: CN(Cc1cccc(-c2cnc(N3CCS(=O)(=O)CC3)nc2)c1)C(=O)CN] | 2HCl |
| 217 | 217 | 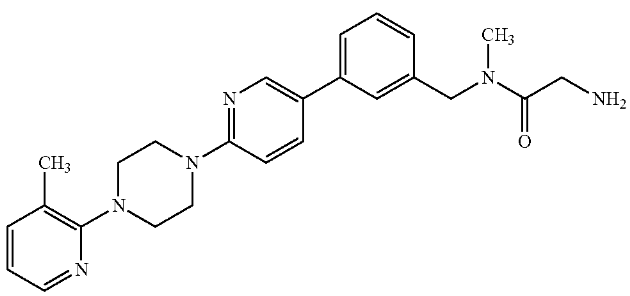 | 3HCl |

TABLE 119

| Ex | Syn | Structure | Acid |
|---|---|---|---|
| 218 | 218 | 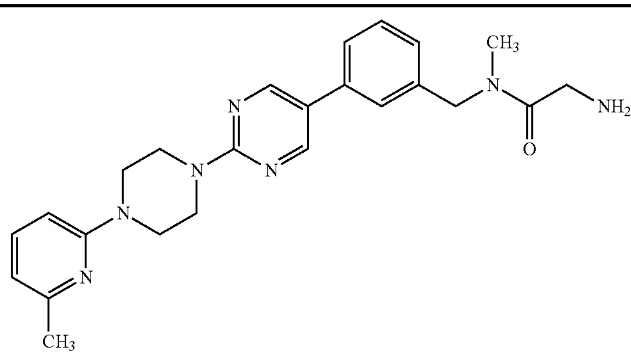 | L—TA |

TABLE 119-continued

| Ex | Syn | Structure | Acid |
|---|---|---|---|
| 219 | 219 | 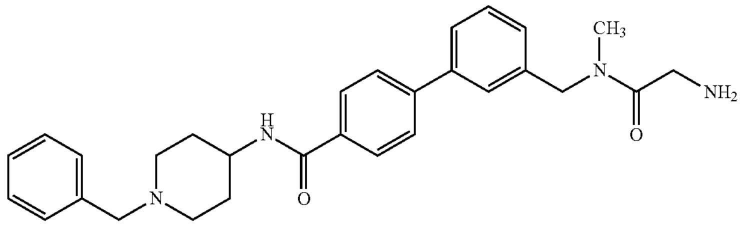 [SMILES: CN(Cc1cccc(-c2ccc(C(=O)NC3CCN(Cc4ccccc4)CC3)cc2)c1)C(=O)CN] | OA |
| 220 | 219 | 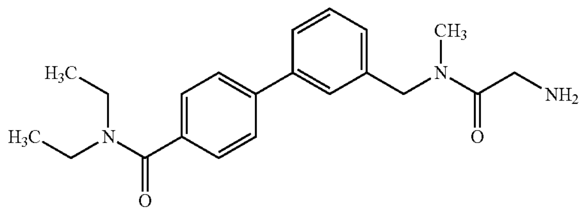 [SMILES: CCN(CC)C(=O)c1ccc(-c2cccc(CN(C)C(=O)CN)c2)cc1] | OA |
| 221 | 219 | 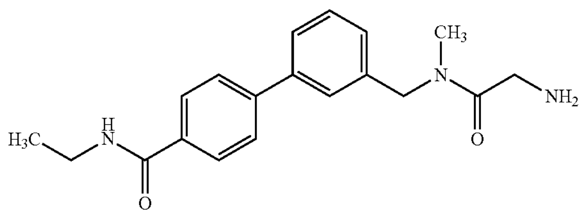 [SMILES: CCNC(=O)c1ccc(-c2cccc(CN(C)C(=O)CN)c2)cc1] | HCl |
| 222 | 222 | 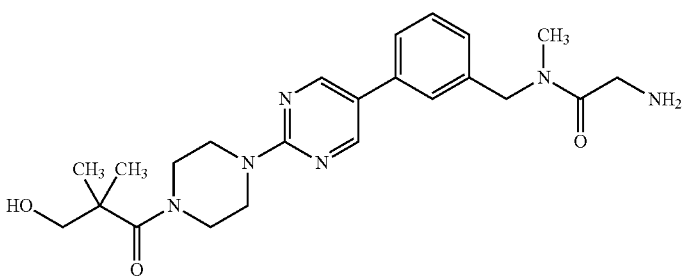 [SMILES: CN(Cc1cccc(-c2cnc(N3CCN(C(=O)C(C)(C)CO)CC3)nc2)c1)C(=O)CN] | L—TA |
| 223 | 222 | 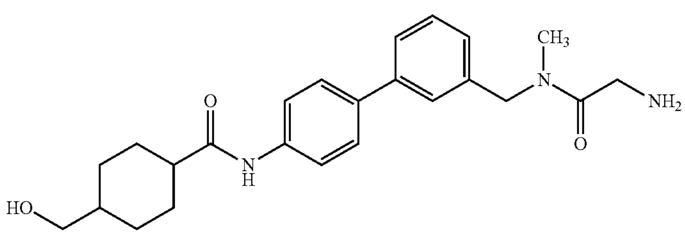 [SMILES: CN(Cc1cccc(-c2ccc(NC(=O)C3CCC(CO)CC3)cc2)c1)C(=O)CN] | L—TA |

TABLE 120

| Ex | Syn | Structure | Acid |
|---|---|---|---|
| 224 | 222 | 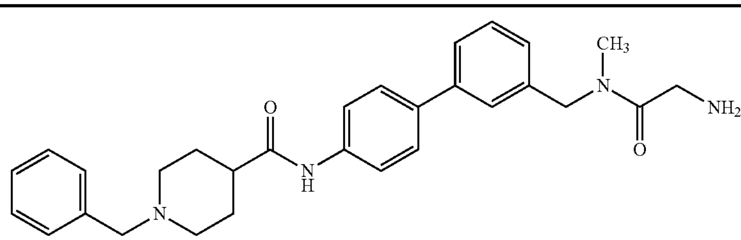 | OA |

TABLE 120-continued

| Ex | Syn | Structure | Acid |
|---|---|---|---|
| 225 | 222 | 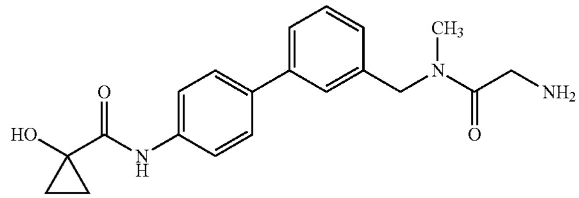 [SMILES: CN(Cc1cccc(-c2ccc(NC(=O)C3(O)CC3)cc2)c1)C(=O)CN] | OA |
| 226 | 226 | 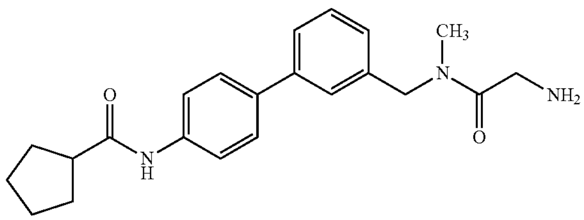 [SMILES: CN(Cc1cccc(-c2ccc(NC(=O)C3CCCC3)cc2)c1)C(=O)CN] | HCl |
| 227 | 226 | 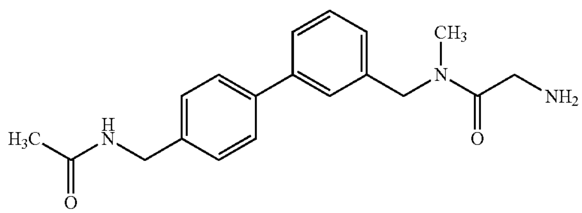 [SMILES: CC(=O)NCc1ccc(-c2cccc(CN(C)C(=O)CN)c2)cc1] | HCl |
| 228 | 228 | 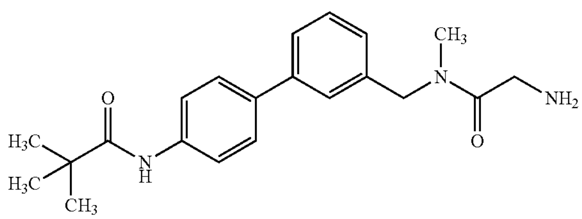 [SMILES: CN(Cc1cccc(-c2ccc(NC(=O)C(C)(C)C)cc2)c1)C(=O)CN] | OA |
| 229 | 19 | 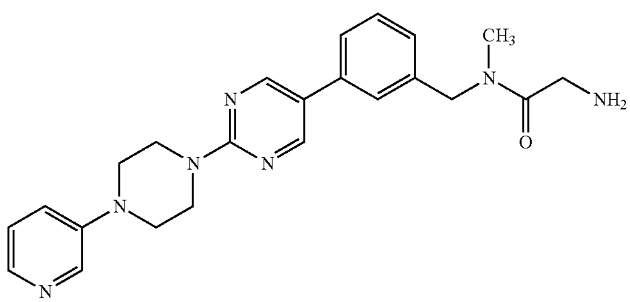 | 3HCl |

TABLE 121

| Ex | Syn | Structure | Acid |
|---|---|---|---|
| 230 | 228 | 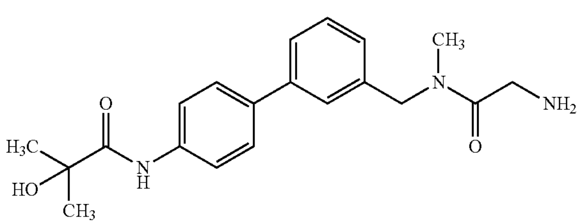 | OA |

TABLE 121-continued
| Ex | Syn | Structure | Acid |
|----|-----|-----------|------|
| 231 | 228 | 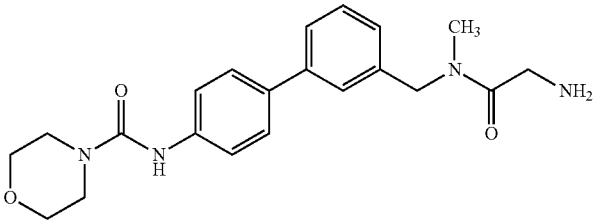 [SMILES: CN(Cc1cccc(-c2ccc(NC(=O)N3CCOCC3)cc2)c1)C(=O)CN] | OA |
| 232 | 228 | 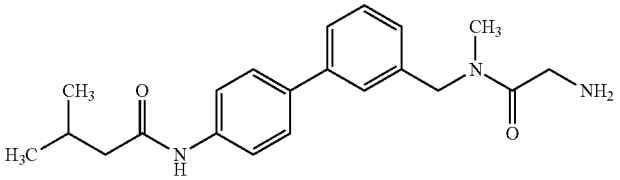 [SMILES: CC(C)CC(=O)Nc1ccc(-c2cccc(CN(C)C(=O)CN)c2)cc1] | OA |
| 233 | 228 | 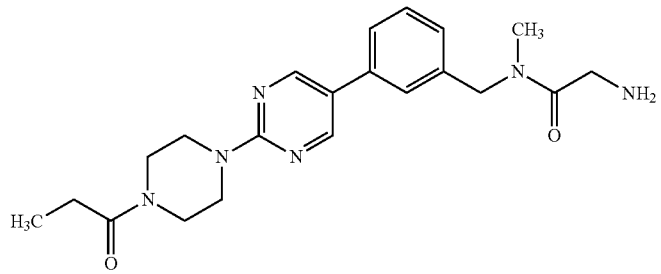 [SMILES: CCC(=O)N1CCN(c2ncc(-c3cccc(CN(C)C(=O)CN)c3)cn2)CC1] | L—TA |
| 234 | 228 | 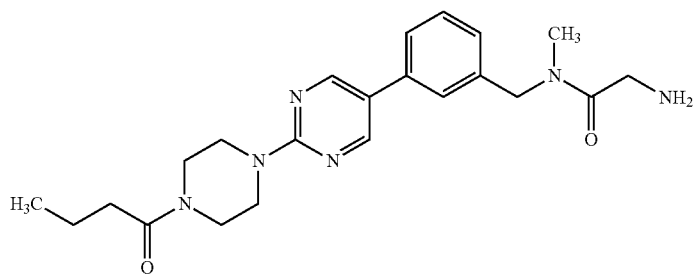 | L—TA |
| 235 | 228 | 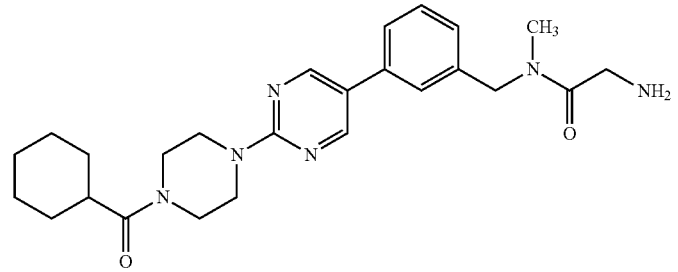 | L—TA |

TABLE 122

| Ex | Syn | Structure | Acid |
|---|---|---|---|
| 236 | 228 | 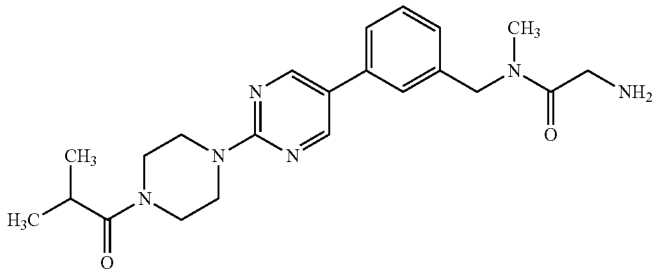 [SMILES: CC(C)C(=O)N1CCN(c2ncc(-c3cccc(CN(C)C(=O)CN)c3)cn2)CC1] | L—TA |
| 237 | 228 | 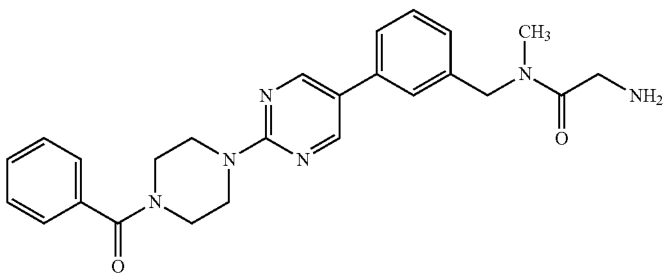 [SMILES: CN(Cc1cccc(-c2cnc(N3CCN(C(=O)c4ccccc4)CC3)nc2)c1)C(=O)CN] | L—TA |
| 238 | 228 | 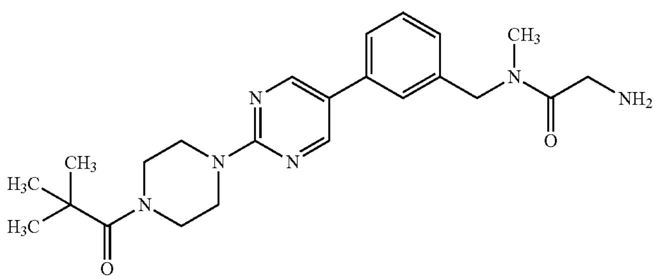 [SMILES: CN(Cc1cccc(-c2cnc(N3CCN(C(=O)C(C)(C)C)CC3)nc2)c1)C(=O)CN] | L—TA |
| 239 | 239 | 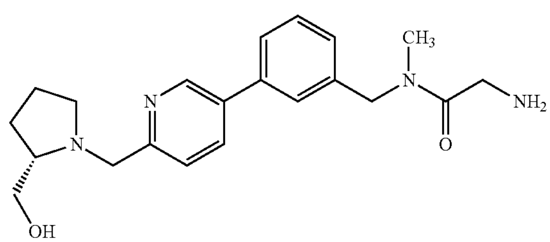 [SMILES: CN(Cc1cccc(-c2ccc(CN3CCC[C@H]3CO)nc2)c1)C(=O)CN] | 3HCl |
| 240 | 239 | 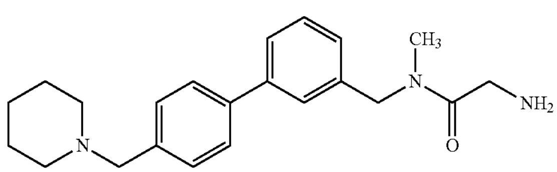 [SMILES: CN(Cc1cccc(-c2ccc(CN3CCCCC3)cc2)c1)C(=O)CN] | 2HCl |
| 241 | 239 | 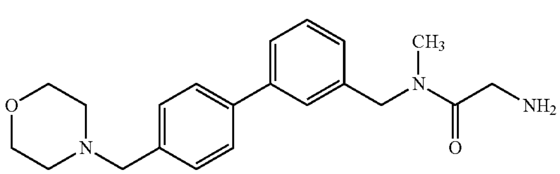 [SMILES: CN(Cc1cccc(-c2ccc(CN3CCOCC3)cc2)c1)C(=O)CN] | 2HCl |

TABLE 123

| Ex | Syn | Structure | Acid |
|---|---|---|---|
| 242 | 239 | 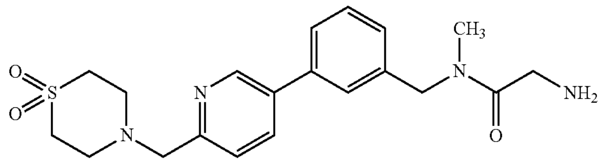 [SMILES: CN(Cc1cccc(-c2ccc(CN3CCS(=O)(=O)CC3)nc2)c1)C(=O)CN] | 3HCl |
| 243 | 239 | 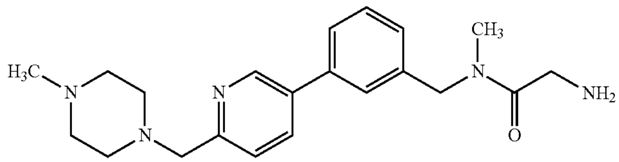 | 4HCl |
| 244 | 244 | 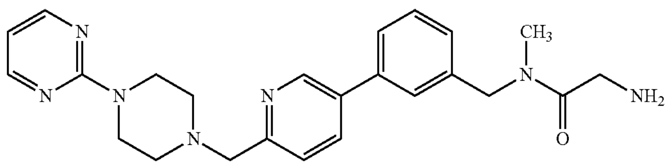 [SMILES: CN(Cc1cccc(-c2ccc(CN3CCN(c4ncccn4)CC3)nc2)c1)C(=O)CN] | L—TA |
| 245 | 244 | 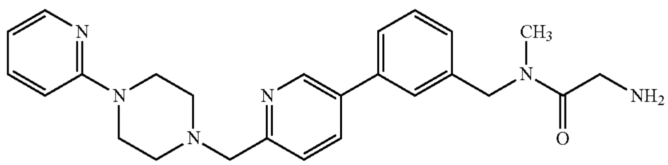 [SMILES: CN(Cc1cccc(-c2ccc(CN3CCN(c4ccccn4)CC3)nc2)c1)C(=O)CN] | L—TA |
| 246 | 244 | 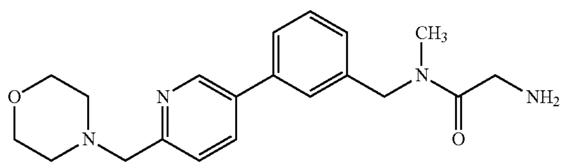 [SMILES: CN(Cc1cccc(-c2ccc(CN3CCOCC3)nc2)c1)C(=O)CN] | L—TA |
| 247 | 244 | 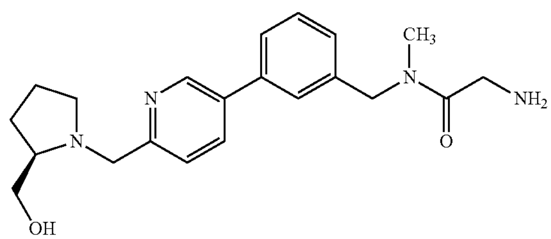 [SMILES: CN(Cc1cccc(-c2ccc(CN3CCC[C@@H]3CO)nc2)c1)C(=O)CN] | L—TA |
| 248 | 248 | 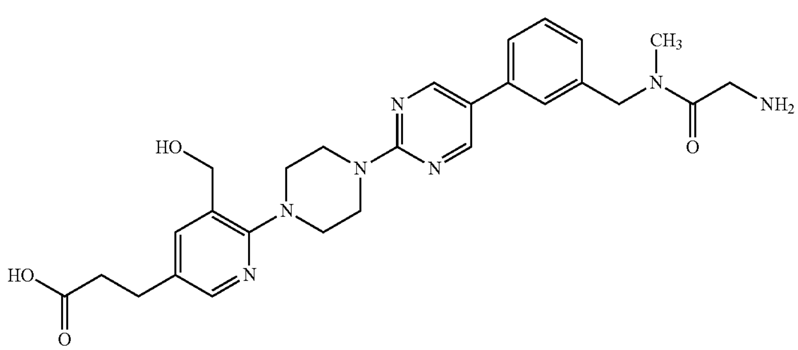 [SMILES: CN(Cc1cccc(-c2cnc(N3CCN(c4ncc(CCC(=O)O)cc4CO)CC3)nc2)c1)C(=O)CN] | 2HCl |

TABLE 124

| Ex | Syn | Structure | Acid |
|---|---|---|---|
| 249 | 248 | 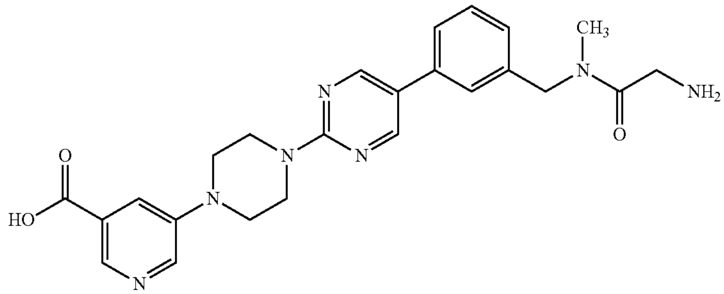 [SMILES: CN(Cc1cccc(-c2cnc(N3CCN(c4cncc(C(=O)O)c4)CC3)nc2)c1)C(=O)CN] | 2HCl |
| 250 | 248 | 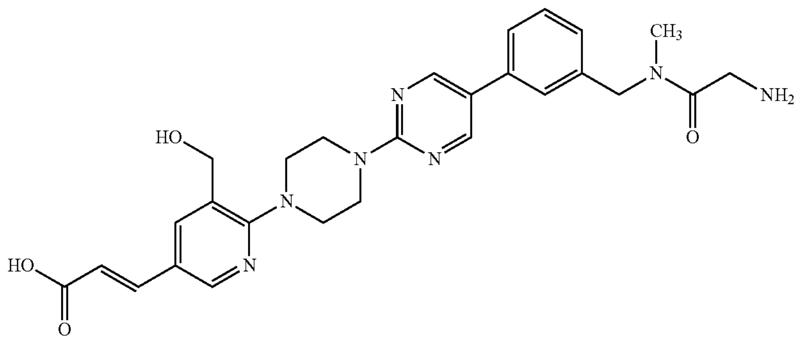 [SMILES: CN(Cc1cccc(-c2cnc(N3CCN(c4ncc(/C=C/C(=O)O)cc4CO)CC3)nc2)c1)C(=O)CN] | 2HCl |
| 251 | 248 | 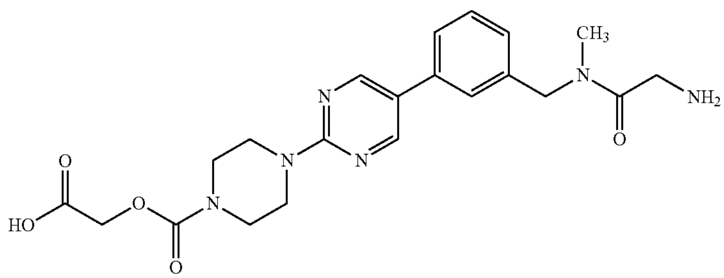 | 2HCl |
| 252 | 248 | 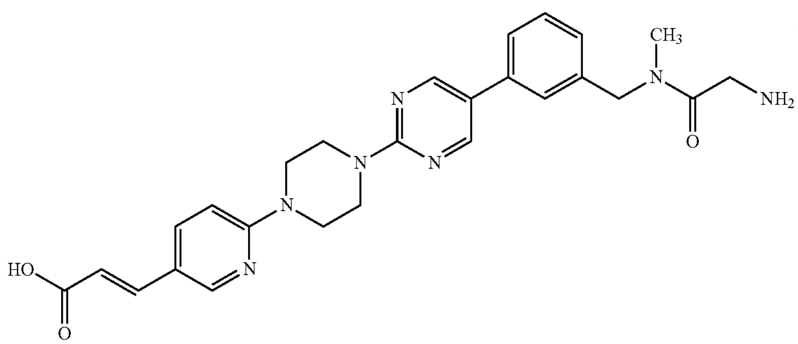 [SMILES: CN(Cc1cccc(-c2cnc(N3CCN(c4ccc(/C=C/C(=O)O)cn4)CC3)nc2)c1)C(=O)CN] | 2HCl |
| 253 | 248 | 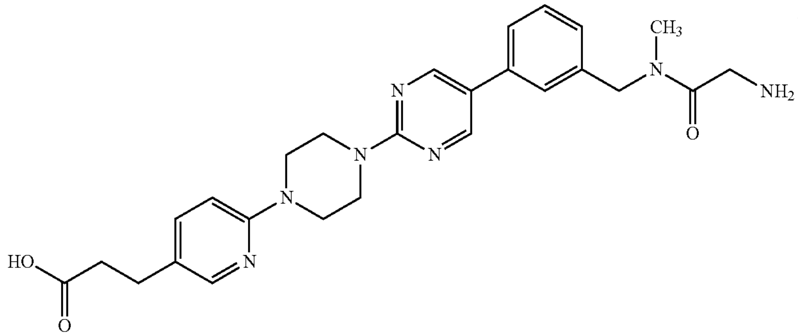 [SMILES: CN(Cc1cccc(-c2cnc(N3CCN(c4ccc(CCC(=O)O)cn4)CC3)nc2)c1)C(=O)CN] | 2HCl |

TABLE 125

| Ex | Syn | Structure | Acid |
|---|---|---|---|
| 254 | 254 | (1-methyl-1,4-diazepan-4-yl)methyl-biphenyl-N-methyl-glycinamide structure | L-TA |
| 255 | 254 | (4-methylpiperazin-1-yl)methyl-biphenyl-N-methyl-glycinamide structure | 3HCl |
| 256 | 254 | (1,1-dioxothiomorpholin-4-yl)methyl-biphenyl-N-methyl-glycinamide structure | HCl |
| 257 | 254 | (azepan-1-yl)methyl-biphenyl-N-methyl-glycinamide structure | L-TA |
| 258 | 254 | ((2S)-2-(hydroxymethyl)pyrrolidin-1-yl)methyl-biphenyl-N-methyl-glycinamide structure | L-TA |
| 259 | 254 | (4-hydroxypiperidin-1-yl)methyl-biphenyl-N-methyl-glycinamide structure | L-TA |
| 260 | 254 | (4-(methylsulfonyl)piperazin-1-yl)methyl-biphenyl-N-methyl-glycinamide structure | L-TA |

TABLE 126
| Ex | Syn | Structure | Acid |
|----|-----|-----------|------|
| 261 | 261 | 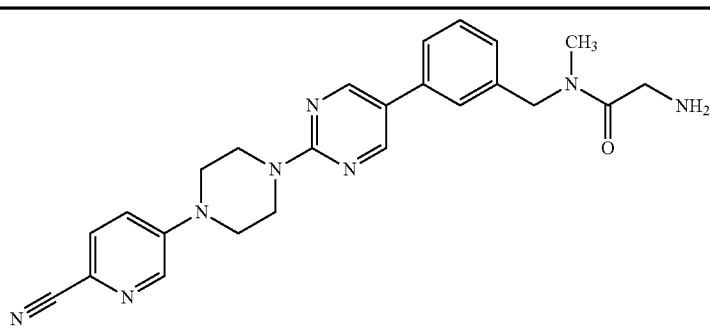 | L-TA |
| 262 | 261 | 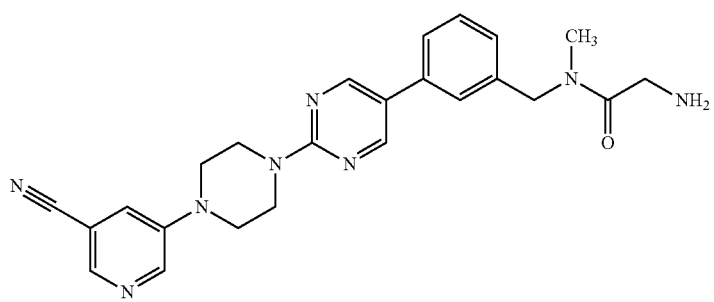 [SMILES: CN(Cc1cccc(-c2cnc(N3CCN(c4cncc(C#N)c4)CC3)nc2)c1)C(=O)CN] | L-TA |
| 263 | 263 | 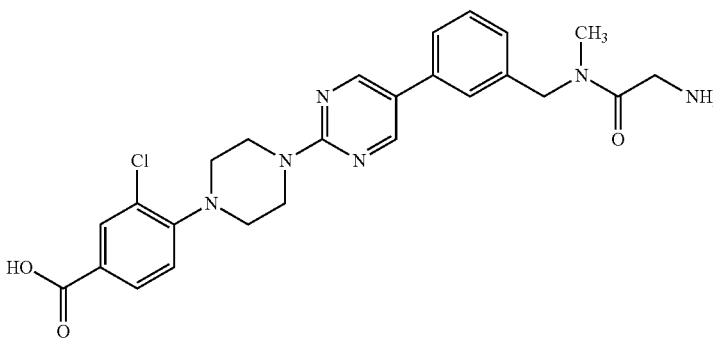 | 2HCl |
| 264 | 264 | 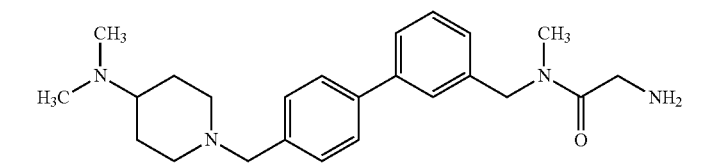 [SMILES: CN(Cc1cccc(-c2ccc(CN3CCC(N(C)C)CC3)cc2)c1)C(=O)CN] | 3HCl |
| 265 | 265 | 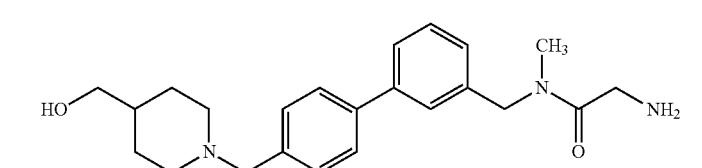 | L-TA |
| 266 | 265 | 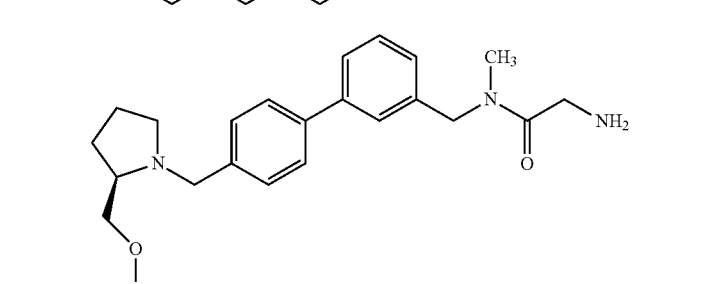 | L-TA |

TABLE 127

| Ex | Syn | Structure | Acid |
|---|---|---|---|
| 267 | 265 | 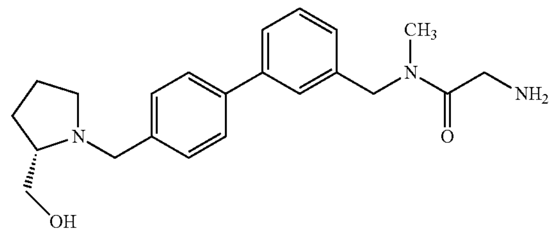 [SMILES: CN(Cc1cccc(-c2ccc(CN3CCC[C@H]3CO)cc2)c1)C(=O)CN] | L-TA |
| 268 | 265 | 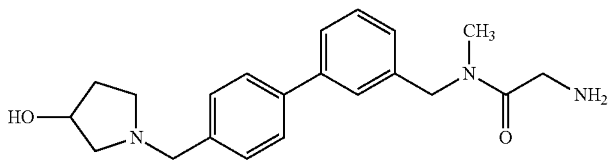 [SMILES: CN(Cc1cccc(-c2ccc(CN3CCC(O)C3)cc2)c1)C(=O)CN] | L-TA |
| 269 | 265 | 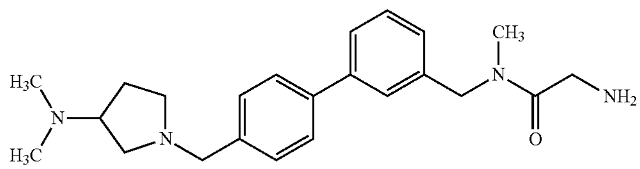 [SMILES: CN(Cc1cccc(-c2ccc(CN3CCC(N(C)C)C3)cc2)c1)C(=O)CN] | L-TA |
| 270 | 270 | 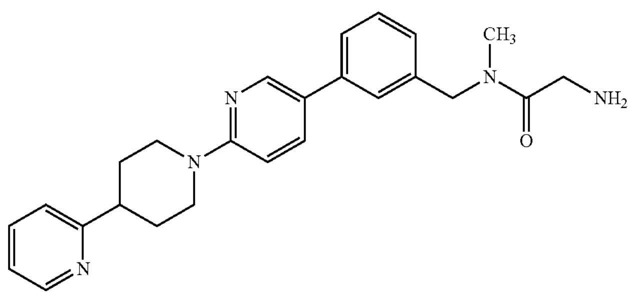 [SMILES: CN(Cc1cccc(-c2ccc(N3CCC(c4ccccn4)CC3)nc2)c1)C(=O)CN] | L-TA |
| 271 | 270 | 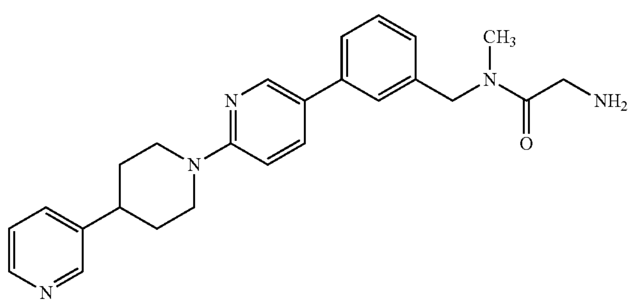 [SMILES: CN(Cc1cccc(-c2ccc(N3CCC(c4cccnc4)CC3)nc2)c1)C(=O)CN] | L-TA |
| 272 | 272 | 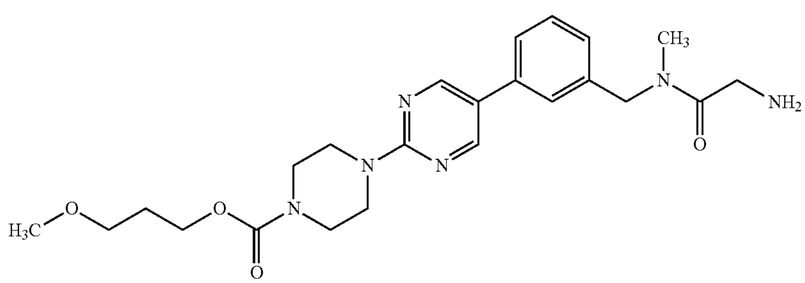 [SMILES: COCCCOC(=O)N1CCN(c2ncc(-c3cccc(CN(C)C(=O)CN)c3)cn2)CC1] | L-TA |

TABLE 128

| Ex | Syn | Structure | Acid |
|---|---|---|---|
| 273 | 272 | 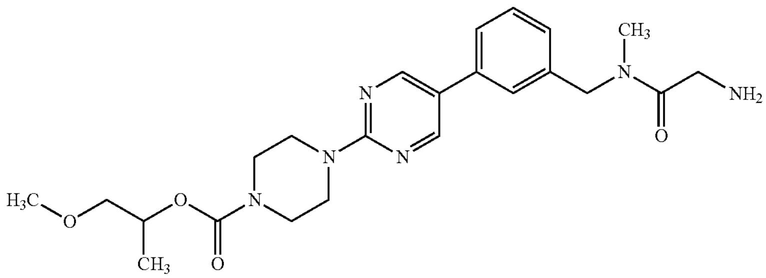 [SMILES: COCC(C)OC(=O)N1CCN(c2ncc(-c3cccc(CN(C)C(=O)CN)c3)cn2)CC1] | L-TA |
| 274 | 272 | 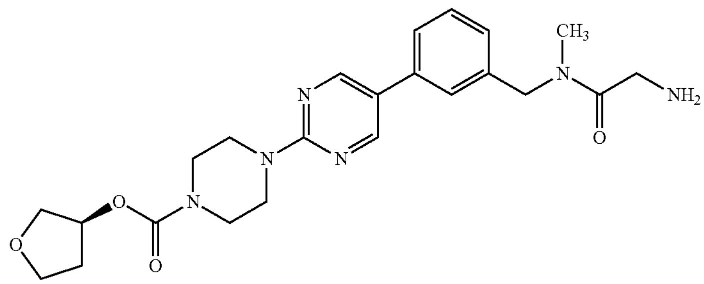 [SMILES: CN(Cc1cccc(-c2cnc(N3CCN(C(=O)O[C@H]4CCOC4)CC3)nc2)c1)C(=O)CN] | L-TA |
| 275 | 272 | 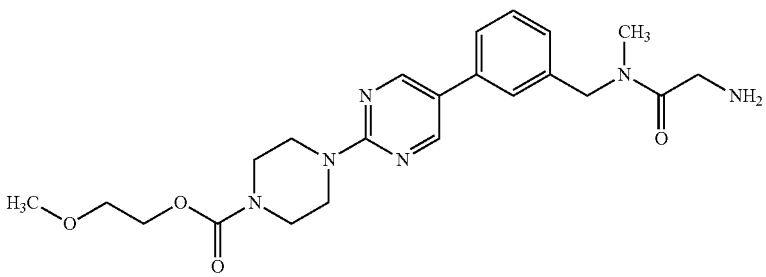 [SMILES: COCCOC(=O)N1CCN(c2ncc(-c3cccc(CN(C)C(=O)CN)c3)cn2)CC1] | L-TA |
| 276 | 272 | 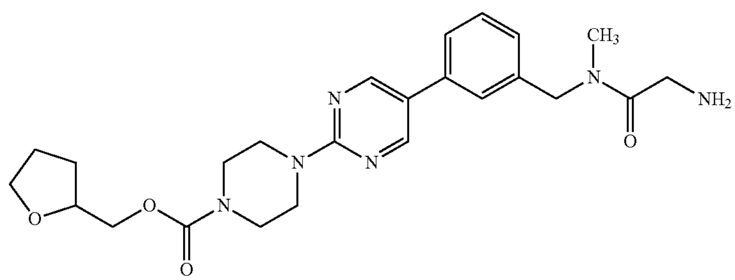 [SMILES: CN(Cc1cccc(-c2cnc(N3CCN(C(=O)OCC4CCCO4)CC3)nc2)c1)C(=O)CN] | L-TA |
| 277 | 272 | 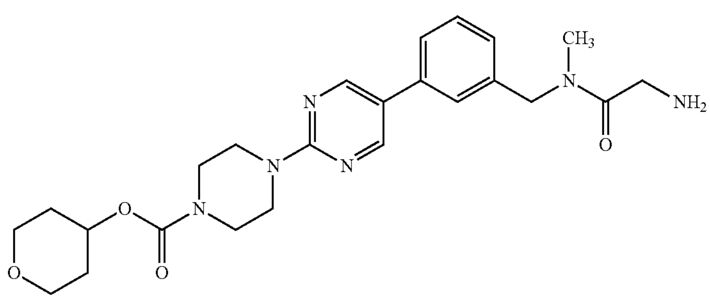 [SMILES: CN(Cc1cccc(-c2cnc(N3CCN(C(=O)OC4CCOCC4)CC3)nc2)c1)C(=O)CN] | L-TA |

TABLE 129

| Ex | Syn | Structure | Acid |
|---|---|---|---|
| 278 | 272 | (structure) | L-TA |
| 279 | 272 | (structure) | L-TA |
| 280 | 272 | (structure) | L-TA |
| 281 | 281 | (structure) | — |
| 282 | 281 | (structure) | — |

TABLE 130

| Ex | Syn | Structure | Acid |
|---|---|---|---|
| 283 | 281 | 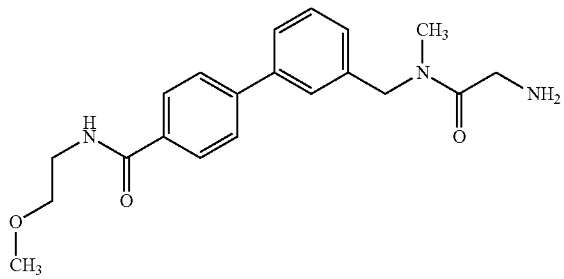 [SMILES: COCCNC(=O)c1ccc(-c2cccc(CN(C)C(=O)CN)c2)cc1] | — |
| 284 | 281 | 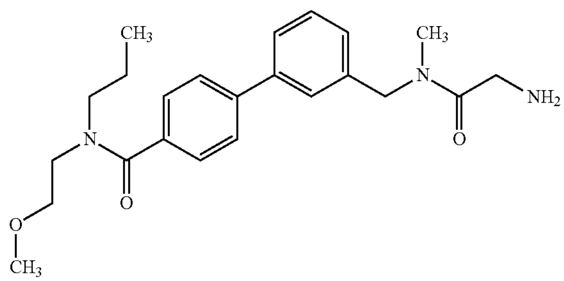 [SMILES: CCCN(CCOC)C(=O)c1ccc(-c2cccc(CN(C)C(=O)CN)c2)cc1] | — |
| 285 | 281 | 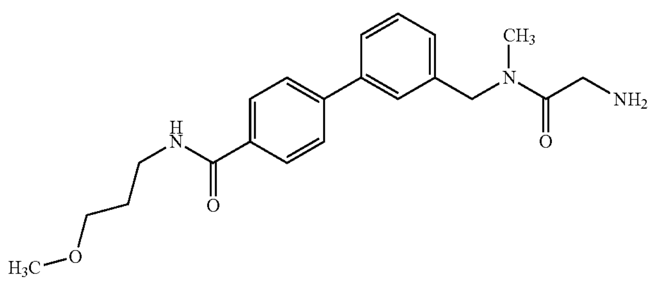 [SMILES: COCCCNC(=O)c1ccc(-c2cccc(CN(C)C(=O)CN)c2)cc1] | — |
| 286 | 281 | 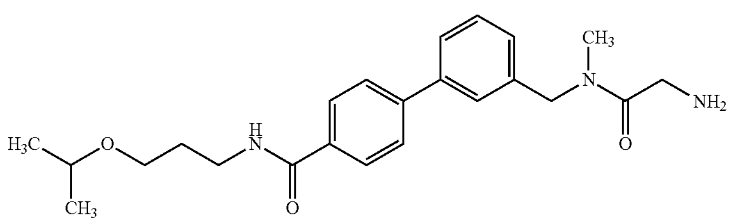 [SMILES: CC(C)OCCCNC(=O)c1ccc(-c2cccc(CN(C)C(=O)CN)c2)cc1] | — |
| 287 | 281 | 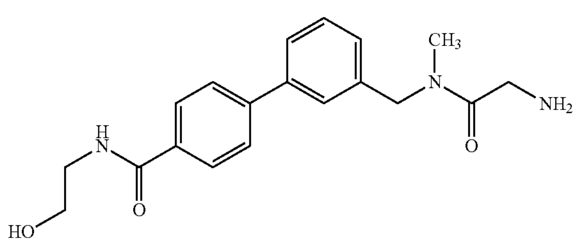 [SMILES: CN(Cc1cccc(-c2ccc(C(=O)NCCO)cc2)c1)C(=O)CN] | — |

TABLE 131

| Ex | Syn | Structure | Acid |
|----|-----|-----------|------|
| 288 | 281 | 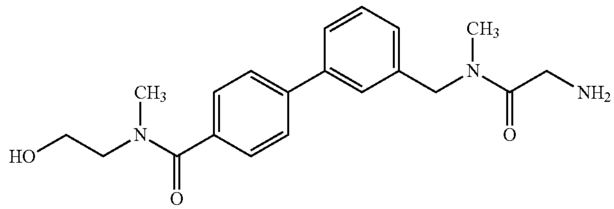 [SMILES: CN(Cc1cccc(-c2ccc(C(=O)N(C)CCO)cc2)c1)C(=O)CN] | — |
| 289 | 281 | 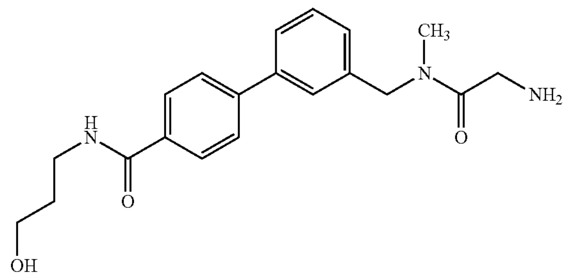 [SMILES: CN(Cc1cccc(-c2ccc(C(=O)NCCCO)cc2)c1)C(=O)CN] | — |
| 290 | 281 | 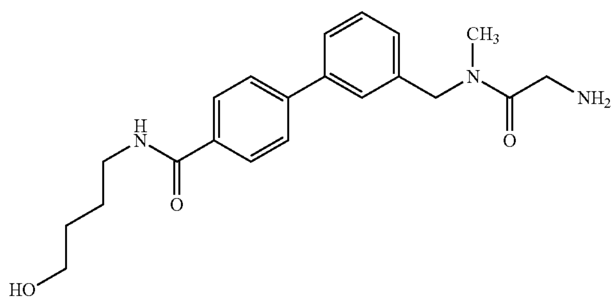 [SMILES: CN(Cc1cccc(-c2ccc(C(=O)NCCCCO)cc2)c1)C(=O)CN] | — |
| 291 | 281 | 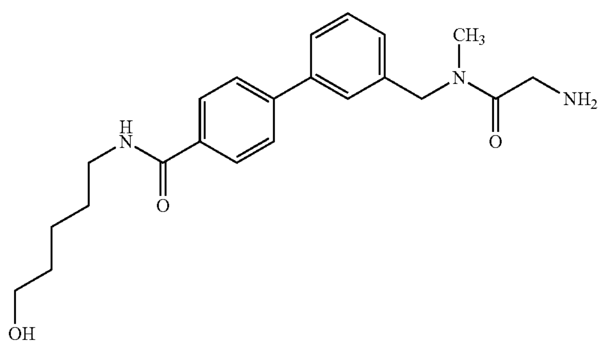 [SMILES: CN(Cc1cccc(-c2ccc(C(=O)NCCCCCO)cc2)c1)C(=O)CN] | — |
| 292 | 281 | 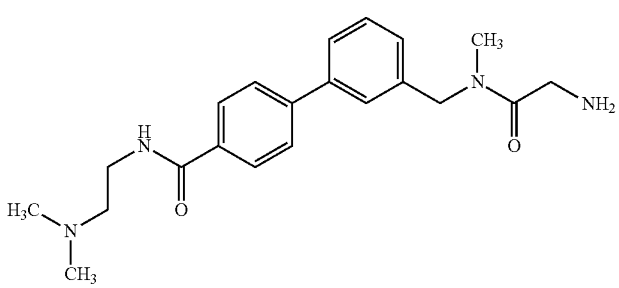 [SMILES: CN(C)CCNC(=O)c1ccc(-c2cccc(CN(C)C(=O)CN)c2)cc1] | — |

TABLE 132
| Ex | Syn | Structure | Acid |
|---|---|---|---|
| 293 | 281 | 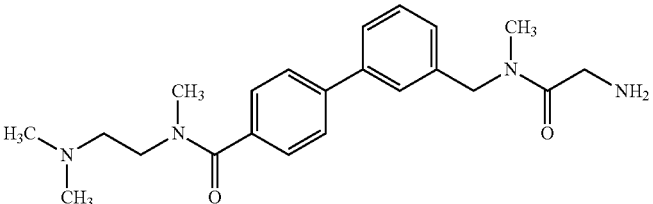 | — |
| 294 | 281 | 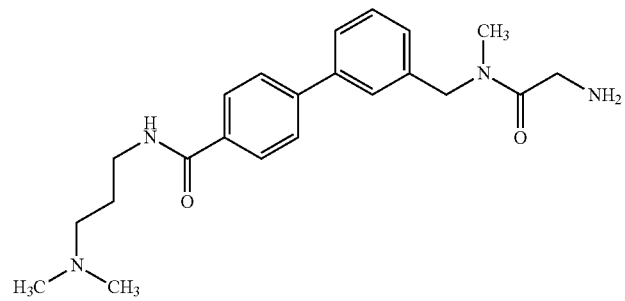 [SMILES: CN(C)CCCNC(=O)c1ccc(-c2cccc(CN(C)C(=O)CN)c2)cc1] | — |
| 295 | 281 | 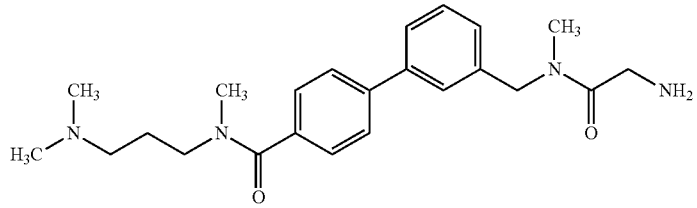 [SMILES: CN(C)CCCN(C)C(=O)c1ccc(-c2cccc(CN(C)C(=O)CN)c2)cc1] | — |
| 296 | 281 | 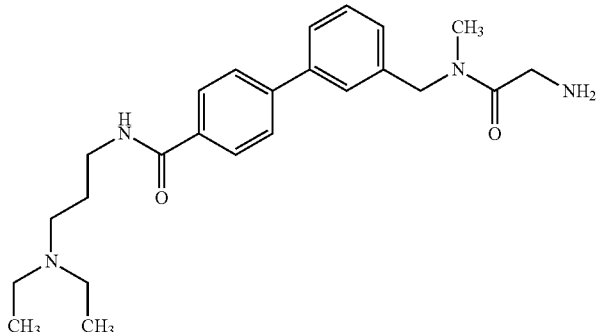 | — |
| 297 | 281 | 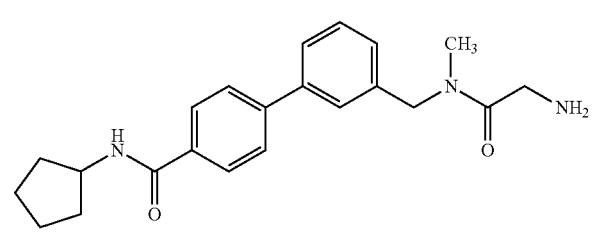 [SMILES: CN(Cc1cccc(-c2ccc(C(=O)NC3CCCC3)cc2)c1)C(=O)CN] | — |

TABLE 133

| Ex | Syn | Structure | Acid |
|----|-----|-----------|------|
| 298 | 281 | 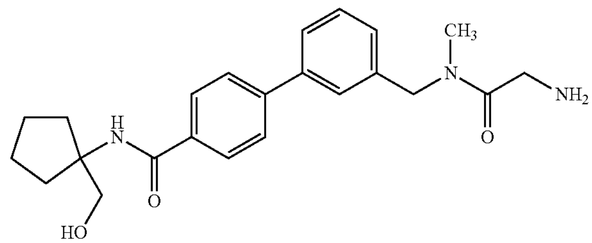 [SMILES: CN(Cc1cccc(-c2ccc(C(=O)NC3(CO)CCCC3)cc2)c1)C(=O)CN] | — |
| 299 | 281 | 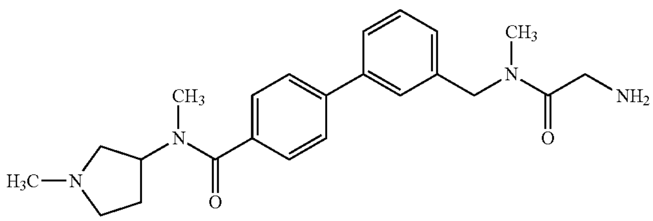 [SMILES: CN1CCC(N(C)C(=O)c2ccc(-c3cccc(CN(C)C(=O)CN)c3)cc2)C1] | — |
| 300 | 281 | 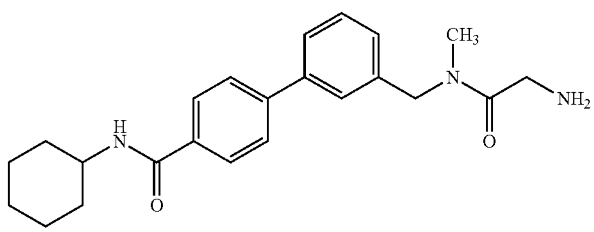 [SMILES: CN(Cc1cccc(-c2ccc(C(=O)NC3CCCCC3)cc2)c1)C(=O)CN] | — |
| 301 | 281 | 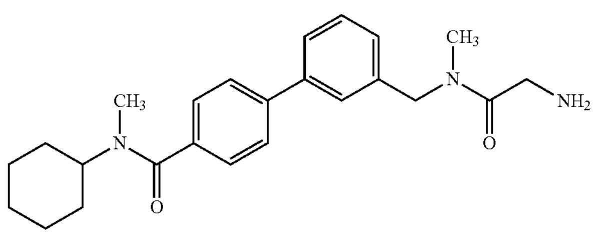 [SMILES: CN(Cc1cccc(-c2ccc(C(=O)N(C)C3CCCCC3)cc2)c1)C(=O)CN] | — |
| 302 | 281 | 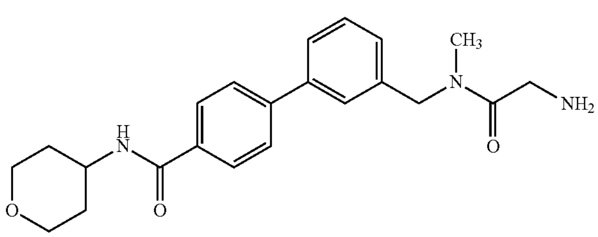 [SMILES: CN(Cc1cccc(-c2ccc(C(=O)NC3CCOCC3)cc2)c1)C(=O)CN] | — |
| 303 | 281 | 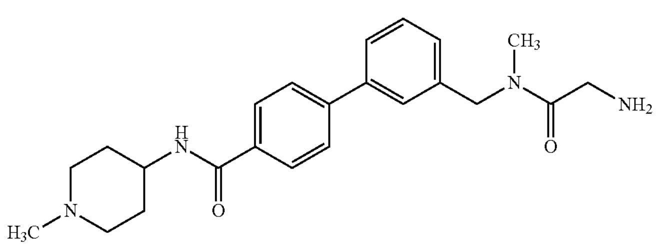 [SMILES: CN1CCC(NC(=O)c2ccc(-c3cccc(CN(C)C(=O)CN)c3)cc2)CC1] | — |

TABLE 134
| Ex | Syn | Structure | Acid |
|---|---|---|---|
| 304 | 281 | 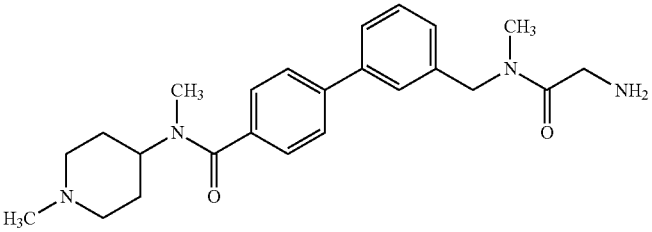 [SMILES: CN1CCC(N(C)C(=O)c2ccc(-c3cccc(CN(C)C(=O)CN)c3)cc2)CC1] | — |
| 305 | 281 | 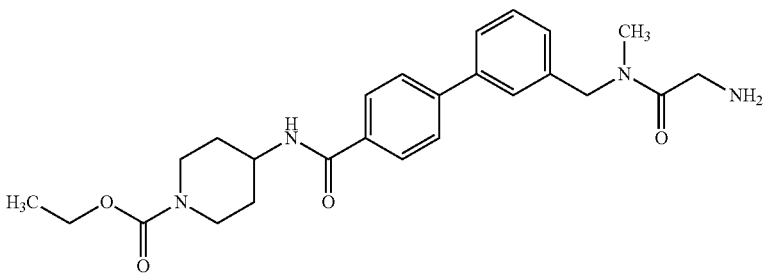 [SMILES: CCOC(=O)N1CCC(NC(=O)c2ccc(-c3cccc(CN(C)C(=O)CN)c3)cc2)CC1] | — |
| 306 | 281 | 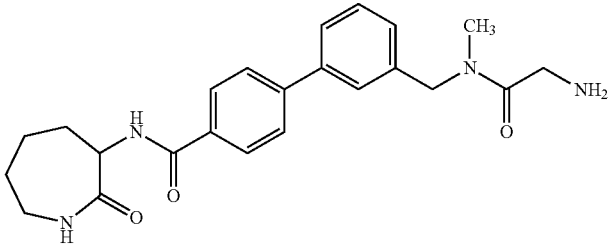 [SMILES: CN(Cc1cccc(-c2ccc(C(=O)NC3CCCCNC3=O)cc2)c1)C(=O)CN] | — |
| 307 | 281 | 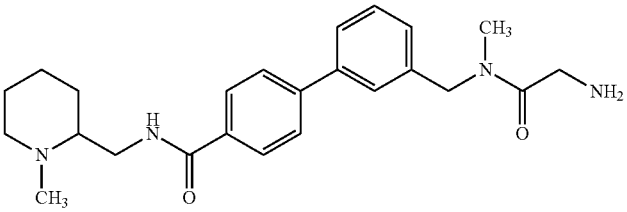 [SMILES: CN(Cc1cccc(-c2ccc(C(=O)NCC3CCCCN3C)cc2)c1)C(=O)CN] | — |
| 308 | 281 | 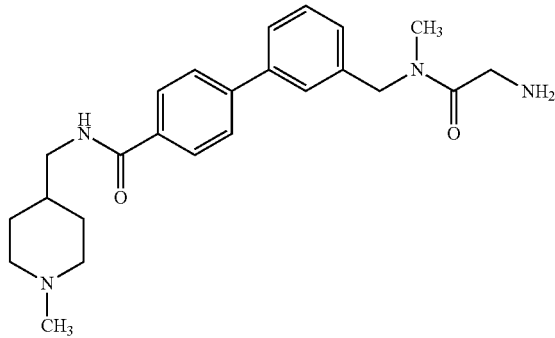 [SMILES: CN1CCC(CNC(=O)c2ccc(-c3cccc(CN(C)C(=O)CN)c3)cc2)CC1] | — |

TABLE 135
| Ex | Syn | Structure | Acid |
|---|---|---|---|
| 309 | 281 | 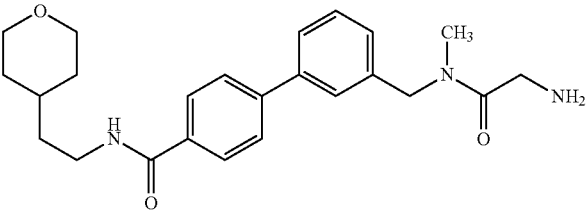 [SMILES: CN(Cc1cccc(-c2ccc(C(=O)NCCC3CCOCC3)cc2)c1)C(=O)CN] | — |
| 310 | 281 | 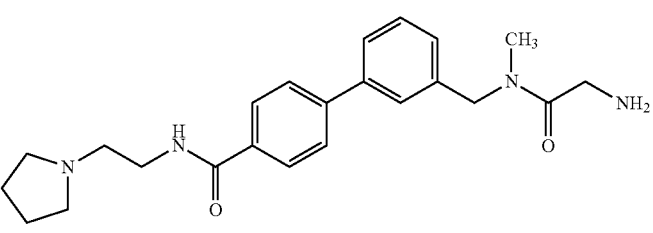 [SMILES: CN(Cc1cccc(-c2ccc(C(=O)NCCN3CCCC3)cc2)c1)C(=O)CN] | — |
| 311 | 281 | 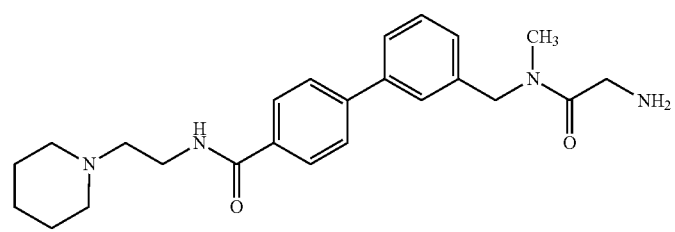 [SMILES: CN(Cc1cccc(-c2ccc(C(=O)NCCN3CCCCC3)cc2)c1)C(=O)CN] | — |
| 312 | 281 | 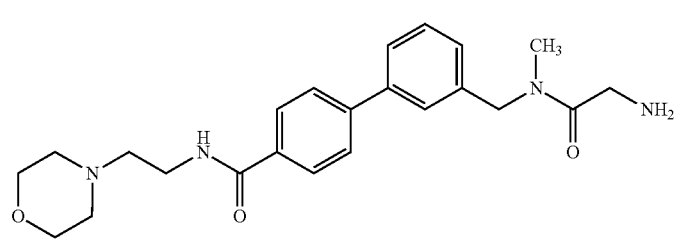 [SMILES: CN(Cc1cccc(-c2ccc(C(=O)NCCN3CCOCC3)cc2)c1)C(=O)CN] | — |
| 313 | 281 | 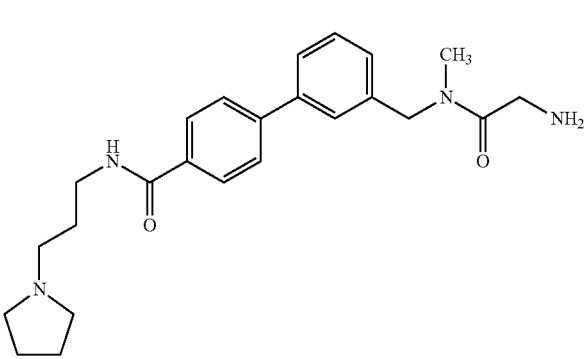 [SMILES: CN(Cc1cccc(-c2ccc(C(=O)NCCCN3CCCC3)cc2)c1)C(=O)CN] | — |
| 314 | 281 | 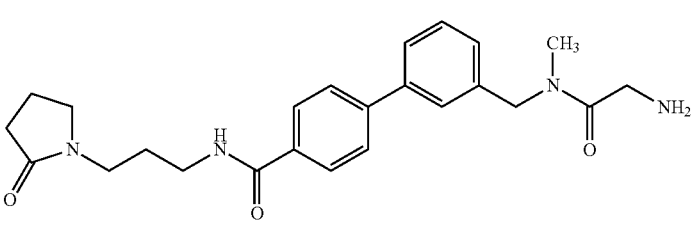 [SMILES: CN(Cc1cccc(-c2ccc(C(=O)NCCCN3CCCC3=O)cc2)c1)C(=O)CN] | — |

TABLE 136

| Ex | Syn | Structure | Acid |
|---|---|---|---|
| 315 | 281 | (structure) | — |
| 316 | 281 | (structure) | — |
| 317 | 281 | (structure) | — |
| 318 | 281 | (structure) | — |
| 319 | 281 | (structure) | — |

TABLE 137

| Ex | Syn | Structure | Acid |
|----|-----|-----------|------|
| 320 | 281 | 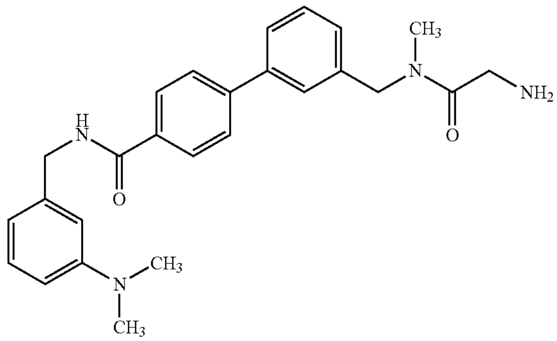 [SMILES: CN(Cc1cccc(-c2ccc(C(=O)NCc3cccc(N(C)C)c3)cc2)c1)C(=O)CN] | — |
| 321 | 281 | 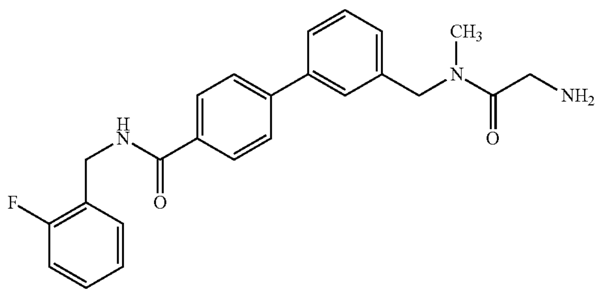 [SMILES: CN(Cc1cccc(-c2ccc(C(=O)NCc3ccccc3F)cc2)c1)C(=O)CN] | — |
| 322 | 281 | 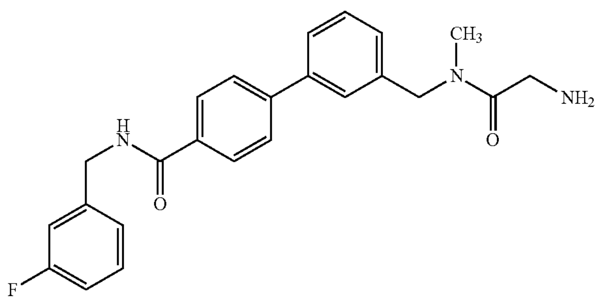 [SMILES: CN(Cc1cccc(-c2ccc(C(=O)NCc3cccc(F)c3)cc2)c1)C(=O)CN] | — |
| 323 | 281 | 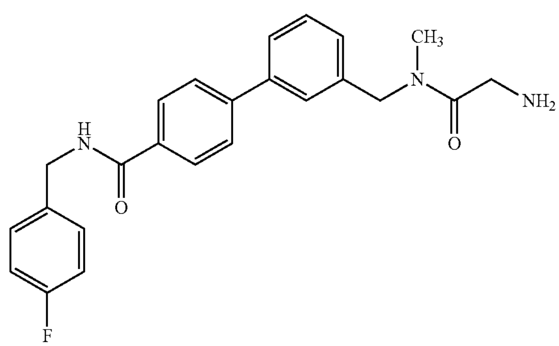 [SMILES: CN(Cc1cccc(-c2ccc(C(=O)NCc3ccc(F)cc3)cc2)c1)C(=O)CN] | — |
| 324 | 281 | 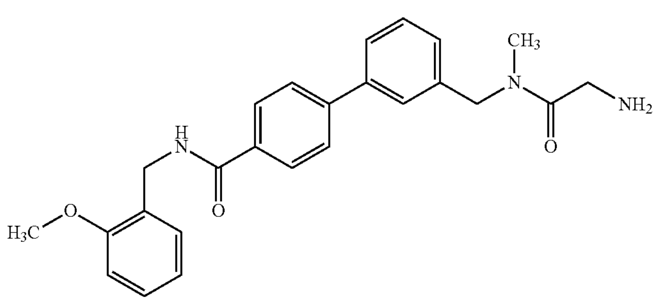 [SMILES: COc1ccccc1CNC(=O)c1ccc(-c2cccc(CN(C)C(=O)CN)c2)cc1] | — |

TABLE 138
| Ex | Syn | Structure | Acid |
|---|---|---|---|
| 325 | 281 | 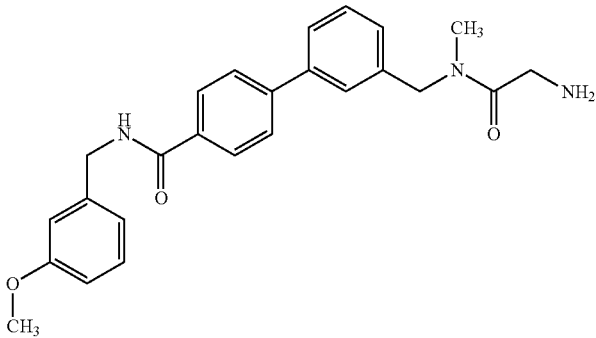 [SMILES: COc1cccc(CNC(=O)c2ccc(-c3cccc(CN(C)C(=O)CN)c3)cc2)c1] | — |
| 326 | 281 | 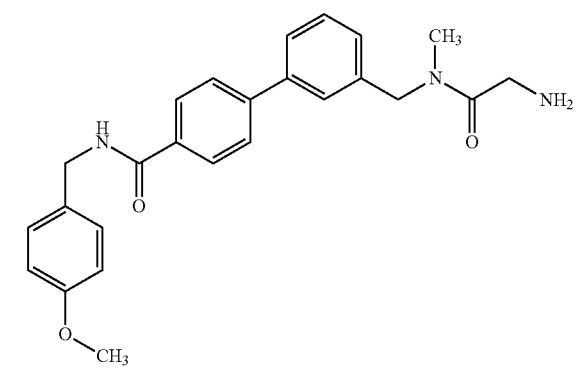 [SMILES: COc1ccc(CNC(=O)c2ccc(-c3cccc(CN(C)C(=O)CN)c3)cc2)cc1] | — |
| 327 | 281 | 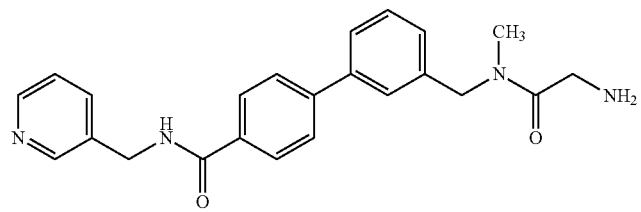 [SMILES: CN(Cc1cccc(-c2ccc(C(=O)NCc3cccnc3)cc2)c1)C(=O)CN] | — |
| 328 | 281 | 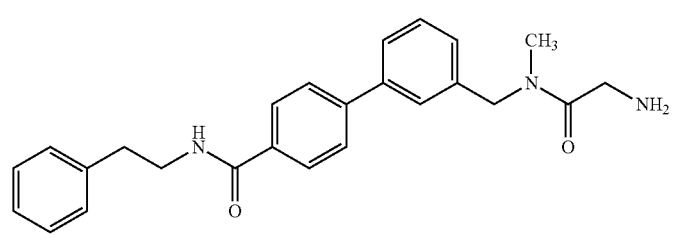 [SMILES: CN(Cc1cccc(-c2ccc(C(=O)NCCc3ccccc3)cc2)c1)C(=O)CN] | — |
| 329 | 281 | 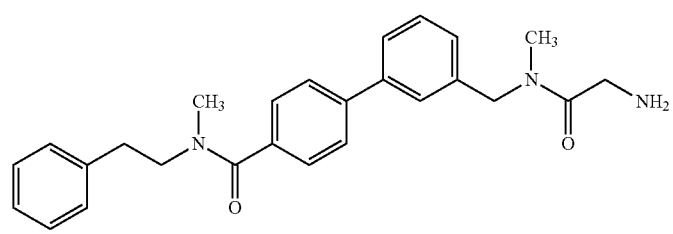 [SMILES: CN(Cc1cccc(-c2ccc(C(=O)N(C)CCc3ccccc3)cc2)c1)C(=O)CN] | — |

TABLE 139
| Ex | Syn | Structure | Acid |
|---|---|---|---|
| 330 | 281 | 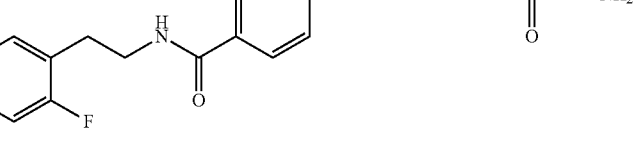 | — |
| 331 | 281 | 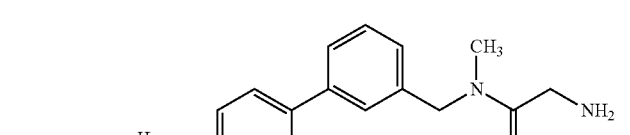 | — |
| 332 | 281 | 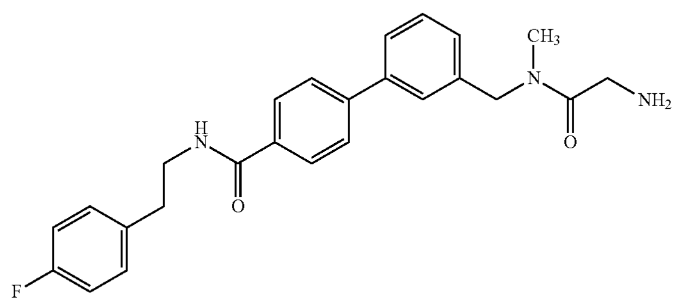 [SMILES: CN(Cc1cccc(-c2ccc(C(=O)NCCc3ccc(F)cc3)cc2)c1)C(=O)CN] | — |
| 333 | 281 | 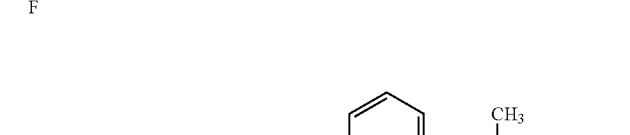 | — |
| 334 | 281 | 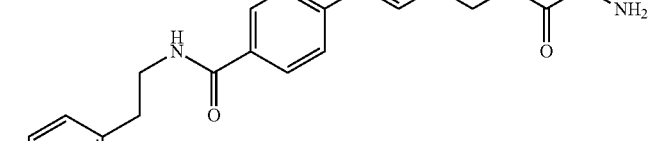 | — |

TABLE 140
| Ex | Syn | Structure | Acid |
|---|---|---|---|
| 335 | 281 | 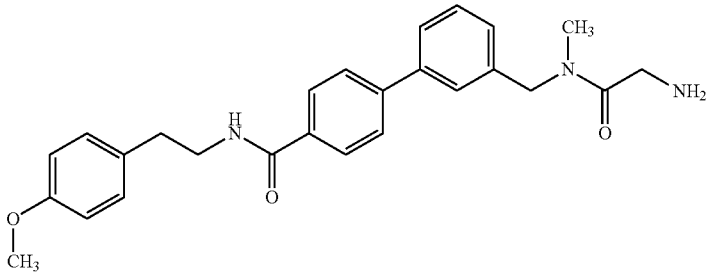 [SMILES: COc1ccc(CCNC(=O)c2ccc(-c3cccc(CN(C)C(=O)CN)c3)cc2)cc1] | — |
| 336 | 281 | 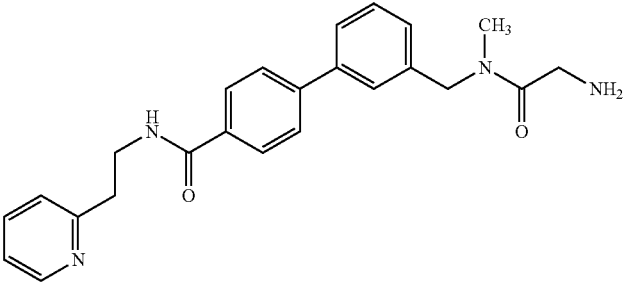 [SMILES: CN(Cc1cccc(-c2ccc(C(=O)NCCc3ccccn3)cc2)c1)C(=O)CN] | — |
| 337 | 281 | 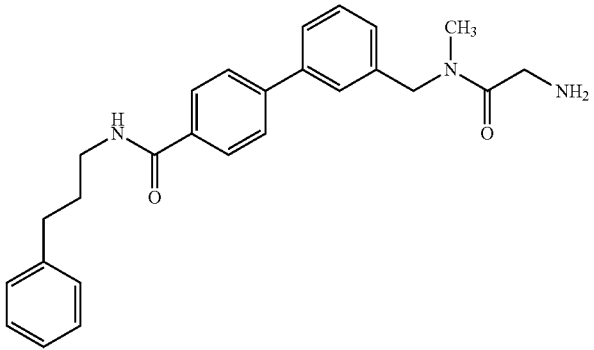 [SMILES: CN(Cc1cccc(-c2ccc(C(=O)NCCCc3ccccc3)cc2)c1)C(=O)CN] | — |
| 338 | 281 | 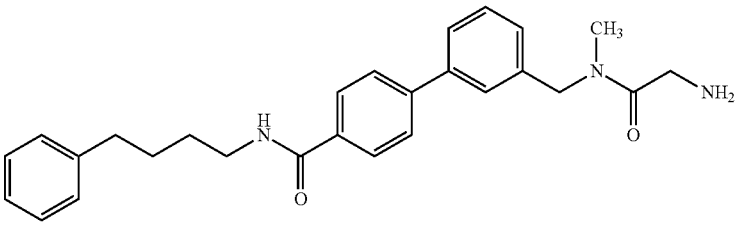 [SMILES: CN(Cc1cccc(-c2ccc(C(=O)NCCCCc3ccccc3)cc2)c1)C(=O)CN] | — |
| 339 | 281 | 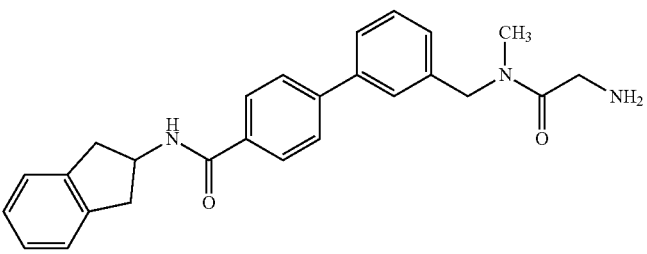 [SMILES: CN(Cc1cccc(-c2ccc(C(=O)NC3Cc4ccccc4C3)cc2)c1)C(=O)CN] | — |

TABLE 141

| Ex | Syn | Structure | Acid |
|---|---|---|---|
| 340 | 281 | 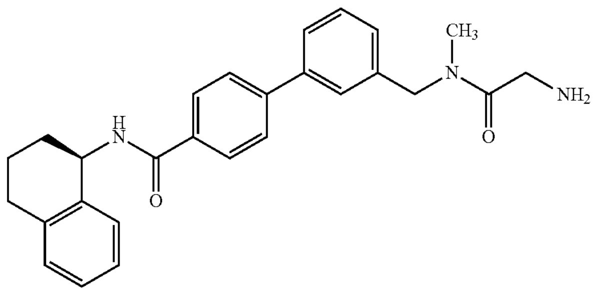 [SMILES: CN(Cc1cccc(-c2ccc(C(=O)N[C@@H]3CCCc4ccccc43)cc2)c1)C(=O)CN] | — |
| 341 | 281 | 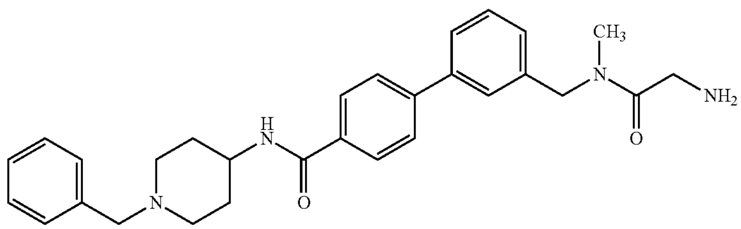 | — |
| 342 | 281 | 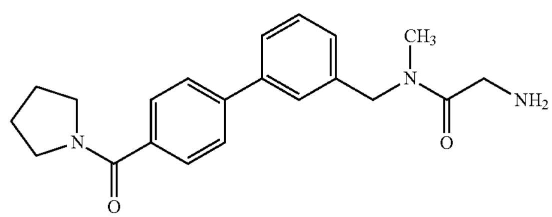 [SMILES: CN(Cc1cccc(-c2ccc(C(=O)N3CCCC3)cc2)c1)C(=O)CN] | — |
| 343 | 281 | 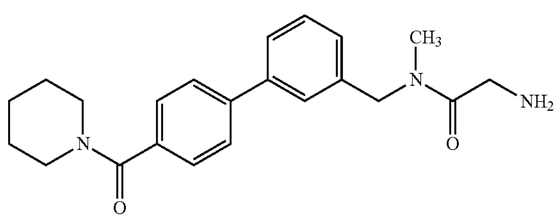 [SMILES: CN(Cc1cccc(-c2ccc(C(=O)N3CCCCC3)cc2)c1)C(=O)CN] | — |
| 344 | 281 | 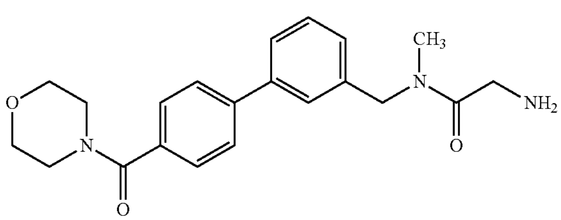 [SMILES: CN(Cc1cccc(-c2ccc(C(=O)N3CCOCC3)cc2)c1)C(=O)CN] | — |
| 345 | 281 | 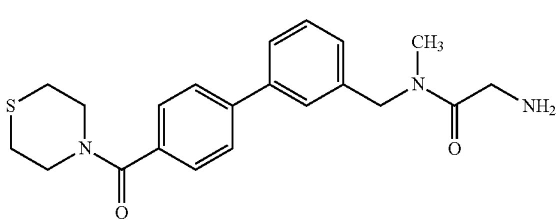 [SMILES: CN(Cc1cccc(-c2ccc(C(=O)N3CCSCC3)cc2)c1)C(=O)CN] | — |

TABLE 142

| Ex | Syn | Structure | Acid |
|---|---|---|---|
| 346 | 281 | 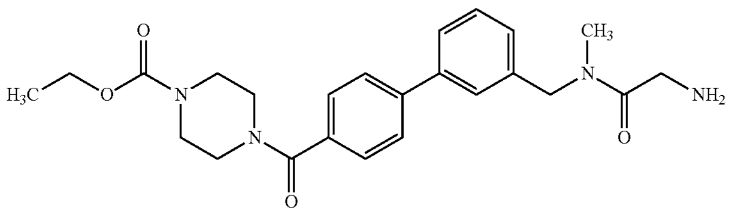 | — |
| 347 | 281 | 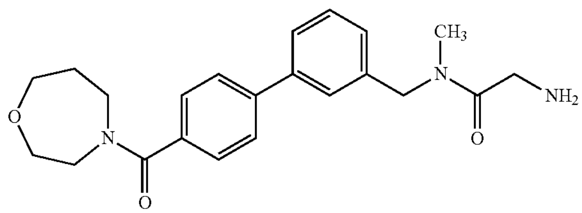 [SMILES: CN(Cc1cccc(-c2ccc(C(=O)N3CCCOCC3)cc2)c1)C(=O)CN] | — |
| 348 | 281 | 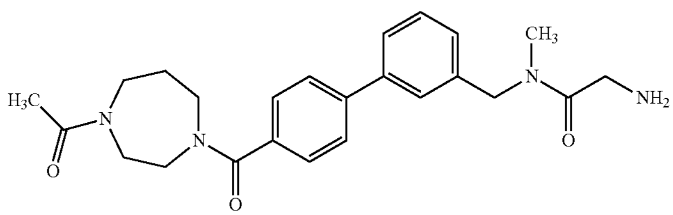 [SMILES: CC(=O)N1CCCN(C(=O)c2ccc(-c3cccc(CN(C)C(=O)CN)c3)cc2)CC1] | — |
| 349 | 281 | 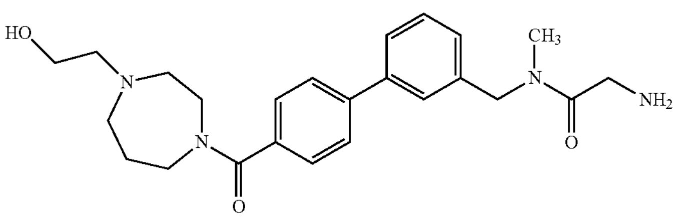 [SMILES: CN(Cc1cccc(-c2ccc(C(=O)N3CCCN(CCO)CC3)cc2)c1)C(=O)CN] | — |
| 350 | 281 | 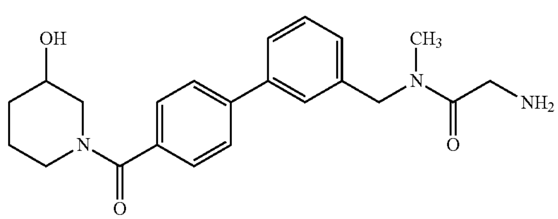 [SMILES: CN(Cc1cccc(-c2ccc(C(=O)N3CCCC(O)C3)cc2)c1)C(=O)CN] | — |
| 351 | 281 | 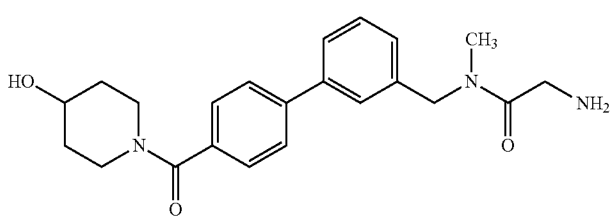 [SMILES: CN(Cc1cccc(-c2ccc(C(=O)N3CCC(O)CC3)cc2)c1)C(=O)CN] | — |

TABLE 143

| Ex | Syn | Structure | Acid |
|---|---|---|---|
| 352 | 281 | 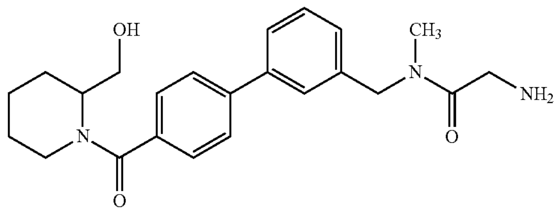 [SMILES: CN(Cc1cccc(-c2ccc(C(=O)N3CCCCC3CO)cc2)c1)C(=O)CN] | — |
| 353 | 281 | 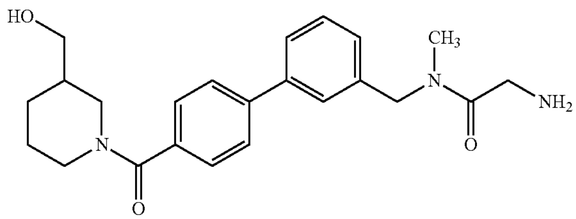 [SMILES: CN(Cc1cccc(-c2ccc(C(=O)N3CCCC(CO)C3)cc2)c1)C(=O)CN] | — |
| 354 | 281 | 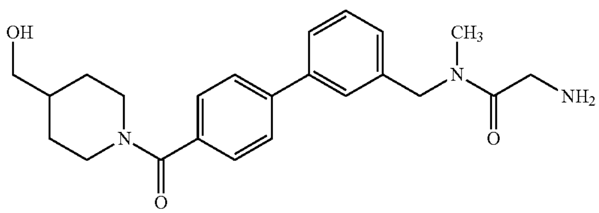 [SMILES: CN(Cc1cccc(-c2ccc(C(=O)N3CCC(CO)CC3)cc2)c1)C(=O)CN] | — |
| 355 | 281 | 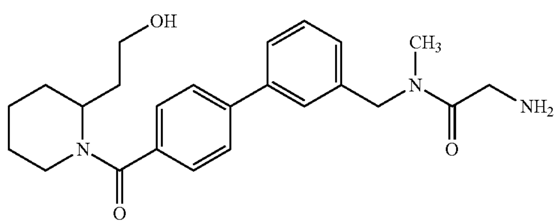 [SMILES: CN(Cc1cccc(-c2ccc(C(=O)N3CCCCC3CCO)cc2)c1)C(=O)CN] | — |
| 356 | 281 | 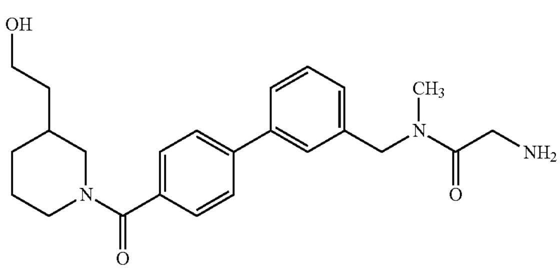 [SMILES: CN(Cc1cccc(-c2ccc(C(=O)N3CCCC(CCO)C3)cc2)c1)C(=O)CN] | — |
| 357 | 281 | 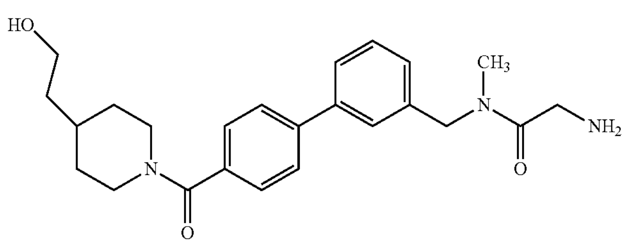 [SMILES: CN(Cc1cccc(-c2ccc(C(=O)N3CCC(CCO)CC3)cc2)c1)C(=O)CN] | — |

TABLE 144

| Ex | Syn | Structure | Acid |
|---|---|---|---|
| 358 | 281 | 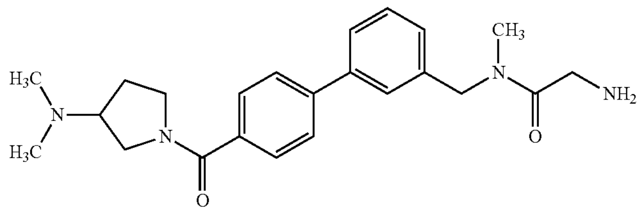 [SMILES: CN(Cc1cccc(-c2ccc(C(=O)N3CCC(N(C)C)C3)cc2)c1)C(=O)CN] | — |
| 359 | 281 | 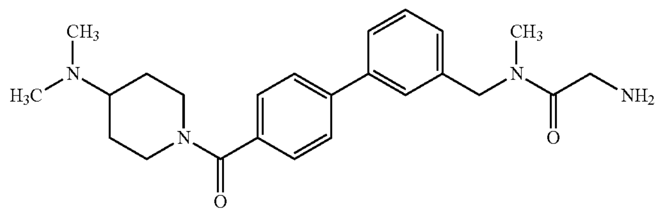 [SMILES: CN(Cc1cccc(-c2ccc(C(=O)N3CCC(N(C)C)CC3)cc2)c1)C(=O)CN] | — |
| 360 | 281 | 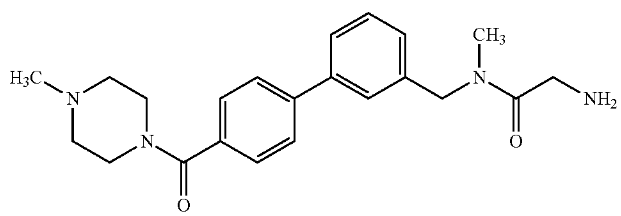 [SMILES: CN1CCN(C(=O)c2ccc(-c3cccc(CN(C)C(=O)CN)c3)cc2)CC1] | — |
| 361 | 281 | 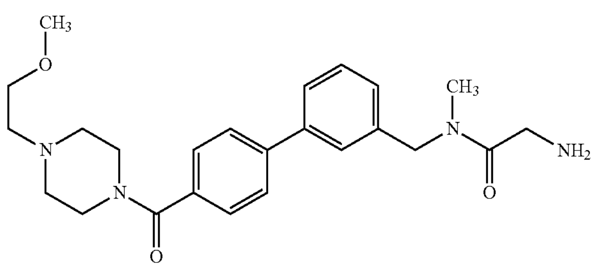 [SMILES: COCCN1CCN(C(=O)c2ccc(-c3cccc(CN(C)C(=O)CN)c3)cc2)CC1] | — |
| 362 | 281 | 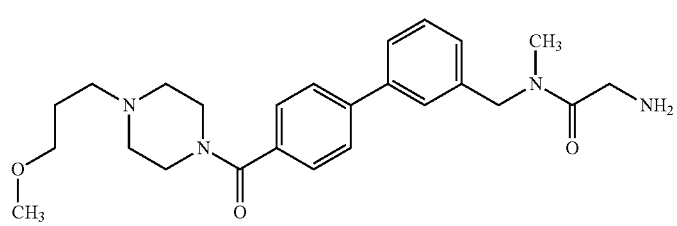 [SMILES: COCCCN1CCN(C(=O)c2ccc(-c3cccc(CN(C)C(=O)CN)c3)cc2)CC1] | — |
| 363 | 281 | 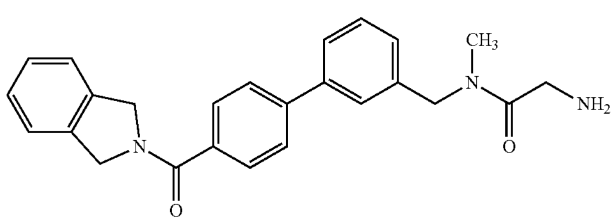 [SMILES: CN(Cc1cccc(-c2ccc(C(=O)N3Cc4ccccc4C3)cc2)c1)C(=O)CN] | — |

TABLE 145

| Ex | Syn | Structure | Acid |
|---|---|---|---|
| 364 | 281 | (3,4-dihydroisoquinolin-2(1H)-yl)carbonyl-biphenyl-CH2-N(CH3)-C(O)-CH2-NH2 | — |
| 365 | 281 | (3-phenylpyrrolidin-1-yl)carbonyl-biphenyl-CH2-N(CH3)-C(O)-CH2-NH2 | — |
| 366 | 281 | (4-phenylpiperidin-1-yl)carbonyl-biphenyl-CH2-N(CH3)-C(O)-CH2-NH2 | — |
| 367 | 281 | (4-(pyridin-4-yl)piperidin-1-yl)carbonyl-biphenyl-CH2-N(CH3)-C(O)-CH2-NH2 | — |
| 368 | 281 | (4-(pyrrolidin-1-yl)piperidin-1-yl)carbonyl-biphenyl-CH2-N(CH3)-C(O)-CH2-NH2 | — |
| 369 | 281 | (4-morpholinopiperidin-1-yl)carbonyl-biphenyl-CH2-N(CH3)-C(O)-CH2-NH2 | — |

TABLE 146

| Ex | Syn | Structure | Acid |
|---|---|---|---|
| 370 | 281 | (structure) | — |
| 371 | 281 | (structure) | — |
| 372 | 281 | (structure) | — |
| 373 | 281 | (structure) | — |
| 374 | 374 | (structure) | — |
| 375 | 374 | (structure) | — |

TABLE 147

| Ex | Syn | Structure | Acid |
|---|---|---|---|
| 376 | 374 | 4'-chloro-biphenyl-3-ylmethyl, N-methyl glycinamide | — |
| 377 | 374 | 4'-methoxy-biphenyl-3-ylmethyl, N-methyl glycinamide | — |
| 378 | 374 | 4'-(hydroxymethyl)-biphenyl-3-ylmethyl, N-methyl glycinamide | — |
| 379 | 374 | 4'-cyano-biphenyl-3-ylmethyl, N-methyl glycinamide | — |
| 380 | 374 | 4'-acetamido-biphenyl-3-ylmethyl, N-methyl glycinamide | — |
| 381 | 374 | 4'-(dimethylamino)-biphenyl-3-ylmethyl, N-methyl glycinamide | — |

TABLE 148

| Ex | Syn | Structure | Acid |
|---|---|---|---|
| 382 | 374 | 4'-morpholino-biphenyl-3-ylmethyl, N-methyl glycinamide | — |

TABLE 148-continued

| Ex | Syn | Structure | Acid |
|----|-----|-----------|------|
| 383 | 374 | 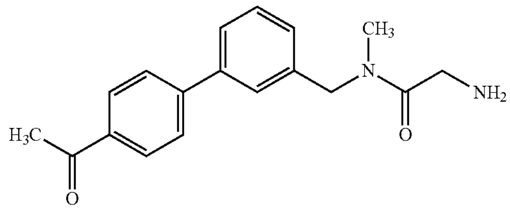 [SMILES: CC(=O)c1ccc(-c2cccc(CN(C)C(=O)CN)c2)cc1] | — |
| 384 | 374 | 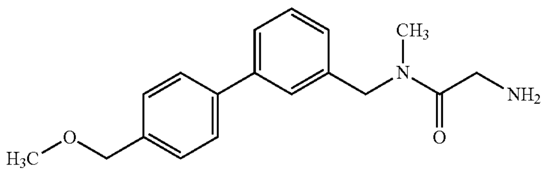 [SMILES: COCc1ccc(-c2cccc(CN(C)C(=O)CN)c2)cc1] | — |
| 385 | 374 | 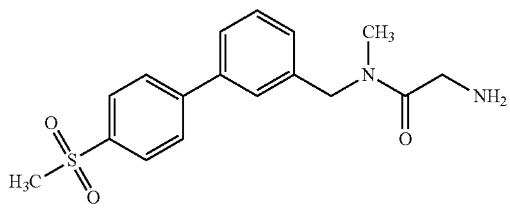 [SMILES: CN(Cc1cccc(-c2ccc(S(C)(=O)=O)cc2)c1)C(=O)CN] | — |
| 386 | 374 | 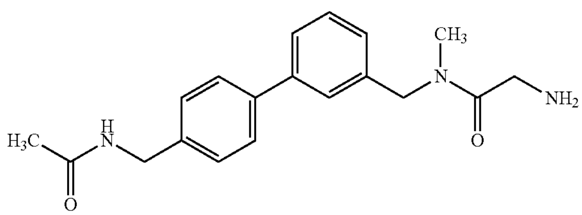 [SMILES: CC(=O)NCc1ccc(-c2cccc(CN(C)C(=O)CN)c2)cc1] | — |
| 387 | 374 | 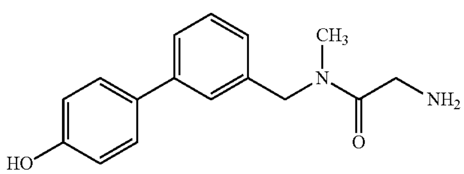 [SMILES: CN(Cc1cccc(-c2ccc(O)cc2)c1)C(=O)CN] | — |

TABLE 149

| Ex | Syn | Structure | Acid |
|----|-----|-----------|------|
| 388 | 374 | 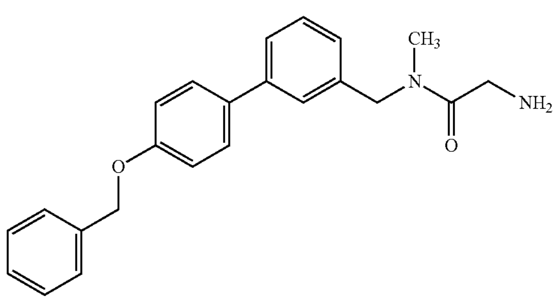 [SMILES: CN(Cc1cccc(-c2ccc(OCc3ccccc3)cc2)c1)C(=O)CN] | — |

TABLE 149-continued

| Ex | Syn | Structure | Acid |
|----|-----|-----------|------|
| 389 | 374 | 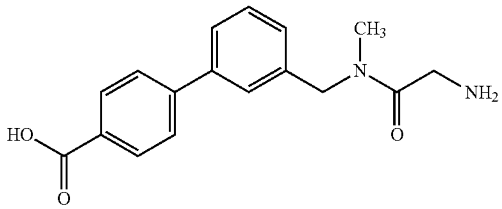 [SMILES: CN(Cc1cccc(-c2ccc(C(=O)O)cc2)c1)C(=O)CN] | — |
| 390 | 374 | 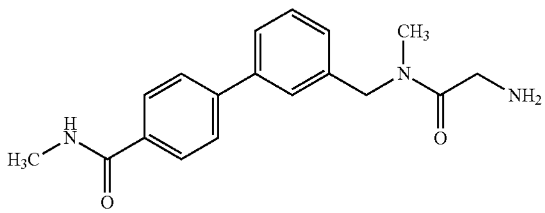 [SMILES: CNC(=O)c1ccc(-c2cccc(CN(C)C(=O)CN)c2)cc1] | — |
| 391 | 374 | 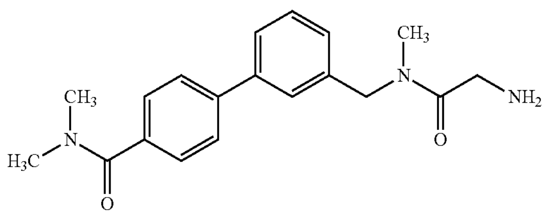 [SMILES: CN(C)C(=O)c1ccc(-c2cccc(CN(C)C(=O)CN)c2)cc1] | — |
| 392 | 374 | 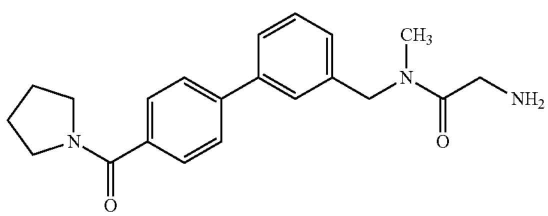 [SMILES: CN(Cc1cccc(-c2ccc(C(=O)N3CCCC3)cc2)c1)C(=O)CN] | — |
| 393 | 374 | 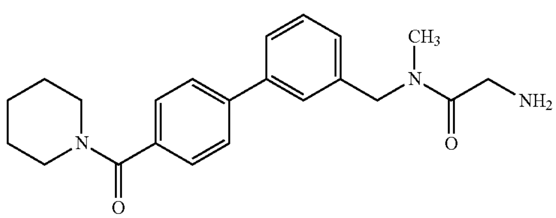 [SMILES: CN(Cc1cccc(-c2ccc(C(=O)N3CCCCC3)cc2)c1)C(=O)CN] | — |

TABLE 150

| Ex | Syn | Structure | Acid |
|----|-----|-----------|------|
| 394 | 374 | 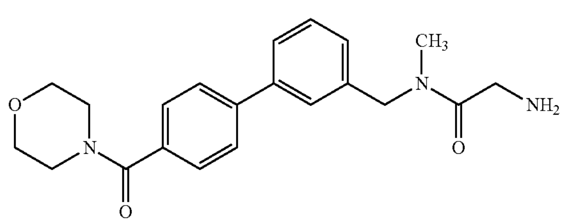 [SMILES: CN(Cc1cccc(-c2ccc(C(=O)N3CCOCC3)cc2)c1)C(=O)CN] | — |

TABLE 150-continued

| Ex | Syn | Structure | Acid |
|---|---|---|---|
| 395 | 374 | 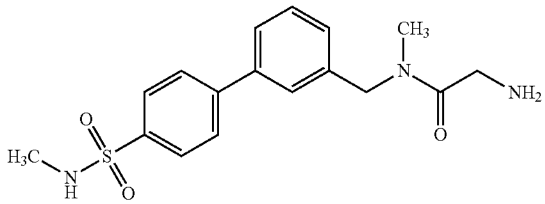 [SMILES: CNS(=O)(=O)c1ccc(-c2cccc(CN(C)C(=O)CN)c2)cc1] | — |
| 396 | 374 | 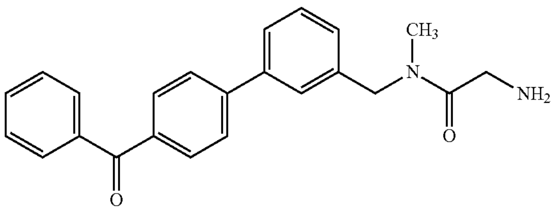 [SMILES: CN(Cc1cccc(-c2ccc(C(=O)c3ccccc3)cc2)c1)C(=O)CN] | — |
| 397 | 374 | 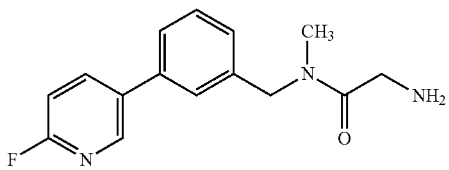 [SMILES: CN(Cc1cccc(-c2ccc(F)nc2)c1)C(=O)CN] | — |
| 398 | 374 | 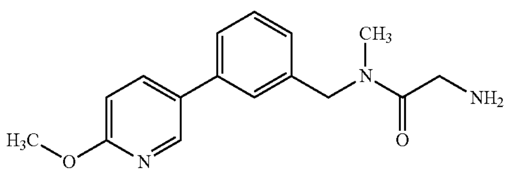 [SMILES: COc1ccc(-c2cccc(CN(C)C(=O)CN)c2)cn1] | — |
| 399 | 374 | 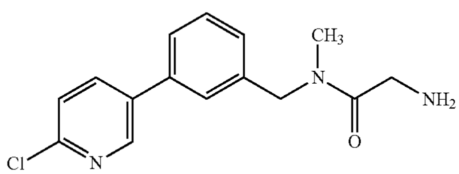 [SMILES: CN(Cc1cccc(-c2ccc(Cl)nc2)c1)C(=O)CN] | — |

TABLE 151

| Ex | Syn | Structure | Acid |
|---|---|---|---|
| 400 | 374 | 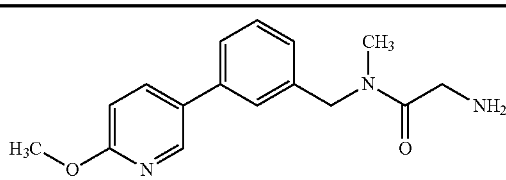 | — |
| 401 | 374 | 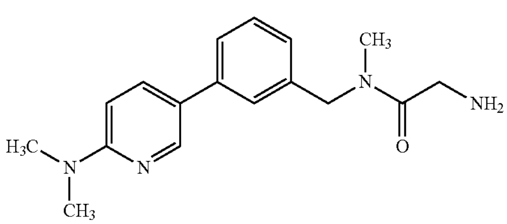 [SMILES: CN(Cc1cccc(-c2ccc(N(C)C)nc2)c1)C(=O)CN] | — |

TABLE 151-continued
| Ex | Syn | Structure | Acid |
|---|---|---|---|
| 402 | 374 | 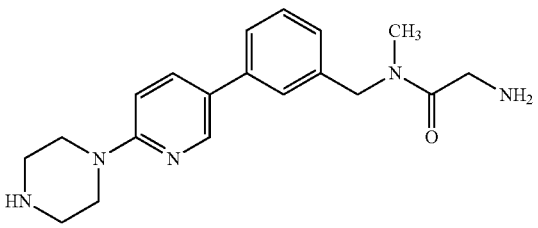 [SMILES: CN(Cc1cccc(-c2ccc(N3CCNCC3)nc2)c1)C(=O)CN] | — |
| 403 | 374 | 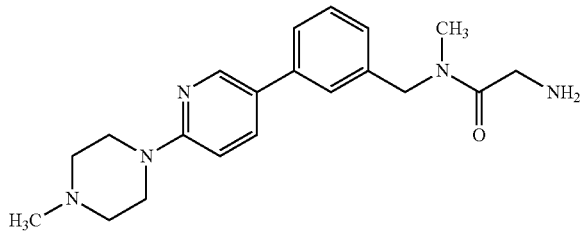 | — |
| 404 | 374 | 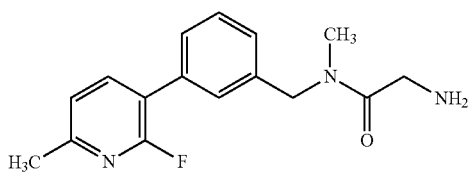 [SMILES: Cc1ccc(-c2cccc(CN(C)C(=O)CN)c2)c(F)n1] | — |
| 405 | 374 | 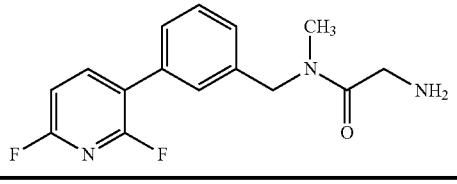 | — |
TABLE 152
| Ex | Syn | Structure | Acid |
|---|---|---|---|
| 406 | 374 | 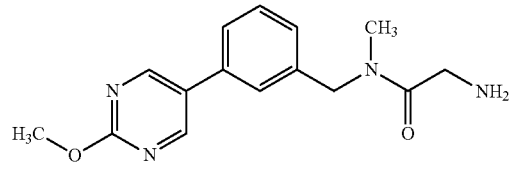 | — |
| 407 | 374 | 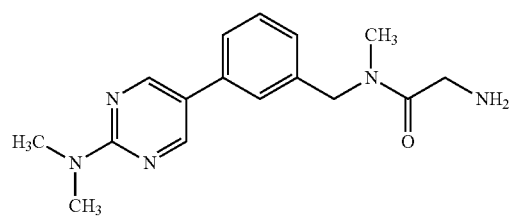 [SMILES: CN(Cc1cccc(-c2cnc(N(C)C)nc2)c1)C(=O)CN] | — |

TABLE 152-continued
| Ex | Syn | Structure | Acid |
|---|---|---|---|
| 408 | 374 | 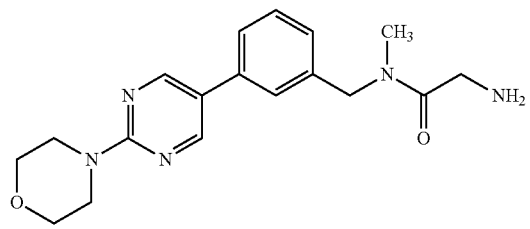 [SMILES: CN(Cc1cccc(-c2cnc(N3CCOCC3)nc2)c1)C(=O)CN] | — |
| 409 | 374 | 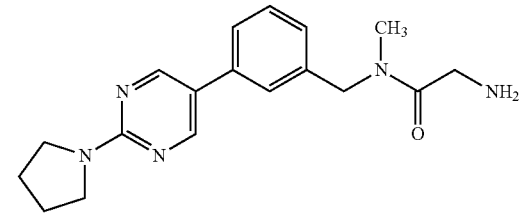 [SMILES: CN(Cc1cccc(-c2cnc(N3CCCC3)nc2)c1)C(=O)CN] | — |
| 410 | 374 | 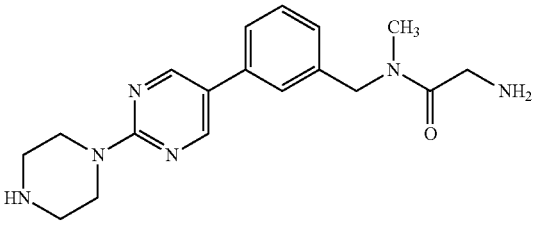 [SMILES: CN(Cc1cccc(-c2cnc(N3CCNCC3)nc2)c1)C(=O)CN] | — |
| 411 | 374 | 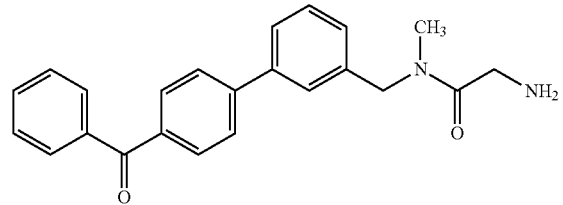 [SMILES: CN(Cc1cccc(-c2ccc(C(=O)c3ccccc3)cc2)c1)C(=O)CN] | — |
TABLE 153
| Ex | Syn | Structure | Acid |
|---|---|---|---|
| 412 | 374 | 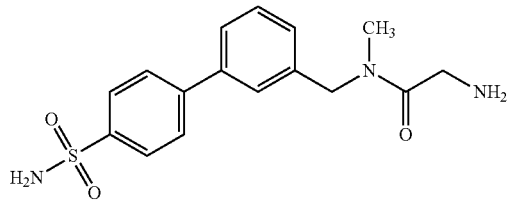 [SMILES: CN(Cc1cccc(-c2ccc(S(N)(=O)=O)cc2)c1)C(=O)CN] | — |
| 413 | 374 | 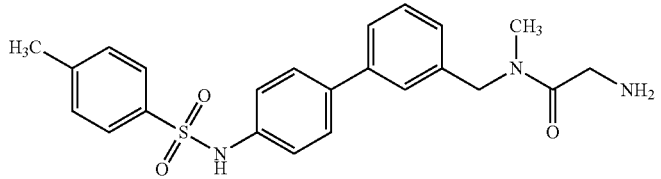 [SMILES: Cc1ccc(S(=O)(=O)Nc2ccc(-c3cccc(CN(C)C(=O)CN)c3)cc2)cc1] | — |

TABLE 153-continued

| Ex | Syn | Structure | Acid |
|---|---|---|---|
| 414 | 374 | (morpholine-phenyl-phenyl-CH2-N(CH3)-C(O)-CH2-NH2) | — |
| 415 | 374 | (CH3-SO2-NH-CH2-phenyl-phenyl-CH2-N(CH3)-C(O)-CH2-NH2) | — |
| 416 | 374 | (HO-(CH2)3-phenyl-phenyl-CH2-N(CH3)-C(O)-CH2-NH2) | — |

TABLE 154

| Ex | Data |
|---|---|
| 1 | ESI+: 313 |
| 2 | FAB+: 312 |
| 3 | ESI+: 432 |
| 4 | ESI+: 431 |
| 5 | ESI+: 486 |
| 6 | ESI+: 430 |
| 7 | ESI+: 453 |
| 8 | ESI+: 457 |
| 9 | ESI+: 452 |
| 10 | ESI+: 413 |
| 11 | ESI+: 406<br>NMR-DMSO-$d_6$: 1.78-1.93 (2H, m), 2.01-2.14 (2H, m), 2.90 (0.9H, s), 2.96 (2.1H, s), 3.06-3.20 (2H, m), 3.82-4.20 (4H, m), 4.47-4.68 (3H, m), 4.74-4.87 (2H, m), 6.18-6.26 (1H, m), 7.17-7.26 (1H, m), 7.37-7.52 (3H, m), 7.53-7.65 (1H, m), 7.75-7.83 (1H, m), 8.72 (1.4H, s), 8.75 (0.6H, s) |
| 12 | ESI+: 423 |
| 13 | ESI+: 409 |
| 14 | FAB+: 340<br>NMR-DMSO-$d_6$: 1.22 (3H, d, J = 6.8 Hz), 1.63-1.75 (1H, m), 1.84-2.12 (3H, m), 2.88 (0.9H, s), 2.93 (2.1H, s), 3.39-3.69 (4H, m), 3.70-3.79 (2H, m), 4.18-4.30 (1H, m), 4.58 (0.6H, s), 4.6 (1.4H, s), 7.13-7.22 (1H, m), 7.35-7.49 (2H, m), 7.49-7.60 (1H, m), 8.67 (1.4H, s), 8.69 (0.6H, s) |
| 15 | FAB+: 344<br>NMR-DMSO-$d_6$: 2.08-2.36 (2H, m), 2.88 (0.9H, s), 2.93 (2.1H, s), 3.38-3.94 (8H, m), 4.56 (0.6H, s), 4.60 (1.4H, s), 5.34-5.56 (1H, m), 7.13-7.24 (1H, m), 7.34-7.50 (2H, m), 7.50-7.62 (1H, m), 8.63-8.78 (2H, m) |
| 16 | FAB+: 344<br>NMR-DMSO-$d_6$: 2.08-2.35 (2H, m), 2.88 (0.9H, s), 2.93 (2.1H, s), 3.38-3.93 (8H, m), 4.57 (0.6H, s), 4.60 (1.4H, s), 5.35-5.56 (1H, m), 7.13-7.23 (1H, m), 7.37-7.50 (2H, m), 7.50-7.62 (1H, m), 8.65-8.76 (2H, m) |

TABLE 155

| Ex | Data |
|---|---|
| 17 | FAB+: 362<br>NMR-DMSO-$d_6$: 2.40-2.64 (2H, m), 2.89 (0.9H, s), 2.95 (2.1H, s), 3.70-3.83 (4H, m), 3.83-4.20 (4H, m), 4.58 (0.6H, s), 4.62 (1.4H, s), 7.16-7.26 (1H, m), 7.37-7.52 (2H, m), 7.52-7.64 (1H, m), 8.68-8.81 (2H, m) |
| 18 | FAB+: 358 |
| 19 | FAB+: 502<br>NMR-DMSO-$d_6$: 2.39 (3H, s), 2.90 (0.9H, s), 2.97 (2.1H, s), 3.35-3.52 (4H, m), 3.87-4.04 (6H, m), 4.57-4.66 (2H, m), 6.56 (1H, d, J = 16.0 Hz), 7.18-7.27 (1H, m), 7.38-7.53 (2H, m), 7.54-7.66 (2H, m), 8.07-8.31 (4H, m), 8.34-8.41 (1H, m), 8.76 (1.6H, s), 8.79 (0.4H, s) |
| 20 | ESI+: 312 |
| 21 | ESI+: 340 |
| 22 | ESI+: 355 |
| 23 | ESI+: 396 |
| 24 | ESI+: 431 |
| 25 | ESI+: 356 |
| 26 | FAB+: 353 |
| 27 | ESI+: 418<br>NMR-DMSO-d6: 2.90 (1.2H, s), 2.97 (1.8H, s), 3.78-4.15 (10H, m), 4.61 (0.8H, s), 4.63 (1.2H, s), 7.17-7.65 (6H, m), 8.18-8.33 (5H, m), 8.78 (1.2H, s), 8.80 (0.8H, s) |
| 28 | ESI+: 419<br>NMR-DMSO-$d_6$: 2.90 (1.2H, s), 2.97 (1.8H, s), 3.50-4.10 (10H, m), 4.60 (0.8H, s), 4.63 (1.2H, s), 6.72 (1H, t, J = 5 Hz), 7.24 (1H, d, J = 7 Hz), 7.40-7.65 (3H, m), 8.07-8.22 (3H, m), 8.44 (2H, d, J = 5 Hz), 8.75 (1.2H, s), 8.77 (0.8H, s) |
| 29 | ESI+: 488<br>NMR-DMSO-$d_6$: 2.38 (3H, s), 3.39-3.44 (4H, m), 3.93-4.04 (6H, m), 4.42 (2H, d, J = 6 Hz), 6.54 (1H, d, J = 16 Hz), 7.28 (1H, d, J = 8 Hz), 7.43 (1H, t, J = 8 Hz), 7.54-7.61 (3H, m), 8.37 (1H, d, J = 2 Hz), 8.76 (2H, s), 8.99 (1H, t, J = 5 Hz) |

TABLE 156

| Ex | Data |
|---|---|
| 30 | ESI+: 516<br>NMR-DMSO-$d_6$: 2.38 (3H, s), 3.39-3.44 (4H, m), 3.93-4.04 (6H, m), 4.42 (2H, d, J = 6 Hz), 6.54 (1H, d, J = 16 Hz), 7.28 (1H, d, J = 8 Hz), 7.43 (1H, t, J = 8 Hz), 7.54-7.61 (3H, m), 8.37 (1H, d, J = 2 Hz), 8.76 (2H, s), 8.99 (1H, t, J = 5 Hz) |

TABLE 156-continued

| Ex | Data |
|---|---|
| 31 | ESI+: 412 |
| 32 | ESI+: 496, 498<br>NMR-DMSO-$d_6$: 2.90 (0.9H, s), 2.97 (2.1H, s), 3.57-3.62 (4H, m), 3.90-4.02 (6H, m), 4.60 (0.6H, s), 4.63 (1.4H, s), 7.24 (1H, d, J = 7.6 Hz), 7.41-7.65 (3H, m), 8.06-8.17 (3H, br), 8.13 (1H, d, J = 2.0 Hz), 8.69 (1H, d, J = 2.0 Hz), 8.75 (1.4H, s), 8.77 (0.6H, s) |
| 33 | ESI+: 522, 524<br>NMR-DMSO-$d_6$: 2.90 (0.9H, s), 2.97 (2.1H, s), 3.46-3.51 (4H, m), 3.90-4.02 (6H, m), 4.60 (0.6H, s), 4.63 (1.4H, s), 6.60 (1H, d, J = 16.0 Hz), 7.24 (1H, d, J = 7.6 Hz), 7.41-7.65 (4H, m), 8.07-8.19 (3H, br), 8.27 (1H, d, J = 2.0 Hz), 8.50 (1H, d, J = 2.0 Hz), 8.75 (1.4H, s), 8.77 (0.6H, s) |
| 34 | ESI+: 397 |
| 35 | ESI+: 338 |
| 36 | ESI+: 375 |
| 37 | ESI+: 375 |
| 38 | ESI+: 380 |
| 39 | ESI+: 396 |
| 40 | FAB+: 355 |
| 41 | ESI+: 356<br>NMR-DMSO-$d_6$: 1.87-2.11 (4H, m), 2.90 (0.9H, s), 2.97 (2.1H, s), 3.37-3.67 (5H, m), 3.87-4.01 (2H, m), 4.12-4.24 (1H, m), 4.60 (0.6H, s), 4.62 (1.4H, s), 7.21-7.26 (1H, m), 7.40-7.52 (2H, m), 7.54-7.64 (1H, m), 8.15-8.32 (3H, br), 8.73 (1.4H, s), 8.76 (0.6H, s) |
| 42 | ESI+: 356<br>NMR-DMSO-$d_6$: 1.87-2.12 (4H, m), 2.90 (0.9H, s), 2.97 (2.1H, s), 3.36-3.67 (5H, m), 3.88-4.01 (2H, m), 4.12-4.24 (1H, m), 4.60 (0.6H, s), 4.62 (1.4H, s), 7.21-7.25 (1H, m), 7.39-7.51 (2H, m), 7.54-7.64 (1H, m), 8.73 (1.4H, s), 8.14-8.30 (3H, br), 8.75 (0.6H, s) |

TABLE 157

| Ex | Data |
|---|---|
| 43 | ESI+: 370<br>NMR-DMSO-$d_6$: 1.87-2.10 (4H, m), 2.89 (0.9H, s), 2.95 (2.1H, s), 3.28 (3H, s), 3.31-3.37 (1H, m), 3.41-3.52 (1H, m) 3.54-3.61 (2H, m), 3.88-4.02 (2H, m), 4.23-4.31 (1H, m), 4.60 (0.6H, s), 4.62 (1.4H, s), 7.20-7.25 (1H, m), 7.39-7.51 (2H, m), 7.53-7.65 (1H, m), 8.07-8.35 (3H, br), 8.72 (1.4H, s), 8.74 (0.6H, s) |
| 44 | ESI+: 417<br>NMR-DMSO-$d_6$: 2.90 (0.9H, s), 2.98 (2.1H, s), 3.35-3.56 (4H, m), 3.87-4.01 (2H, m), 4.06-4.32 (4H, m), 4.61 (0.6H, s), 4.63 (1.4H, s), 7.10-7.29 (2H, m), 7.34-7.69 (7H, m), 8.15-8.35 (3H, br), 8.79 (1.4H, s), 8.81 (0.6H, s) |
| 45 | ESI+: 461 |
| 46 | ESI+: 447 |
| 47 | ESI+: 377 |
| 48 | ESI+: 391 |
| 49 | ESI+: 383 |
| 50 | ESI+: 354 |
| 51 | ESI+: 425 |
| 52 | ESI+: 438 |
| 53 | ESI+: 363 |
| 54 | ESI+: 377 |
| 55 | ESI+: 446 |
| 56 | ESI+: 432 |
| 57 | ESI+: 460 |
| 58 | ESI+: 433 |
| 59 | ESI+: 467 |
| 60 | ESI+: 397 |
| 61 | ESI+: 506<br>NMR-DMSO-$d_6$: 2.90 (0.9H, s), 2.97 (2.1H, s), 3.25-3.36 (4H, m), 3.87-4.05 (6H, m), 4.19 (2H, s), 4.57-4.66 (4H, m), 7.09-7.16 (1H, m), 7.21-7.26 (1H, m), 7.41-7.52 (2H, m), 7.55-7.65 (1H, m), 7.87-7.94 (1H, m), 8.05-8.19 (3H, br), 8.21-8.26 (1H, m), 8.75 (1.4H, s), 8.77 (0.6H, s) |
| 62 | FAB+: 386 |
| 63 | ESI+: 454 |
| 64 | FAB+: 452 |

TABLE 158

| Ex | Data |
|---|---|
| 65 | ESI+: 441 |
| 66 | FAB+: 504<br>NMR-DMSO-$d_6$: 2.41 (3H, s), 2.57-2.64 (2H, m), 2.78-2.87 (2H, m), 2.90 (0.9H, s), 2.97 (2.1H, s), 3.40-3.53 (4H, m), 3.86-4.03 (6H, m), 4.58-4.66 (2H, m), 7.20-7.28 (1H, m), 7.41-7.53 (2H, m), 7.55-7.66 (1H, m), 7.97-8.07 (2H, m), 8.13-8.30 (3H, m), 8.77 (1.4H, s), 8.80 (0.6H, s) |
| 67 | ESI+: 462<br>NMR-DMSO-$d_6$: 2.90 (0.9H, s), 2.97 (2.1H, s), 3.79-3.87 (4H, m), 3.89-4.02 (6H, m), 4.55-4.68 (2H, m), 7.04 (1H, d, J = 9.2 Hz), 7.24 (1H, d, J = 7.7 Hz), 7.39-7.53 (2H, m), 7.54-7.66 (1H, m), 7.98-8.07 (1H, m), 8.08-8.27 (3H, m), 8.62 (1H, d, J = 2.3 Hz), 8.76 (1.4H, s), 8.78 (0.6H, s) |
| 68 | ESI+: 461<br>NMR-DMSO-$d_6$: 2.90 (0.9H, s), 2.97 (2.1H, s), 3.40-3.50 (4H, m), 3.89-4.03 (6H, m), 4.60 (0.6H, s), 4.63 (1.4H, s), 7.03 (2H, d, J = 9.1 Hz), 7.24 (1H, d, J = 7.5 Hz), 7.39-7.53 (2H, m), 7.53-7.65 (1H, m), 7.81 (2H, d, J = 9.0 Hz), 8.10-8.31 (3H, m), 8.75 (1.4H, s), 8.77 (0.6H, s) |
| 69 | ESI+: 342<br>NMR-DMSO-$d_6$: 2.88 (1.2H, s), 2.93 (1.8H, s), 3.66-3.70 (4H, m), 3.73-3.77 (4H, m), 4.56 (0.8H, s), 4.60 (1.2H, s), 7.18-7.22 (1H, m), 7.40-7.61 (3H, m), 8.72 (1.2H, s), 8.74 (0.8H, s) |
| 70 | ESI+: 485 |
| 71 | ESI+: 485 |
| 72 | ESI+: 501.3 |
| 73 | ESI+: 341 |
| 74 | ESI+: 486 |
| 75 | ESI+: 326<br>NMR-DMSO-$d_6$: 1.85-2.04 (4H, m), 2.89 (1.2H, s), 2.96 (1.8H, s), 3.47-3.60 (4H, m), 3.88 (2H, s), 3.91 (0.8H, s), 3.96 (1.2H, s), 4.58 (0.8H, s), 4.62 (1.2H, s), 7.20 (1H, d, J = 8 Hz), 7.40-7.62 (3H, m), 8.68 (1.2H, s), 8.70 (0.8H, s) |
| 76 | ESI+: 341 |

TABLE 159

| Ex | Data |
|---|---|
| 77 | ESI+: 368 |
| 78 | NMR-DMSO-$d_6$: 1.16 (3H, s), 1.17 (3H, s), 2.54-2.62 (2H, m), 2.89 (1.2H, s), 2.96 (1.8H, s), 3.51-3.61 (2H, m), 3.83 (2H, s), 3.88 (0.8H, s), 3.94 (1.2H, s), 4.55 (2H, d, J = 13 Hz), 4.58 (0.8H, s), 4.62 (1.2H, s), 7.22 (1H, d, J = 8 Hz), 7.39-7.66 (3H, m), 8.70 (1.2H, s), 8.73 (0.8H, s) |
| 79 | ESI+: 372 |
| 80 | ESI+: 369 |
| 81 | ESI+: 344 |
| 82 | ESI+: 353 |
| 83 | ESI+: 370 |
| 84 | ESI+: 356 |
| 85 | ESI+: 418<br>NMR-DMSO-$d_6$: 2.88 (1.2H, s), 2.93 (1.8H, s), 3.58-3.65 (4H, m), 3.70-3.75 (2H, m), 3.87-3.94 (4H, m), 4.56 (0.8H, s), 4.61 (1.2H, s), 6.64-6.70 (1H, m), 6.89 (1H, d, J = 9 Hz), 7.17-7.24 (1H, m), 7.40-7.63 (4H, m), 8.13-8.16 (1H, m), 8.73 (1.2H, s), 8.75 (0.8H, s) |
| 86 | NMR-DMSO-$d_6$: 2.21 (3H, s), 2.30-2.36 (4H, m), 2.90 (0.8H, s), 2.94 (1.2H, s), 3.43-3.48 (4H, m), 3.80 (2H, s), 3.83 (0.8H, s), 3.89 (1.2H, s), 4.59 (0.8H, s), 4.62 (1.2H, s), 7.16-7.21 (1H, m), 7.37-7.60 (7H, m), 8.60 (0.6H, s), 8.61 (0.4H, s) |
| 87 | ESI+: 415 |
| 88 | FAB+: 432 |
| 89 | ESI+: 490 |
| 90 | FAB+: 432<br>NMR-DMSO-$d_6$: 2.90 (1.2H, s), 2.96 (1.8H, s), 2.26-2.32 (4H, m), 3.84-3.98 (8H, m), 4.59 (0.8H, s), 4.63 (1.2H, s), 7.20-7.25 (2H, m), 7.41-7.64 (3H, m), 7.88 (1H, s), 8.17 (1H, d, J = 3 Hz), 8.74 (1.2H, s), 8.76 (0.8H, s) |
| 91 | ESI+: 432<br>NMR-DMSO-$d_6$: 2.90 (1.2H, s), 2.97 (1.8H, s), 2.92-2.99 (4H, m), 3.90-4.00 (6H, m), 4.09 (3H, s), 4.59 (0.8H, s), 4.63 (1.2H, s), 7.16-7.26 (2H, m), 7.40-7.65 (4H, m), 8.16 (1H, dd, J = 2.5 Hz), 8.74 (1.2H, s), 8.77 (0.8H, s) |
| 92 | ESI+: 424 |

TABLE 160

| Ex | Data |
|---|---|
| 93 | ESI+: 384 |
| 94 | FAB+: 412 |
| 95 | ESI+: 375<br>NMR-DMSO-$d_6$: 2.91 (1.2H, s), 2.98 (1.8H, s), 3.89-4.04 (2H, m), 4.62 (0.8H, s), 4.64 (1.2H, s), 4.94-5.03 (4H, m), 7.23 (1H, d, J = 8 Hz), 7.46 (1H, t, J = 8 Hz), 7.49-7.68 (3H, m), 8.15-8.32 (4H, m), 8.68 (1H, d, J = 5 Hz), 8.84 (1.2H, s), 8.87 (0.8H, s) |
| 96 | FAB+: 433<br>NMR-DMSO-$d_6$: 1.90-1.98 (2H, m), 2.88 (1.2H, s), 2.93 (1.8H, s), 3.64-4.03 (10H, m), 4.56 (0.8H, s), 4.60 (1.2H, s), 7.17-7.22 (1H, m), 7.37-7.58 (3H, m), 7.73 (1H, d, J = 3 Hz), 7.99-8.02 (1H, m), 8.19 (1H, d, J = 2 Hz), 8.66 (1.2H, s), 8.68 (0.8H, s) |
| 97 | ESI+: 384 |
| 98 | FAB+: 402 |
| 99 | ESI+: 370<br>NMR-DMSO-$d_6$: 1.69-1.79 (1H, m), 2.02-2.12 (1H, m), 2.53-2.61 (1H, m), 2.89 (1.2H, s), 2.96 (1.8H, s), 3.24-3.54 (7H, m), 3.61-3.71 (2H, m), 3.84 (2H, s), 3.88 (0.8H, s), 3.95 (1.2H, s), 4.58 (0.8H, s), 4.62 (1.2H, s), 7.20 (1H, d, J = 8 Hz), 7.38-7.61 (3H, m), 8.68 (1.2H, s), 8.70 (0.8H, s) |
| 100 | ESI+: 427 |
| 101 | FAB+: 397 |
| 102 | ESI+: 409 |
| 103 | FAB+: 447 |
| 104 | ESI+: 343 |
| 105 | ESI+: 398 |
| 106 | ESI+: 342 |
| 107 | ESI+: 358 |
| 108 | ESI+: 352 |
| 109 | ESI+: 396 |
| 110 | ESI+: 396 |
| 111 | ESI+: 384 |
| 112 | ESI+: 354 |
| 113 | FAB+: 395 |
| 114 | FAB+: 358 |

TABLE 161

| Ex | Data |
|---|---|
| 115 | ESI+: 358 |
| 116 | ESI+: 374 |
| 117 | ESI+: 397 |
| 118 | ESI+: 370<br>NMR-DMSO-$d_6$: 1.87-2.09 (4H, m), 2.89 (0.9H, s), 2.95 (2.1H, s), 3.28 (3H, s), 3.30-3.37 (1H, m), 3.42-3.51 (1H, m), 3.52-3.61 (2H, m), 3.80 (2H, s), 3.85 (0.6H, s), 3.92 (1.4H, s), 4.23-4.28 (1H, m), 4.58 (0.6H, s), 4.61 (1.4H, s), 7.18-7.24 (1H, m), 7.39-7.50 (2H, m), 7.52-7.61 (1H, m), 8.70 (1.4H, s), 8.72 (0.6H, s) |
| 119 | FAB+: 473 |
| 120 | ESI+: 419<br>NMR-DMSO-$d_6$: 2.90 (0.9H, s), 2.97 (2.1H, s), 3.68-3.73 (4H, m), 3.89-4.03 (8H, m), 4.59 (0.6H, s), 4.63 (1.4H, s), 7.21-7.26 (1H, m), 7.41-7.52 (2H, m), 7.55-7.65 (1H, m), 7.86-7.89 (1H, m), 8.10-8.13 (1H, m), 8.37-8.40 (1H, m), 8.75 (1.4H, s), 8.77 (0.6H, s) |
| 121 | FAB+: 431 |
| 122 | FAB+: 435 |
| 123 | ESI+: 451 |
| 124 | ESI+: 432 |
| 125 | ESI+: 454 |
| 126 | ESI+: 385 |
| 127 | ESI+: 413 |
| 128 | ESI+: 433 |
| 129 | ESI+: 364 |
| 130 | ESI+: 377 |
| 131 | ESI+: 369 |
| 132 | ESI+: 387 |
| 133 | ESI+: 432 |
| 134 | ESI+: 490 |
| 135 | ESI+: 443 |

TABLE 162

| Ex | Data |
|---|---|
| 136 | ESI+: 446<br>NMR-DMSO-$d_6$: 0.96-1.01 (3H, m), 1.22-1.29 (3H, m), 2.90 (0.9H, s), 2.97 (2.1H, s), 3.26-3.32 (1H, m), 3.41-3.56 (2H, m), 3.89-3.99 (4H, m), 4.20-4.31 (1H, m), 4.47-4.54 (1H, m), 4.59 (0.6H, s), 4.63 (1.4H, s), 4.98-5.08 (1H, m), 7.20-7.25 (2H, m), 7.30-7.35 (1H, m), 7.41-7.51 (2H, m), 7.54-7.64 (1H, m), 7.94-7.98 (1H, m), 8.29-8.33 (1H, m), 8.73 (1.4H, s), 8.75 (0.6H, s) |
| 137 | ESI+: 476 |
| 138 | ESI+: 452 |
| 139 | ESI+: 432 |
| 140 | ESI+: 446 |
| 141 | ESI+: 446 |
| 142 | ESI+: 417 |
| 143 | FAB+: 417 |
| 144 | ESI+: 416 |
| 145 | FAB+: 418<br>NMR-DMSO-$d_6$: 1.66-1.79 (2H, m), 1.98-2.08 (2H, m), 2.90 (0.9H, s), 2.96 (2.1H, s), 3.09-3.24 (3H, m), 3.80 (2H, s), 3.85 (0.6H, s), 3.92 (1.4H, s), 4.58 (0.6H, s), 4.62 (1.4H, s), 4.74-4.83 (2H, m), 7.19-7.24 (1H, m), 7.34-7.37 (1H, m), 7.40-7.51 (1H, m), 7.53-7.63 (1H, m), 8.70 (1.4H, s), 8.73 (0.6H, s), 8.75 (2H, d, J = 4.9 Hz) |
| 146 | ESI+: 443 |
| 147 | ESI+: 452 |
| 148 | ESI+: 486 |
| 149 | ESI+: 417 |
| 150 | ESI+: 417<br>NMR-DMSO-$d_6$: 1.52-1.66 (2H, m), 1.86-1.94 (2H, m), 2.85-3.08 (6H, m), 3.82 (2H, s), 3.87 (0.6H, s), 3.94 (1.4H, s), 4.58 (0.6H, s), 4.62 (1.4H, s), 4.84-4.92 (2H, m), 7.19-7.24 (1H, m), 7.28-7.32 (2H, m), 7.40-7.51 (2H, m), 7.54-7.63 (1H, m), 8.46-8.49 (2H, m), 8.71 (1.4H, s), 8.73 (0.6H, s) |
| 151 | ESI+: 436 |
| 152 | ESI+: 431 |
| 153 | ESI+: 435 |
| 154 | ESI+: 453 |

TABLE 163

| Ex | Data |
|---|---|
| 155 | ESI+: 436 |
| 156 | ESI+: 452 |
| 157 | ESI+: 496, 498 |
| 158 | ESI+: 448 |
| 159 | ESI+: 448 |
| 160 | ESI+: 432 |
| 161 | ESI+: 419<br>NMR-DMSO-$d_6$: 2.90 (0.9H, s), 2.97 (2.1H, s), 3.70-3.76 (4H, m), 3.88-3.99 (8H, m), 4.59 (0.6H, s), 4.63 (1.4H, s), 7.20-7.25 (1H, m), 7.29-7.34 (1H, m), 7.39-7.52 (3H, m), 7.55-7.65 (1H, m), 8.57-8.60 (1H, m), 8.75 (1.4H, s), 8.77 (0.6H, s) |
| 162 | ESI+: 467 |
| 163 | ESI+: 383 |
| 164 | ESI+: 423 |
| 165 | ESI+: 382 |
| 166 | ESI+: 411 |
| 167 | ESI+: 356<br>NMR-DMSO-$d_6$: 2.00-2.14 (2H, m), 2.89 (0.9H, s), 2.96 (2.1H, s), 3.27 (3H, s), 3.45-3.53 (1H, m), 3.55-3.70 (3H, m), 3.85 (2H, s), 3.90 (0.6H, s), 3.96 (1.4H, s), 4.05-4.11 (1H, m), 4.58 (0.6H, s), 4.62 (1.4H, s), 7.17-7.24 (1H, m), 7.38-7.50 (2H, m), 7.51-7.62 (1H, m), 8.69 (1.4H, s), 8.71 (0.6H, s) |
| 168 | ESI+: 356<br>NMR-DMSO-$d_6$: 2.00-2.14 (2H, m), 2.89 (0.9H, s), 2.96 (2.1H, s), 3.24 (3H, s), 3.44-3.54 (1H, m), 3.55-3.71 (3H, m), 3.83 (2H, s), 3.88 (0.6H, s), 3.95 (1.4H, s), 4.06-4.11 (1H, m), 4.58 (0.6H, s), 4.62 (1.4H, s), 7.18-7.24 (1H, m), 7.39-7.50 (2H, m), 7.51-7.62 (1H, m), 8.69 (1.4H, s), 8.71 (0.6H, s) |
| 169 | ESI+: 398 |
| 170 | FAB+: 383 |
| 171 | ESI+: 405 |
| 172 | ESI+: 399 |

TABLE 163-continued

| Ex | Data |
|---|---|
| 173 | ESI+: 427 |
| 174 | ESI+: 427 |
| 175 | ESI+: 441 |

TABLE 164

| Ex | Data |
|---|---|
| 176 | ESI+: 439 |
| 177 | ESI+: 451 |
| 178 | ESI+: 453 |
| 179 | ESI+: 479 |
| 180 | ESI+: 412 |
| 181 | FAB+: 453 |
| 182 | FAB+: 451 |
| 183 | FAB+: 437 |
| 184 | FAB+: 440 |
| 185 | ESI+: 412 |
| 186 | FAB+: 398 |
| 187 | ESI+: 381 |
| 188 | ESI+: 395 |
| 189 | FAB+: 367 |
| 190 | ESI+: 417<br>NMR-DMSO-$d_6$: 1.52-1.72 (2H, m), 1.82-1.95 (2H, m), 2.85-3.09 (6H, m), 3.88-4.03 (4H, m), 4.59 (0.6H, s), 4.63 (1.4H, s), 4.83-4.95 (2H, m), 7.17-7.25 (1H, m), 7.29-7.35 (1H, m), 7.38-7.52 (2H, m), 7.53-7.64 (1H, m), 7.66-7.72 (1H, m), 8.38-8.46 (1H, m), 8.47-8.55 (1H, m), 8.71 (1.4H, s), 8.73 (0.6H, s) |
| 191 | ESI+: 415 |
| 192 | ESI+: 414 |
| 193 | ESI+: 414 |
| 194 | ESI+: 377 |
| 195 | ESI+: 340 |
| 196 | ESI+: 340 |
| 197 | ESI+: 356 |
| 198 | ESI+: 342 |
| 199 | ESI+: 457 |
| 200 | ESI+: 457 |
| 201 | ESI+: 395 |
| 202 | ESI+: 396 |
| 203 | FAB+: 438 |
| 204 | FAB+: 396 |
| 205 | ESI+ 368 |

TABLE 165

| Ex | Data |
|---|---|
| 206 | ESI+: 411 |
| 207 | ESI+: 452, 454 |
| 208 | FAB+: 418<br>NMR-DMSO-$d_6$: 2.90 (0.9H, s), 2.97 (2.1H, s), 3.26-3.35 (4H, m), 3.90-4.04 (8H, m), 4.59 (0.6H, s), 4.63 (1.4H, s), 7.20-7.28 (2H, m), 7.36-7.52 (3H, m), 7.55-7.65 (1H, m), 8.00-8.05 (1H, m), 8.34-8.39 (1H, m), 8.74 (1.4H, s), 8.77 (0.6H, s) |
| 209 | ESI+: 432 |
| 210 | ESI+: 432 |
| 211 | ESI+: 417<br>NMR-DMSO-$d_6$: 1.59-1.76 (2H, m), 1.84-1.97 (2H, m), 2.85-3.12 (6H, m), 3.81-3.99 (4H, m), 4.59 (0.6H, s), 4.63 (1.4H, s), 4.78-4.91 (2H, m), 7.16-7.25 (2H, m), 7.27-7.33 (1H, m), 7.38-7.51 (2H, m), 7.53-7.64 (1H, m), 7.67-7.76 (1H, m), 8.42-8.52 (1H, m), 8.71 (1.4H, s), 8.73 (0.6H, s) |
| 212 | ESI+: 476 |
| 213 | FAB+: 288 |
| 214 | FAB+: 298 |
| 215 | ESI+: 326 |
| 216 | ESI+: 390 |
| 217 | FAB+: 431 |
| 218 | ESI+: 432 |

TABLE 165-continued

| Ex | Data |
|---|---|
| 219 | ESI+: 471 |
| 220 | FAB+: 354 |
| 221 | ESI+: 326 |
| 222 | ESI+: 441 |
| 223 | ESI+: 410 |
| 224 | ESI+: 471 |
| 225 | ESI+: 354 |
| 226 | ESI+: 366 |
| 227 | ESI+: 326 |
| 228 | FAB+: 354 |
| 229 | ESI+: 418 |
| 230 | ESI+: 356 |
| 231 | ESI+: 383 |

TABLE 166

| Ex | Data |
|---|---|
| 232 | FAB+: 354 |
| 233 | ESI+: 397 |
| 234 | ESI+: 411 |
| 235 | ESI+: 451 |
| 236 | FAB+: 411 |
| 237 | FAB+: 445 |
| 238 | ESI+: 425 |
| 239 | FAB+: 369 |
| 240 | ESI+: 352 |
| 241 | ESI+: 354 |
| 242 | FAB+: 403 |
| 243 | FAB+: 368 |
| 244 | ESI+: 432 |
| 245 | ESI+: 431 |
| 246 | ESI+: 355 |
| 247 | ESI+: 369 |
| 248 | ESI+: 520<br>NMR-DMSO-$d_6$: 2.55-2.62 (2H, m), 2.82-2.87 (2H, m), 2.90 (0.9H, s), 2.97 (2.1H, s), 3.32-3.45 (4H, m), 3.87-4.02 (6H, m), 4.57 (2H, s), 4.60 (0.6H, s), 4.63 (1.4H, s), 7.21-7.28 (1H, m), 7.40-7.52 (2H, m), 7.55-7.65 (1H, m), 8.00-8.07 (2H, m), 8.08-8.22 (3H, br), 8.75 (1.4H, s), 8.78 (0.6H, s) |
| 249 | ESI+: 462 |
| 250 | ESI+: 518 |
| 251 | ESI+: 443 |
| 252 | ESI+: 488 |
| 253 | ESI+: 490 |
| 254 | ESI+: 381 |
| 255 | ESI+ 367 |
| 256 | ESI+: 402 |
| 257 | ESI+: 366 |
| 258 | ESI+: 368 |
| 259 | ESI+: 368 |
| 260 | ESI+: 431 |
| 261 | ESI+: 443 |

TABLE 167

| Ex | Data |
|---|---|
| 262 | ESI+: 443 |
| 263 | ESI+: 495, 497<br>NMR-DMSO-$d_6$: 2.90 (0.9H, s), 2.97 (2.1H, s), 3.11-3.22 (4H, m), 3.88-4.02 (6H, m), 4.60 (0.6H, s), 4.63 (1.4H, s), 7.19-7.30 (2H, m), 7.40-7.53 (2H, m), 7.54-7.65 (1H, m), 7.83-8.89 (1H, m), 7.89-7.93 (1H, m), 8.05-8.25 (3H, m), 8.75 (1.4H, s), 8.77 (0.6H, s) |
| 264 | FAB+: 395 |
| 265 | ESI+: 382 |
| 266 | FAB+: 382 |
| 267 | FAB+: 368 |
| 268 | FAB+: 354 |
| 269 | FAB+: 381 |
| 270 | ESI+: 416 |

TABLE 167-continued

| Ex | Data |
|---|---|
| 271 | ESI+: 416<br>NMR-DMSO-d$_6$: 1.58-1.74 (2H, m), 1.80-1.93 (2H, m), 2.80-3.00 (6H, m), 3.60-3.82 (4H, m), 4.44-4.65 (4H, m), 6.92-7.20 (1H, m), 7.11-7.21 (1H, m), 7.27-7.35 (1H, m), 7.36-7.49 (2H, m), 7.49-7.60 (1H, m), 7.64-7.72 (1H, m), 7.78-7.89 (1H, m), 8.36-8.48 (2H, m), 8.48-8.54 (1H, m) |
| 272 | ESI+: 457 |
| 273 | FAB+: 457 |
| 274 | FAB+: 455 |
| 275 | FAB+: 443 |
| 276 | FAB+: 469 |
| 277 | FAB+: 469 |
| 278 | ESI+: 471 |
| 279 | ESI+: 443 |
| 280 | ESI+: 455 |
| 281 | ESI+: 326 |
| 282 | ESI+: 368 |
| 283 | ESI+: 356 |
| 284 | ESI+: 398 |
| 285 | ESI+: 370 |
| 286 | ESI+: 398 |

TABLE 168

| Ex | Data |
|---|---|
| 287 | ESI+: 342 |
| 288 | ESI+: 356 |
| 289 | ESI+: 356 |
| 290 | ESI+: 370 |
| 291 | ESI+: 384 |
| 292 | ESI+: 369 |
| 293 | ESI+: 383 |
| 294 | ESI+: 383 |
| 295 | ESI+: 397 |
| 296 | ESI+: 411 |
| 297 | ESI+: 366 |
| 298 | ESI+: 396 |
| 299 | ESI+: 395 |
| 300 | ESI+: 380 |
| 301 | ESI+: 394 |
| 302 | ESI+: 382 |
| 303 | ESI+: 395 |
| 304 | ESI+: 409 |
| 305 | ESI+: 453 |
| 306 | ESI+: 409 |
| 307 | ESI+: 409 |
| 308 | ESI+: 409 |
| 309 | ESI+: 410 |
| 310 | ESI+: 395 |
| 311 | ESI+: 409 |
| 312 | ESI+: 411 |
| 313 | ESI+: 409 |
| 314 | ESI+: 423 |
| 315 | ESI+: 425 |
| 316 | ESI+: 388 |
| 317 | ESI+: 402 |
| 318 | ESI+: 432 |
| 319 | ESI+: 431 |
| 320 | ESI+: 431 |

TABLE 169

| Ex | Data |
|---|---|
| 321 | ESI+: 406 |
| 322 | ESI+: 406 |
| 323 | ESI+: 406 |
| 324 | ESI+: 418 |
| 325 | ESI+: 418 |
| 326 | ESI+: 418 |
| 327 | ESI+: 389 |
| 328 | ESI+: 402 |

TABLE 169-continued

| Ex | Data |
|---|---|
| 329 | ESI+: 416 |
| 330 | ESI+: 420 |
| 331 | ESI+: 420 |
| 332 | ESI+: 420 |
| 333 | ESI+: 432 |
| 334 | ESI+: 432 |
| 335 | ESI+: 432 |
| 336 | ESI+: 403 |
| 337 | ESI+: 416 |
| 338 | ESI+: 430 |
| 339 | ESI+: 414 |
| 340 | ESI+: 428 |
| 341 | ESI+: 471 |
| 342 | ESI+: 352 |
| 343 | ESI+: 366 |
| 344 | ESI+: 368 |
| 345 | ESI+: 384 |
| 346 | ESI+: 439 |
| 347 | ESI+: 382 |
| 348 | ESI+: 423 |
| 349 | ESI+: 425 |
| 350 | ESI+: 382 |
| 351 | ESI+: 382 |
| 352 | ESI+: 396 |
| 353 | ESI+: 396 |
| 354 | ESI+: 396 |

TABLE 170

| Ex | Data |
|---|---|
| 355 | ESI+: 410 |
| 356 | ESI+: 410 |
| 357 | ESI+: 410 |
| 358 | ESI+: 395 |
| 359 | ESI+: 409 |
| 360 | ESI+: 381 |
| 361 | ESI+: 425 |
| 362 | ESI+: 439 |
| 363 | ESI+: 400 |
| 364 | ESI+: 414 |
| 365 | ESI+: 428 |
| 366 | ESI+: 442 |
| 367 | ESI+: 443 |
| 368 | ESI+: 435 |
| 369 | ESI+: 451 |
| 370 | ESI+: 443 |
| 371 | ESI+: 461 |
| 372 | ESI+: 461 |
| 373 | ESI+: 461 |
| 374 | ESI+: 340 |
| 375 | ESI+: 273 |
| 376 | ESI+: 289 |
| 377 | ESI+: 285 |
| 378 | ESI+: 285 |
| 379 | ESI+: 280 |
| 380 | ESI+: 312 |
| 381 | ESI+: 298 |
| 382 | ESI+: 340 |
| 383 | ESI+: 297 |
| 384 | ESI+: 299 |
| 385 | ESI+: 333 |
| 386 | ESI+: 326 |
| 387 | ESI+: 271 |
| 388 | ESI+: 361 |

TABLE 171

| Ex | Data |
|---|---|
| 389 | ESI+: 299 |
| 390 | ESI+: 312 |
| 391 | ESI+: 326 |

TABLE 171-continued

| Ex | Data |
|---|---|
| 392 | ESI+: 352 |
| 393 | ESI+: 366 |
| 394 | ESI+: 368 |
| 395 | ESI+: 348 |
| 396 | ESI+: 359 |
| 397 | ESI+: 274 |
| 398 | ESI+: 286 |
| 399 | ESI+: 290 |
| 400 | ESI+: 286 |
| 401 | ESI+: 299 |
| 402 | ESI+: 340 |
| 403 | ESI+: 354 |
| 404 | ESI+: 288 |

TABLE 171-continued

| Ex | Data |
|---|---|
| 405 | ESI+: 292 |
| 406 | ESI+: 287 |
| 407 | ESI+: 300 |
| 408 | ESI+: 342 |
| 409 | ESI+: 326 |
| 410 | ESI+: 341 |
| 411 | ESI+: 359 |
| 412 | ESI+: 334 |
| 413 | ESI+: 424 |
| 414 | ESI+: 340 |
| 415 | ESI+: 362 |
| 416 | ESI+: 313 |

TABLE 172

| Ex | Syn | Structure | Acid |
|---|---|---|---|
| 417 | 417 | 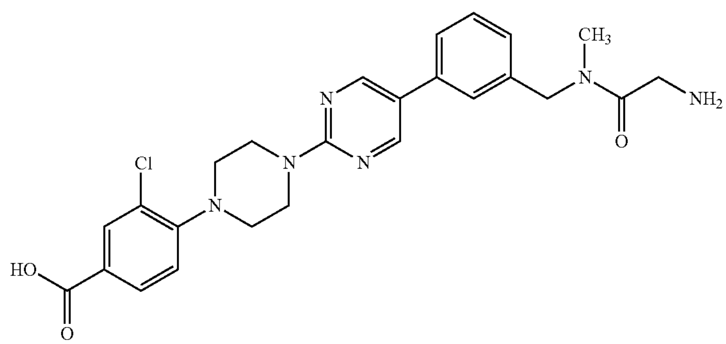 [SMILES: CN(Cc1cccc(-c2cnc(N3CCN(c4ccc(C(=O)O)cc4Cl)CC3)nc2)c1)C(=O)CN] | 1/2 FA |
| 418 | 418 | 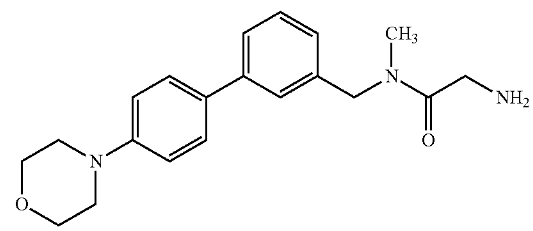 [SMILES: CN(Cc1cccc(-c2ccc(N3CCOCC3)cc2)c1)C(=O)CN] | 1/2 SA |
| 419 | 418 | 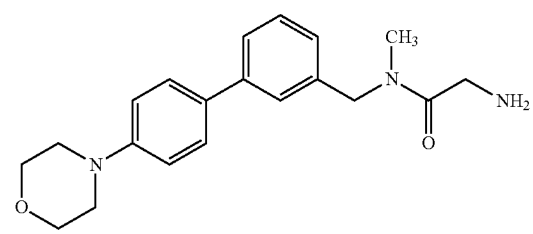 [SMILES: CN(Cc1cccc(-c2ccc(N3CCOCC3)cc2)c1)C(=O)CN] | 1/2 FA |
| 420 | 418 | 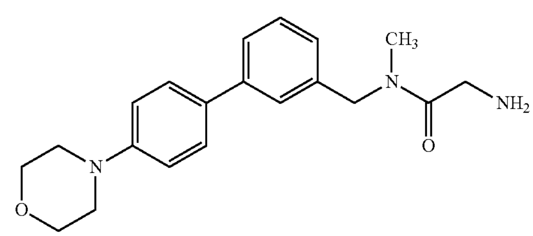 [SMILES: CN(Cc1cccc(-c2ccc(N3CCOCC3)cc2)c1)C(=O)CN] | L-TA |

TABLE 173

| Ex | Data |
|---|---|
| 417 | ESI+: 495<br>NMR-DMSO-$d_6$: 2.91 (3H, s), 3.18-3.22 (4H, m), 3.56 (2H, s), 3.97-3.99 (4H, m), 4.58 (1H, s), 6.54 (1H, s), 7.19-7.23 (2H, m), 7.40-7.57 (2H, m), 7.52-7.54 (1H, m), 7.83-7.84 (1H, m), 7.89-7.90 (1H, m), 8.69 (2H, s).<br>Powder X-ray Diffraction using Cu-K$\alpha$:<br>2$\theta$(°): 12.5, 14.8, 17.6, 18.2, 22.0 and 23.4 |
| 418 | ESI+: 340<br>NMR-DMSO-$d_6$: 2.26 (2H, s), 2.89 (1H, s), 2.92 (2H, s), 3.14-3.16 (4H, m), 3.64 (0.7H, s), 3.70 (1.3H, s), 3.74-3.77 (4H, m), 4.57 (0.7H, s), 4.59 (1.3H, s), 7.01-7.36 (2H, m), 7.11-7.16 (1H, m), 7.36-7.56 (5H, m).<br>Powder X-ray Diffraction using Cu-K$\alpha$:<br>2$\theta$(°): 4.9, 7.4, 15.6, 16.2, 17.7, 20.7 and 22.0 |
| 419 | ESI+: 340<br>NMR-DMSO-$d_6$: 2.88 (1H, s), 2.91 (2H, s), 3.14-3.16 (4H, m), 3.65 (0.7H, s), 3.70 (1.3H, s), 3.74-3.77 (4H, m), 4.56 (0.7H, s), 4.59 (1.3H, s), 6.41 (2H, s), 7.01-7.03 (2H, m), 7.12-7.16 (1H, m), 7.35-7.57 (5H, m).<br>Powder X-ray Diffraction using Cu-K$\alpha$:<br>2$\theta$(°): 4.9, 7.4, 15.8, 16.4, 17.9, 20.8 and 22.6 |
| 420 | ESI+: 340<br>NMR-DMSO-$d_6$: 2.90 (1H, s), 2.94 (2H, s), 3.14-3.17 (4H, m), 3.75-3.77 (4H, m), 3.83-3.91 (4H, m), 4.58 (0.7H, s), 4.61 (1.3H, s), 6.41 (2H, s), 7.01-7.04 (2H, m), 7.14-7.18 (1H, m), 7.36-7.57 (5H, m).<br>Powder X-ray Diffraction using Cu-K$\alpha$:<br>2$\theta$(°): 3.9, 18.4, 18.8, 20.0, 21.0 and 21.9 |

INDUSTRIAL APPLICABILITY

The compound of the formula (I) or a salt thereof has a VAP-1 inhibitory action, and it can be used as an agent for preventing and/or treating VAP-1-related diseases.

The invention claimed is:

1. A compound represented by the formula (I) or a salt thereof:

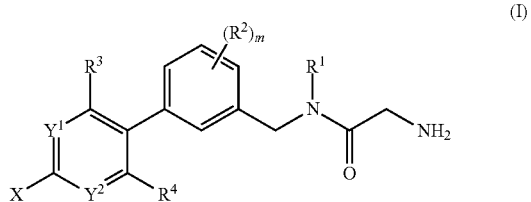

(I)

wherein
$R^1$ is H or lower alkyl which may be substituted with halogen,
$R^2$ is halogen,
$R^3$ and $R^4$ are the same as or different from each other, and are H or halogen,
m is 0, 1, 2, 3, or 4,
$Y^1$ and $Y^2$ are both N,
X is Z—,
Z is

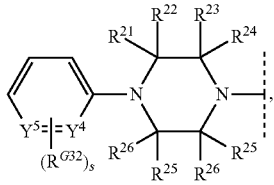

$R^{21}$, $R^{22}$, $R^{23}$, $R^{24}$, $R^{25}$ and $R^{26}$ are H, $Y^4$ is N or $CR^{Y41}$, $Y^5$ is N or $CR^{Y51}$, $R^{Y41}$, $R^{Y51}$, and $R^{G32}$ are H, halogen, —OH, —O-lower alkyl (in which the lower alkyl may be substituted with 1 to 3 OH, halogen, —O-lower alkyl (in which the lower alkyl may be substituted with one or more —COOH groups), or aryl groups), —CHO, —CO-lower alkyl (in which the lower alkyl may be substituted with 1 to 3 halogen atoms), —CO-cycloalkyl (in which cycloalkyl may be substituted with one or more —O-lower alkyl groups), —CO-aryl, a —CO-monocyclic saturated hetero ring group, cyano, —COOH, —COO-lower alkyl (in which the lower alkyl may be substituted with 1 to 3 halogen atoms), lower alkyl which may be substituted with —COOH or —O-lower alkyl, or lower alkenyl which may be substituted with —COOH or —O-lower alkyl, and s is 0, 1, 2, or 3.

2. The compound or a salt thereof according to claim 1, wherein Z is

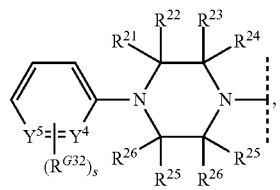

$R^{21}$, $R^{22}$, $R^{23}$, $R^{24}$, $R^{25}$ and $R^{26}$ are H, and

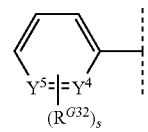

is 3-methylpyridin-2-yl, 5-(2-carboxyvinyl)-3-methyl-pyridin-2-yl, 5-(2-carboxyethyl)-3-methyl-pyridin-2-yl, 5-carboxy-3-chloro-pyridin-2-yl, 5-(2-carboxyvinyl)-3-chloro-pyridin-2-yl, 4-carboxy-6-chloro-phenyl, 6-cyanopyridin-3-yl, 2-methylpyridin-3-yl, or 3-chloropyridin-2-yl.

3. The compound or a salt thereof according to claim 2, wherein $R^1$ is lower alkyl which may be substituted with halogen.

4. The compound or a salt thereof according to claim 3, wherein $R^3$ and $R^4$ are H.

5. The compound or a salt thereof according to claim 4, wherein m is 0.

6. The compound or a salt thereof according to claim 1, which is a compound selected from the group consisting of:
(2E)-3-(6-{4-[5-(3-{[glycyl(methyl)amino] methyl}phenyl)pyrimidin-2-yl]piperazin-1-yl}-5-methylpyridin-3-yl)acrylic acid,
3-chloro-4-{4-[5-(3-{[glycyl(methyl)amino] methyl}phenyl)pyrimidin-2-yl]piperazin-1-yl}benzoic acid, and
N-methyl-N-(3-{2-[4-(2-methylpyridin-3-yl)piperazin-1-yl]pyrimidin-5-yl}benzyl)glycinamide;
or a salt of said compound.

7. A pharmaceutical composition, comprising a compound or a salt thereof according to claim 6 and a pharmaceutically acceptable excipient.

8. A method for treating a VAP-1-related disease selected from the group consisting of diabetic nephropathy and diabetic macular edema, comprising administering to a patient in need thereof an effective amount of a compound or a salt thereof according to claim 6.

9. The method according to claim 8, wherein the administration of the effective amount comprises at least one selected from the group consisting of administration via tablets, pills, capsules, granules, powders, solutions, parenteral application, intraarticular, intravenous, and intramuscular injections, suppositories, ophthalmic solutions, eye ointments, transdermal liquid preparations, ointments, transdermal patches, transmucosal liquid preparations, transmucosal patches, and inhalers.

10. The compound or a salt thereof according to claim 6, which is:

3-chloro-4-{4-[5-(3-{[glycyl(methyl)amino]methyl}phenyl)pyrimidin-2-yl]piperazin-1-yl}benzoic acid or a salt thereof.

11. The compound or a salt thereof according to claim 6, which is:

(2E)-3-(6-{4-[5-(3-{[glycyl(methyl)amino]methyl}phenyl)pyrimidin-2-yl]piperazin-1-yl}-5-methylpyridin-3-yl)acrylic acid or a salt thereof.

12. The compound or a salt thereof according to claim 6, which is:

N-methyl-N-(3-{2-[4-(2-methylpyridin-3-yl)piperazin-1-yl]pyrimidin-5-yl}benzyl)glycinamide or a salt thereof.

* * * * *